US010260038B2

(12) United States Patent
Swee et al.

(10) Patent No.: US 10,260,038 B2
(45) Date of Patent: Apr. 16, 2019

(54) PROTEIN MODIFICATION OF LIVING CELLS USING SORTASE

(71) Applicant: Whitehead Institute for Biomedical Research, Cambridge, MA (US)

(72) Inventors: Lee Kim Swee, Heidelberg (DE); Hidde L. Ploegh, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 262 days.

(21) Appl. No.: 14/890,296

(22) PCT Filed: May 9, 2014

(86) PCT No.: PCT/US2014/037545
§ 371 (c)(1),
(2) Date: Nov. 10, 2015

(87) PCT Pub. No.: WO2014/183066
PCT Pub. Date: Nov. 13, 2014

(65) Prior Publication Data
US 2016/0122707 A1  May 5, 2016

Related U.S. Application Data

(60) Provisional application No. 61/943,094, filed on Feb. 21, 2014, provisional application No. 61/822,092, filed on May 10, 2013.

(51) Int. Cl.
| | | |
|---|---|---|
| C12N 5/07 | (2010.01) | |
| A61K 39/395 | (2006.01) | |
| A61K 47/68 | (2017.01) | |
| A61K 47/66 | (2017.01) | |
| A61K 47/65 | (2017.01) | |
| C12N 5/00 | (2006.01) | |
| A61K 39/00 | (2006.01) | |
| C12N 5/0783 | (2010.01) | |
| C12N 9/50 | (2006.01) | |

(52) U.S. Cl.
CPC ........ *C12N 5/0006* (2013.01); *A61K 39/0011* (2013.01); *A61K 47/65* (2017.08); *A61K 47/66* (2017.08); *A61K 47/68* (2017.08); *C12N 5/0636* (2013.01); *C12N 5/0638* (2013.01); *C12N 9/50* (2013.01); *A61K 2039/5158* (2013.01); *C12Y 304/2207* (2013.01)

(58) Field of Classification Search
None
See application file for complete search history.

(56) References Cited

U.S. PATENT DOCUMENTS

| 5,728,369 A | 3/1998 | Griffiths et al. |
|---|---|---|
| 8,940,501 B2 | 1/2015 | Ploegh et al. |
| 2003/0022178 A1 | 1/2003 | Schneewind et al. |
| 2004/0213795 A1 | 10/2004 | Collins et al. |
| 2011/0195068 A1 | 8/2011 | Langermann et al. |
| 2011/0321183 A1 | 12/2011 | Ploegh et al. |
| 2012/0039906 A1 | 2/2012 | Olive |
| 2012/0114649 A1 | 5/2012 | Langermann et al. |
| 2013/0095098 A1 | 4/2013 | Tyson |
| 2013/0108651 A1 | 5/2013 | Carven et al. |
| 2013/0109843 A1 | 5/2013 | Carven et al. |
| 2013/0237580 A1 | 9/2013 | Sasikumar et al. |
| 2014/0030697 A1 | 1/2014 | Ploegh et al. |
| 2014/0057317 A1 | 2/2014 | Liu et al. |
| 2014/0249296 A1 | 9/2014 | Ploegh et al. |
| 2015/0086576 A1 | 3/2015 | Ploegh et al. |
| 2016/0082046 A1 | 3/2016 | Lodish et al. |
| 2016/0097773 A1 | 4/2016 | Pasqual et al. |
| 2016/0287734 A1 | 10/2016 | Rashidian et al. |

FOREIGN PATENT DOCUMENTS

| JP | 2010115136 A | 5/2010 |
|---|---|---|
| WO | WO 2000/62804 A2 | 10/2000 |
| WO | WO 2005/051976 A2 | 6/2005 |
| WO | WO 2010/087994 A2 | 8/2010 |
| WO | WO 2011/133704 A2 | 10/2011 |
| WO | WO 2012/142659 A1 | 10/2012 |
| WO | WO 2013/003555 A1 | 1/2013 |

(Continued)

OTHER PUBLICATIONS

Yamamoto "Expansion of the sortase-mediated labeling method for site-specific N-terminal labeling of cell surface proteins on living cells", Chemical Communications, 2009, No. 9, 1022-1024, and supplemental information. (Year: 2009).*
Xiao "Protein N-Terminal Processing: Substated Specificity of *Escherichia coli* and Human Methionine Aminopeptidases" Biochemistry, 2010, 49(26), 5588-5599. (Year: 2010).*
Ta ("Enzymatic Single Chain Antibody Tagging", Circulation Research, 2011, 365-373, and Supplemental Material) (Year: 2011).*
Creative Biolabs ("Single Domain Antibody Library", available at www.creative-biolabs.com/single-domain-antibody-library-service.html?gclid=eaiaiqobchnninozno5qo3givibczch3uhqhneaayaiaaegk-sfd_bwe, captured on Oct. 17, 2018) (Year: 2018).*

(Continued)

*Primary Examiner* — Robert J Yamasaki
*Assistant Examiner* — Charles Zoltan Constantine
(74) *Attorney, Agent, or Firm* — Wolf, Greenfield & Sacks, P.C.

(57) ABSTRACT

Non-genetically engineered mammalian cells modified by sortase-mediated conjugation of an agent thereto are provided. Methods of conjugating agents to nongenetically engineered mammalian cells using sortase are provided. Methods of using the cells, e.g. a method of modulating an immune response of a subject to an entity of interest, a method of neutralizing a substance in the body of a subject, a method of treating a subject in need of treatment for deficiency of a protein, and a method of treating a subject in need of treatment for a disease, are provided.

17 Claims, 15 Drawing Sheets
Specification includes a Sequence Listing.

(56) References Cited

FOREIGN PATENT DOCUMENTS

| WO | WO 2014/183006 A2 | 11/2014 |
|----|----|----|
| WO | WO 2015/073746 A2 | 5/2015 |

OTHER PUBLICATIONS

Moreno ("Immunohistochemical analysis of B3 integrin (CD61): expression in pig tissues and human tumors" Histology and Histopathology, 2002, 17:347-352) (Year: 2002).*
Extended European Search Report, dated Nov. 30, 2012, in connection with EP 10736161.0.
Invitation to Pay Additional Fees, dated Nov. 8, 2010, in connection with PCT/US2010/000274.
International Search Report and Written Opinion, dated Dec. 22, 2010, in connection with PCT/US2010/000274.
International Preliminary Report on Patentability, dated Aug. 11, 2011, in connection with PCT/US2010/000274.
Extended European Search Report, dated Nov. 26, 2014, in connection with EP 12804570.5.
International Search Report and Written Opinion, dated Nov. 15, 2012, in connection with PCT/US2012/044584.
International Preliminary Report on Patentability, dated Jan. 16, 2014, in connection with PCT/US2012/044584.
Invitation to Pay Additional Fees, dated Sep. 5, 2014, in connection with PCT/US2014/037554.
International Search Report and Written Opinion, dated Nov. 6, 2014, in connection with PCT/US2014/037554.
International Preliminary Report on Patentability, dated Nov. 19, 2015, in connection with PCT/US2014/037554.
International Search Report and Written Opinion, dated Oct. 27, 2014, in connection with PCT/US2014/037545.
International Preliminary Report on Patentability, dated Nov. 19, 2015, in connection with PCT/US2014/037545.
Invitation to Pay Additional Fees, dated Mar. 20, 2015, in connection with PCT/US14/65574.
International Search Report and Written Opinion, dated Jun. 4, 2015, in connection with PCT/US14/65574.
Antos et al., A straight path to circular proteins. J Biol Chem. Jun. 5, 2009;284(23):16028-36. Epub Apr. 9, 2009.
Antos et al., Lipid modification of proteins through sortase-catalyzed transpeptidation. J Am Chem Soc. Dec. 3, 2008;130(48):16338-43.
Antos et al., Site-specific N- and C-terminal labeling of a single polypeptide using sortases of different specificity. J Am Chem Soc. Aug. 12, 2009;131(31):10800-1. doi: 10.1021/ja902681k.
Barnett et al., Differential recognition of surface proteins in *Streptococcus pyogenes* by two sortase gene homologs. J Bacteriol. Apr. 2002;184(8):2181-91.
Boonyarattanakalin et al., Synthesis of an artificial cell surface receptor that enables oligohistidine affinity tags to func-tion as metal-dependent cell-penetrating peptides. J Am Chem Soc. Mar. 18, 2006;128(14):4917.
Chan et al., Covalent attachment of proteins to solid supports and surfaces via Sortase-mediated ligation. PLoS One. Nov. 14, 2007;2(11):e1164. 5 pages.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Clow et al., Immobilization of proteins to biacore sensor chips using *Staphylococcus aureus* sortase A. Biotechnol Lett. Sep. 2008;30(9):1603-7. Epub Apr. 15, 2008.
Kruger et al., Analysis of the substrate specificity of the *Staphylococcus aureus* sortase transpeptidase SrtA. Biochemistry. Feb. 17, 2004;43(6):1541-51.
Levary et al., Protein-protein fusion catalyzed by sortase A. PLoS One. Apr. 6, 2011;6(4):e18342. doi: 10.1371/journal.pone.0018342. 6 pages.
Mao et al., Sortase-Mediated Protein Ligation: A New Method for Portein Engineering. J Am Chem Soc. Feb. 10, 2004;126:2670-1.
Mao, A self-cleavable sortase fusion for one-step purification of free recombinant proteins. Protein Expr Purif. Sep. 2004;37(1):253-63.
Maresso et al., Surface protein IsdC and Sortase B are required for heme-iron scavenging of Bacillus anthracis. J Bacteriol. Dec. 2006;188(23):8145-52. Epub Sep. 29, 2006.
Mariscotti et al., The Listeria monocytogenes sortase-B recognizes varied amino acids at position 2 of the sorting motif. J Biol Chem. Mar. 6, 2009;284(10):6140-6. Epub Jan. 7, 2009.
Marraffini et al., Sortase C-mediated anchoring of BasI to the cell wall envelope of Bacillus anthracis. J Bacteriol. Sep. 2007;189(17):6425-36. Epub Jun. 22, 2007.
Matsumoto et al., Site-specific tetrameric streptavidin-protein conjugation using sortase A. J Biotechnol. Mar. 10, 2011;152(1-2):37-42. doi: 10.1016/j.jbiotec.2011.01.008. Epub Jan. 22, 2011.
Mazmanian et al., An iron-regulated sortase anchors a class of surface protein during *Staphylococcus aureus* pathogenesis. Proc Natl Acad Sci U S A. Feb. 19, 2002;99(4):2293-8. Epub Feb. 5, 2002.
Mazmanian et al., Sortase-catalysed anchoring of surface proteins to the cell wall of *Staphylococcus aureus*. Mol Microbial. Jun. 2001;40(5):1049-57. Review.
Namavari et al., A novel method far direct site-specific radiolabeling of peptides using [18F]FDG. Bioconjug Chem. Mar. 18, 2009;20(3):432-6. doi: 10.1021/bc800422b.
Ning et al., Visualizing metabolically labeled glycoconjugates of living cells by copper-free and fast huisgen cycloadditions. Angew Chem Int Ed Engl. 2008;47(12):2253-5.
Pallen et al., An embarrassment of sortases—a richness of substrates? Trends Microbiol. Mar. 2001;9(3):97-101.
Parthasarathy et al., Sortase A as a novel molecular "stapler" for sequence-specific protein conjugation. Bioconjug Chem. Mar.-Apr. 2007;18(2):469-76. Epub Feb. 16, 2007.
Paterson et al., Enzyme-mediated site-specific bioconjugation of metal complexes to proteins: sortase-mediated coupling of copper-64 to a single-chain antibody. Angew Chem Int Ed Engl. Jun. 10, 2014;53(24):6115-9. doi: 10.1002/anie.201402613. Epub Apr. 28, 2014.
Pellois et al., A ligation and photorelease strategy for the temporal and spatial control of protein function in living cells. Angew Chem Int Ed Engl. Sep. 5, 2005;44(35):5713-7.
Piotukh et al., D. Directed evolution of sortase A mutants with altered substrate selectivity profiles. J Am Chem Soc. Nov. 9, 2011;133(44):17536-9. doi: 10.1021/ja205630g. Epub Oct. 13, 2011.
Popp et al., Making and breaking peptide bonds: protein engineering using sortase. Angew Chem Int Ed Engl. May 23, 2011;50(22):5024-32. doi:10.1002/anie.201008267. Epub Apr. 27, 2011.
Popp et al., Site-specific protein labeling via sortase-mediated transpeptidation. Curr Protoc Protein Sci. Apr. 2009;Chapter 15:Unit 15.3. doi: 10.1002/0471140864.ps1503s56.
Popp et al., Sortagging: a versatile method for protein labeling. Nat Chem Biol. Nov. 2007;3(11):707-8. Epub Sep. 23, 2007.
Popp et al., Sortase-catalyzed transformations that improve the properties of cytokines. Proc Natl Acad Sci USA. Feb. 22, 2011;108(8):3169-74. doi: 10.1073/pnas.1016863108. Epub Feb. 4, 2011.
Popp et al., Substrate filtering by the active site crossover loop in UCHL3 revealed by sortagging and gain-of-function mutations. J Biol Chem. Feb. 6, 2009;284(6):3593-602. Epub Dec. 1, 2008.
Samantaray et al., Peptide-sugar ligation catalyzed by transpeptidase sortase: a facile approach to neoglycoconjugate synthesis. J Am Chem Soc. Feb. 20, 2008;130(7):2132-3. Epub Jan. 30, 2008.
Strijbis et al., Protein ligation in living cells using sortase. Traffic. Jun. 2012;13(6):780-9. doi: 10.1111/j.1600-0854.2012.01345.x. Epub Mar. 23, 2012.
Swee et al., Sortase-mediated modification of αDEC205 affords optimization of antigen presentation and immunization against a set of viral epitopes. Proc Natl Acad Sci USA. Jan. 22, 2013;110(4):1428-33. doi: 10.1073/pnas.1214994110. Epub Jan. 7, 2013.
Tanaka et al., Site-specific protein modification on living cells catalyzed by Sortase. Chembiochem. Mar. 25, 2008;9(5):802-7.

(56) References Cited

OTHER PUBLICATIONS

Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.
Ton-That et al., Anchoring of surface proteins to the cell wall of Staphylococcus aureus. Sortase catalyzed in vitro transpeptidation reaction using LPXTG peptide and NH(2)-Gly(3) substrates. J Biol Chem. Mar. 31, 2000;275(13):9876-81.
Ton-That et al., Protein sorting to the cell wall envelope of Gram-positive bacteria. Biochim Biophys Acta. Nov. 11, 2004;1694(1-3):269-78.
Ton-That et al., Purification and characterization of sortase, the transpeptidase that cleaves surface proteins of Staphylococcus aureus at the LPXTG motif. Proc Natl Acad Sci U S A. Oct. 26, 1999;96(22):12424-9.
Witte et al., Preparation of unnatural N-to-N and C-to-C protein fusions. Proc Natl Acad Sci U S A. Jul. 24, 2012;109(30):11993-8. doi: 10.1073/pnas.1205427109. Epub Jul. 9, 2012.
Witte et al., Production of unnaturally linked chimeric proteins using a combination of sortase-catalyzed transpeptidation and click chemistry. Nat Protoc. Sep. 2013;8(9):1808-19. doi: 10.1038/nprot.2013.103. Epub Apr. 4, 2014. 16 pages.
Wu et al., Sortase A-catalyzed transpeptidation of glycosylphosphatidylinositol derivatives for chemoenzymatic synthesis of GPI-anchored proteins. J Am Chem Soc. Feb. 10, 2010;132(5):1567-71. doi: 10.1021/ja906611x.
Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.
EP 14795167.7, Nov. 9, 2016, Extended European Search Report.
EP 14795120.6, Oct. 13, 2016, Extended European Search Report.
U.S. Appl. No. 15/934,177, filed Mar. 23, 2018, Lodish et al.
U.S. Appl. No. 15/764,087, filed Mar. 28, 2018, Rashidian et al.
PCT/US2016/055074, Apr. 12, 2018, International Preliminary Report on Patentability.
PCT/US2016/055074, Dec. 1, 2016, Invitation to Pay Additional Fees.
PCT/US2016/055074, Feb. 6, 2017, International Search Report and Written Opinion.
Chudakov et al., Fluorescent proteins and their applications in imaging living cells and tissues.Physiol Rev. Jul. 2010;90(3):1103-63. doi: 10.1152/physrev.00038.2009.
Denk et al., Development of a (18) F-labeled tetrazine with favorable pharmacokinetics for bioorthogonal PET imaging. Angew Chem Int Ed Engl. Sep. 1, 2014;53(36):9655-9. doi:10.1002/anie.201404277. Epub Jul. 2, 2014.
Matsumura et al., Emerging principles for the recognition of peptide antigens by MHC class 1 molecules, Sci. 1992;257:927-934.
Tsukiji et al., Sortase-mediated ligation: A Gift from Gram-Positive Bacteria to Protein Engineering, ChemBioChem 2009;10:787-798.
Wriggers et al., Control of Protein Functional Dynamics by Peptide Linkers, Prat. Function. Dynam. 2005;80:736-746.
Extended European Search Report, dated Nov. 9, 2016, in connection with EP 14795167.7.
Extended European Search Report, dated Oct. 13, 2016, in connection with EP 14795120.6.
Ahlgren et al., Targeting of HER2-expressing tumors with a site-specifically 99mTc-labeled recombinant affibody molecule, ZHER2:2395, with C-terminally engineered cysteine. J Nucl Med. May 2009;50(5):781-9. doi: 10.2967/jnumed.108.056929. Epub Apr. 16, 2009.
Chang et al., Development and characterization of 89Zr-labeled panitumumab for immuno-positron emission tomographic imaging of the epidermal growth factor receptor. Mol Imaging. Jan.-Feb. 2013;12(1):17-27.
De Meyer et al., Nanobody-based products as research and diagnostic tools. Trends Biotechnol. May 2014;32(5):263-70. doi:10.1016/j.tibtech.2014.03.001. Epub Apr. 1, 2014.
Delgado, et al. "Stabilities of divalent and trivalent metal ion complexes of macrocyclic triazatriacetic acids.", Inorg. Chem. 1999; 32, 3320-3326.
Dijkers et al., Biodistribution of 89Zr-trastuzumab and PET imaging of HER2-positive lesions in patients with metastatic breast cancer. Clin Pharmacol Ther. May 2010;87(5):586-92. doi:10.1038/clpt.2010.12. Epub Mar. 31, 2010.
Dorr et al., Reprogramming the specificity of sortase enzymes. Proc Natl Acad Sci U S A. Sep. 16, 2014;111(37):13343-8. doi:10.1073/pnas.1411179111. Epub Sep. 3, 2014.
Engfeldt et al., Chemical synthesis of triple-labelled three-helix bundle binding proteins for specific fluorescent detection of unlabelled protein. Chembiochem. Jun. 2005;6(6):1043-50.
GenPept Accession No. YP 187332.1. Gill et al. Dec. 17, 2014.
Goldenberg et al., Novel radiolabeled antibody conjugates. Oncogene. May 28, 2007;26(25):3734-44.
Groheux et al., Correlation of high 18F-FDG uptake to clinical, pathological and biological prognostic factors in breast cancer. Eur J Nucl Med Mol Imaging. Mar. 2011;38(3):426-35. doi:10.1007/s00259-010-1640-9. Epub Nov. 6, 2010.
Hackenberger et al., Chemoselective ligation and modification strategies for peptides and proteins. Angew Chem Int Ed Engl. 2008;47(52):10030-74. doi: 10.1002/anie.200801313.
Hochuli et al., Genetic Approach to Facilitate Purification of Recombinant Proteins with a Novel Metal Chelate Adsorbent. Nature Biotechnology. 1988, 6, 1321-1325.
Holm et al., Electrophilic affibodies forming covalent bonds to protein targets. J Biol Chem. Nov. 20, 2009;284(47):32906-13. doi:10.1074/jbc.M109.034322. Epub Sep. 15, 2009.
Keliher et al., High-yielding, two-step 18F labeling strategy for 18F-PARP1 inhibitors. ChemMedChem. Mar. 7, 2011;6(3):424-7. doi: 10.1002/cmdc.201000426. Epub Jan. 4, 2011.
Knowles et al., Advances in immuno-positron emission tomography: antibodies for molecular imaging in oncology. J Clin Oncol. Nov. 1, 2012;30(31):3884-92. doi: 10.1200/JCO.2012.42.4887. Epub Sep. 17, 2012.
Langenhan et al., "Recent Carbohydrate-Based Chemoselective Ligation Applications." Current Organic Synthesis. 2005; 2, 59-81.
Lu et al. Biologic properties and enucleation of red blood cells from human embryonic stem cells. Blood. Dec. 1, 2008;112(12):4475-84. doi:10.1182/blood-2008-05-157198. Epub Aug. 19, 2008.
Lundberg et al., Site-specifically conjugated anti-HER2 Affibody molecules as one-step reagents for target expression analyses on cells and xenograft samples. J Immunol Methods. Jan. 30, 2007;319(1-2):53-63. Epub Nov. 21, 2006.
Nair-Gill et al., Non-invasive imaging of adaptive immunity using positron emission tomography. Immunol Rev. Feb. 2008;221:214-28. doi: 10.1111/j.1600-065X.2008.00585.x.
Nayak et al., PET and MRI of metastatic peritoneal and pulmonary colorectal cancer in mice with human epidermal growth factor receptor 1-targeted 89Zr-labeled panitumumab. J Nucl Med. Jan. 2012;53(1):113-20. doi: 10.2967/jnumed.111.094169.
Orlova et al., Evaluation of [(111/114m)In]CHX-AΔ-DTPA-ZHER2:342, an affibody ligand coniugate for targeting of HER2-expressing malignant tumors. Q J Nucl Med Mol Imaging. 2007.
Orlova et al., Tumor imaging using a picomolar affinity HER2 binding affibody molecule. Cancer Res. Apr. 15, 2006;66(8):4339-48.
Park et al., Anchoring foreign substances on live cell surfaces using Sortase A specific binding peptide. Chem Commun (Camb). Oct. 25, 2013;49(83):9585-7. doi: 10.1039/c3cc44753g.
Pishesha et al., Engineered erythrocytes covalently linked to antigenic peptides can protect against autoimmune disease. Proc Natl Acad Sci U S A. Mar. 21, 2017;114(12):3157-3162. doi:10.1073/pnas.1701746114. Epub Mar. 7, 2017.
Poli et al., Radretumab radioimmunotherapy in patients with brain metastasis: a 124I-L19SIP dosimetric PET study. Cancer Immunol Res. Aug. 2013;l(2):134-43. doi: 10.1158/2326-6066.CIR-13/0007. Epub May 20, 2013.
Rashidian et al., A highly efficient catalyst for oxime ligation and hydrazone-oxime exchange suitable for bioconjugation. Bioconjug Chem. Mar. 20, 2013;24(3):333-42. doi: 10.1021/bc3004167.Epub Mar. 6, 2013.

(56) References Cited

OTHER PUBLICATIONS

Rashidian et al., Enzymatic labeling of proteins: techniques and approaches. Bioconjug Chem. Aug. 21, 2013;24(8):1277-94.
Salsano et al., "PET imaging using radiolabeled antibodies: future direction in tumor diagnosis and correlate applications." Research and Reports in Nuclear Medicine. 2013: 3; 9-17.
Shi et al. Engineered red blood cells as carriers for systemic delivery of a wide array of functional probes. Proc Natl Acad Sci U S A. Jul. 15, 2014;111(28):10131-6. doi: 10.1073/pnas.1409861111. Epub Jun. 30, 2014.
Siontorou, Nanobodies as novel agents for disease diagnosis and therapy. Int J Nanomedicine. 2013;8:4215-27. doi: 10.2147/IJN. S39428. Epub Jan. 11, 2013.
Spicer et al., Selective chemical protein modification. Nat Commun. Sep. 5, 2014;5:4740. doi: 10.1038/ncomms5740.
Swee et al., One-step enzymatic modification of the cell surface redirects cellular cytotoxicity and parasite tropism. ACS Chem Biol. Feb. 20, 2015;10(2):460-5. doi: 10.1021/cb500462t.
Ta et al., Enzymatic single-chain antibody tagging: a universal approach to targeted molecular imaging and cell homing in cardiovascular disease. Circ Res. Aug. 5, 2011;109(4):365-73. doi: 10.1161/CIRCRESAHA.111.249375.
Tanaka et al., PET (positron emission tomography) imaging of biomolecules using metal-DOTA complexes: a new collaborative challenge by chemists, biologists, and physicians for future diagnostics and exploration of in vivo dynamics. Org Biomol Chem. Mar. 7, 2008;6(5):815-28. doi: 10.1039/b718157b. Epub Feb. 1, 2008.
Tolmachev et al., Radionuclide therapy of HER2-positive microxenografts using a 177Lu-labeled HER2-specific Affibody molecule. Cancer Res. Mar. 15, 2007;67(6):2773-82.
Tran et al., (99m)Tc-maEEE-Z(HER2:342), an Affibody molecule-based tracer for the detection of HER2 expression in malignant tumors. Bioconjug Chem. Nov.-Dec. 2007;18(6):1956-64. Epub Oct. 19, 2007.
Truong et al., Copper-catalyzed, directing group-assisted fluorination of arene and heteroarene C—H bonds. J Am Chem Soc. Jun. 26, 2013;135(25):9342-5. doi: 10.1021/ja4047125. Epub Jun. 12, 2013.
Vaidyanathan et al., Synthesis of N-succinimidyl 4-[18F]fluorobenzoate, an agent for labeling proteins and peptides with 18F. Nat Protoc. 2006;1(4):1655-61.
Vosjan et al., Conjugation and radiolabeling of monoclonal antibodies with zirconium-89 for PET imaging using the bifunctional chelate p-isothiocyanatobenzyl-desferrioxamine. Nat Protoc. Apr. 2010;5(4):739-43. doi: 10.1038/nprot.2010.13. Epub Mar. 25, 2010.
Waldherr et al., Monitoring antiproliferative responses to kinase inhibitor therapy in mice with 3'-deoxy-3'-18F-fluorothymidine PET. J Nucl Med. Jan. 2005;46(1):114-20.
Wu et al., The use of sortase-mediated ligation for the immobilisation of bacterial adhesins onto fluorescence-labelled microspheres: a novel approach to analyse bacterial adhesion to host cells. Biotechnol Lett. Nov. 2010;32(11):1713-8. doi: 10.1007/s10529-010-0349-y.
Youssef et al., The use of 18F-FDG PET in the diagnosis of cardiac sarcoidosis: a systematic review and metaanalysis including the Ontario experience. J Nucl Med. Feb. 2012;53(2):241-8. doi:10.2967/jnumed.111.090662. Epub Jan. 6, 2012.
Zhang et al., Positron emission tomography imaging of CD105 expression with a 64Cu-labeled monoclonal antibody: NOTA is superior to DOTA. PLoS One. 2011;6(12):e28005. doi:10.1371/journal.pone.0028005. Epub Dec. 9, 2011.
Zong et al., Crystal structures of *Staphylococcus aureus* sortase A and its substrate complex. J Biol Chem. Jul. 23, 2004;279(30):31383-9. Epub Apr. 26, 2004.

* cited by examiner (A)

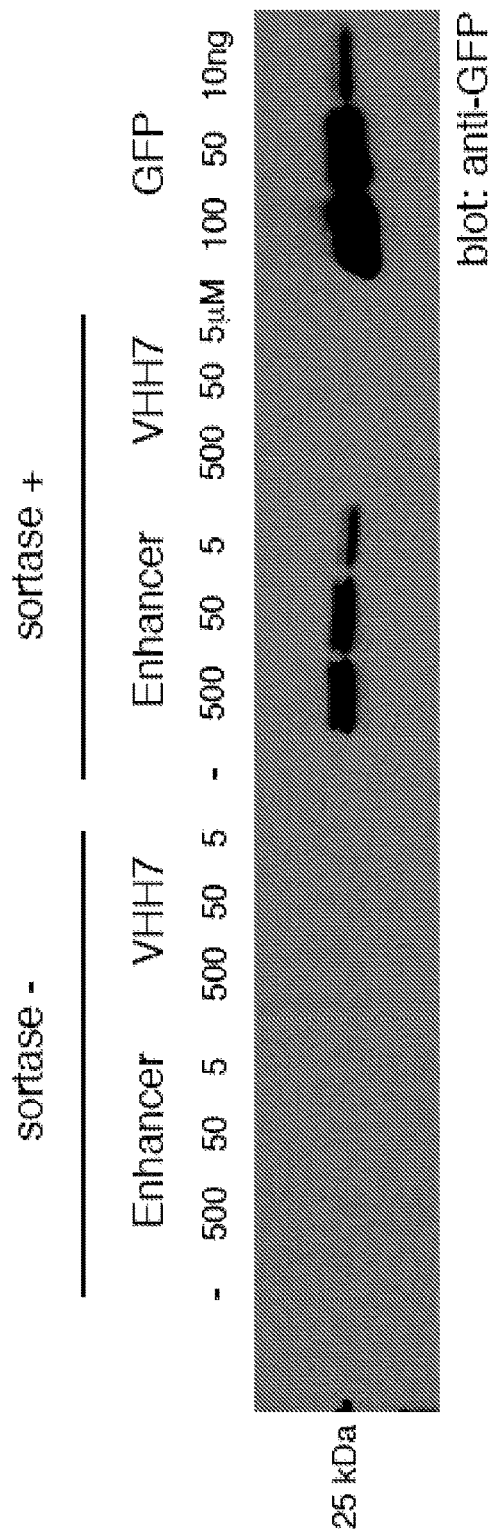

SEQUENCE LISTING

```
<160> NUMBER OF SEQ ID NOS: 138

<210> SEQ ID NO 1
<211> LENGTH: 206
<212> TYPE: PRT
<213> ORGANISM: S. aureus

<400> SEQUENCE: 1

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 2
<211> LENGTH: 206
<212> TYPE: PRT
<213> ORGANISM: S. aureus

<400> SEQUENCE: 2

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
```

```
                  20                  25                  30

Leu His Asp Lys Asp Lys Asp Glu Lys Ile Glu Gln Tyr Asp Lys Asn
            35                  40                  45

Val Lys Glu Gln Ala Ser Lys Asp Lys Gln Ala Lys Pro Gln
 50                  55                  60

Ile Pro Lys Asp Lys Ser Lys Val Ala Gly Tyr Ile Glu Ile Pro Asp
 65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
            130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
            195                 200                 205

<210> SEQ ID NO 3
<211> LENGTH: 148
<212> TYPE: PRT
<213> ORGANISM: S. aureus

<400> SEQUENCE: 3

Met Gln Ala Lys Pro Gln Ile Pro Lys Asp Lys Ser Lys Val Ala Gly
 1               5                  10                  15

Tyr Ile Glu Ile Pro Asp Ala Asp Ile Lys Glu Pro Val Tyr Pro Gly
                20                  25                  30

Pro Ala Thr Arg Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
 50                  55                  60

Ile Asp Arg Pro Asn Tyr Gln Phe Thr Asn Leu Lys Ala Ala Lys Lys
 65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
            115                 120                 125

Tyr Asn Glu Glu Thr Gly Val Trp Glu Thr Arg Lys Ile Phe Val Ala
            130                 135                 140

Thr Glu Val Lys
145

<210> SEQ ID NO 4
<211> LENGTH: 148
<212> TYPE: PRT
<213> ORGANISM: S. aureus
```

<400> SEQUENCE: 4

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Arg Glu Gln Leu Asn Arg Gly Val Ser Phe Ala Lys Glu
            35                  40                  45

Asn Gln Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
130                 135                 140

Thr Glu Val Lys
145

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is Val or Ile
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Asp Xaa Glu Xaa Asn Pro Gly
1               5

<210> SEQ ID NO 6
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 6

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 7
<211> LENGTH: 156
<212> TYPE: PRT
<213> ORGANISM: Artificial Sequence
<220> FEATURE:
<223> OTHER INFORMATION: Synthetic Polypeptide

<400> SEQUENCE: 7

-continued

```
Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Arg Glu Gln Leu Asn Arg Gly Val Ser Phe Ala Lys Glu
        35                  40                  45

Asn Gln Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
    130                 135                 140

Thr Glu Val Lys Leu Glu His His His His His His
145                 150                 155
```

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

```
Leu Pro Xaa Thr Gly
1               5
```

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 9

```
Leu Pro Xaa Thr Gly Gly
1               5
```

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

```
Leu Pro Glu Thr Gly Gly
1               5
```

<210> SEQ ID NO 11

-continued

```
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Lys Leu Pro Xaa Thr Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 12

Leu Pro Glu Thr Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 13

Ser Ile Ile Asn Phe Glu Lys Leu
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Leu Pro Glu Thr Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 15

Leu Pro Glu Thr Gly
1               5

<210> SEQ ID NO 16
<211> LENGTH: 4
<212> TYPE: PRT
<213> ORGANISM: Artificial Sequence
<220> FEATURE:
<221> NAME/KEY: misc_feature
<222> LOCATION: (4)..(4)
<223> OTHER INFORMATION: Ser can be replaced by Thr, Gly or Ala

<400> SEQUENCE: 16
```

Gly Gly Gly Ser
1

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Gly Gly Gly Gly Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 18

Leu Xaa Pro Thr Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 19

His His His His His His
1               5

<210> SEQ ID NO 20

<400> SEQUENCE: 20

000

<210> SEQ ID NO 21

<400> SEQUENCE: 21

000

<210> SEQ ID NO 22
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 22

Gly Gly Gly Gly
1

<210> SEQ ID NO 23
<211> LENGTH: 5
<212> TYPE: PRT
<213> ORGANISM: Artificial Sequence
<220> FEATURE:

<223> OTHER INFORMATION: Synthetic Polypeptide

<400> SEQUENCE: 23

Gly Gly Gly Gly Gly
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 24

Ala Ala Ala Ala
1

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 25

Ala Ala Ala Ala Ala
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 26

Leu Pro Lys Thr Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 27

Leu Pro Ala Thr Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Leu Pro Asn Thr Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 29

Leu Pro Xaa Ala Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 30

Leu Pro Asn Ala Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 31

Leu Pro Xaa Thr Ala
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 32

Leu Pro Asn Thr Ala
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 33

Leu Gly Xaa Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34
```

```
Leu Gly Ala Thr Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 35

Ile Pro Xaa Thr Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 36

Ile Pro Asn Thr Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

Ile Pro Glu Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 38

Thr Leu Xaa Thr Cys
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Gln or Lys
<220> FEATURE:
<221> NAME/KEY: misc_feature
<222> LOCATION: (4)..(4)
<223> OTHER INFORMATION: Xaa is Thr or Ser
```

```
<220> FEATURE:
<221> NAME/KEY: misc_feature
<222> LOCATION: (5)..(5)
<223> OTHER INFORMATION: Xaa is Asn, Gly or Ser

<400> SEQUENCE: 39

Asn Pro Xaa Xaa Xaa
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 40

Asn Pro Gln Thr Asn
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Asn Pro Lys Thr Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 42

Asn Ser Lys Thr Ala
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Asn Pro Gln Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Asn Ala Lys Thr Asn
1               5

<210> SEQ ID NO 45
<211> LENGTH: 5
<212> TYPE: PRT
```

```
<213> ORGANISM: Artificial Sequence
<220> FEATURE:
<223> OTHER INFORMATION: Synthetic Polypeptide

<400> SEQUENCE: 45

Asn Pro Gln Ser Ser
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 46

Asn Ala Xaa Thr Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 47

Leu Ala Xaa Thr Gly
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 48

Gln Val Pro Thr Gly Val
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is Ala or Ser

<400> SEQUENCE: 49

Leu Pro Xaa Thr Xaa
1               5

<210> SEQ ID NO 50
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 50

Leu Pro Ser Thr Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 51

Ser Pro Xaa Thr Xaa
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 52

Leu Ser Xaa Thr Xaa
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Asp, Glu, Ala, Asn, Gln, Lys or Arg
<220> FEATURE:
<221> NAME/KEY: misc_feature
<222> LOCATION: (5)..(5)
<223> OTHER INFORMATION: Xaa is Gly or Ser

<400> SEQUENCE: 53

Asn Pro Xaa Thr Xaa
1               5

<210> SEQ ID NO 54
<211> LENGTH: 5
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Asp, Glu, Ala, Asn, Gln, Lys or Arg
<220> FEATURE:
<221> NAME/KEY: misc_feature
<222> LOCATION: (5)..(5)
<223> OTHER INFORMATION: Xaa is Gly or Ser

<400> SEQUENCE: 54

Val Pro Xaa Thr Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Asp, Glu, Ala, Asn, Gln, Lys or Arg
<220> FEATURE:
<221> NAME/KEY: misc_feature
<222> LOCATION: (5)..(5)
<223> OTHER INFORMATION: Xaa is Gly or Ser

<400> SEQUENCE: 55

Ile Pro Xaa Thr Xaa
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa is Asp, Glu, Ala, Asn, Gln, Lys or Arg
<220> FEATURE:
<221> NAME/KEY: misc_feature
<222> LOCATION: (5)..(5)
<223> OTHER INFORMATION: Xaa is Gly or Ser

<400> SEQUENCE: 56

Tyr Pro Xaa Arg Xaa
1               5

<210> SEQ ID NO 57
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 57

Leu Pro Lys Thr
1

<210> SEQ ID NO 58
<211> LENGTH: 4
<212> TYPE: PRT
<213> ORGANISM: Artificial Sequence
<220> FEATURE:
<223> OTHER INFORMATION: Synthetic Polypeptide
```

```
<400> SEQUENCE: 58

Leu Pro Ile Thr
1

<210> SEQ ID NO 59
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 59

Leu Pro Asp Thr
1

<210> SEQ ID NO 60
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 60

Ser Pro Lys Thr
1

<210> SEQ ID NO 61
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 61

Leu Ala Glu Thr
1

<210> SEQ ID NO 62
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 62

Leu Ala Ala Thr
1

<210> SEQ ID NO 63
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 63

Leu Ala Ser Thr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 64
```

Leu Pro Leu Thr
1

<210> SEQ ID NO 65
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 65

Leu Ser Arg Thr
1

<210> SEQ ID NO 66
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 66

Leu Pro Glu Thr
1

<210> SEQ ID NO 67
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 67

Val Pro Asp Thr
1

<210> SEQ ID NO 68
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 68

Ile Pro Gln Thr
1

<210> SEQ ID NO 69
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 69

Tyr Pro Arg Arg
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 70

Leu Pro Met Thr
1

<210> SEQ ID NO 71
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 71

Leu Ala Phe Thr
1

<210> SEQ ID NO 72
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 72

Leu Pro Gln Thr
1

<210> SEQ ID NO 73
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 73

Asn Ser Lys Thr
1

<210> SEQ ID NO 74
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 74

Asn Pro Gln Thr
1

<210> SEQ ID NO 75
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 75

Asn Ala Lys Thr
1

<210> SEQ ID NO 76
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 76

Asn Pro Gln Ser

```
<210> SEQ ID NO 77
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 77

Leu Pro Lys Thr Gly
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 78

Leu Pro Ile Thr Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 79

Leu Pro Asp Thr Ala
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 80

Ser Pro Lys Thr Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 81

Leu Ala Glu Thr Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 82

Leu Ala Ala Thr Gly
1               5
```

```
<210> SEQ ID NO 83
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 83

Leu Ala His Thr Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 84

Leu Ala Ser Thr Gly
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 85

Leu Ala Glu Thr Gly
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 86

Leu Pro Leu Thr Gly
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 87

Leu Ser Arg Thr Gly
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 88

Leu Pro Glu Thr Gly
1               5
```

```
<210> SEQ ID NO 89
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 89

Val Pro Asp Thr Gly
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 90

Ile Pro Gln Thr Gly
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 91

Tyr Pro Arg Arg Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 92

Leu Pro Met Thr Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 93

Leu Pro Leu Thr Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 94

Leu Ala Phe Thr Gly
1               5
```

```
<210> SEQ ID NO 95
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 95

Leu Pro Gln Thr Ser
1               5

<210> SEQ ID NO 96
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 96

Leu Pro Ser Thr
1

<210> SEQ ID NO 97
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 97

Arg Ala Lys Arg
1

<210> SEQ ID NO 98
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 98

Thr Thr Cys Cys Gly Leu Arg Gln Tyr
1               5

<210> SEQ ID NO 99
<211> LENGTH: 303
<212> TYPE: PRT
<213> ORGANISM: Artificial Sequence
<220> FEATURE:
<223> OTHER INFORMATION: Synthetic Polypeptide

<400> SEQUENCE: 99

Ile Lys Gly Gly Leu Phe Ala Asp Ile Ala Ser His Pro Trp Gln Ala
1               5                   10                  15

Ala Ile Phe Ala Lys His His Arg Arg Gly Gly Glu Arg Phe Leu Cys
                20                  25                  30

Gly Gly Ile Leu Ile Ser Ser Cys Trp Ile Leu Ser Ala Ala His Cys
            35                  40                  45

Phe Gln Gln Gln Gln Gln Glu Glu Glu Glu Arg Arg Arg Arg
    50                  55                  60

Phe Phe Phe Phe Phe Pro Pro Pro Pro Pro His His Leu Thr Val
65                  70                  75                  80

Ile Leu Gly Arg Thr Tyr Arg Val Val Pro Gly Glu Glu Glu Gln Lys
                85                  90                  95
```

```
Phe Glu Val Glu Lys Tyr Ile Val His Lys Glu Phe Asp Asp Thr
            100                 105                 110

Tyr Asp Asn Asp Ile Ala Leu Leu Gln Leu Lys Ser Ser Ser Ser
            115                 120                 125

Asp Asp Asp Asp Asp Ser Ser Ser Ser Ser Ser Ser Ser Ser Arg
            130                 135                 140

Arg Arg Arg Arg Cys Ala Gln Glu Ser Ser Val Val Arg Thr Val Cys
145                 150                 155                 160

Leu Pro Pro Ala Asp Leu Gln Leu Pro Asp Trp Thr Glu Cys Glu Leu
                    165                 170                 175

Ser Gly Tyr Gly Lys His Glu Ala Leu Ser Pro Phe Tyr Ser Glu Arg
                    180                 185                 190

Leu Lys Glu Ala His Val Arg Leu Tyr Pro Ser Ser Arg Cys Thr Thr
            195                 200                 205

Thr Ser Ser Ser Gln Gln Gln His Leu Leu Asn Arg Thr Val Thr Asp
            210                 215                 220

Asn Met Leu Cys Ala Gly Asp Thr Thr Thr Arg Arg Arg Ser Ser Ser
225                 230                 235                 240

Asn Asn Asn Leu His Asp Ala Cys Gln Gly Asp Ser Gly Gly Pro Leu
                    245                 250                 255

Val Cys Leu Asn Asp Gly Arg Met Thr Leu Val Gly Ile Ile Ser Trp
                    260                 265                 270

Gly Leu Gly Cys Gly Gly Gln Lys Asp Val Pro Gly Val Tyr Thr
                275                 280                 285

Lys Val Thr Asn Tyr Leu Asp Trp Ile Arg Asp Asn Met Arg Pro
    290                 295                 300

<210> SEQ ID NO 100
<211> LENGTH: 255
<212> TYPE: PRT
<213> ORGANISM: Artificial Sequence
<220> FEATURE:
<223> OTHER INFORMATION: Synthetic Polypeptide

<400> SEQUENCE: 100

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Glu Thr Thr Gly
        35                  40                  45

Val Lys Ile Thr Val Val Ala Gly Glu His Asn Ile Glu Glu Thr Glu
50                  55                  60

His Thr Glu Gln Lys Arg Asn Val Ile Arg Ile Ile Pro His His Asn
65                  70                  75                  80

Tyr Asn Asn Asn Ala Ala Ala Ala Ala Ile Asn Lys Tyr Asn His
                85                  90                  95

Asp Ile Ala Leu Leu Glu Leu Asp Glu Pro Leu Val Leu Asn Ser Tyr
            100                 105                 110

Val Thr Pro Ile Cys Ile Ala Asp Lys Glu Tyr Thr Thr Thr Asn Asn
            115                 120                 125

Asn Ile Ile Ile Phe Leu Lys Phe Gly Ser Gly Tyr Val Ser Gly Trp
        130                 135                 140

Gly Arg Val Phe His Lys Gly Arg Ser Ala Leu Val Leu Gln Tyr Leu
145                 150                 155                 160
```

-continued

```
Arg Val Pro Leu Val Asp Arg Ala Thr Cys Leu Arg Ser Thr Lys Phe
            165                 170                 175

Thr Ile Tyr Asn Asn Met Phe Cys Ala Gly Gly Phe His Glu Gly
        180                 185                 190

Gly Gly Arg Arg Asp Ser Cys Gln Gly Asp Ser Gly Pro His Val
            195                 200                 205

Thr Glu Val Glu Gly Thr Ser Phe Leu Thr Gly Ile Ile Ser Trp Gly
        210                 215                 220

Glu Glu Cys Ala Ala Met Met Lys Gly Lys Tyr Gly Ile Tyr Thr Lys
225                 230                 235                 240

Val Ser Arg Tyr Val Asn Trp Ile Lys Glu Lys Thr Lys Leu Thr
            245                 250                 255

<210> SEQ ID NO 101
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 101

Met Thr Cys Asn Ile Lys Asn Gly Arg Cys Glu Gln Phe Cys Lys Asn
1               5                   10                  15

Ser Ala Asp Asn Lys Val Val Cys Ser Cys Thr Glu Gly Tyr Arg Leu
            20                  25                  30

Ala Glu Asn Gln Lys Ser Cys Glu Pro Ala Val Pro Phe Pro Cys Gly
        35                  40                  45

Arg Val Ser Val Ser Gln Thr Ser Lys
        50                  55

<210> SEQ ID NO 102
<211> LENGTH: 496
<212> TYPE: PRT
<213> ORGANISM: Artificial Sequence
<220> FEATURE:
<223> OTHER INFORMATION: Synthetic Polypeptide

<400> SEQUENCE: 102

Glu Phe Ala Arg Pro Cys Ile Pro Lys Ser Phe Gly Tyr Ser Ser Val
1               5                   10                  15

Val Cys Val Cys Asn Ala Thr Tyr Cys Asp Ser Phe Asp Pro Pro Ala
            20                  25                  30

Leu Gly Thr Phe Ser Arg Tyr Glu Ser Thr Arg Ser Gly Arg Arg Met
        35                  40                  45

Glu Leu Ser Met Gly Pro Ile Gln Ala Asn His Thr Gly Thr Gly Leu
    50                  55                  60

Leu Leu Thr Leu Gln Pro Glu Gln Lys Phe Gln Lys Val Lys Gly Phe
65                  70                  75                  80

Gly Gly Ala Met Thr Asp Ala Ala Ala Leu Asn Ile Leu Ala Leu Ser
                85                  90                  95

Pro Pro Ala Gln Asn Leu Leu Leu Lys Ser Tyr Phe Ser Glu Glu Gly
            100                 105                 110

Ile Gly Tyr Asn Ile Ile Arg Val Pro Met Ala Ser Cys Asp Phe Ser
        115                 120                 125

Ile Arg Thr Tyr Thr Tyr Ala Asp Thr Pro Asp Asp Phe Gln Leu His
    130                 135                 140

Asn Phe Ser Leu Pro Glu Glu Asp Thr Lys Leu Lys Ile Pro Leu Ile
145                 150                 155                 160
```

His Arg Ala Leu Gln Leu Ala Gln Arg Pro Val Ser Leu Leu Ala Ser
            165                 170                 175

Pro Trp Thr Ser Pro Thr Trp Leu Lys Thr Asn Gly Ala Val Asn Gly
        180                 185                 190

Lys Gly Ser Leu Lys Gly Gln Pro Gly Asp Ile Tyr His Gln Thr Trp
            195                 200                 205

Ala Arg Tyr Phe Val Lys Phe Leu Asp Ala Tyr Ala Glu His Lys Leu
        210                 215                 220

Gln Phe Trp Ala Val Thr Ala Glu Asn Glu Pro Ser Ala Gly Leu Leu
225                 230                 235                 240

Ser Gly Tyr Pro Phe Gln Cys Leu Gly Phe Thr Pro Glu His Gln Arg
            245                 250                 255

Asp Phe Ile Ala Arg Asp Leu Gly Pro Thr Leu Ala Asn Ser Thr His
            260                 265                 270

His Asn Val Arg Leu Leu Met Leu Asp Asp Gln Arg Leu Leu Leu Pro
        275                 280                 285

His Trp Ala Lys Val Val Leu Thr Asp Pro Glu Ala Ala Lys Tyr Val
        290                 295                 300

His Gly Ile Ala Val His Trp Tyr Leu Asp Phe Leu Ala Pro Ala Lys
305                 310                 315                 320

Ala Thr Leu Gly Glu Thr His Arg Leu Phe Pro Asn Thr Met Leu Phe
            325                 330                 335

Ala Ser Glu Ala Cys Val Gly Ser Lys Phe Trp Glu Gln Ser Val Arg
            340                 345                 350

Leu Gly Ser Trp Asp Arg Gly Met Gln Tyr Ser His Ser Ile Ile Thr
        355                 360                 365

Asn Leu Leu Tyr His Val Val Gly Trp Thr Asp Trp Asn Leu Ala Leu
    370                 375                 380

Asn Pro Glu Gly Gly Pro Asn Trp Val Arg Asn Phe Val Asp Ser Pro
385                 390                 395                 400

Ile Ile Val Asp Ile Thr Lys Asp Thr Phe Tyr Lys Gln Pro Met Phe
            405                 410                 415

Tyr His Leu Gly His Phe Ser Lys Phe Ile Pro Glu Gly Ser Gln Arg
            420                 425                 430

Val Gly Leu Val Ala Ser Gln Lys Asn Asp Leu Asp Ala Val Ala Leu
        435                 440                 445

Met His Pro Asp Gly Ser Ala Val Val Val Leu Asn Arg Ser Ser
    450                 455                 460

Lys Asp Val Pro Leu Thr Ile Lys Asp Pro Ala Val Gly Phe Leu Glu
465                 470                 475                 480

Thr Ile Ser Pro Gly Tyr Ser Ile His Thr Tyr Leu Trp His Arg Gln
            485                 490                 495

<210> SEQ ID NO 103
<211> LENGTH: 390
<212> TYPE: PRT
<213> ORGANISM: Artificial Sequence
<220> FEATURE:
<223> OTHER INFORMATION: Synthetic Polypeptide

<400> SEQUENCE: 103

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

```
Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
 65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
            290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
370                 375                 380

Gln Leu Glu Asn Thr Met
385                 390
```

<210> SEQ ID NO 104
<211> LENGTH: 479
<212> TYPE: PRT
<213> ORGANISM: Artificial Sequence
<220> FEATURE:
<223> OTHER INFORMATION: Synthetic Polypeptide

<400> SEQUENCE: 104

```
Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Pro Ser Arg Ala Ala Leu Leu Thr Gly Arg Leu Pro Val Arg
50                  55                  60

Met Gly Met Tyr Pro Gly Val Leu Val Pro Ser Ser Arg Gly Gly Leu
65                  70                  75                  80

Pro Leu Glu Glu Val Thr Val Ala Glu Val Leu Ala Ala Arg Gly Tyr
                85                  90                  95

Leu Thr Gly Met Ala Gly Lys Trp His Leu Gly Val Gly Pro Glu Gly
                100                 105                 110

Ala Phe Leu Pro Pro His Gln Gly Phe His Arg Phe Leu Gly Ile Pro
            115                 120                 125

Tyr Ser His Asp Gln Gly Pro Cys Gln Asn Leu Thr Cys Phe Pro Pro
        130                 135                 140

Ala Thr Pro Cys Asp Gly Gly Cys Asp Gln Gly Leu Val Pro Ile Pro
145                 150                 155                 160

Leu Leu Ala Asn Leu Ser Val Glu Ala Gln Pro Pro Trp Leu Pro Gly
                165                 170                 175

Leu Glu Ala Arg Tyr Met Ala Phe Ala His Asp Leu Met Ala Asp Ala
                180                 185                 190

Gln Arg Gln Asp Arg Pro Phe Phe Leu Tyr Tyr Ala Ser His His Thr
            195                 200                 205

His Tyr Pro Gln Phe Ser Gly Gln Ser Phe Ala Glu Arg Ser Gly Arg
        210                 215                 220

Gly Pro Phe Gly Asp Ser Leu Met Glu Leu Asp Ala Ala Val Gly Thr
225                 230                 235                 240

Leu Met Thr Ala Ile Gly Asp Leu Gly Leu Leu Glu Glu Thr Leu Val
                245                 250                 255

Ile Phe Thr Ala Asp Asn Gly Pro Glu Thr Met Arg Met Ser Arg Gly
                260                 265                 270

Gly Cys Ser Gly Leu Leu Arg Cys Gly Lys Gly Thr Thr Tyr Glu Gly
            275                 280                 285

Gly Val Arg Glu Pro Ala Leu Ala Phe Trp Pro Gly His Ile Ala Pro
290                 295                 300

Gly Val Thr His Glu Leu Ala Ser Ser Leu Asp Leu Leu Pro Thr Leu
305                 310                 315                 320

Ala Ala Leu Ala Gly Ala Pro Leu Pro Asn Val Thr Leu Asp Gly Phe
                325                 330                 335

Asp Leu Ser Pro Leu Leu Gly Thr Gly Lys Ser Pro Arg Gln Ser
            340                 345                 350

Leu Phe Phe Tyr Pro Ser Tyr Pro Asp Glu Val Arg Gly Val Phe Ala
        355                 360                 365

Val Arg Thr Gly Lys Tyr Lys Ala His Phe Phe Thr Gln Gly Ser Ala
370                 375                 380

His Ser Asp Thr Thr Ala Asp Pro Ala Cys His Ala Ser Ser Ser Leu
385                 390                 395                 400

Thr Ala His Glu Pro Pro Leu Leu Tyr Asp Leu Ser Lys Asp Pro Gly
                405                 410                 415
```

-continued

Glu Asn Tyr Asn Leu Leu Gly Ala Thr Pro Glu Val Leu Gln Ala Leu
        420                 425                 430

Lys Gln Leu Gln Leu Leu Lys Ala Gln Leu Asp Ala Ala Val Thr Phe
        435                 440                 445

Gly Pro Ser Gln Val Ala Arg Gly Glu Asp Pro Ala Leu Gln Ile Cys
        450                 455                 460

Cys His Pro Gly Cys Thr Pro Arg Pro Ala Cys Cys His Cys Pro
465                 470                 475

<210> SEQ ID NO 105
<211> LENGTH: 474
<212> TYPE: PRT
<213> ORGANISM: Artificial Sequence
<220> FEATURE:
<223> OTHER INFORMATION: Synthetic Polypeptide

<400> SEQUENCE: 105

Ser Arg Pro Pro His Leu Val Phe Leu Leu Ala Asp Asp Leu Gly Trp
1               5                   10                  15

Asn Asp Val Gly Phe His Gly Ser Arg Ile Arg Thr Pro His Leu Asp
                20                  25                  30

Ala Leu Ala Ala Gly Gly Val Leu Leu Asp Asn Tyr Tyr Thr Gln Pro
        35                  40                  45

Leu Thr Pro Ser Arg Ser Gln Leu Leu Thr Gly Arg Tyr Gln Ile Arg
    50                  55                  60

Thr Gly Leu Gln His Gln Ile Ile Trp Pro Cys Gln Pro Ser Cys Val
65              70                  75                  80

Pro Leu Asp Glu Lys Leu Leu Pro Gln Leu Leu Lys Glu Ala Gly Tyr
                85                  90                  95

Thr Thr His Met Val Gly Lys Trp His Leu Gly Met Tyr Arg Lys Glu
            100                 105                 110

Cys Leu Pro Thr Arg Arg Gly Phe Asp Thr Tyr Phe Gly Tyr Leu Leu
        115                 120                 125

Gly Ser Glu Asp Tyr Tyr Ser His Glu Arg Cys Thr Leu Ile Asp Ala
    130                 135                 140

Leu Asn Val Thr Arg Cys Ala Leu Asp Phe Arg Asp Gly Glu Glu Val
145                 150                 155                 160

Ala Thr Gly Tyr Lys Asn Met Tyr Ser Thr Asn Ile Phe Thr Lys Arg
                165                 170                 175

Ala Ile Ala Leu Ile Thr Asn His Pro Pro Glu Lys Pro Leu Phe Leu
            180                 185                 190

Tyr Leu Ala Leu Gln Ser Val His Glu Pro Leu Gln Val Pro Glu Glu
        195                 200                 205

Tyr Leu Lys Pro Tyr Asp Phe Ile Gln Asp Lys Asn Arg His His Tyr
    210                 215                 220

Ala Gly Met Val Ser Leu Met Asp Glu Ala Val Gly Asn Val Thr Ala
225                 230                 235                 240

Ala Leu Lys Ser Ser Gly Leu Trp Asn Asn Thr Val Phe Ile Phe Ser
                245                 250                 255

Thr Asp Asn Gly Gly Gln Thr Leu Ala Gly Gly Asn Asn Trp Pro Leu
            260                 265                 270

Arg Gly Arg Lys Trp Ser Leu Trp Glu Gly Gly Val Arg Gly Val Gly
        275                 280                 285

Phe Val Ala Ser Pro Leu Leu Lys Gln Lys Gly Val Lys Asn Arg Glu
    290                 295                 300

```
Leu Ile His Ile Ser Asp Trp Leu Pro Thr Leu Val Lys Leu Ala Arg
305                 310                 315                 320

Gly His Thr Asn Gly Thr Lys Pro Leu Asp Gly Phe Asp Val Trp Lys
                325                 330                 335

Thr Ile Ser Glu Gly Ser Pro Ser Pro Arg Ile Glu Leu Leu His Asn
            340                 345                 350

Ile Asp Pro Asn Phe Val Asp Ser Ser Pro Cys Ser Ala Phe Asn Thr
        355                 360                 365

Ser Val His Ala Ala Ile Arg His Gly Asn Trp Lys Leu Leu Thr Gly
    370                 375                 380

Tyr Pro Gly Cys Gly Tyr Trp Phe Pro Pro Ser Gln Tyr Asn Val
385                 390                 395                 400

Ser Glu Ile Pro Ser Ser Asp Pro Pro Thr Lys Thr Leu Trp Leu Phe
                405                 410                 415

Asp Ile Asp Arg Asp Pro Glu Glu Arg His Asp Leu Ser Arg Glu Tyr
                420                 425                 430

Pro His Ile Val Thr Lys Leu Leu Ser Arg Leu Gln Phe Tyr His Lys
                435                 440                 445

His Ser Val Pro Val Tyr Phe Pro Ala Gln Asp Pro Arg Cys Asp Pro
            450                 455                 460

Lys Ala Thr Gly Val Trp Gly Pro Trp Met
465                 470

<210> SEQ ID NO 106
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 106

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
                20                  25                  30

Gln Pro Gly Cys Ser Val Leu Asp Glu Ala Phe Gln Arg Tyr Arg Asp
            35                  40                  45

Leu Leu Phe Gly Thr Leu Glu Lys Asn Val Leu Val Ser Val Val
        50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190
```

Pro Val Thr His Ile Tyr Thr Ala Gln Asp Val Lys Glu Val Ile Glu
            195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
            275                 280                 285

Asp Phe Thr Cys Trp Lys Ser Asn Pro Glu Ile Gln Asp Phe Met Arg
290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
            340                 345                 350

Ile Gln Val Trp Arg Glu Asp Ile Pro Val Asn Tyr Met Lys Glu Leu
            355                 360                 365

Glu Leu Val Thr Lys Ala Gly Phe Arg Ala Leu Leu Ser Ala Pro Trp
370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
            435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 107
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 107

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
        35                  40                  45

Leu Leu Phe Gly Thr Leu Glu Lys Asn Val Leu Val Val Ser Val Val
    50                  55                  60

```
Thr Pro Gly Cys Asn Gln Leu Pro Thr Leu Glu Ser Val Glu Asn Tyr
 65                  70                  75                  80

Thr Leu Thr Ile Asn Asp Asp Gln Cys Leu Leu Leu Ser Glu Thr Val
                 85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr
    130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
        195                 200                 205

Tyr Ala Arg Leu Arg Gly Ile Arg Val Leu Ala Glu Phe Asp Thr Pro
    210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
        275                 280                 285

Asp Phe Thr Cys Trp Lys Ser Asn Pro Glu Ile Gln Asp Phe Met Arg
    290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
            340                 345                 350

Ile Gln Val Trp Arg Glu Asp Ile Pro Val Asn Tyr Met Lys Glu Leu
        355                 360                 365

Glu Leu Val Thr Lys Ala Gly Phe Arg Ala Leu Leu Ser Ala Pro Trp
    370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
        435                 440                 445

Trp Ser Asn Lys Leu Thr Ser Asp Leu Thr Phe Ala Tyr Glu Arg Leu
    450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
```

<210> SEQ ID NO 108
<211> LENGTH: 480
<212> TYPE: PRT
<213> ORGANISM: Artificial Sequence
<220> FEATURE:
<223> OTHER INFORMATION: Synthetic Polypeptide

<400> SEQUENCE: 108

```
Pro Ala Leu Trp Pro Leu Pro Leu Ser Val Lys Met Thr Pro Asn Leu
1               5                   10                  15

Leu His Leu Ala Pro Glu Asn Phe Tyr Ile Ser His Ser Pro Asn Ser
            20                  25                  30

Thr Ala Gly Pro Ser Cys Thr Leu Leu Glu Glu Ala Phe Arg Arg Tyr
        35                  40                  45

His Gly Tyr Ile Phe Gly Thr Gln Val Gln Leu Leu Val Ser Ile
    50                  55                  60

Thr Leu Gln Ser Glu Cys Asp Ala Phe Pro Asn Ile Ser Ser Asp Glu
65                  70                  75                  80

Ser Tyr Thr Leu Leu Val Lys Glu Pro Val Ala Val Leu Lys Ala Asn
                85                  90                  95

Arg Val Trp Gly Ala Leu Arg Gly Leu Glu Thr Phe Ser Gln Leu Val
            100                 105                 110

Tyr Gln Asp Ser Tyr Gly Thr Phe Thr Ile Asn Glu Ser Thr Ile Ile
        115                 120                 125

Asp Ser Pro Arg Phe Ser His Arg Gly Ile Leu Ile Asp Thr Ser Arg
    130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                165                 170                 175

Phe Pro Tyr Gln Ser Ile Thr Phe Pro Glu Leu Ser Asn Lys Gly Ser
            180                 185                 190

Tyr Ser Leu Ser His Val Tyr Thr Pro Asn Asp Val Arg Met Val Ile
        195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Asp Ser Phe Gly Pro Ile Asn Pro Thr Leu Asn Thr
                245                 250                 255

Thr Tyr Ser Phe Leu Thr Thr Phe Phe Lys Glu Ile Ser Glu Val Phe
            260                 265                 270

Pro Asp Gln Phe Ile His Leu Gly Gly Asp Glu Val Glu Phe Lys Cys
        275                 280                 285

Trp Glu Ser Asn Pro Lys Ile Gln Asp Phe Met Arg Gln Lys Gly Phe
    290                 295                 300

Gly Thr Asp Phe Lys Lys Leu Glu Ser Phe Tyr Ile Gln Lys Val Leu
305                 310                 315                 320

Asp Ile Ile Ala Thr Ile Asn Lys Gly Ser Ile Val Trp Gln Glu Val
                325                 330                 335

Phe Asp Asp Lys Ala Lys Leu Ala Pro Gly Thr Ile Val Glu Val Trp
            340                 345                 350

Lys Asp Ser Ala Tyr Pro Glu Glu Leu Ser Arg Val Thr Ala Ser Gly
```

```
                    355                 360                 365

Phe Pro Val Ile Leu Ser Ala Pro Trp Tyr Leu Asp Leu Ile Ser Tyr
    370                 375                 380

Gly Gln Asp Trp Arg Lys Tyr Tyr Lys Val Glu Pro Leu Asp Phe Gly
385                 390                 395                 400

Gly Thr Gln Lys Gln Lys Gln Leu Phe Ile Gly Gly Glu Ala Cys Leu
                    405                 410                 415

Trp Gly Glu Tyr Val Asp Ala Thr Asn Leu Thr Pro Arg Leu Trp Pro
                420                 425                 430

Arg Ala Ser Ala Val Gly Glu Arg Leu Trp Ser Ser Lys Asp Val Arg
            435                 440                 445

Asp Met Asp Asp Ala Tyr Asp Arg Leu Thr Arg His Arg Cys Arg Met
        450                 455                 460

Val Glu Arg Gly Ile Ala Ala Gln Pro Leu Tyr Ala Gly Tyr Cys Asn
465                 470                 475                 480

<210> SEQ ID NO 109
<211> LENGTH: 481
<212> TYPE: PRT
<213> ORGANISM: Artificial Sequence
<220> FEATURE:
<223> OTHER INFORMATION: Synthetic Polypeptide

<400> SEQUENCE: 109

Pro Ala Leu Trp Pro Leu Pro Leu Ser Val Lys Met Thr Pro Asn Leu
1               5                   10                  15

Leu His Leu Ala Pro Glu Asn Phe Tyr Ile Ser His Ser Pro Asn Ser
                20                  25                  30

Thr Ala Gly Pro Ser Cys Thr Leu Leu Glu Glu Ala Phe Arg Arg Tyr
            35                  40                  45

His Gly Tyr Ile Phe Gly Thr Gln Val Gln Gln Leu Leu Val Ser Ile
        50                  55                  60

Thr Leu Gln Ser Glu Cys Asp Ala Phe Pro Asn Ile Ser Ser Asp Glu
65                  70                  75                  80

Ser Tyr Thr Leu Leu Val Lys Glu Pro Val Ala Val Leu Lys Ala Asn
                85                  90                  95

Arg Val Trp Gly Ala Leu Arg Gly Leu Glu Thr Phe Ser Gln Leu Val
            100                 105                 110

Tyr Gln Asp Ser Tyr Gly Thr Phe Thr Ile Asn Glu Ser Thr Ile Ile
        115                 120                 125

Asp Ser Pro Arg Phe Ser His Arg Gly Ile Leu Ile Asp Thr Ser Arg
    130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                165                 170                 175

Phe Pro Tyr Gln Ser Ile Thr Phe Pro Glu Leu Ser Asn Lys Gly Ser
            180                 185                 190

Tyr Ser Leu Ser His Val Tyr Thr Pro Asn Asp Val Arg Met Val Ile
        195                 200                 205

Glu Tyr Ala Arg Leu Arg Gly Ile Arg Val Leu Pro Glu Phe Asp Thr
    210                 215                 220

Pro Gly His Thr Leu Ser Trp Gly Lys Gly Gln Lys Asp Leu Leu Thr
225                 230                 235                 240

Pro Cys Tyr Ser Leu Asp Ser Phe Gly Pro Ile Asn Pro Thr Leu Asn
```

```
                245             250                 255
Thr Thr Tyr Ser Phe Leu Thr Thr Phe Phe Lys Glu Ile Ser Glu Val
            260                 265                 270

Phe Pro Asp Gln Phe Ile His Leu Gly Gly Asp Glu Val Glu Phe Lys
            275                 280                 285

Cys Trp Glu Ser Asn Pro Lys Ile Gln Asp Phe Met Arg Gln Lys Gly
            290                 295                 300

Phe Gly Thr Asp Phe Lys Lys Leu Glu Ser Phe Tyr Ile Gln Lys Val
305                 310                 315                 320

Leu Asp Ile Ile Ala Thr Ile Asn Lys Gly Ser Ile Val Trp Gln Glu
                325                 330                 335

Val Phe Asp Asp Lys Ala Lys Leu Ala Pro Gly Thr Ile Val Glu Val
            340                 345                 350

Trp Lys Asp Ser Ala Tyr Pro Glu Glu Leu Ser Arg Val Thr Ala Ser
            355                 360                 365

Gly Phe Pro Val Ile Leu Ser Ala Pro Trp Tyr Leu Asp Leu Ile Ser
            370                 375                 380

Tyr Gly Gln Asp Trp Arg Lys Tyr Tyr Lys Val Glu Pro Leu Asp Phe
385                 390                 395                 400

Gly Gly Thr Gln Lys Gln Lys Gln Leu Phe Ile Gly Gly Glu Ala Cys
                405                 410                 415

Leu Trp Gly Glu Tyr Val Asp Ala Thr Asn Leu Thr Pro Arg Leu Trp
            420                 425                 430

Pro Arg Ala Ser Ala Val Gly Glu Arg Leu Trp Ser Ser Lys Asp Val
            435                 440                 445

Arg Asp Met Asp Asp Ala Tyr Asp Arg Leu Thr Arg His Arg Cys Arg
            450                 455                 460

Met Val Glu Arg Gly Ile Ala Ala Gln Pro Leu Tyr Ala Gly Tyr Cys
465                 470                 475                 480

Asn

<210> SEQ ID NO 110
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 110

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
            35                  40                  45

Leu Leu Phe Gly Thr Leu Glu Lys Asn Val Leu Val Val Ser Val Val
            50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
            115                 120                 125
```

Pro Arg Phe Pro His Arg Gly Leu Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
                180                 185                 190

Pro Val Thr His Ile Tyr Thr Ala Gln Asp Val Lys Glu Val Ile Glu
                195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
                260                 265                 270

Ser Ser Val Phe Pro Asp Phe Tyr Leu His Leu Gly Gly Asp Glu Val
                275                 280                 285

Asp Phe Thr Cys Trp Lys Ser Asn Pro Glu Ile Gln Asp Phe Met Arg
290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
                340                 345                 350

Ile Gln Val Trp Arg Glu Asp Ile Pro Val Asn Tyr Met Lys Glu Leu
                355                 360                 365

Glu Leu Val Thr Lys Ala Gly Phe Arg Ala Leu Leu Ser Ala Pro Trp
370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
                420                 425                 430

Leu Val Pro Arg Leu Trp Pro Arg Ala Gly Ala Val Ala Glu Arg Leu
435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 111
<211> LENGTH: 307
<212> TYPE: PRT
<213> ORGANISM: Artificial Sequence
<220> FEATURE:
<223> OTHER INFORMATION: Synthetic Polypeptide

<400> SEQUENCE: 111

```
Val Pro Trp Phe Pro Arg Thr Ile Gln Glu Leu Asp Arg Phe Ala Asn
1               5                   10                  15

Gln Ile Leu Ser Tyr Gly Ala Glu Leu Asp Ala Asp His Pro Gly Phe
            20                  25                  30

Lys Asp Pro Val Tyr Arg Ala Arg Arg Lys Gln Phe Ala Asp Ile Ala
        35                  40                  45

Tyr Asn Tyr Arg His Gly Gln Pro Ile Pro Arg Val Glu Tyr Met Glu
50                  55                  60

Glu Glu Lys Lys Thr Trp Gly Thr Val Phe Lys Thr Leu Lys Ser Leu
65                  70                  75                  80

Tyr Lys Thr His Ala Cys Tyr Glu Tyr Asn His Ile Phe Pro Leu Leu
                85                  90                  95

Glu Lys Tyr Cys Gly Phe His Glu Asp Asn Ile Pro Gln Leu Glu Asp
            100                 105                 110

Val Ser Gln Phe Leu Gln Thr Cys Thr Gly Phe Arg Leu Arg Pro Val
        115                 120                 125

Ala Gly Leu Leu Ser Ser Arg Asp Phe Leu Gly Gly Leu Ala Phe Arg
    130                 135                 140

Val Phe His Cys Thr Gln Tyr Ile Arg His Gly Ser Lys Pro Met Tyr
145                 150                 155                 160

Thr Pro Glu Pro Asp Ile Cys His Glu Leu Leu Gly His Val Pro Leu
                165                 170                 175

Phe Ser Asp Arg Ser Phe Ala Gln Phe Ser Gln Glu Ile Gly Leu Ala
            180                 185                 190

Ser Leu Gly Ala Pro Asp Glu Tyr Ile Glu Lys Leu Ala Thr Ile Tyr
        195                 200                 205

Trp Phe Thr Val Glu Phe Gly Leu Cys Lys Gln Gly Asp Ser Ile Lys
    210                 215                 220

Ala Tyr Gly Ala Gly Leu Leu Ser Ser Phe Gly Glu Leu Gln Tyr Cys
225                 230                 235                 240

Leu Ser Glu Lys Pro Lys Leu Leu Pro Leu Glu Leu Glu Lys Thr Ala
                245                 250                 255

Ile Gln Asn Tyr Thr Val Thr Glu Phe Gln Pro Leu Tyr Tyr Val Ala
            260                 265                 270

Glu Ser Phe Asn Asp Ala Lys Glu Lys Val Arg Asn Phe Ala Ala Thr
        275                 280                 285

Ile Pro Arg Pro Phe Ser Val Arg Tyr Asp Pro Tyr Thr Gln Arg Ile
    290                 295                 300

Glu Val Leu
305
```

<210> SEQ ID NO 112
<211> LENGTH: 452
<212> TYPE: PRT
<213> ORGANISM: Artificial Sequence
<220> FEATURE:
<223> OTHER INFORMATION: Synthetic Polypeptide

<400> SEQUENCE: 112

```
Ala Pro Asp Gln Asp Glu Ile Gln Arg Leu Pro Gly Leu Ala Lys Gln
1               5                   10                  15

Pro Ser Phe Arg Gln Tyr Ser Gly Tyr Leu Lys Ser Ser Gly Ser Lys
            20                  25                  30

His Leu His Tyr Trp Phe Val Glu Ser Gln Lys Asp Pro Glu Asn Ser
        35                  40                  45
```

```
Pro Val Val Leu Trp Leu Asn Gly Gly Pro Gly Cys Ser Ser Leu Asp
    50                  55                  60

Gly Leu Leu Thr Glu His Gly Pro Phe Leu Val Gln Pro Asp Gly Val
 65              70                  75                  80

Thr Leu Glu Tyr Asn Pro Tyr Ser Trp Asn Leu Ile Ala Asn Val Leu
                85                  90                  95

Tyr Leu Glu Ser Pro Ala Gly Val Gly Phe Ser Tyr Ser Asp Asp Lys
            100                 105                 110

Phe Tyr Ala Thr Asn Asp Thr Glu Val Ala Gln Ser Asn Phe Glu Ala
        115                 120                 125

Leu Gln Asp Phe Phe Arg Leu Phe Pro Glu Tyr Lys Asn Asn Lys Leu
    130                 135                 140

Phe Leu Thr Gly Glu Ser Tyr Ala Gly Ile Tyr Ile Pro Thr Leu Ala
145                 150                 155                 160

Val Leu Val Met Gln Asp Pro Ser Met Asn Leu Gln Gly Leu Ala Val
            165                 170                 175

Gly Asn Gly Leu Ser Ser Tyr Glu Gln Asn Asp Asn Ser Leu Val Tyr
            180                 185                 190

Phe Ala Tyr Tyr His Gly Leu Leu Gly Asn Arg Leu Trp Ser Ser Leu
        195                 200                 205

Gln Thr His Cys Cys Ser Gln Asn Lys Cys Asn Phe Tyr Asp Asn Lys
    210                 215                 220

Asp Leu Glu Cys Val Thr Asn Leu Gln Glu Val Ala Arg Ile Val Gly
225                 230                 235                 240

Asn Ser Gly Leu Asn Ile Tyr Asn Leu Tyr Ala Pro Cys Ala Gly Gly
            245                 250                 255

Val Pro Ser His Phe Arg Tyr Glu Lys Asp Thr Val Val Val Gln Asp
            260                 265                 270

Leu Gly Asn Ile Phe Thr Arg Leu Pro Leu Lys Arg Met Trp His Gln
    275                 280                 285

Ala Leu Leu Arg Ser Gly Asp Lys Val Arg Met Asp Pro Pro Cys Thr
    290                 295                 300

Asn Thr Thr Ala Ala Ser Thr Tyr Leu Asn Asn Pro Tyr Val Arg Lys
305                 310                 315                 320

Ala Leu Asn Ile Pro Glu Gln Leu Pro Gln Trp Asp Met Cys Asn Phe
            325                 330                 335

Leu Val Asn Leu Gln Tyr Arg Arg Leu Tyr Arg Ser Met Asn Ser Gln
        340                 345                 350

Tyr Leu Lys Leu Leu Ser Ser Gln Lys Tyr Gln Ile Leu Leu Tyr Asn
    355                 360                 365

Gly Asp Val Asp Met Ala Cys Asn Phe Met Gly Asp Glu Trp Phe Val
    370                 375                 380

Asp Ser Leu Asn Gln Lys Met Glu Val Gln Arg Arg Pro Trp Leu Val
385                 390                 395                 400

Lys Tyr Gly Asp Ser Gly Glu Gln Ile Ala Gly Phe Val Lys Glu Phe
            405                 410                 415

Ser His Ile Ala Phe Leu Thr Ile Lys Gly Ala Gly His Met Val Pro
        420                 425                 430

Thr Asp Lys Pro Leu Ala Ala Phe Thr Met Phe Ser Arg Phe Leu Asn
    435                 440                 445

Lys Gln Pro Tyr
    450
```

<210> SEQ ID NO 113
<211> LENGTH: 145
<212> TYPE: PRT
<213> ORGANISM: Artificial Sequence
<220> FEATURE:
<223> OTHER INFORMATION: Synthetic Polypeptide

<400> SEQUENCE: 113

```
Leu Pro Gln Ser Phe Leu Leu Lys Cys Leu Glu Gln Val Arg Lys Ile
1               5                   10                  15

Gln Gly Asp Gly Ala Ala Leu Gln Glu Lys Leu Cys Ala Thr Tyr Lys
            20                  25                  30

Leu Cys His Pro Glu Glu Leu Val Leu Leu Gly His Ser Leu Gly Ile
        35                  40                  45

Pro Trp Ala Pro Leu Leu Ala Gly Cys Leu Ser Gln Leu His Ser Gly
    50                  55                  60

Leu Phe Leu Tyr Gln Gly Leu Leu Gln Ala Leu Glu Gly Ile Ser Pro
65                  70                  75                  80

Glu Leu Gly Pro Thr Leu Asp Thr Leu Gln Leu Asp Val Ala Asp Phe
                85                  90                  95

Ala Thr Thr Ile Trp Gln Gln Met Glu Glu Leu Gly Met Met Pro Ala
            100                 105                 110

Phe Ala Ser Ala Phe Gln Arg Arg Ala Gly Gly Val Leu Val Ala Ser
        115                 120                 125

His Leu Gln Ser Phe Leu Glu Val Ser Tyr Arg Val Leu Arg His Leu
    130                 135                 140

Ala
145
```

<210> SEQ ID NO 114
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 114

```
Glu His Val Asn Ala Ile Gln Glu Ala Arg Arg Leu Leu Asn Leu Ser
1               5                   10                  15

Arg Asp Thr Ala Ala Glu Met Asn Glu Thr Val Glu Val Ile Ser Glu
            20                  25                  30

Met Phe Asp Leu Gln Glu Pro Thr Cys Leu Gln Thr Arg Leu Glu Leu
        35                  40                  45

Tyr Lys Gln Gly Leu Arg Gly Ser Leu Thr Lys Leu Lys Gly Pro Leu
    50                  55                  60

Thr Met Met Ala Ser His Tyr Lys Gln His Cys Pro Pro Thr Pro Glu
65                  70                  75                  80

Thr Ser Cys Ala Thr Gln Ile Ile Thr Phe Glu Ser Phe Lys Glu Asn
                85                  90                  95

Leu Lys Asp Phe Leu Leu Val Ile Pro
            100                 105
```

<210> SEQ ID NO 115
<211> LENGTH: 165
<212> TYPE: PRT
<213> ORGANISM: Artificial Sequence
<220> FEATURE:
<223> OTHER INFORMATION: Synthetic Polypeptide

```
<400> SEQUENCE: 115

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 116
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 116

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

```
<210> SEQ ID NO 117
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 117

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Arg Asp Asp Phe Glu Lys Leu
                85                  90                  95

Thr Asn Tyr Ser Val Thr Asp Leu Asn Val Gln Arg Lys Ala Ile Asp
            100                 105                 110

Glu Leu Ile Gln Val Met Ala Glu Leu Gly Ala Asn Val Ser Gly Glu
        115                 120                 125

Phe Val Lys Glu Ala Glu Asn Leu Lys Lys Tyr Phe Asn Asp Asn Gly
    130                 135                 140

Thr Leu Phe Leu Gly Ile Leu Lys Asn Trp Lys Glu Glu Ser Asp Arg
145                 150                 155                 160

Lys Ile Met Gln Ser Gln Ile Val Ser Phe Tyr Phe Lys Leu Phe Lys
                165                 170                 175

Asn Phe Lys Asp Asp Gln Ser Ile Gln Lys Ser Val Glu Thr Ile Lys
            180                 185                 190

Glu Asp Met Asn Val Lys Phe Phe Asn Ser Asn Lys Lys Lys Arg Asp
        195                 200                 205

Asp Phe Glu Lys Leu Thr Asn Tyr Ser Val Thr Asp Leu Asn Val Gln
    210                 215                 220

Arg Lys Ala Ile His Glu Leu Ile Gln Val Met Ala Glu Leu Ser Pro
225                 230                 235                 240

Ala Ala

<210> SEQ ID NO 118
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 118

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Tyr Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Asn Phe His Leu Arg Pro Arg Asp Leu Ile Ser
```

```
                65                  70                  75                  80
Asn Ile Asn Val Ile Val Leu Glu Leu Lys Gly Phe Met Cys Glu Tyr
                    85                  90                  95
Ala Asp Glu Thr Ala Thr Ile Val Glu Phe Leu Asn Arg Trp Ile Thr
                    100                 105                 110
Phe Cys Gln Ser Ile Ile Ser Thr Leu Thr
                    115                 120

<210> SEQ ID NO 119
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 119

Ala Pro Val Arg Ser Leu Asn Cys Thr Leu Arg Asp Ser Gln Gln Lys
1               5                   10                  15
Ser Leu Val Met Ser Gly Pro Tyr Glu Leu Lys Ala Leu His Leu Gln
                20                  25                  30
Gly Gln Asp Met Glu Gln Gln Val Val Phe Ser Met Ser Phe Val Gln
            35                  40                  45
Gly Glu Glu Ser Asn Asp Lys Ile Pro Val Ala Leu Gly Leu Lys Glu
        50                  55                  60
Lys Asn Leu Tyr Leu Ser Cys Val Leu Lys Asp Asp Lys Pro Thr Leu
65                  70                  75                  80
Gln Leu Glu Ser Val Asp Pro Lys Asn Tyr Pro Lys Lys Lys Met Glu
                85                  90                  95
Lys Arg Phe Val Phe Asn Lys Ile Glu Ile Asn Asn Lys Leu Glu Phe
                100                 105                 110
Glu Ser Ala Gln Phe Pro Asn Trp Tyr Ile Ser Thr Ser Gln Ala Glu
            115                 120                 125
Asn Met Pro Val Phe Leu Gly Gly Thr Lys Gly Gly Gln Asp Ile Thr
        130                 135                 140
Asp Phe Thr Met Gln Phe Val Ser
145                 150

<210> SEQ ID NO 120
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 120

Asp Lys Pro Val Ala His Val Val Ala Asn Pro Gln Ala Glu Gly Gln
1               5                   10                  15
Leu Gln Trp Ser Asn Arg Arg Ala Asn Ala Leu Leu Ala Asn Gly Val
                20                  25                  30
Glu Leu Arg Asp Asn Gln Leu Val Val Pro Ile Glu Gly Leu Phe Leu
            35                  40                  45
Ile Tyr Ser Gln Val Leu Phe Lys Gly Gln Gly Cys Pro Ser Thr His
        50                  55                  60
Val Leu Leu Thr His Thr Ile Ser Arg Ile Ala Val Ser Tyr Gln Thr
65                  70                  75                  80
Lys Val Asn Leu Leu Ser Ala Ile Lys Ser Pro Cys Gln Arg Glu Thr
                85                  90                  95
```

```
Pro Glu Gly Ala Glu Ala Lys Pro Trp Tyr Glu Pro Ile Tyr Leu Gly
            100                 105                 110

Gly Val Phe Gln Leu Gly Lys Gly Asp Arg Leu Ser Ala Glu Ile Asn
        115                 120                 125

Arg Pro Asp Tyr Leu Asp Phe Ala Glu Ser Gly Gln Val Tyr Phe Gly
    130                 135                 140

Ile Ile Ala Leu
145

<210> SEQ ID NO 121
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 121

Lys Pro Ala Ala His Leu Ile Gly Asp Pro Ser Lys Gln Asn Ser Leu
1               5                   10                  15

Leu Trp Arg Ala Asn Thr Asp Arg Ala Phe Leu Gln Asp Gly Phe Ser
            20                  25                  30

Leu Ser Asn Asn Ser Leu Leu Val Pro Thr Ser Gly Ile Tyr Phe Val
        35                  40                  45

Tyr Ser Gln Val Val Phe Ser Gly Lys Ala Tyr Ser Pro Lys Ala Thr
    50                  55                  60

Ser Ser Pro Leu Tyr Leu Ala His Glu Val Gln Leu Phe Ser Ser Gln
65                  70                  75                  80

Tyr Pro Phe His Val Pro Leu Leu Ser Ser Gln Lys Met Val Tyr Pro
                85                  90                  95

Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
        115                 120                 125

His Leu Val Leu Ser Pro Ser Thr Val Phe Phe Gly Ala Phe Ala Leu
    130                 135                 140

<210> SEQ ID NO 122
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 122

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110
```

```
Gly Ala Gln Lys Glu Ala Ile Ser Asn Ser Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 123
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 123

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 124
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 124

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 125
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 125

Phe Pro Thr Ile Pro Leu Ser Arg Leu Ala Asp Asn Ala Trp Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Ile His Ser Phe Trp Trp Asn Pro
        35                  40                  45

Gln Thr Ser Leu Cys Pro Ser Glu Ser Ile Pro Thr Pro Ser Asn Lys
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125
```

Glu Ala Leu Leu Lys Asn Tyr Gly Leu Leu Tyr Cys Phe Asn Lys Asp
            130                 135                 140

Met Ser Lys Val Ser Thr Tyr Leu Arg Thr Val Gln Cys Arg Ser Val
145                 150                 155                 160

Glu Gly Ser Cys Gly Phe
                165

<210> SEQ ID NO 126
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 126

Cys His His Arg Ile Cys His Cys Ser Asn Arg Val Phe Leu Cys Gln
1               5                   10                  15

Glu Ser Lys Val Thr Glu Ile Pro Ser Asp Leu Pro Arg Asn Ala Ile
            20                  25                  30

Glu Leu Arg Phe Val Leu Thr Lys Leu Arg Val Ile Gln Lys Gly Ala
        35                  40                  45

Phe Ser Gly Phe Gly Asp Leu Glu Lys Ile Glu Ile Ser Gln Asn Asp
    50                  55                  60

Val Leu Glu Val Ile Glu Ala Asp Val Phe Ser Asn Leu Pro Lys Leu
65                  70                  75                  80

His Glu Ile Arg Ile Glu Lys Ala Asn Asn Leu Leu Tyr Ile Asn Pro
                85                  90                  95

Glu Ala Phe Gln Asn Leu Pro Asn Leu Gln Tyr Leu Leu Ile Ser Asn
            100                 105                 110

Thr Gly Ile Lys His Leu Pro Asp Val His Lys Ile His Ser Leu Gln
        115                 120                 125

Lys Val Leu Leu Asp Ile Gln Asp Asn Ile Asn Ile His Thr Ile Glu
    130                 135                 140

Arg Asn Ser Phe Val Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Asn Leu Glu Glu Leu
            180                 185                 190

Pro Asn Asp Val Phe His Gly Ala Ser Gly Pro Val Ile Leu Asp Ile
        195                 200                 205

Ser Arg Thr Arg Ile His Ser Leu Pro Ser Tyr Gly Leu Glu Asn Leu
    210                 215                 220

Lys Lys Leu Arg Ala Arg Ser Thr Tyr Asn Leu Lys Lys Leu Pro Thr
225                 230                 235                 240

Leu Glu

<210> SEQ ID NO 127
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 127

Ile Gln Lys Val Gln Asp Asp Thr Lys Thr Leu Ile Lys Thr Ile Val
1               5                   10                  15

```
Thr Arg Ile Asn Asp Ile Leu Asp Phe Ile Pro Gly Leu His Pro Ile
            20                  25                  30

Leu Thr Leu Ser Lys Met Asp Gln Thr Leu Ala Val Tyr Gln Gln Ile
        35                  40                  45

Leu Thr Ser Met Pro Ser Arg Asn Val Ile Gln Ile Ser Asn Asp Leu
    50                  55                  60

Glu Asn Leu Arg Asp Leu Leu His Val Leu Ala Phe Ser Lys Ser Cys
65                  70                  75                  80

His Leu Pro Glu Ala Ser Gly Leu Glu Thr Leu Asp Ser Leu Gly Gly
                85                  90                  95

Val Leu Glu Ala Ser Gly Tyr Ser Thr Glu Val Val Ala Leu Ser Arg
            100                 105                 110

Leu Gln Gly Ser Leu Gln Asp Met Leu Trp Gln Leu Asp Leu Ser Pro
        115                 120                 125

Gly Cys
    130
```

<210> SEQ ID NO 128
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 128

```
Pro Glu Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Arg Ala Pro Gln Thr Gly Ile Val Asp Glu Cys Cys Phe
        35                  40                  45

Arg Ser Cys Asp Leu Arg Arg Leu Glu Met Tyr Cys Ala Pro
    50                  55                  60
```

<210> SEQ ID NO 129
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 129

```
Met Tyr Arg Ser Ala Phe Ser Val Gly Leu Glu Thr Arg Val Thr Val
1               5                   10                  15

Pro Asn Val Pro Ile Arg Phe Thr Lys Ile Phe Tyr Asn Gln Gln Asn
            20                  25                  30

His Tyr Asp Gly Ser Thr Gly Lys Phe Tyr Cys Asn Ile Pro Gly Leu
        35                  40                  45

Tyr Tyr Phe Ser Tyr His Ile Thr Val Tyr Met Lys Asp Val Lys Val
    50                  55                  60

Ser Leu Phe Lys Lys Asp Lys Ala Val Leu Phe Thr Tyr Asp Gln Tyr
65                  70                  75                  80

Gln Glu Asn Val Asp Gln Ala Ser Gly Ser Val Leu Leu His Leu Glu
                85                  90                  95

Val Gly Asp Gln Val Trp Leu Gln Val Tyr Tyr Ala Asp Asn Val Asn
            100                 105                 110

Asp Ser Thr Phe Thr Gly Phe Leu Leu Tyr His Asp Thr
        115                 120                 125
```

```
<210> SEQ ID NO 130
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 130

Met Tyr Arg Ser Ala Phe Ser Val Gly Leu Pro Asn Val Pro Ile Arg
1               5                   10                  15

Phe Thr Lys Ile Phe Tyr Asn Gln Gln Asn His Tyr Asp Gly Ser Thr
            20                  25                  30

Gly Lys Phe Tyr Cys Asn Ile Pro Gly Leu Tyr Tyr Phe Ser Tyr His
        35                  40                  45

Ile Thr Val Tyr Met Lys Asp Val Lys Val Ser Leu Phe Lys Lys Asp
    50                  55                  60

Lys Val Leu Phe Thr Tyr Asp Gln Tyr Gln Glu Lys Val Asp Gln Ala
65                  70                  75                  80

Ser Gly Ser Val Leu Leu His Leu Glu Val Gly Asp Gln Val Trp Leu
                85                  90                  95

Gln Val Tyr Asp Ser Thr Phe Thr Gly Phe Leu Leu Tyr His Asp
            100                 105                 110

<210> SEQ ID NO 131
<211> LENGTH: 102
<212> TYPE: PRT
<213> ORGANISM: Artificial Sequence
<220> FEATURE:
<223> OTHER INFORMATION: Synthetic Polypeptide

<400> SEQUENCE: 131

Met Tyr Arg Ser Ala Phe Ser Val Gly Leu Glu Thr Arg Val Thr Val
1               5                   10                  15

Pro Ile Arg Phe Thr Lys Ile Phe Tyr Asn Gln Gln Asn His Tyr Asp
            20                  25                  30

Gly Ser Thr Gly Lys Phe Tyr Cys Asn Ile Pro Gly Leu Tyr Tyr Phe
        35                  40                  45

Ser Tyr His Ile Thr Val Asp Val Lys Val Ser Leu Phe Lys Lys Asp
    50                  55                  60

Lys Ala Val Leu Phe Thr Gln Ala Ser Gly Ser Val Leu Leu His Leu
65                  70                  75                  80

Glu Val Gly Asp Gln Val Trp Leu Gln Asn Asp Ser Thr Phe Thr Gly
                85                  90                  95

Phe Leu Leu Tyr His Asp
            100

<210> SEQ ID NO 132
<211> LENGTH: 693
<212> TYPE: PRT
<213> ORGANISM: Artificial Sequence
<220> FEATURE:
<223> OTHER INFORMATION: Synthetic Polypeptide

<400> SEQUENCE: 132

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30
```

```
Arg Val Pro Lys Ser Phe Pro Phe Asn Thr Ser Val Tyr Lys Lys
            35                  40                  45

Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ala Ala Ser Ala Arg Ala Trp Pro Lys Met
    210                 215                 220

His Thr Val Asn Gly Tyr Val Asn Arg Ser Leu Pro Gly Leu Ile Gly
225                 230                 235                 240

Cys His Arg Lys Ser Val Tyr Trp His Val Ile Gly Met Gly Thr Thr
                245                 250                 255

Pro Glu Val His Ser Ile Phe Leu Glu Gly His Thr Phe Leu Val Arg
            260                 265                 270

Asn His Arg Gln Ala Ser Leu Glu Ile Ser Pro Ile Thr Phe Leu Thr
            275                 280                 285

Ala Gln Thr Leu Leu Met Asp Leu Gly Gln Phe Leu Leu Phe Cys His
        290                 295                 300

Ile Ser Ser His Gln His Asp Gly Met Glu Ala Tyr Val Lys Val Asp
305                 310                 315                 320

Ser Cys Pro Glu Glu Pro Gln Phe Asp Asp Asn Ser Pro Ser Phe
                325                 330                 335

Ile Gln Ile Arg Ser Val Ala Lys Lys His Pro Lys Thr Trp Val His
            340                 345                 350

Tyr Ile Ala Ala Glu Glu Glu Asp Trp Asp Tyr Ala Pro Leu Val Leu
            355                 360                 365

Ala Pro Asp Asp Arg Ser Tyr Lys Ser Gln Tyr Leu Asn Asn Gly Pro
        370                 375                 380

Gln Arg Ile Gly Arg Lys Tyr Lys Lys Val Arg Phe Met Ala Tyr Thr
385                 390                 395                 400

Asp Glu Thr Phe Lys Thr Arg Glu Ala Ile Gln His Glu Ser Gly Ile
                405                 410                 415

Leu Gly Pro Leu Leu Tyr Gly Glu Val Gly Asp Thr Leu Leu Ile Ile
            420                 425                 430

Phe Lys Asn Gln Ala Ser Arg Pro Tyr Asn Ile Tyr Pro His Gly Ile
        435                 440                 445

Thr Asp Val Arg Pro Leu Tyr Ser Arg Arg Leu Pro Lys Gly Val Lys
```

```
            450                 455                 460
His Leu Lys Asp Phe Pro Ile Leu Pro Gly Glu Ile Phe Lys Tyr Lys
465                 470                 475                 480

Trp Thr Val Thr Val Glu Asp Gly Pro Thr Lys Ser Asp Pro Arg Cys
                    485                 490                 495

Leu Thr Arg Tyr Tyr Ser Ser Phe Val Asn Met Glu Arg Asp Leu Ala
                500                 505                 510

Ser Gly Leu Ile Gly Pro Leu Leu Ile Cys Tyr Lys Glu Ser Val Asp
            515                 520                 525

Gln Arg Gly Asn Gln Ile Met Ser Asp Lys Arg Asn Val Ile Leu Phe
        530                 535                 540

Ser Val Phe Asp Glu Asn Arg Ser Trp Tyr Leu Thr Glu Asn Ile Gln
545                 550                 555                 560

Arg Phe Leu Pro Asn Pro Ala Gly Val Gln Leu Glu Asp Pro Glu Phe
                565                 570                 575

Gln Ala Ser Asn Ile Met His Ser Ile Asn Gly Tyr Val Phe Asp Ser
                580                 585                 590

Leu Gln Leu Ser Val Cys Leu His Glu Val Ala Tyr Trp Tyr Ile Leu
            595                 600                 605

Ser Ile Gly Ala Gln Thr Asp Phe Leu Ser Val Phe Phe Ser Gly Tyr
        610                 615                 620

Thr Phe Lys His Lys Met Val Tyr Glu Asp Thr Leu Thr Leu Phe Pro
625                 630                 635                 640

Phe Ser Gly Glu Thr Val Phe Met Ser Met Glu Asn Pro Gly Leu Trp
                645                 650                 655

Ile Leu Gly Cys His Asn Ser Asp Phe Arg Asn Arg Gly Met Thr Ala
                660                 665                 670

Leu Leu Lys Val Ser Ser Cys Asp Lys Asn Thr Gly Asp Tyr Tyr Glu
            675                 680                 685

Asp Ser Tyr Glu Asp
    690

<210> SEQ ID NO 133
<211> LENGTH: 644
<212> TYPE: PRT
<213> ORGANISM: Artificial Sequence
<220> FEATURE:
<223> OTHER INFORMATION: Synthetic Polypeptide

<400> SEQUENCE: 133

Arg Ser Phe Gln Lys Lys Thr Arg His Tyr Phe Ile Ala Ala Val Glu
1               5                   10                  15

Arg Leu Trp Asp Tyr Gly Met Ser Ser Ser Pro His Val Leu Arg Asn
                20                  25                  30

Arg Ala Gln Ser Gly Ser Val Pro Gln Phe Lys Lys Val Val Phe Gln
            35                  40                  45

Glu Phe Thr Asp Gly Ser Phe Thr Gln Pro Leu Tyr Arg Gly Glu Leu
        50                  55                  60

Asn Glu His Leu Gly Leu Leu Gly Pro Tyr Ile Arg Ala Glu Val Glu
65                  70                  75                  80

Asp Asn Ile Met Val Thr Phe Arg Asn Gln Ala Ser Arg Pro Tyr Ser
                85                  90                  95

Phe Tyr Ser Ser Leu Ile Ser Tyr Glu Glu Asp Gln Arg Gln Gly Ala
                100                 105                 110

Glu Pro Arg Lys Asn Phe Val Lys Pro Asn Glu Thr Lys Thr Tyr Phe
```

-continued

```
            115                 120                 125
Trp Lys Val Gln His His Met Ala Pro Thr Lys Asp Glu Phe Asp Cys
130                 135                 140

Lys Ala Trp Ala Tyr Ser Ser Asp Val Asp Leu Glu Lys Asp Val His
145                 150                 155                 160

Ser Gly Leu Ile Gly Pro Leu Leu Val Cys His Thr Asn Thr Leu Asn
                165                 170                 175

Pro Ala His Gly Arg Gln Val Thr Val Gln Glu Phe Ala Leu Phe Phe
                180                 185                 190

Thr Ile Phe Asp Glu Thr Lys Ser Trp Tyr Phe Thr Glu Asn Met Glu
                195                 200                 205

Arg Asn Cys Arg Ala Pro Cys Asn Ile Gln Met Glu Asp Pro Thr Phe
                210                 215                 220

Lys Glu Asn Tyr Arg Phe His Ala Ile Asn Gly Tyr Ile Met Asp Thr
225                 230                 235                 240

Leu Pro Gly Leu Val Met Ala Gln Asp Gln Arg Ile Arg Trp Tyr Leu
                245                 250                 255

Leu Ser Met Gly Ser Asn Glu Asn Ile His Ser Ile His Phe Ser Gly
                260                 265                 270

His Val Phe Thr Val Arg Lys Lys Glu Glu Tyr Lys Met Ala Leu Tyr
                275                 280                 285

Asn Leu Tyr Pro Gly Val Phe Glu Thr Val Glu Met Leu Pro Ser Lys
290                 295                 300

Ala Gly Ile Trp Arg Val Glu Cys Leu Ile Gly Glu His Leu His Ala
305                 310                 315                 320

Gly Met Ser Thr Leu Phe Leu Val Tyr Ser Asn Lys Cys Gln Thr Pro
                325                 330                 335

Leu Gly Met Ala Ser Gly His Ile Arg Asp Phe Gln Ile Thr Ala Ser
                340                 345                 350

Gly Gln Tyr Gly Gln Trp Ala Pro Lys Leu Ala Arg Leu His Tyr Ser
                355                 360                 365

Gly Ser Ile Asn Ala Trp Ser Thr Lys Glu Pro Phe Ser Trp Ile Lys
370                 375                 380

Val Asp Leu Leu Ala Pro Met Ile Ile His Gly Ile Lys Thr Gln Gly
385                 390                 395                 400

Ala Arg Gln Lys Phe Ser Ser Leu Tyr Ile Ser Gln Phe Ile Ile Met
                405                 410                 415

Tyr Ser Leu Asp Gly Lys Lys Trp Gln Thr Tyr Arg Gly Asn Ser Thr
                420                 425                 430

Gly Thr Leu Met Val Phe Phe Gly Asn Val Asp Ser Ser Gly Ile Lys
                435                 440                 445

His Asn Ile Phe Asn Pro Pro Ile Ile Ala Arg Tyr Ile Arg Leu His
                450                 455                 460

Pro Thr His Tyr Ser Ile Arg Ser Thr Leu Arg Met Glu Leu Met Gly
465                 470                 475                 480

Cys Asp Leu Asn Ser Cys Ser Met Pro Leu Gly Met Glu Ser Lys Ala
                485                 490                 495

Ile Ser Asp Ala Gln Ile Thr Ala Ser Ser Tyr Phe Thr Asn Met Phe
                500                 505                 510

Ala Thr Trp Ser Pro Ser Lys Ala Arg Leu His Leu Gln Gly Arg Ser
                515                 520                 525

Asn Ala Trp Arg Pro Gln Val Asn Asn Pro Lys Glu Trp Leu Gln Val
530                 535                 540
```

```
Asp Phe Gln Lys Thr Met Lys Val Thr Gly Val Thr Gln Gly Val
545                 550                 555                 560

Lys Ser Leu Leu Thr Ser Met Tyr Val Lys Glu Phe Leu Ile Ser Ser
                565                 570                 575

Ser Gln Asp Gly His Gln Trp Thr Leu Phe Phe Gln Asn Gly Lys Val
            580                 585                 590

Lys Val Phe Gln Gly Asn Gln Asp Ser Phe Thr Pro Val Val Asn Ser
                595                 600                 605

Leu Asp Pro Pro Leu Leu Thr Arg Tyr Leu Arg Ile His Pro Gln Ser
610                 615                 620

Trp Val His Gln Ile Ala Leu Arg Met Glu Val Leu Gly Cys Glu Ala
625                 630                 635                 640

Gln Asp Leu Tyr

<210> SEQ ID NO 134
<211> LENGTH: 578
<212> TYPE: PRT
<213> ORGANISM: Artificial Sequence
<220> FEATURE:
<223> OTHER INFORMATION: Synthetic Polypeptide

<400> SEQUENCE: 134

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
                20                  25                  30

Glu Asp His Val Lys Leu Val Asn Glu Val Thr Glu Phe Ala Lys Thr
            35                  40                  45

Cys Val Ala Asp Glu Ser Ala Glu Asn Cys Asp Lys Ser Leu His Thr
        50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255
```

```
Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
        435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
        515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala

<210> SEQ ID NO 135
<211> LENGTH: 578
<212> TYPE: PRT
<213> ORGANISM: Artificial Sequence
<220> FEATURE:
<223> OTHER INFORMATION: Synthetic Polypeptide

<400> SEQUENCE: 135

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
```

```
                35                  40                  45
Cys Val Ala Asp Glu Ser Ala Glu Asn Cys Asp Lys Ser Leu His Thr
 50                  55                  60
Leu Phe Gly Asp Lys Leu Cys Thr Val Ala Thr Leu Arg Glu Thr Tyr
 65                  70                  75                  80
Gly Glu Met Ala Asp Cys Cys Ala Lys Gln Glu Pro Glu Arg Asn Glu
                 85                  90                  95
Cys Phe Leu Gln His Lys Asp Asp Asn Pro Asn Leu Pro Arg Leu Val
                100                 105                 110
Arg Pro Glu Val Asp Val Met Cys Thr Ala Phe His Asp Asn Glu Glu
                115                 120                 125
Thr Phe Leu Lys Lys Tyr Leu Tyr Glu Ile Ala Arg Arg His Pro Tyr
                130                 135                 140
Phe Tyr Ala Pro Glu Leu Leu Phe Phe Ala Lys Arg Tyr Lys Ala Ala
145                 150                 155                 160
Phe Thr Glu Cys Cys Gln Ala Ala Asp Lys Ala Ala Cys Leu Leu Pro
                165                 170                 175
Lys Leu Asp Glu Leu Arg Asp Glu Gly Lys Ala Ser Ser Ala Lys Gln
                180                 185                 190
Arg Leu Lys Cys Ala Ser Leu Gln Lys Phe Gly Glu Arg Ala Phe Lys
                195                 200                 205
Ala Trp Ala Val Ala Arg Leu Ser Gln Arg Phe Pro Lys Ala Glu Phe
210                 215                 220
Ala Glu Val Ser Lys Leu Val Thr Asp Leu Thr Lys Val His Thr Glu
225                 230                 235                 240
Cys Cys His Gly Asp Leu Leu Glu Cys Ala Asp Asp Arg Ala Asp Leu
                245                 250                 255
Ala Lys Tyr Ile Cys Glu Asn Gln Asp Ser Ile Ser Ser Lys Leu Lys
                260                 265                 270
Glu Cys Cys Glu Lys Pro Leu Leu Glu Lys Ser His Cys Ile Ala Glu
                275                 280                 285
Val Glu Asn Asp Glu Met Pro Ala Asp Leu Pro Ser Leu Ala Ala Asp
                290                 295                 300
Phe Val Glu Ser Lys Asp Val Cys Lys Asn Tyr Ala Glu Ala Lys Asp
305                 310                 315                 320
Val Phe Leu Gly Met Phe Leu Tyr Glu Tyr Ala Arg Arg His Pro Asp
                325                 330                 335
Tyr Ser Val Val Leu Leu Leu Arg Leu Ala Lys Thr Tyr Glu Thr Thr
                340                 345                 350
Leu Glu Lys Cys Cys Ala Ala Ala Asp Pro His Glu Cys Tyr Ala Lys
                355                 360                 365
Val Phe Asp Glu Phe Lys Pro Leu Val Glu Glu Pro Gln Asn Leu Ile
                370                 375                 380
Lys Gln Asn Cys Glu Leu Phe Glu Gln Leu Gly Glu Tyr Lys Phe Gln
385                 390                 395                 400
Asn Ala Leu Leu Val Arg Tyr Thr Lys Lys Val Pro Gln Val Ser Thr
                405                 410                 415
Pro Thr Leu Val Glu Val Ser Arg Asn Leu Gly Lys Val Gly Ser Lys
                420                 425                 430
Cys Cys Lys His Pro Glu Ala Lys Arg Met Pro Cys Ala Glu Asp Tyr
                435                 440                 445
Leu Ser Val Val Leu Asn Gln Leu Cys Val Leu His Glu Lys Thr Pro
                450                 455                 460
```

```
Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
            485                 490                 495

Glu Phe Asn Ala Glu Thr Phe Thr Phe His Ala Asp Ile Cys Thr Leu
                500                 505                 510

Ser Glu Lys Glu Arg Gln Ile Lys Lys Gln Thr Ala Leu Val Glu Leu
            515                 520                 525

Val Lys His Lys Pro Lys Ala Thr Lys Glu Gln Leu Lys Ala Val Met
530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala

<210> SEQ ID NO 136
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 136

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
        50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 137
<211> LENGTH: 146
<212> TYPE: PRT
<213> ORGANISM: Artificial Sequence
<220> FEATURE:
<223> OTHER INFORMATION: Synthetic Polypeptide

<400> SEQUENCE: 137

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
            35                  40                  45
```

```
Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
                100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
        130                 135                 140

Tyr His
145

<210> SEQ ID NO 138
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 138

His Ala Leu Pro Glu Thr Gly
1               5
```

PROTEIN MODIFICATION OF LIVING CELLS USING SORTASE

CROSS-REFERENCE TO RELATED APPLICATION

This application is a national stage filing under 35 U.S.C. § 371 of international PCT application, PCT/US2014/037545, filed May 9, 2014, which claims priority under 35 U.S.C. § 119(e) to U.S. Provisional Application Ser. No. 61/822,092, filed on May 10, 2013, and to U.S. Provisional Application Ser. No. 61/943,094, filed on Feb. 21, 2014, the contents of each of which are hereby incorporated by reference in their entirety.

GOVERNMENT SUPPORT

The invention was made with government support under Grant No. R01 A1087879 awarded by the National Institutes of Health. The government has certain rights in the invention.

BACKGROUND

Bacterial sortases were originally identified as enzymes that covalently attach proteins to the bacterial cell wall. For example, *Staphylococcus aureus* sortase A recognizes a set of diverse substrates via a sortase recognition motif (e.g., LPXTG) and cleaves the peptide bond between threonine and glycine, thereby releasing the residues C-terminal to the threonine and yielding an amide linkage with the N terminus of a pentaglycine nucleophile, which is provided in vivo by a cell wall precursor.

The transpeptidation reaction catalyzed by sortases has emerged as a versatile method for site-specific modification of proteins and has been applied to a variety of in vitro reactions. The method has proved versatile in part because the enzyme tolerates a wide variety of substrates in proximity of the cleavage site and in nucleophiles. In many sortase-based protein modification methods a protein to be modified is engineered to contain a sortase recognition motif (e.g., LPXTG) at or near its C-terminus. When incubated with sortase and a synthetic peptide containing one or more N-terminal glycine residues, such artificial sortase substrates undergo a transacylation reaction resulting in the exchange of residues C-terminal to the threonine residue with the synthetic peptide, resulting in the protein C-terminus being ligated to the N-terminus of the synthetic peptide. In some cases, a protein to be modified is engineered to contain one or more N-terminal glycine residues near its N-terminus. When incubated with sortase and a synthetic peptide containing a sortase recognition motif and a sortase, the transacylation reaction results in the exchange of residues C-terminal to the threonine residue in the synthetic peptide with the modified protein, resulting in the synthetic peptide being ligated to the N-terminus of the protein. The synthetic peptides used in either approach may be fused or conjugated to any of a number of different moieties. When the synthetic peptide and protein are conjugated via sortase-mediated transacylation, such moieties become attached to the protein.

The sortase-catalyzed reaction has been used for, among other things, ligating proteins and/or peptides to one another in vitro, conjugating a protein or peptide to a solid support or polymer, and linking a label to a protein or peptide.

SUMMARY

Some aspects of this invention relate to sortase-mediated modification of proteins expressed by living animal cells, wherein the cells are not genetically engineered to express a protein comprising a sortase recognition sequence or a sequence capable of serving as a nucleophilic acceptor sequence in a sortase-mediated reaction. In some embodiments the animal cells are not genetically engineered. In some embodiments the animal cells are mammalian cells, e.g., human cells. In some embodiments the cells are immune system cells. In some embodiments the methods provide for attaching any moiety of interest to a living animal cell, without requiring that the animal cell be genetically engineered and without requiring the use of crosslinking reagents.

Any of a wide variety of agents may be conjugated to a protein expressed by an animal cell in accordance with various embodiments. In some embodiments, a protein is modified by the conjugation of a sortase substrate comprising an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle, or moiety comprising a reactive chemical group, e.g., a click chemistry handle.

In some embodiments, a method comprises contacting a living animal cell with a sortase and a sortase substrate comprising a sortase recognition motif, wherein the animal cell is not genetically engineered to express a protein comprising a sortase recognition sequence or a sequence capable of serving as a nucleophilic acceptor sequence in a reaction catalyzed by the sortase. In some embodiments the animal cell is not genetically engineered. In some embodiments contacting is performed under conditions suitable for the sortase to transamidate the sortase substrate and a polypeptide exposed at the surface of the animal cell, thereby conjugating the sortase substrate to the polypeptide. In some embodiments the sortase substrate comprises a sortase recognition motif and a moiety of interest, e.g., an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle, or a click chemistry handle. Conjugating the sortase substrate to the polypeptide exposed at the surface of animal cell attaches the moiety of interest to the cell expressing the polypeptide.

In some embodiments a sortase substrate comprises an antibody, e.g., a single chain antibody such as a camelid antibody, a single-domain antibody, a VHH domain, a nanobody, or an scFv. In some embodiments a sortase substrate comprises a binding moiety. In some embodiments a binding moiety may comprise an antibody, polypeptide, affibody, adnectin, anticalin, or aptamer. In some embodiments a binding moiety may serve as a targeting moiety. In some embodiments a binding moiety binds to a cell surface marker of a target cell. In some embodiments a target cell is a cancer cell, infected cell, or other abnormal or diseased cell. In some embodiments a target cell is a normal cell.

In some embodiments a sortase substrate comprises a click chemistry handle. Click chemistry handles are chemical moieties that provide a reactive group that can partake in a click chemistry reaction. Click chemistry reactions and suitable chemical groups for click chemistry reactions are well known to those of skill in the art, and include, but are not limited to terminal alkynes, azides, strained alkynes, dienes, dieneophiles, alkoxyamines, carbonyls, phosphines, hydrazides, thiols, and alkenes. For example, in some embodiments, an azide and an alkyne are used in a click chemistry reaction. In some embodiments a reactive group of first click chemistry handle attached to an animal cell via a sortase-catalyzed reaction is reacted with a second reactive group attached to a second entity, thereby conjugating the second entity to the animal cell. The second reactive group may be a second click chemistry handle that is compatible with the first click chemistry handle. The entity may be, e.g., an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle, or a cell. In some embodiments the entity may be an antibody, e.g., a single chain antibody such as a camelid antibody, a single-domain antibody, a VHH domain, a nanobody, or an scFv. In some embodiments the entity comprises a binding moiety. In some embodiments a binding moiety may comprise an antibody, polypeptide, affibody, adnectin, anticalin, or aptamer.

Some aspects of this invention provide animal cells comprising one or more modified endogenous, non-genetically engineered proteins comprising an agent conjugated at or near its N-terminus. In some embodiments the agent comprises a moiety of interest, e.g., an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle, or a click chemistry handle. In some embodiments, the modified endogenous protein comprises an antigen-binding domain, for example, an antigen-binding domain of an antibody, e.g., a camelid antibody, a single-domain antibody, a VHH domain, a nanobody, or an ScFv.

Some aspects of this invention comprise administering modified mammalian cells, e.g., modified human cells, to subjects, e.g., human subjects. In some embodiments the modified mammalian cells enhance the subject's immune response to a cancer cell, infected cell, or other abnormal cell, or directly attack a cancer cell, infected cell, or other abnormal cell. In some embodiments the modified mammalian cells have a therapeutic agent or detection agent conjugated to an endogenous protein and serve to deliver the agent to the subject.

Some embodiments of this invention provide chimeric proteins, for example, chimeric proteins that have been generated by conjugation of two proteins, wherein at least one of the proteins is an endogenous protein expressed by a living animal cell. Some embodiments provide living animal cells, e.g., mammalian cells, having one or more such chimeric proteins attached to their surface.

Some embodiments provide modified endogenous mammalian proteins comprising a sortase recognition motif (e.g., LPXTG) and a moiety attached to the sortase recognition motif. For example, a moiety may be attached directly to one of the amino acids of the sortase recognition motif or may be attached via a linker. In some embodiments, the modified endogenous mammalian protein comprises an antigen-binding domain, e.g., an antibody or an antigen-binding antibody fragment. Exemplary, modified mammalian proteins provided herein may comprise, e.g., single chain antibody, camelid antibody, a VHH domain, a single-domain antibody, a nanobody, an scFv, an adnectin, an affibody, an anticalin, an aptamer, or a click chemistry handle. In some embodiments the sortase recognition motif is positioned N-terminal with respect to the endogenous polypeptide. In some embodiments the moiety is attached to the N-terminal amino acid of the sortase recognition motif or to an amino acid positioned N-terminal to the N-terminal amino acid of the sortase recognition motif.

In some aspects, the present disclosure provides a method of conjugating an agent to an animal cell, the method comprising: contacting an animal cell with a sortase substrate that comprises a sortase recognition sequence and an agent in the presence of a sortase under conditions suitable for the sortase to conjugate the sortase substrate to an endogenous, non-engineered polypeptide expressed by the animal cell. In some embodiments the sortase substrate is conjugated to an extracellular portion of an endogenous, non-engineered polypeptide expressed by the cell. In some embodiments the animal cell is a mammalian cell, e.g., a human cell. In some embodiments the cell is an immune system cell, e.g., a lymphocyte (e.g., a T cell or NK cell), dendritic cell. In some embodiments the cell is a cytotoxic cell. In some embodiments the cell is a non-immortalized cell. In some embodiments the cell is a primary cell. In some embodiments the animal cell is not genetically engineered to express a polypeptide comprising a sortase recognition sequence, a sequence comprising one or more glycines, or both. In some embodiments the animal cell is not genetically engineered to express a polypeptide comprising a sortase recognition sequence, a sequence comprising one or more alanines, or both. In some embodiments the animal cell is not genetically engineered to express a polypeptide comprising a sequence that renders the polypeptide usable in a sortase-catalyzed reaction. In some embodiments, the animal cell is not chemically engineered to present a polypeptide comprising a sortase recognition sequence, a sequence comprising one or more glycines, or both, on its surface. In some embodiments, the animal cell is not chemically engineered to present a polypeptide comprising a sortase recognition sequence, a sequence comprising one or more alanines, or both, on its surface. In some embodiments the animal cell is not chemically engineered to present at its surface a moiety that renders the polypeptide usable in a sortase-catalyzed reaction. In some embodiments the animal cell is not chemically engineered to present at its surface a polypeptide comprising a sequence that renders the polypeptide usable in a sortase-catalyzed reaction. In some embodiments the cell is not stably or transiently transfected or infected with a nucleic acid construct or vector encoding a protein comprising a sortase recognition sequence, nucleophilic acceptor sequence, or both. In some embodiments the cell is not genetically engineered. In some embodiments the cell originates from a subject in need of evaluation or treatment for a disease of interest or from a donor who is immunocompatible with the subject. In some embodiments the cell originates from a subject in need of evaluation or treatment for a disease characterized by the presence of abnormal or excessive cells or pathogens in the subject's body or from a donor who is immunocompatible with the subject. In some embodiments the cell originates from a subject in need treatment for a disease characterized by deterioration or dysfunction of a tissue or organ, wherein regenerative medicine therapy may be useful. In some embodiments the cell originates from a subject in need of evaluation or treatment for cancer, an autoimmune disease, or an infection or from a donor who is immunocompatible with the subject. In some embodiments the sortase is a Sortase A, e.g., *Staphylococcus aureus* Sortase A. In some embodiments the sortase recognition sequence comprises LPXTG. In some embodiments the agent comprises an amino acid, a peptide, a protein, a polynucleotide, a carbohydrate, a tag, a metal atom, a chelating agent, a contrast agent, a catalyst, a polymer, a recognition element, a small molecule, a lipid, a label, an epitope, an antigen, a therapeutic agent, a cross-linker, a toxin, a radioisotope, an antibody, an antibody domain, a click chemistry handle, a virus, a cell, or a particle. In some embodiments the agent comprises a targeting moiety that binds to an epitope or antigen of interest. In some embodiments the targeting moiety binds to a tumor antigen or a viral, bacterial, fungal, or parasite antigen, or a cellular marker. In some embodiments the agent comprises one or more of the following: (a) a targeting moiety, (b) a costimulatory domain, (c) a signaling domain, (d) a receptor domain, (e) an activating domain, (f) an antigen-binding portion of an antigen receptor; (g) an enzyme; (h) a cytolytic domain; (i) a pro-apoptotic domain. In some embodiments the method comprises obtaining the cell or an ancestor of the animal cell from a subject in need of evaluation or treatment for a disease of interest or from a donor who is immunocompatible with the subject. In some embodiments the method comprises separating the animal cell that has the sortase substrate conjugated thereto from the sortase, unconjugated sortase substrate, or both. In some embodiments the method comprises detecting the agent conjugated to the animal cell. In some embodiments the method comprises administering the animal cell having the agent conjugated thereto to a subject. In some aspects, the disclosure provides an isolated animal cell or population of isolated animal cells prepared according to any of the methods. In some embodiments the cell or population of cells is suitable for administration to a human subject.

In some aspects, the disclosure provides an isolated animal cell comprising an endogenous, non-engineered polypeptide comprising a sortase recognition sequence that has an agent conjugated thereto. In some embodiments the sortase substrate is conjugated to an extracellular portion of an endogenous, non-engineered polypeptide expressed by the cell. In some embodiments the cell is a mammalian cell, e.g., a human cell. In some embodiments the cell is an immune system cell, e.g., a lymphocyte (e.g., a T cell), NK cell, dendritic cell. In some embodiments the cell is a non-immortalized cell. In some embodiments the cell is a primary cell. In some embodiments the animal cell is not genetically engineered to express a polypeptide comprising a sortase recognition sequence, a sequence comprising one or more glycines, or both. In some embodiments the animal cell is not genetically engineered to express a polypeptide comprising a sortase recognition sequence, a sequence comprising one or more alanines, or both. In some embodiments the cell is not genetically engineered. In some embodiments the cell is not chemically engineered. In some embodiments the cell originates from a subject in need of evaluation or treatment for a disease of interest or from a donor who is immunocompatible with the subject. In some embodiments the cell originates from a subject in need of evaluation or treatment for a disease characterized by the presence of abnormal or excessive cells or pathogens in the subject's body or from a donor who is immunocompatible with the subject. In some embodiments the cell originates from a subject in need of evaluation or treatment for cancer, an autoimmune disease, or an infection or from a donor who is immunocompatible with the subject. In some embodiments the sortase recognition sequence comprises LPXTG. In some embodiments the agent comprises an amino acid, a peptide, a protein, a polynucleotide, a carbohydrate, a tag, a metal atom, a chelating agent, a contrast agent, a catalyst, a polymer, a recognition element, a small molecule, a lipid, a label, an epitope, an antigen, a therapeutic agent, a cross-linker, a toxin, a radioisotope, an antibody, an antibody domain, a click chemistry handle, a virus, a cell, or a particle. In some embodiments the agent comprises a targeting moiety that binds to an epitope or antigen of interest. In some embodiments the agent comprises a targeting moiety that binds to a tumor antigen or a viral, bacterial, fungal, or parasite antigen. In some embodiments the agent comprises one or more of the following: (a) a targeting moiety, (b) a costimulatory domain, (c) a signaling domain, (d) a receptor domain, (e) an activating domain, (f) an antigen-binding portion of an antigen receptor; (g) an enzyme; (h) a cytolytic domain; (i) a pro-apoptotic domain. In some embodiments the agent is detectable by fluorescence activated cell sorting (FACS), fluorescence microscopy, Western blot, ELISA, chromatography, or mass spectrometry after being conjugated to the cell.

In some aspects, the disclosure provides a method of administering an agent to a subject comprising: (a) providing the isolated animal cell or population of animal cells described herein and (b) administering the isolated animal cell or population of animal cells to the subject.

In some aspects, the disclosure provides composition comprising: (i) an animal cell comprising an endogenous, non-engineered polypeptide comprising a sequence capable as serving as a nucleophile in a sortase-mediated reaction; (ii) a sortase substrate comprising a sortase recognition motif; and (iii) a sortase. In some embodiments the animal cell is a mammalian cell, e.g., a human cell. In some embodiments the sortase is a sortase A. In some embodiments the animal cell is an immune system cell, e.g., a lymphocyte (e.g., a T cell or NK cell) or dendritic cell. In some embodiments the cell is a cytotoxic cell. In some embodiments the cell is a non-immortalized cell. In some embodiments the cell is a primary cell. In some embodiments the cell is not genetically engineered to express a polypeptide comprising a sortase recognition sequence, a sequence comprising one or more glycines, or both. In some embodiments the cell is not genetically engineered to express a polypeptide comprising a sortase recognition sequence, a sequence comprising one or more alanines, or both. In some embodiments the cell is not genetically engineered. In some embodiments the cell is not chemically engineered. In some embodiments the cell originates from a subject in need of evaluation or treatment for a disease of interest or from a donor who is immunocompatible with the subject. In some embodiments the cell originates from a subject in need of evaluation or treatment for a disease characterized by the presence of abnormal or excessive cells or pathogens in the subject's body or from a immunocompatible donor. In some embodiments the cell originates from a subject in need of evaluation or treatment for cancer, an autoimmune disease, or an infection or from a donor who is immunocompatible with the subject. In some embodiments the sortase is a Sortase A, e.g., *Staphylococcus aureus* Sortase A. In some embodiments the sortase recognition sequence comprises LPXTG. In some embodiments the agent comprises an amino acid, a peptide, a protein, a polynucleotide, a carbohydrate, a tag, a metal atom, a chelating agent, a contrast agent, a catalyst, a polymer, a recognition element, a small molecule, a lipid, a label, an epitope, an antigen, a therapeutic agent, a cross-linker, a toxin, a radioisotope, an antibody, an antibody domain, a click chemistry handle, a virus, a cell, or a particle. In some embodiments the agent comprises a targeting moiety that binds to an epitope or antigen of interest. In some embodiments the agent comprises a targeting moiety that binds to a tumor antigen or a viral, bacterial, fungal, or parasite antigen. In some embodiments the agent comprises one or more of the following: (a) a targeting moiety, (b) a costimulatory domain, (c) a signaling domain, (d) a receptor domain, (e) an activating domain, (f) an antigen-binding portion of an antigen receptor; (g) an enzyme; (h) a cytolytic domain; (i) a pro-apoptotic domain. In some embodiments the cell originates from a subject in need of evaluation or treatment for a disease of interest or from a donor who is immunocompatible with the subject.

In some aspects, the disclosure provides a method of modulating an immune response of a subject to an entity of interest, the method comprising administering to the subject an animal cell that comprises an endogenous, non-engineered polypeptide comprising a sortase recognition sequence that has an agent conjugated thereto, wherein the agent comprises an antigen or epitope of the entity of interest or a targeting moiety that binds to an antigen or epitope of the entity of interest. In some embodiments the cell is a mammalian cell, e.g., a human cell. In some embodiments the cell is an immune system cell, e.g., a lymphocyte (e.g., a T cell or NK cell) or dendritic cell. In some embodiments the entity of interest is a cancer cell, an infected cell, or a pathogen. In some embodiments the antigen is a tumor antigen or a viral, bacterial, fungal, or parasite antigen. In some embodiments modulating an immune response comprises stimulating an immune response directed towards the entity of interest. In some embodiments the entity of interest is a self cell or structure. In some embodiments the entity of interest is an environmental allergen. In some embodiments modulating an immune response comprises inhibiting an immune response directed towards the entity of interest. In some embodiments modulating an immune response comprises increasing or inducing tolerance towards the entity of interest. In some embodiments the agent comprises one or more of the following: (a) a targeting moiety, (b) a costimulatory domain, (c) a signaling domain, (d) a receptor domain, (e) an activating domain, (f) an antigen-binding portion of an antigen receptor; (h) a cytolytic domain; (i) a pro-apoptotic domain.

In some aspects, the disclosure provides a method of neutralizing a substance in the body of a subject, the method comprising administering to the subject an animal cell that comprises an endogenous, non-engineered polypeptide comprising a sortase recognition sequence that has an agent conjugated thereto, wherein the agent binds to the substance. In some embodiments the substance comprises a toxin. In some embodiments the substance comprises an inflammatory cytokine. In some embodiments the agent comprises an antibody or antigen-binding fragment thereof or a portion of a receptor that binds to the substance.

In some aspects, the disclosure provides a method of treating a subject in need of treatment for deficiency of a protein, the method comprising administering to the subject an animal cell that comprises an endogenous, non-engineered polypeptide comprising a sortase recognition sequence that has an agent conjugated thereto, wherein the agent comprises the protein. In some embodiments the protein is an enzyme. In some embodiments the protein is normally found in the blood.

In some aspects, the disclosure provides a method of treating a subject in need of treatment for a disease, the method comprising administering to the subject an animal cell that comprises an endogenous, non-engineered polypeptide comprising a sortase recognition sequence that has an agent conjugated thereto, wherein the agent comprises a therapeutic agent effective for treating the disease. In some embodiments the therapeutic agent comprises a chemotherapy drug, anti-infective agent (e.g., antibacterial, antiviral, antifungal, or antiparasite agent), enzyme, or monoclonal antibody. In some embodiments the cell is a human cell. In some embodiments the cell originates from the subject or from an immunocompatible donor.

In some embodiments of any method comprising administering a cell to a subject, the subject is a human subject.

In some embodiments of any method comprising administering a cell to a subject, the cell is a human cell (e.g., an autologous or immunocompatible cell) and the subject is a human subject.

In some embodiments of any method comprising administering a cell, the cell is administered into the circulatory system, e.g., intravenously.

The above summary is intended to give an overview over some aspects of this invention, and is not to be construed to limit the invention in any way. Additional aspects, advantages, and embodiments of this invention are described herein, and further embodiments will be apparent to those of skill in the art based on the instant disclosure. The entire contents of all references cited in this document are hereby incorporated by reference.

The practice of certain aspects of the present invention may employ conventional techniques of molecular biology, cell culture, recombinant nucleic acid (e.g., DNA) technology, immunology, transgenic biology, microbiology, nucleic acid and polypeptide synthesis, detection, manipulation, and quantification, and RNA interference that are within the ordinary skill of the art. See, e.g., Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008 or more recent editions; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988. Information regarding various diseases and diagnosis and certain treatments of such diseases is found in Longo, D., et al. (eds.), Harrison's Principles of Internal Medicine, 18th Edition; McGraw-Hill Professional, 2011. Information regarding various therapeutic agents and human diseases is found in Brunton, L., et al. (eds.) Goodman and Gilman's The Pharmacological Basis of Therapeutics, $12^{th}$ Ed., McGraw Hill, 2010 and/or Katzung, B. (ed.) Basic and Clinical Pharmacology, McGraw-Hill/Appleton & Lange; 11th edition (July 2009). Information regarding the immune system, immune system cells, and proteins and other molecules produced by immune system cells and/or that play a role in the immune system or immune response may be found in standard immunology textbooks such as Paul, W E (ed.), Fundamental Immunology, Lippincott Williams & Wilkins; 6th ed., 2008; Murphy, K, Janeway's Immunobiology, 8th ed., Garland Science, Taylor & Francis Group, London and New York (2012). All patents, patent applications, books, articles, documents, databases, websites, publications, references, etc., mentioned in this document are incorporated by reference in their entirety. In case of a conflict between the specification and any of the incorporated references, the specification (including any amendments thereof), shall control. Applicants reserve the right to amend the specification based, e.g., on any of the incorporated material and/or to correct obvious errors. None of the content of the incorporated material shall limit the invention.

BRIEF DESCRIPTION OF THE DRAWING

The patent or application file contains at least one drawing executed in color. Copies of this patent or patent application publication with color drawings will be provided by the Office upon request and payment of the necessary fee.

DEFINITIONS

Figure 1:
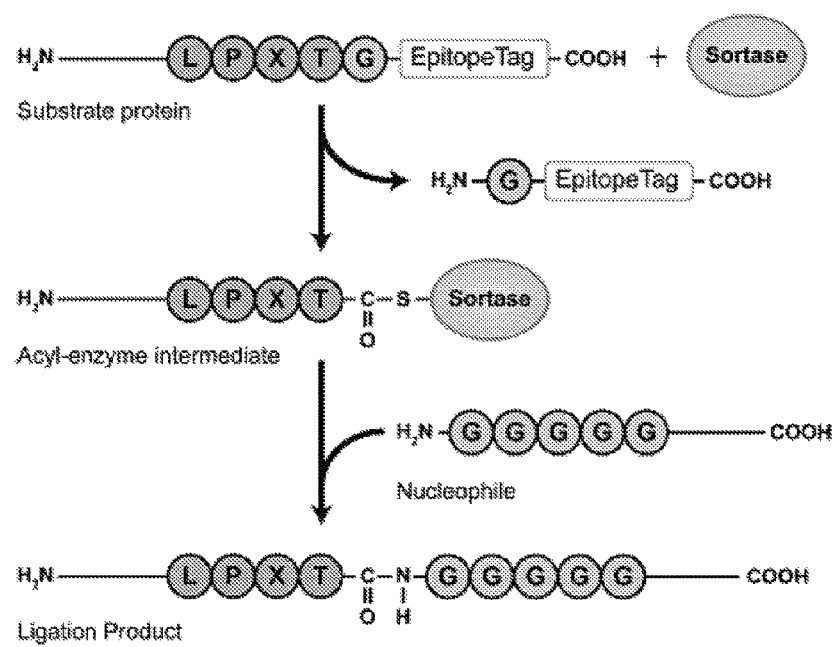
FIG. 1. (A) Schematic representation of a sortase-catalyzed transacylation reaction in which a sortase substrate protein is conjugated to a nucleophile, with release of a portion of the substrate protein comprising an epitope tag. (B) Schematic representation of sortase-catalyzed conjugation of G(n)-Probe to the C-terminus of a LPETG-tagged protein using sortase A. (C) Schematic representation of sortase-catalyzed conjugation of Probe-LPETG to the N-terminus to a G(n)-tagged protein using sortase A. (D) Schematic representation of sortase-catalyzed conjugation of LPETG-tagged probe or protein to naturally exposed N-terminal glycine residues at the surface of cells. (G)n in FIGS. 1(B), 1(C), and 1(D) represents a sequence of one or more glycines.
Figure 1:
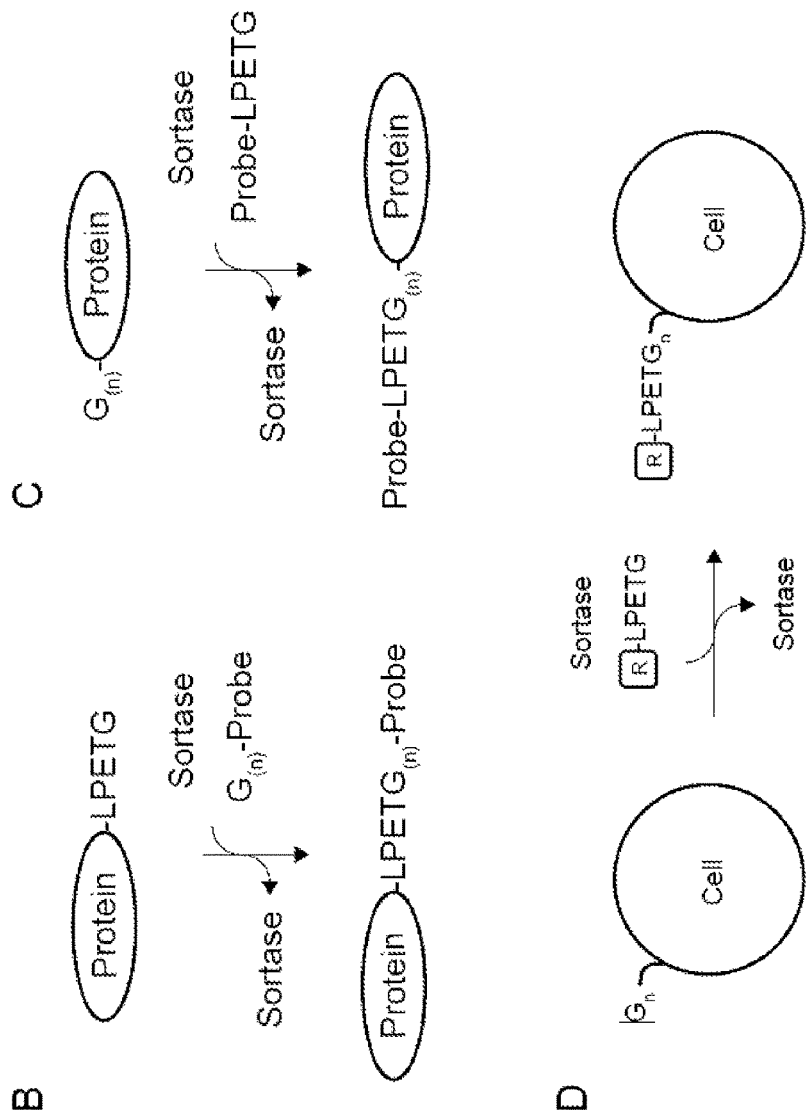

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "carbocyclic" or "carbocyclyl" as used herein, refers to an as used herein, refers to a cyclic aliphatic group containing 3-10 carbon ring atoms ($C_{3-10}$carbocyclic). Carbocyclic group substituents include, but are not limited to, any of the substituents described herein, that result in the formation of a stable moiety.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms ($C_{1-20}$heteroaliphatic). In certain embodiments, the heteroaliphatic group contains 1-10 carbon atoms and 1-4 heteroatoms ($C_{1-10}$heteroaliphatic). In certain embodiments, the heteroaliphatic group contains 1-6 carbon atoms and 1-3 heteroatoms ($C_{1-6}$heteroaliphatic). In certain embodiments, the heteroaliphatic group contains 1-5 carbon atoms and 1-3 heteroatoms ($C_{1-5}$heteroaliphatic). In certain embodiments, the heteroaliphatic group contains 1-4 carbon atoms and 1-2 heteroatoms ($C_{1-4}$heteroaliphatic). In certain embodiments, the heteroaliphatic group contains 1-3 carbon atoms and 1 heteroatom ($C_{1-3}$heteroaliphatic). In certain embodiments, the heteroaliphatic group contains 1-2 carbon atoms and 1 heteroatom ($C_{1-2}$heteroaliphatic). Heteroaliphatic group substituents include, but are not limited to, any of the substituents described herein, that result in the formation of a stable moiety.

The term "heteroalkyl," as used herein, refers to an alkyl moiety, as defined herein, which contain one or more heteroatoms (e.g., oxygen, sulfur, nitrogen, phosphorus, or silicon atoms) in between carbon atoms. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms ($C_{1-10}$ heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety.

The term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms ($C_{2-20}$ heteroalkenyl). In certain embodiments, the heteroalkenyl group contains 2-10 carbon atoms and 1-4 heteroatoms ($C_{2-10}$ heteroalkenyl). In certain embodiments, the heteroalkenyl group contains 2-6 carbon atoms and 1-3 heteroatoms ($C_{2-6}$ heteroalkenyl). In certain embodiments, the heteroalkenyl group contains 2-5 carbon atoms and 1-3 heteroatoms ($C_{2-5}$ heteroalkenyl). In certain embodiments, the heteroalkenyl group contains 2-4 carbon atoms and 1-2 heteroatoms ($C_{2-4}$ heteroalkenyl). In certain embodiments, the heteroalkenyl group contains 2-3 carbon atoms and 1 heteroatom ($C_{2-3}$ heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms ($C_{2-20}$ heteroalkynyl). In certain embodiments, the heteroalkynyl group contains 2-10 carbon atoms and 1-4 heteroatoms ($C_{2-10}$ heteroalkynyl). In certain embodiments, the heteroalkynyl group contains 2-6 carbon atoms and 1-3 heteroatoms ($C_{2-6}$ heteroalkynyl). In certain embodiments, the heteroalkynyl group contains 2-5 carbon atoms and 1-3 heteroatoms ($C_{2-5}$ heteroalkynyl). In certain embodiments, the heteroalkynyl group contains 2-4 carbon atoms and 1-2 heteroatoms ($C_{2-4}$ heteroalkynyl). In certain embodiments, the heteroalkynyl group contains 2-3 carbon atoms and 1 heteroatom ($C_{2-3}$ heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety. The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety. The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

The term "acyl," as used herein, is a subset of a substituted alkyl group, and refers to a group having the general formula —C(=O)$R^A$, —C(=O)O$R^A$, —C(=O)—O—C(=O)$R^A$, —C(=O)S$R^A$, —C(=O)N($R^A$)$_2$, —C(=S)$R^A$, —C(=S)N($R^A$)$_2$, and —C(=S)S($R^A$), —C(=N$R^A$)$R^A$, —C(=N$R^A$)O$R^A$, —C(=N$R^A$)S$R^A$, and —C(=N$R^A$)N($R^A$)$_2$, wherein $R^A$ is hydrogen; halogen; substituted or unsubstituted hydroxyl; substituted or unsubstituted thiol; substituted or unsubstituted amino; acyl; optionally substituted aliphatic; optionally substituted heteroaliphatic; optionally substituted alkyl; optionally substituted alkenyl; optionally substituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety.

The term "acylene," as used herein, is a subset of a substituted alkylene, substituted alkenylene, substituted alkynylene, substituted heteroalkylene, substituted heteroalkenylene, or substituted heteroalkynylene group, and refers to an acyl group having the general formulae: —$R^O$—(C=$X^1$)—$R^O$—, —$R^O$—$X^2$(C=$X^1$)—$R^O$, or —$R^O$—$X^2$(C=$X^1$)$X^3$—$R^O$—, where $X^1$, $X^2$, and $X^3$ is, independently, oxygen, sulfur, or NW, wherein $R^r$ is hydrogen or optionally substituted aliphatic, and $R^O$ is an optionally substituted alkylene, alkenylene, alkynylene, heteroalkylene, heteroalkenylene, or heteroalkynylene group, as defined herein. Exemplary acylene groups wherein $R^O$ is alkylene includes —(CH$_2$)$_T$—O(C=O)—(CH$_2$)$_T$—; —(CH$_2$)$_T$—NR$^r$(C=O)—(CH$_2$)$_T$—; —(CH$_2$)$_T$—O(C=NR$^r$)—(CH$_2$)$_T$—; —(CH$_2$)$_T$—NR$^r$(C=NR$^r$)—(CH$_2$)$_T$—; —(CH$_2$)$_T$—(C=O)—(CH$_2$)$_T$—; —(CH$_2$)$_T$—(C=NR$^r$)—(CH$_2$)$_T$—; —(CH$_2$)$_T$—S(C=S)—(CH$_2$)$_T$—; —(CH$_2$)$_T$—NR$^r$(C=S)—(CH$_2$)$_T$—; —(CH$_2$)$_T$—S(C=NR$^r$)—(CH$_2$)$_T$—; —(CH$_2$)$_T$—O(C=S)—(CH$_2$)$_T$—; —(CH$_2$)$_T$—(C=S)(CH$_2$)$_T$—; or —(CH$_2$)$_T$—S(C=O)—(CH$_2$)$_T$—, and the like, which may bear one or more substituents; and wherein each instance of T is, independently, an integer between 0 to 20. Acylene substituents include, but are not limited to, any of the substituents described herein, that result in the formation of a stable moiety.

The term "amino," as used herein, refers to a group of the formula (—NH$_2$). A "substituted amino" refers either to a mono-substituted amine (—NHR$^h$) of a disubstituted amine (—NR$^h_2$), wherein the R$^h$ substituent is any substituent as described herein that results in the formation of a stable moiety (e.g., an amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the disubstituted amino group (—$NR^h_2$) form a 5- to 6-membered heterocyclic ring.

The term "hydroxy" or "hydroxyl," as used herein, refers to a group of the formula (—OH). A "substituted hydroxyl" refers to a group of the formula (—$OR^i$), wherein $R^i$ can be any substituent which results in a stable moiety (e.g., a hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "thio" or "thiol," as used herein, refers to a group of the formula (—SH). A "substituted thiol" refers to a group of the formula (—$SR^r$), wherein $R^r$ can be any substituent that results in the formation of a stable moiety (e.g., a thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "imino," as used herein, refers to a group of the formula (=$NR^r$), wherein $R^r$ corresponds to hydrogen or any substituent as described herein, that results in the formation of a stable moiety (for example, an amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "azide" or "azido," as used herein, refers to a group of the formula (—$N_3$).

The terms "halo" and "halogen," as used herein, refer to an atom selected from fluorine (fluoro, —F), chlorine (chloro, —Cl), bromine (bromo, —Br), and iodine (iodo, —I).

A "leaving group" is an art-understood term referring to a molecular fragment that departs with a pair of electrons in heterolytic bond cleavage, wherein the molecular fragment is an anion or neutral molecule. See, for example, Smith, March's Advanced Organic Chemistry 6th ed. (501-502). Exemplary leaving groups include, but are not limited to, halo (e.g., chloro, bromo, iodo) and activated substituted hydroxyl groups, e.g., of the formula —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —P($R^{cc}$)$_2$, —OP($R^{cc}$)$_3$, —OP(=O)$_2R^{aa}$, —PP(=O)($R^{aa}$)$_2$, —OP(=O)($OR^{cc}$)$_2$, —OP(=O)$_2$N($R^{bb}$)$_2$, or —OP(=O)($NR^{bb}$)$_2$ wherein $R^{aa}$ is optionally substituted aliphatic, optionally substituted heteroaliphatic, optionally substituted aryl, or optionally substituted heteroaryl; $R^{bb}$ is hydrogen, an amino protecting group, optionally substituted aliphatic, optionally substituted heteroaliphatic, optionally substituted aryl, or optionally substituted heteroaryl; and $R^{cc}$ is hydrogen, optionally substituted aliphatic, optionally substituted heteroaliphatic, optionally substituted aryl, or optionally substituted heteroaryl.

The term "agent," as used herein, refers to any molecule, entity, or moiety that can be conjugated to a sortase recognition motif. For example, an agent may be a protein, an amino acid, a peptide, a polynucleotide, a carbohydrate, a detectable label, a binding agent, a tag, a metal atom, a contrast agent, a catalyst, a non-polypeptide polymer, a synthetic polymer, a recognition element, a lipid, a linker, or chemical compound, such as a small molecule. In some embodiments, the agent is a binding agent, for example, a ligand or a ligand-binding molecule, streptavidin, biotin, an antibody or an antibody fragment. In some embodiments, the agent cannot be genetically encoded. In some such embodiments, the agent is a lipid, a carbohydrate, or a small molecule. Additional agents suitable for use in embodiments of the present invention will be apparent to the skilled artisan. The invention is not limited in this respect.

The term "amino acid," as used herein, includes any naturally occurring and nonnaturally occurring amino acid. Amino acids include without limitation, natural alpha-amino acids such as the 20 common naturally occurring alpha-amino acids found in polypeptides and proteins (A, R, N, C, D, Q, E, G, H, I, L, K, M, F, P, S, T, W, Y, V, also referred to as standard amino acids), non-standard alpha-amino acids, and beta-amino acids. There are many known non-standard, e.g., non-natural, amino acids any of which may be included in the polypeptides or proteins described herein. See, for example, S. Hunt, The Non-Protein Amino Acids in *Chemistry and Biochemistry of the Amino Acids*, edited by G. C. Barrett, Chapman and Hall, 1985 and/or Hughes, B. (ed.), Amino Acids, Peptides and Proteins in Organic Chemistry, Volumes 1-4, Wiley-VCH (2009-2011); Blaskovich, M., Handbook on Syntheses of Amino Acids General Routes to Amino Acids, Oxford University Press, 2010. As used herein in the context of amino acid sequences, the term X or Xaa represents any amino acid residue, e.g., any naturally occurring and/or any non-naturally occurring amino acid residue.

The term "binding agent" or "binding moiety" as used herein refers to any molecule or entity that binds another molecule or entity with high affinity. In some embodiments, a binding agent binds its binding partner with high specificity. Examples of binding agents include, without limitation, antibodies, antibody fragments, receptors, ligands, aptamers, and adnectins.

The term "click chemistry" refers to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallisation or distillation).

The term "click chemistry handle," as used herein, refers to a reactant, or a reactive group, that can partake in a click chemistry reaction. For example, a strained alkyne, e.g., a cyclooctyne, is a click chemistry handle, since it can partake in a strain-promoted cycloaddition (see, e.g., Table 1). In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables 1 and 2. Other suitable click chemistry handles are known to those of skill in the art.

The terms "protein," "peptide" and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. In some embodiments a peptide is between 3 and 60 amino acids long, e.g., between 3 and 15, 15 and 30, 30 and 45, or 45 and 60 amino acids long.

The term "conjugated" or "conjugation" refers to an association of two molecules, for example, two proteins or a protein and a small molecule or other entity, with one another in a way that they are linked by a direct or indirect covalent or non-covalent interaction. In the context of conjugation via a sortase mediated reaction, the conjugation is via a covalent bond the formation of which is catalyzed by sortase. In the context of conjugation via click chemistry, the conjugation is via a covalent bond formed by the reaction of two click chemistry handles. In some embodiments, a protein is post-translationally conjugated to another molecule, for example, a second protein, by forming a covalent bond between the protein and the other molecule after the protein has been translated, and, in some embodiments, after the protein has been isolated. In some embodiments, two molecules are conjugated directly to each other. In some embodiments two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, a protein N-terminus is conjugated to or near a C-terminus of a second protein generating an N—C conjugated chimeric protein. In some embodiments, two proteins are conjugated at their respective C-termini, generating a C—C conjugated chimeric protein. In some embodiments, two proteins are conjugated at their respective N-termini, generating an N—N conjugated chimeric protein.

As used herein, a "detectable label" refers to a moiety that has at least one element, isotope, or functional group incorporated into the moiety which enables detection of the molecule, e.g., a protein or polypeptide, or other entity, to which the label is attached. Labels can be directly attached (i.e., via a bond) or can be attached by a tether (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a tether). It will be appreciated that the label may be attached to or incorporated into a molecule, for example, a protein, polypeptide, or other entity, at any position.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-99m), $^{111}In$, $^{123}I$, $^{125}I$, $^{131}I$, $^{153}Gd$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluoresceinisothiocyanate (FITC); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluoresceinisothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, *Renilla*, or *Gaussia* luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, mTomato, T-Sapphire, mAmetrine, mKeima. See, e.g., Chalfie, M. and Kain, S R (eds.) Green fluorescent protein: properties, applications, and protocols (Methods of biochemical analysis, v. 47). Wiley-Interscience, Hoboken, N.J., 2006, and/or Chudakov, D M, et al., Physiol Rev. 90(3):1103-63, 2010 for discussion of GFP and numerous other fluorescent or luminescent proteins. In some embodiments, a label comprises a dark quencher, e.g., a substance that absorbs excitation energy from a fluorophore and dissipates the energy as heat.

The term "adjuvant" encompasses substances that accelerate, prolong, or enhance the immune response to an antigen. In some embodiments an adjuvant serves as a lymphoid system activator that enhances the immune response in a relatively non-specific manner, e g., without having any specific antigenic effect itself. For example, in some embodiments an adjuvant stimulates one or more components of the innate immune system. In certain embodiments an adjuvant enhances antigen-specific immune responses when used in combination with a specific antigen or antigens, e.g., as a component of a vaccine. Adjuvants include, but are not limited to, aluminum salts (alum) such as aluminum hydroxide or aluminum phosphate, complete Freund's adjuvant, incomplete Freund's adjuvant, surface active substances such as lysolecithin, pluronic polyols, Amphigen, Avridine, bacterial lipopolysaccharides, 3-O-deacylated monophosphoryl lipid A, synthetic lipid A analogs or aminoalkyl glucosamine phosphate compounds (AGP), or derivatives or analogs thereof (see, e.g., U.S. Pat. No. 6,113,918), L121/squalene, muramyl dipeptide, polyanions, peptides, saponins, oil or hydrocarbon and water emulsions, particles such as ISCOMS (immunostimulating complexes), etc. In some embodiments an adjuvant stimulates dendritic cell maturation. In some embodiments an adjuvant stimulates expression of one or more costimulator(s), such as B7 or a B7 family member, by antigen presenting cells (APCs), e.g., dendritic cells. In some embodiments an adjuvant comprises a CD40 agonist. In some embodiments a CD40 agonist comprises an anti-CD40 antibody. In some embodiments a CD40 agonist comprises a CD40 ligand, such as CD40L. In some embodiments an adjuvant comprises a ligand for a Toll-like receptor (TLR). In some embodiments an agent is a ligand for one or more of TLRs 1-13, e.g., at least for TLR3, TLR4, and/or TLR9. In some embodiments an adjuvant comprises a pathogen-derived molecular pattern (PAMP) or mimic thereof. In some embodiments an adjuvant comprises an immunostimulatory nucleic acid, e.g., a double-stranded nucleic acid, e.g., double-stranded RNA or an analog thereof. For example, in some embodiments an adjuvant comprises polyriboinosinic:polyribocytidylic acid (polyIC). In some embodiments an adjuvant comprises a nucleic acid comprising unmethylated nucleotides, e.g., a single-stranded CpG oligonucleotide. In some embodiments an adjuvant comprises a cationic polymer, e.g., a poly(amino acid) such as poly-L-lysine, poly-L-arginine, or poly-L-ornithine. In some embodiments an adjuvant comprises a nucleic acid (e.g., dsRNA, polyIC) and a cationic polymer. For example, in some embodiments an adjuvant comprises polyIC and poly-L-lysine. In some embodiments an adjuvant comprises a complex comprising polyIC, poly-L-lysine, and carboxymethylcellulose (referred to as polyICLC). In some embodiments an adjuvant comprises a CD40 agonist and a TLR ligand. For example, in some embodiments an adjuvant comprises (i) an anti-CD40 antibody and (ii) an immunostimulatory nucleic acid and/or a cationic polymer. In some embodiments an adjuvant comprises an anti-CD40 antibody, an immunostimulatory nucleic acid, and a cationic polymer. In some embodiments an adjuvant comprises (i) an anti-CD40 antibody and (ii) poly(IC) or poly(ICLC). Exemplary adjuvants of use in various embodiments are disclosed in, e.g., WO/2007/137427 and/or in WO/2009/086640 and/or in one or more references therein. In certain embodiments an adjuvant is pharmaceutically acceptable for administration to a human subject. In certain embodiments an adjuvant is pharmaceutically acceptable for administration to a non-human subject, e.g., for veterinary purposes.

The term "antibody", as used herein, refers to a glycoprotein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from non-mammalian species (e.g., from birds, reptiles, amphibia) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab') fragment (or F(ab')2 fragment), retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab'), Fab, Fv, and Fd fragments; antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, the present invention provides for so-called single chain antibodies (e.g., scFv), (single) domain antibodies (sdAb), and other antibodies, which, in some embodiments, find use as intracellular antibodies. A single-chain variable fragment (scFv) is a protein comprising the variable regions of the heavy (VH) and light chains (VL) of an immunoglobulin, connected with a short linker peptide of, e.g., about 10 to about 25 amino acids. A divalent (or bivalent) single-chain variable fragment (di-scFvs, bi-scFvs) can be engineered by linking two scFvs, e.g., by producing a single peptide chain with two VH and two VL regions, yielding tandem scFvs. Two sdAbs or an sdAb and an scFv can also be linked by producing them as single polypeptide chains. In some embodiments two scFv are joined in the form of a diabody. By using a linker that is too short to allow pairing between the two domains (VH and VL) on the same scFv chain (e.g., less than about 10 amino acids, e.g., about 5 amino acids) the domains instead pair with the complementary domains of another scFv chain and thereby create two antigen-binding sites. A bispecific agent may be created by linking the VH and VL of two different antibodies A and B to form two different "cross-over" chains $VH_A$-$VL_B$ and $VH_B$-$VL_A$, whereby the chains recreate both antigen-binding sites on association (see, e.g., P., et al., Proc Natl Acad Sci USA. 1993; 90(14):6444-8). Domain antibodies, camelid and camelized antibodies and fragments thereof, for example, VHH domains, or nanobodies, such as those described in patents and published patent applications of Ablynx NV and Domantis are also encompassed in the term antibody. Also encompassed are VH domains obtained or derived from immunoglobulin novel (or new) antigen receptors (IgNAR) found in cartilaginous fish (e.g., sharks, skates and rays). See, e.g., WO 05/18629; Barelle, C., et al., Adv Exp Med Biol. (2009) 655:49-62, and/or the chapter by Flajnik and Dooley in Antibody Phage Display: Methods and Protocols, Methods in Molecular Biology, 2009. The term "antigen-binding antibody fragment," as used herein, refers to a fragment of an antibody that comprises the paratope, or a fragment of the antibody that binds to the antigen to which the antibody binds, with similar specificity and affinity as the intact antibody. Where the present disclosure refers to antibodies, the disclosure provides embodiments pertaining to or using antigen-binding fragments of such antibodies.

Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) *Phage Display in Biotechnology and Drug Discovery* (Drug Discovery Series; CRC Press; 1$^{st}$ ed., 2005; Aitken, R. (ed.) *Antibody Phage Display: Methods and Protocols* (Methods in Molecular Biology) Humana Press; 2nd ed., 2009. In some embodiments, a monoclonal antibody is produced using recombinant methods in suitable host cells, e.g., prokaryotic or eukaryotic host cells. In some embodiments microbial host cells (e.g., bacteria, fungi) are used. Nucleic acids encoding antibodies or portions thereof may be isolated and their sequence determined. Such nucleic acid sequences may be inserted into suitable vectors (e.g., plasmids) and, e.g., introduced into host cells for expression. In some embodiments insect cells are used. In some embodiments mammalian cells, e.g., human cells, are used. In some embodiments, an antibody is secreted by host cells that produce it and may be isolated, e.g., from culture medium. Methods for production and purification of recombinant proteins are well known to those of ordinary skill in the art. It will be understood that such methods may be applied to produce and, optionally, purify, any protein of interest herein.

The term "chimeric antigen receptor" (CAR) refers to a polypeptide comprising a cell activation domain fused to a binding domain, e.g., a domain comprising an antigen binding moiety. A cell that expresses a chimeric antigen receptor may be referred to as a "CAR cell". In general, the binding domain is or is located in an extracellular domain of the polypeptide, and the activation domain is located inside the cell in the cytoplasm (cytoplasmic domain). Upon binding of binding moiety to a ligand, the activation domain transmits an activation signal to the CAR cell, and the cell becomes activated as a result of signaling via the activation domain. For example, upon binding of the antigen binding moiety to its cognate antigen (e.g., a protein, lipid, or other molecule) the activation domain transmits an activation signal to the CAR cell, and the cell becomes activated as a result of signaling via the activation domain. If the antigen is expressed by a target cell, the antigen binding moiety directs the specificity of the CAR cell to a target cell of interest. Effector functions of the CAR cell, such as cell-mediated cytotoxicity, are directed to the target cell. In some embodiments the CAR cell is a T cell. In some embodiments the CAR cell is an NK cell. In some embodiments the binding domain, e.g., antigen binding domain, comprises a single chain variable fragment. The binding domain is typically preceded by a signal peptide to direct the nascent CAR to the endoplasmic reticulum and subsequent surface expression. In general, any eukaryotic signal peptide sequence may be used. In some embodiments the signal peptide natively attached to the amino-terminal most component of the CAR is used. It will be appreciated that the signal peptide is cleaved and therefore absent in the mature CAR. In some embodiments the cell activation domain comprises a biologically active portion of the signaling domain of an antigen receptor such as the T cell receptor complex (TCR-CD3 complex). For example, in some embodiments the cell activation domain comprises at least a portion of the cytoplasmic domain (endodomain) of the T cell receptor CD3 ζ (zeta) chain (CD247) or CD3ε (epsilon) chain that is sufficient to activate T cells. In some embodiments a CAR comprises all or substantially all of the cytoplasmic domain of the CD3 ζ chain. In some embodiments, at least a portion of CD3 ζ comprising 1, 2, or 3 ITAM motifs is used. A CAR typically comprises a transmembrane domain (TMD) between the extracellular and cytoplasmic domains. In general, a TMD may comprise at least a portion of a TMD found in any transmembrane protein, e.g., any human transmembrane protein. In some embodiments the transmembrane protein is a protein that spans the plasma membrane. In some embodiments the sequence of a TMD of a CAR comprises at least the sequence of an alpha helical region of a naturally occurring transmembrane protein. In some embodiments a TMD is derived from the alpha or beta chain of the T-cell receptor, CD28, CD3 zeta, CD3 epsilon, CD45, CD4, CD5, CD8, CD9, CD16, CD22, CD33, CD37, CD64, CD80, CD86, CD134, CD137, or CD154. In some embodiments a synthetic TMD may be used. One of ordinary skill in the art will be aware of numerous transmembrane proteins and can readily select a TMD or design a synthetic TMD (see, e.g., Sharpe, H J, et al, Cell. 20101 142(1):158-69 for discussion of features of TMDs and numerous examples of such domains (e.g., in Table S2)). In some embodiments a CAR comprises the CD3zeta transmembrane domain and endodomain. In some embodiments a CAR comprises a spacer region one or more amino acids long (e.g., a polypeptide linker) that links the binding domain to the transmembrane domain. A spacer region sufficiently flexible to allow the binding domain to orient in different directions to facilitate antigen recognition may be selected. Exemplary spacer regions may comprise, e.g., the hinge region from an immunoglobulin, e.g., from IgG1, the $C_H2$ $C_H3$ region of an immunoglobulin, or portions of CD3. In some embodiments the cytoplasmic domain of a CAR comprises an activation domain and at least one domain that provides co-stimulatory signals. Examples of proteins containing such co-stimulatory domains include CD28, 4-1BB, DAP10, ICOS, OX40, CD30, CD40, lymphocyte function-associated antigen-1 (LFA-1), CD2, CD7, LIGHT, NKNKG2C, B7-H3, a ligand that specifically binds with CD83, and any combination thereof) to the cytoplasmic portion of the CAR to provide additional signals to the T cell. In some embodiments a CAR comprises multiple co-stimulatory domains, which may increase potency and/or persistence/proliferation of CAR cells that express the CAR, resulting in designs such as CD3zeta-CD28-4-1BB or CD3zeta-CD28-OX40 (wherein in each case the name of the molecule indicates the protein in which the particular signaling domain is found in nature). The order of such domains described herein is not to be considered limiting. In some embodiments the transmembrane domain of the CAR is the transmembrane domain of the most membrane proximal component of the cytoplasmic domain of the CAR. For example, if the cytoplasmic domain of the CAR comprises CD3zeta-CD28-4-1BB, with the CD3zeta component being located closest to the inner face of the plasma membrane (i.e., separated from the inner face of the plasma membrane by the fewest amino acids), the CAR comprises the transmembrane domain of CD3zeta. It should be understood that any of the domains of a CAR may be connected via a spacer rather than being directly fused to one another. Nucleic acid constructs encoding CARs may be introduced into cells by any suitable method, e.g., by lentiviral or gamma-retroviral vector gene transfer or by electroporation.

Examples of CARs, CAR cells, methods of making, culturing, manipulating, storing, and using CARs and CAR cells, reagents useful for generating CAR cells such as nucleic acid constructs and vectors encoding CARs, are described in the following publications: U.S. Pat. Pub. Nos: 20040038886, 20110158957; 20120148552, 20130071414, 20130266551, 20130280285; 20130287748; PCT application publications WO/2012/079000 (PCT/US11/064191) and/or Finney, H M, et al., J Immunol. 2004; 172(1):104-13; Kalos, M., et al., Sci. Transl. Med. 3, 95ra73 (2011); Porter, D L, et al., N Engl J Med 2011; 365:725-33. Such CARs, CAR cells, methods of making, culturing, manipulating, storing, and using CARs and CAR cells, reagents useful for generating CAR cells such as nucleic acid constructs and vectors encoding CARs, may be used in certain embodiments of the present invention. Furthermore, methods, compositions reagents, media, or devices described in any of the foregoing references may, wherever applicable, be used in embodiments of the present invention that pertain to CAR cells or that do not pertain to CAR cells. Such methods, reagents, media, or devices may, for example, pertain to obtaining, culturing, maintaining, manipulating, expanding, storing, and/or administering cells. In some aspects, methods described herein of sortagging cells, wherein an agent is conjugated to an endogenous, non-genetically engineered polypeptide expressed by a cell, may be applied to CAR cells described in or generated as described in any of the afore-mentioned references. In some embodiments, sortagged CAR cells may be used to treat a cancer that contains cells that express an antigen to which the CAR binds or to treat an infection in which infected cells express an antigen to which the CAR binds. In some embodiments, any CAR that comprises an antigen binding moiety that binds to a particular antigen or epitope may be modified by replacing the antigen binding moiety with a different antigen binding moiety that binds to the same antigen or epitope. In some embodiments, any CAR that comprises an antigen-binding moiety that binds to a particular antigen may be modified by replacing the antigen-binding moiety with an antigen-binding moiety that binds to a different antigen, to generate a CAR that binds to such different antigen or epitope. Such modification may be accomplished by modifying the nucleic acid construct used to produce the CAR, e.g., by replacing the sequence that encodes the antigen-binding moiety with a sequence that encodes a different antigen-binding moiety. CAR T cells and CAR NK cells that express CARs that specifically bind to various tumor antigens (e.g., CD19, CD20, etc.) have been tested in clinical trials for the treatment of human subjects with cancer (e.g., hematologic malignancies) and shown benefit in some patients. The present invention contemplates the sortagging of any CAR cells that have shown reasonable safety in a clinical trial.

The term "chimeric antibody," as used herein, refers to an antibody, or an antigen-binding antibody fragment, conjugated to another molecule, for example, to a second antibody, or antigen-binding antibody fragment. Any antibody or antigen-binding antibody fragment, or antigen-binding protein domain can be used to generate a chimeric antibody. In some embodiments, a chimeric antibody comprises two conjugated antibodies, or antibody fragments, or one antibody conjugated to an antibody fragment, wherein the antigen-binding domains of the conjugated molecules bind different antigens or different epitopes of the same antigen. Such chimeric antibodies are referred to herein as "bi-specific," since they bind two different antigens/epitopes.

The term "costimulator" refers to a molecule that provides a stimulus (or second signal) that promotes or is required, in addition to antigen, for stimulation of naïve immune system cells, e.g., naïve T cells or naïve B cells, and/or that contributes to sustaining or modifying the response. Naturally occurring costimulators include various molecules expressed on the surface of or secreted by APCs, which molecules bind to receptors on the surfaces of, e.g., T cells. Examples of receptors to which costimulators bind include, e.g., CD28 family members (e.g., CD28 and inducible costimulator (ICOS)) and CD2 family members (e.g., CD2, SLAM). Examples of costimulators include various members of the B7 family of molecules such as B7-1 and B7-2 (which bind to CD28) and ICOS ligand (which binds to ICOS). In some embodiments a costimulator is a TNF alpha family member. For example, CD70 on DCs binding to its receptor CD27 on naïve T cells delivers costimulatory signals; 4-1BBL (also called CD137L) on APCs delivers costimulatory signals by binding to its receptor CD137 on T cells. It will be appreciated that the effects of an interaction may be bidirectional, e.g., APCs may receive costimulation via their interaction with cells that they stimulate. OX40 (CD134) is a secondary costimulatory molecule, expressed after typically about 24 to 72 hours following activation; its ligand, OX40L, is expressed on APCs following their activation. In some embodiments expression of costimulator(s) by APCs is stimulated by an adjuvant, e.g., a CD40 ligand, PAMP or PAMP mimic, or TLR ligand. In some embodiments a costimulator is a soluble molecule. In some embodiments a soluble costimulator is a recombinantly produced polypeptide comprising at least a functional portion of the extracellular domain of a naturally occurring costimulator or a functional variant thereof.

The term "endogenous polypeptide" refers to a naturally occurring polypeptide that originates naturally from or is naturally produced by a cell, e.g., a polypeptide that is an expression product of a gene that both (i) is present in the genetic material (nuclear or mitochondrial genome) of the cell (an "endogenous gene") and (ii) has not been modified or introduced into the cell or an ancestor of the cell by the hand of man or by a virus or other vector. It will be understood that endogenous genes of a particular species (e.g., humans) may include sequences introduced by retroviruses, transposons, or other vectors but that have been present in the genome of at least some members of the species for sufficiently long to be considered endogenous. For purposes hereof, genetic elements that can be shown to have been present in the genome of at least some individuals of a particular species, e.g., at a particular chromosomal location, for at least 1000 years are considered endogenous to that species. One of ordinary skill in the art will be aware of endogenous genes and polypeptides of animal cells, e.g., mammalian cells, e.g., human cells. For purposes hereof, "introducing" a nucleic acid into a cell encompasses introducing the nucleic acid itself or introducing a nucleic acid that can undergo one or more rounds of copying, reverse transcription, and/or processing in the cell to yield the nucleic acid. An endogenous polypeptide may be processed or modified during or after its synthesis. For example an N-terminal amino acid or secretion signal sequence may be removed or a loop may be cleaved. In certain embodiments of any aspect of the disclosure, "endogenous polypeptides" are also not chemically modified as defined below.

The terms "genetically engineered" or "genetically modified", or "recombinant" encompass nucleic acids whose sequence comprises a non-naturally occurring sequence, (a sequence invented or generated by man and not occurring in nature or not known to occur in nature), comprises two or more naturally occurring sequences joined together that are not found joined to one another in their naturally occurring state, or comprises a deletion, insertion, rearrangement, or other alteration of or in a naturally occurring sequence, wherein the deletion, insertion, rearrangement, or other alteration is brought about by the hand of man. The terms "genetically engineered", "genetically modified", or "recombinant" polypeptide encompass polypeptides encoded by genetically engineered nucleic acids. In some embodiments the sequence of a genetically engineered polypeptide expressed by a cell is distinct from those polypeptides that are endogenous to the cell. The terms "genetically engineered cell", "genetically modified cell", or "recombinant" cell" encompass cells into which a nucleic acid has been introduced by the hand of man and their descendants that inherit at least a portion of the introduced nucleic acid. In some embodiments a genetically engineered cell has had its genome altered by the hand of man, e.g., by insertion of an exogenous nucleic acid sequence and/or deletion of an endogenous nucleic acid sequence, or is descended from such a cell and has inherited a copy of at least a portion of the original alteration. In some embodiments the nucleic acid or a portion thereof, or a copy of the nucleic acid or a portion thereof, may be integrated into the genome of the cell. "Non-genetically engineered, "non-genetically modified", and "non-recombinant" refer to not being genetically engineered, absence of genetic modification, etc. Non-genetically engineered polypeptides encompass endogenous polypeptides. In certain embodiments a non-genetically engineered cell, gene, or genome does not contain non-endogenous nucleic acid, e.g., DNA or RNA that originates from a vector, from a different species, or that comprises an artificial sequence, e.g., DNA or RNA that was introduced by the hand of man. In certain embodiments a non-genetically engineered cell has not been intentionally contacted with a nucleic acid that is capable of causing a heritable genetic alteration under conditions suitable for uptake of the nucleic acid by the cells.

The terms "chemically engineered" or "chemically modified" encompass modifications made to endogenous proteins or cells to introduce a "linker" as described below, to an endogenous protein or cell. Chemical modifications can be any known in the art. Examples of such modifications are provided in Ta et al. Circ. Res. 2011; 109: 365-373 and International Publication No. WO 2012/142659, both incorporated by reference herein in their entireties. Other chemical modifications that can be made to biomolecules, e.g., polypeptides, are known to those of ordinary skill in the art. See, e.g., Hermanson, G., *Bioconjugate Techniques*, Academic Press; 2nd edition (2008). In certain embodiments, chemical modification of cells includes introducing a reactive functional group, such as a sulfhydryl or maleimide, to cell surfaces, e.g., by attachment (e.g., via a covalent bond) to an extracellular domain of an endogenous polypeptide, followed by labelling the cells with a moiety capable of serving as a nucleophile in a sortase-catalyzed reaction, such as a $(G)_n$- or $(A)_n$-containing peptide, via reaction with such reactive functional group. In certain embodiments, chemical modification of cells includes introducing sulfhydryls to cell surfaces via reaction with primary amines using, e.g., 2-Iminothiolane or Traut's reagent followed by labelling cells with $NH_2GGG$-tags via specific reaction of sulfhydryls on the cell surface and maleimide groups on $NH_2$-GGG-maleimide peptides.

The term "immunomodulator" refers to substances that are capable either by themselves or together with other agent(s) of inducing, enhancing, suppressing, or regulating an immune response. (It will be understood that the term generally does not refer to those entities that are the target of the immune response such as pathogens, tumor cells, grafts, or self antigens in the case of autoimmune disease). Immunomodulators include substances capable of modulating the activation, proliferation, differentiation, and/or biological activity of immune system cells. Examples, include, e.g., cytokines, costimulators, adjuvants.

The term "linker" as used herein, refers to a chemical group or molecule covalently linked to a molecule, for example, a protein, and a chemical group or moiety. In some embodiments, the linker is positioned between, or flanked by, two groups, molecules, or moieties and connected to each one via a covalent bond, thus connecting the two. In some embodiments, the linker is an amino acid or a plurality of amino acids. In some embodiments, the linker is an organic molecule, group, or chemical moiety. In some embodiments a linker connects two or more polypeptides. In some embodiments a linker comprises or consists of a polypeptide. In some embodiments a linker may comprise or consist of one or more glycine residues and, in some embodiments, one or more serine, and/or threonine residues. In some embodiments, the linker comprises 1, 2, 3, 4, 5, 6, 7, 8, 9, 10, 11, 12, 13, 14, 15, 16, 17, 18, 19, 20, or more than 20 amino acids. In some embodiments, the linker comprises an oligoglycine sequence. In some embodiments a linker may comprise at least 50% glycine residues and, in some embodiments, between 5% and 50% of the amino acids are serine or threonine (i.e., S+T is between 5% and 50%, where S is the percentage of serine residues and T is the percentage of threonine residues). Examples of linkers include, e.g., (Gly-Ser)$_n$; (Gly-Gly-Ser)$_n$; (Gly-Gly-Gly-Ser)$_n$; (Gly-Gly-Gly-Gly-Ser)$_n$, where n is a number sufficient to produce a desired linker length, e.g., about 5-15 amino acids, e.g., up to about 25-50 amino acids. The afore-mentioned sequences can be permuted and/or concatenated in any order and/or may be truncated and/or any of the Ser residues may be replaced by Thr and/or any of the Gly or Ser residues may be replaced by Ala. In some embodiments a linker comprises an aliphatic, alicyclic, heteroaliphatic, heteroalicyclic, aromatic, or heteroaromatic linker which, in some embodiments, comprises between 1 and 6, 6 and 12, or 12-30 carbon atoms in the main chain connecting the moieties at each end. In some embodiments a linker comprises a linear saturated or unsaturated hydrocarbon chain, an oligo(ethylene glycol) chain, one or more amino acids (e.g., a peptide), an alicyclic structure, or an aromatic ring. In some embodiments a linker is sufficiently long and flexible so as to permit linked polypeptides to assemble to form a proper three dimensional structure (e.g., as found in nature) and/or retain one or more activities such as binding, enzymatic activity, and/or appropriate interaction with its typical interaction partners. In some embodiments a linker may comprise a protease recognition site or labile bond, which allows release of one or both of the linked moieties under appropriate conditions, e.g., in the presence of a protease that recognizes the protease recognition site and cleaves within or near the linker.

The term "marker" or "cellular marker" refers to any molecular moiety (e.g., protein, peptide, carbohydrate, polysaccharide, nucleic acid (mRNA or other RNA species, DNA), lipid, or a combination thereof) that characterizes, indicates, or identifies one or more cell type(s), tissue type(s), cell lineages, or embryological tissue of origin and/or that characterizes, indicates, or identifies a particular physiological or pathological state, e.g., an activation state, cell cycle state, metabolic state, differentiation state, apoptotic state, diseased state, etc. In some embodiments, the presence, absence, or amount of certain marker(s) may indicate a particular physiological or diseased state of a subject, organ, tissue, or cell. In some embodiments a cell surface marker is a "cluster of differentiation" (CD) molecule. Numerous CD molecules are known in the art. See, e.g., H. Zola, et al., Leukocyte and Stromal Cell Molecules: the CD Markers, Wiley, N.J., 2007 and/or databases cited therein; Proceedings of the 9th International Workshop on Human Leukocyte Differentiation Antigens published in Immunology Letters, Volume 134, Issue 2, Pages 103-188 (30 Jan. 2011); Human Cell Differentiation Molecules database available at http://www.hcdm.org/MoleculeInformation/tabid/54/Default.aspx; and/or Human and Mouse CD Handbook, available at http://www.bdbiosciences.com/documents/cd_marker_handbook.pdf (BD Biosciences, San Jose, Calif., 2010). In some embodiments a cellular marker is cell type specific. For example, a cell type specific marker is typically present at a higher level on or in a particular cell type or cell types of interest than on or in many other cell types. In some instances a cell type specific marker is present at detectable levels only on or in a particular cell type of interest. However, it will be appreciated that useful cell type specific markers need not be absolutely specific for the cell type of interest. In some embodiments a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. In some embodiments a cell type specific marker is present at levels at least 4-5 fold, between 5-10 fold, or more than 10-fold greater than its average expression in a reference population. In some embodiments detection or measurement of a cell type specific marker can distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc.

The term "naturally occurring" as applied to an entity (e.g., a molecule, substance, etc.) refers to the fact that the entity can be found in nature as distinct from being artificially created or modified by man. For example, a polypeptide or polynucleotide sequence that is naturally present in a virus or in a prokaryotic (bacteria) or eukaryotic (e.g., fungal, protozoa, insect, plant, vertebrate) cell, tissue, or organism and/or that can be isolated from a source in nature and which has not been intentionally modified by man (e.g., in the laboratory) is naturally occurring. "Non-naturally occurring" (also referred to as "synthetic" or "artificial") as applied to an entity means that the entity is not naturally occurring, i.e., it cannot be found in nature as distinct from being artificially produced by man. It will be appreciated that a "naturally occurring" entity may be produced by man, e.g., through recombinant nucleic acid techniques or chemical synthesis and/or may be isolated or purified. Such an entity is still considered naturally occurring so long as it does not otherwise differ materially from the entity as found in nature.

The term "purified" refers to agents that have been separated from some, many, or most of the components with which they are associated in nature or when originally generated. In general, such purification involves action of the hand of man. In some embodiments a purified agent is, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, 99.5%, 99.9%, 99.95%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, 99.5%, 99.9%, 99.95%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" or "at least partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate or, in the case of a molecule that is secreted by a cell, the molecule has been separated from at least some components of the medium or environment into which it was secreted. In some embodiments, any agent disclosed herein is purified. In some embodiments a composition comprises one or more purified agents.

The term "RNA interference" (RNAi) encompasses processes in which a molecular complex known as an RNA-induced silencing complex (RISC) silences or "knocks down" gene expression in a sequence-specific manner in, e.g., eukaryotic cells, e.g., vertebrate cells, or in an appropriate in vitro system. RISC may incorporate a short nucleic acid strand (e.g., about 16-about 30 nucleotides (nt) in length) that pairs with and directs or "guides" sequence-specific degradation or translational repression of RNA (e.g., mRNA) to which the strand has complementarity. The short nucleic acid strand may be referred to as a "guide strand" or "antisense strand". An RNA strand to which the guide strand has complementarity may be referred to as a "target RNA". The complementarity of the structure formed by hybridization of a target RNA and the guide strand may be such that the strand can (i) guide cleavage of the target RNA in the RNA-induced silencing complex (RISC) and/or (ii) cause translational repression of the target RNA. Reduction of expression due to RNAi may be essentially complete (e.g., the amount of a gene product is reduced to background levels) or may be less than complete in various embodiments. For example, mRNA and/or protein level may be reduced by 50%, 60%, 70%, 75%, 80%, 85%, 90%, 95%, or more, in various embodiments. As known in the art, the complementarity between the guide strand and a target RNA need not be perfect (100%) but need only be sufficient to result in inhibition of gene expression. For example, in some embodiments 1, 2, 3, 4, 5, or more nucleotides of a guide strand may not be matched to a target RNA. In some embodiments a guide strand has at least about 80%, 85%, or 90%, e.g., least about 91%, 92%, 93%, 94%, 95%, 96%, 97%, 98%, 99%, or 100% sequence complementarity to a target RNA over a continuous stretch of at least about 15 nt, e.g., between 15 nt and 30 nt, between 17 nt and 29 nt, between 18 nt and 25 nt, between 19 nt and 23 nt, of the target RNA. In some embodiments at least the seed region of a guide strand (the nucleotides in positions 2-7 or 2-8 of the guide strand) is perfectly complementary to a target RNA. As used herein, the term "RNAi agent" encompasses nucleic acids that can be used to achieve RNAi in eukaryotic cells. Short interfering RNA (siRNA), short hairpin RNA (shRNA), and microRNA (miRNA) are examples of RNAi agents. siRNAs typically comprise two separate nucleic acid strands that are hybridized to each other to form a structure that contains a double stranded (duplex) portion at least 15 nt in length, e.g., about 15-about 30 nt long, e.g., between 17-27 nt long, e.g., between 18-25 nt long, e.g., between 19-23 nt long, e.g., 15, 16, 17, 18, 19, 20, 21, 22, 23, 24, 25, 26, 27, 28, 29, or 30 nucleotides. In some embodiments the strands of an siRNA are perfectly complementary to each other within the duplex portion. In some embodiments the duplex portion may contain one or more unmatched nucleotides, e.g., one or more mismatched (non-complementary) nucleotide pairs or bulged nucleotides. In some embodiments either or both strands of an siRNA may contain up to about 1, 2, 3, or 4 unmatched nucleotides within the duplex portion. In some embodiments a strand may have a length of between 15-35 nt, e.g., between 17-29 nt, e.g., 19-25 nt, e.g., 21-23 nt. Strands may be equal in length or may have different lengths in various embodiments. In some embodiments strands may differ by between 1-10 nt in length. A strand may have a 5' phosphate group and/or a 3' hydroxyl (—OH) group. Either or both strands of an siRNA may comprise a 3' overhang of, e.g., about 1-10 nt (e.g., 1-5 nt, e.g., 2 nt). shRNAs are nucleic acid molecules that comprise a stem-loop structure and a length typically between about 40-150 nt, e.g., about 50-100 nt, e.g., 60-80 nt. A "stem-loop structure" (also referred to as a "hairpin" structure) refers to a nucleic acid having a secondary structure that includes a region of nucleotides which are known or predicted to form a double strand (stem portion; duplex) that is linked on one side by a region of (usually) predominantly single-stranded nucleotides (loop portion). Such structures are well known in the art and the term is used consistently with its meaning in the art. A guide strand sequence may be positioned in either arm of the stem, i.e., 5' with respect to the loop or 3' with respect to the loop in various embodiments. As is known in the art, the stem structure does not require exact base-pairing (perfect complementarity). Thus, the stem may include one or more unmatched residues or the base-pairing may be exact, i.e., it may not include any mismatches or bulges. In some embodiments the stem is between 15-30 nt, e.g., between 17-29 nt, e.g., 19-25 nt. In some embodiments the stem is between 15-19 nt. In some embodiments the stem is between 19-30 nt. In some embodiments the loop is between 1 and 20 nt in length, e.g., 1-15 nt, e.g., 4-9 nt. The shRNA structure may comprise a 5' or 3' overhang. As known in the art, an shRNA may undergo intracellular processing to remove the loop and generate an siRNA. Mature endogenous miRNAs are short (typically 18-24 nt, e.g., about 22 nt), single-stranded RNAs that are generated by intracellular processing from larger, endogenously encoded precursor RNA molecules termed miRNA precursors (see, e.g., Bartel, D., Cell. 116(2):281-97 (2004); Bartel D P. Cell. 136(2):215-33 (2009); Winter, J., et al., Nature Cell Biology 11: 228-234 (2009). Artificial miRNA may be designed to take advantage of the endogenous RNAi pathway in order to silence a target RNA of interest. An RNAi agent that contains a strand sufficiently complementary to an RNA of interest so as to result in reduced expression of the RNA of interest (e.g., as a result of degradation or repression of translation of the RNA) in a cell or in an in vitro system capable of mediating RNAi and/or that comprises a sequence that is at least 80%, 90%, 95%, or more (e.g., 100%) complementary to a sequence comprising at least 10, 12, 15, 17, or 19 consecutive nucleotides of an RNA of interest may be referred to as being "targeted to" the RNA of interest. An RNAi agent targeted to an RNA transcript may also considered to be targeted to a gene from which the transcript is transcribed. In some embodiments an RNAi agent is a vector (e.g., an expression vector) suitable for causing intracellular expression of one or more transcripts that give rise to a siRNA, shRNA, or miRNA in the cell.

Such a vector may be referred to as an "RNAi vector". An RNAi vector may comprise a template that, when transcribed, yields transcripts that may form a siRNA (e.g., as two separate strands that hybridize to each other), shRNA, or miRNA precursor (e.g., pri-miRNA or pre-mRNA).

The term "sortagging," as used herein, refers to the process of attaching (conjugating) a tag to a target entity, e.g., a molecule, for example, a protein, using a sortase. The term "sortagging" encompasses attaching a tag to a protein expressed by a living cell using a sortase, thereby attaching the tag to the cell. The term "tag" is used in a broad sense to encompass any of a wide variety of entities. Examples of suitable tags include, but are not limited to, amino acids, peptides, proteins, nucleic acids, polynucleotides, sugars, carbohydrates, polymers, lipids, fatty acids, and small molecules. Other suitable tags will be apparent to those of skill in the art and the invention is not limited in this aspect. In some embodiments a tag is covalently or noncovalently attached to, physically associated with, or part of another entity, such as a virus, cell, particle, or other supramolecular complex, and attaching the tag to the target entity (sortagging the target entity) attaches the entity to the target entity. In some embodiments, a tag comprises a sequence useful for purifying, expressing, solubilizing, and/or detecting a polypeptide. In some embodiments, a tag may comprise two or more moieties, which may be conjugated to each other. In some embodiments a tag may serve multiple functions. In some embodiments a tag is a relatively small polypeptide, e.g., ranging from a few amino acids up to about 100 amino acids long. In some embodiments a tag is more than 100 amino acids long, e.g., up to about 500 amino acids long, or more. In some embodiments, a tag comprises an HA, TAP, Myc, 6xHis, Flag, V5, or GST tag, to name few examples. A tag (e.g., any of the afore-mentioned tags) that comprises an epitope against which an antibody, e.g., a monoclonal antibody, is available (e.g., commercially available) or known in the art may be referred to as an "epitope tag". In some embodiments a tag comprises a solubility-enhancing tag (e.g., a SUMO tag, NUS A tag, SNUT tag, a Strep tag, or a monomeric mutant of the Ocr protein of bacteriophage T7). See, e.g., Esposito D and Chatterjee D K. Curr Opin Biotechnol.; 17(4):353-8 (2006). In some embodiments, a tag is cleavable, so that at least a portion of it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., PCT/US05/05763. In some embodiments, sortagging involves coupling a tag to an endogenous protein on the surface of a cell.

The term "sortase" refers to an enzyme that has transamidase activity. Sortases, also referred to as transamidases, can form a peptide linkage (i.e., amide linkage) between an appropriate acyl donor compound and a nucleophilic acyl acceptor containing a $NH_2$—$CH_2$-moiety, such as an N-terminal glycine. Sortases recognize substrates comprising a sortase recognition motif, e.g., the amino acid sequence LPXTG. A molecule recognized by a sortase (i.e., comprising a sortase recognition motif) is sometimes termed a "sortase substrate" herein. After recognition of such a motif by sortase the catalytic residue (e.g., cysteine) in the enzyme's active site serves as a nucleophile to cleave a peptide bond in the motif (e.g., the peptide bond between threonine and glycine in LXPTG). Cleavage occurs with concomitant formation of a thioacyl intermediate between substrate and enzyme. This intermediate is resolved by reaction with an appropriate nucleophile, thereby creating a new bond that links the substrate to the nucleophile. Sortases tolerate a wide variety of moieties in proximity to the cleavage site, thus allowing for the versatile conjugation of diverse entities so long as the substrate contains a suitably exposed sortase recognition motif and a suitable nucleophile is available. The terms "sortase-mediated transacylation reaction", "sortase-catalyzed transacylation reaction", "sortase-mediated reaction", "sortase-catalyzed reaction", "sortase reaction" and like terms, are used interchangeably herein to refer to such a reaction. The terms "sortase recognition motif", "sortase recognition sequence", and "transamidase recognition sequence" (sometimes abbreviated as "TRS") with respect to sequences recognized by a transamidase or sortase, are used interchangeably herein. The term "nucleophilic acceptor sequence" refers to an amino acid sequence capable of serving as a nucleophile in a sortase-catalyzed reaction, e.g., a sequence comprising an N-terminal glycine (e.g., 1, 2, 3, 4, or 5 N-terminal glycines) or in some embodiments comprising an N-terminal alanine (e.g., 1, 2, 3, 4, or 5 N-terminal alanines).

Substrates suitable for sortase-mediated conjugation can readily be designed. For example, polypeptides can be modified to include a sortase recognition motif at or near their C-terminus, thereby allowing them to serve as substrates for sortase. The sortase recognition motif need not be positioned at the very C-terminus of a substrate but should typically be sufficiently accessible by the enzyme to participate in the sortase reaction. In some embodiments a sortase recognition motif is considered to be "near" a C-terminus if there are no more than 5, 6, 7, 8, 9, 10, 12, 15, 20, or 25 amino acids between the most N-terminal amino acid in the sortase recognition motif (e.g., L) and the C-terminal amino acid of the polypeptide. In some embodiments there is at least 1, 2, 3, or 4 additional amino acids C-terminal to a G or A in a sortase recognition motif. In some embodiments at least one additional amino acid is G or A. For example, the sortase substrate may comprise LPXTGG, e.g., LPETGG. In some embodiments a tag (e.g., a 6xHis tag or other small peptide tag) is located C-terminal to the sortase recognition motif, optionally separated from it by a spacer. Upon cleavage, the tag is released. The free tag may be detected, which may be useful to monitor the progress or extent of the reaction. In some embodiments a sortase recognition motif is located in a flexible loop of a polypeptide. The flexible loop may be exposed at the surface of a properly folded polypeptide. The loop may be cleaved by a protease so as to position the sortase recognition motif at or near the C-terminus of a resulting cleavage product. A polypeptide comprising a sortase recognition motif may be modified by incorporating or attaching any of a wide variety of moieties thereto. The resulting modified polypeptide can serve as a sortase substrate, resulting in conjugation of the moiety to the nucleophile. Suitable nucleophiles that can be used in a sortase reaction typically comprise a short run (e.g., 1-10) of glycine residues, although even an alkylamine suffices to allow the reaction to proceed. Polypeptides can be modified to comprise a nucleophilic acceptor sequence, e.g., a sequence comprising one or more glycines, at their N-terminus and the resulting polypeptide may be used as a nucleophile in a sortase-catalyzed reaction. Such a reaction can result in installation of any of a wide variety of entities (comprising a sortase sortase recognition motif) at the N-terminus of the polypeptide.

A "subject" may be any vertebrate organism in various embodiments. A subject may be individual to whom an agent, cell, substance, or composition is administered, e.g., for experimental, diagnostic, and/or therapeutic purposes or from whom a sample is obtained or on whom a procedure is performed. In some embodiments a subject is a mammal, e.g. a human, non-human primate, rodent (e.g., mouse, rat, rabbit), ungulate (e.g., ovine, bovine, equine, caprine species), canine, or feline. In some embodiments a subject is an avian. In some embodiments a subject is a non-human animal that serves as a model for a disease or disorder that affects humans. An animal model may be used, e.g., in preclinical studies, e.g., to assess efficacy and/or determine a suitable dose.

The term "small molecule" is used herein to refer to molecules, whether naturally occurring or artificially created (e.g., via chemical synthesis) that have a relatively low molecular weight. Typically, a small molecule is an organic compound. A small molecule may contain multiple carbon-carbon bonds, stereocenters, and other functional groups (e.g., amines, hydroxyl, carbonyls, heterocyclic rings, etc.). In some embodiments, a small molecule is monomeric. In some embodiments, a small molecule has a molecular weight of less than about 1500 g/mol. In some embodiments, a small molecule has a molecular weight of less than about 1000 g/mol or less than about 500 g/mol. In certain embodiments a small molecule is a compound that has been deemed safe and effective for use as a diagnostic or therapeutic agent in humans or animals by an appropriate governmental agency or regulatory body.

As used herein, a "support" may be any entity or plurality of entities having a surface to which a substance may be attached or on which a substance may be placed. Examples, include, e.g., particles, slides, filters, interior wall or bottom of a vessel (e.g., a culture vessel such as a plate or flask, well of a microwell plate, tube), chips, etc. A support may be composed, e.g., of glass, metal, gels (e.g., agarose), ceramics, polymers, or combinations thereof.

The term "tumor" as used herein encompasses abnormal growths comprising aberrantly proliferating cells. Tumors are typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclear:cytoplasmic ratio, atypical mitoses, etc.); invasion of adjacent tissues (e.g., breaching a basement membrane); and/or metastasis. In certain embodiments a tumor is a malignant tumor, also referred to herein as a "cancer". Malignant tumors have a tendency for sustained growth and an ability to spread, e.g., to invade locally and/or metastasize regionally and/or to distant locations, whereas benign tumors often remain localized at the site of origin and are often self-limiting in terms of growth. The term "tumor" includes malignant solid tumors (e.g., carcinomas, sarcomas) and malignant growths in which there may be no detectable solid tumor mass (e.g., certain hematologic malignancies). The term "cancer" is generally used interchangeably with "tumor" herein and/or to refer to a disease characterized by one or more tumors, e.g., one or more malignant or potentially malignant tumors. Cancer includes, but is not limited to: breast cancer; biliary tract cancer; bladder cancer; brain cancer (e.g., glioblastomas, medulloblastomas); cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma, oral cancer including squamous cell carcinoma; ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullary carcinoma. It will be appreciated that a variety of different tumor types can arise in certain organs, which may differ with regard to, e.g., clinical and/or pathological features and/or molecular markers. Tumors arising in a variety of different organs are discussed, e.g., in DeVita, Hellman, and Rosenberg's Cancer: Principles and Practice of Oncology (Cancer: Principles & Practice), Lippincott Williams & Wilkins; Ninth, North American Edition (May 16, 2011) or in the WHO Classification of Tumours series, $4^{th}$ ed, or $3^{rd}$ ed (Pathology and Genetics of Tumours series), by the International Agency for Research on Cancer (IARC), WHO Press, Geneva, Switzerland.

"Treat", "treating" and similar terms refer to providing medical and/or surgical management of a subject. Treatment may include, but is not limited to, administering an agent or composition (e.g., a pharmaceutical composition) to a subject. Treatment is typically undertaken in an effort to alter the course of a disease (which term is used to indicate any disease, disorder, or undesirable condition warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease.

A "variant" of a particular polypeptide or polynucleotide has one or more alterations (e.g., additions, substitutions, and/or deletions) with respect to a reference polypeptide or polynucleotide, which may be referred to as the "original polypeptide" or "original polynucleotide", respectively. An addition may be an insertion or may be at either terminus. A variant may be shorter or longer than the reference polypeptide or polynucleotide. The term "variant" encompasses "fragments". A "fragment" is a continuous portion of a polypeptide or polynucleotide that is shorter than the reference polypeptide or polynucleotide. In some embodiments a variant comprises or consists of a fragment. In some embodiments a fragment or variant is at least 20%, 30%, 40%, 50%, 60%, 70%, 80%, 90%, 92.5%, 95%, 96%, 97%, 98%, 99%, or more as long as the reference polypeptide or polynucleotide. In some embodiments a fragment may lack an N-terminal and/or C-terminal portion of a reference polypeptide. For example, a fragment may lack up to 5%, 10%, 15%, 20%, or 25% of the length of the polypeptide from either or both ends. A fragment may be an N-terminal, C-terminal, or internal fragment. In some embodiments a variant polypeptide comprises or consists of at least one domain of a reference polypeptide. In some embodiments a variant polynucleotide hybridizes to a reference polynucleotide under art-recognized stringent conditions, e.g., high stringency conditions, for sequences of the length of the reference polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the reference polypeptide or polynucleotide over at least 20%, 30%, 40%, 50%, 60%, 70%, 80%, 90%, 95%, 96%, 97%, 98%, 99%, or 100% of the reference polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the reference polypeptide over at least 20%, 30%, 40%, 50%, 60%, 70%, 80%, 90%, 95%, 96%, 97%, 98%, 99%, or 100% of the reference polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the reference polypeptide over at least 20%, 30%, 40%, 50%, 60%, 70%, 80%, 90%, 95%, 96%, 97%, 98%, 99%, or 100% of the reference polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to a reference sequence, wherein N is any integer between 1 and 10 or between 1 and 20 or any integer up to 1%, 2%, 5%, or 10% of the number of amino acids in the reference polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
|---|---|---|
| | | I L V |
| | Polar - uncharged | C S T M |
| | | N Q |
| | Polar - charged | D E |
| | | K R |
| Aromatic | | H F W Y |

In some embodiments, proline (P) is considered to be in an individual group. In some embodiments, cysteine (C) is considered to be in an individual group. In some embodiments, proline (P) and cysteine (C) are each considered to be in an individual group. Within a particular group, certain substitutions may be of particular interest in certain embodiments, e.g., replacements of leucine by isoleucine (or vice versa), serine by threonine (or vice versa), or alanine by glycine (or vice versa).

In some embodiments a variant is a functional variant, i.e., the variant at least in part retains at least one activity of the reference polypeptide or polynucleotide. In some embodiments a variant at least in part retains more than one or substantially all known activities of the reference polypeptide or polynucleotide. An activity may be, e.g., a catalytic activity, binding activity, ability to perform or participate in a biological function or process, etc. In some embodiments an activity is one that has (or the lack of which has) a detectable effect on an observable phenotype of a cell or organism. In some embodiments an activity of a variant may be at least 10%, 20%, 30%, 40%, 50%, 60%, 70%, 80%, 90%, 95%, or more, of the activity of the reference polypeptide or polynucleotide, up to approximately 100%, approximately 125%, or approximately 150% of the activity of the reference polypeptide or polynucleotide, in various embodiments. In some embodiments a variant, e.g., a functional variant, comprises or consists of a polypeptide at least 80%, 90%, 92.5%, 95%, 96%, 97%, 98%, 99%. 99.5% or 100% identical to an reference polypeptide or polynucleotide over at least 70%, 75%, 80%, 85%, 90%, 95%, 96%, 97%, 98%, or 99% or 100% of the full length of the reference polypeptide or polynucleotide or over at least 70%, 75%, 80%, 85%, 90%, 92.5%, 95%, 96%, 97%, 98%, or 99% or 100% of a functional fragment of the reference polypeptide or polynucleotide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. In some embodiments nucleotide(s), amino acid(s), or region(s) exhibiting lower degrees of conservation across species as compared with other amino acids or regions may be selected for alteration. Variants may be tested in one or more suitable assays to assess activity. In certain embodiments a polypeptide or polynucleotide sequence in the NCBI RefSeq database may be used as a reference sequence. In some embodiments a variant or fragment of a naturally occurring polypeptide or polynucleotide is a naturally occurring variant or fragment. In some embodiments a variant or fragment of a naturally occurring polypeptide or polynucleotide is not naturally occurring. Calculations of sequence identity can be performed as follows. Sequences are aligned for optimal comparison purposes and gaps can be introduced in one or both of a first and a second sequence for optimal alignment. When a position in the first sequence is occupied by the same residue as the corresponding position in the second sequence, the sequences are deemed to be identical at that position. The percent identity between the two sequences is a function of the number of identical positions shared by the sequences, taking into account the number of gaps, and the length of each gap, introduced for optimal alignment of the two sequences. Sequences can be aligned and/or percent identity determined with the use of a variety of algorithms and computer programs known in the art. For example, computer programs such as BLAST2, BLASTN, BLASTP, Gapped BLAST, etc., may be used to generate alignments and/or to obtain a percent identity. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. MoI. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm.nih.gov and/or McGinnis, S. and Madden, T L, W20-W25 Nucleic Acids Research, 2004, Vol. 32, Web server issue. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.) The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of TGA and TGB (here TGA and TGB are the sum of the number of residues and internal gap positions in sequences A and B in the alignment), and multiplying by 100. Percent identity may be evaluated over a window of evaluation. In some embodiments a window of evaluation may have a length of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more, e.g., 100%, of the length of the shortest of the sequences being compared. In some embodiments a window of evaluation is at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments no more than 20%, 10%, 5%, or 1% of positions in either sequence or in both sequences over a window of evaluation are occupied by a gap. In some embodiments no more than 20%, 10%, 5%, or 1% of positions in either sequence or in both sequences are occupied by a gap.

A "vector" may be any of a number of nucleic acid molecules or viruses or portions thereof that are capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, transposons (e.g., Sleeping Beauty transposon), etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses, gamma retroviruses), vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA such as an shRNA or miRNA precursor). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), e.g., a promoter for transcription of ribosomal RNA (other than 5S rRNA) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), e.g., a promoter for transcription of U6, H1, 7SK or tRNA promoter or a functional variant thereof) or a functional variant thereof is used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. Examples of virus vectors that may be used in mammalian cells include, e.g., adenoviruses, adeno-associated viruses, poxviruses such as vaccinia viruses and attenuated poxviruses, retroviruses (e.g., lentiviruses), Semliki Forest virus, Sindbis virus, etc. In some embodiments, regulatable (e.g., inducible or repressible) expression control element(s), e.g., a regulatable promoter, is/are used so that expression can be regulated, e.g., turned on or increased or turned off or decreased. For example, the tetracycline-regulatable gene expression system (Gossen & Bujard, Proc. Natl. Acad. Sci. 89:5547-5551, 1992) or variants thereof (see, e.g., Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390 for examples) can be employed to provide inducible or repressible expression. Other inducible/repressible systems may be used in various embodiments. For example, expression control elements that can be regulated by small molecules such as artificial or naturally occurring hormone receptor ligands (e.g., steroid receptor ligands such as naturally occurring or synthetic estrogen receptor or glucocorticoid receptor ligands), tetracycline or analogs thereof, metal-regulated systems (e.g., metallothionein promoter) may be used in certain embodiments. In some embodiments, tissue-specific or cell type specific regulatory element(s) may be used, e.g., in order to direct expression in one or more selected tissues or cell types.

In some embodiments a vector is used to insert exogenous DNA into the genome of a cell. In general, any suitable vector may be used. In some embodiments the vector is a viral vector, e.g., a retroviral vector such as a lentiviral vector or gamma retroviral vector, or an adenoviral or AAV vector. In some embodiments the vector is a plasmid, e.g., a DNA plasmid. In some embodiments, the plasmid comprises DNA to be inserted into the genome of a cell, wherein the DNA is located between binding sites for a transposase ("transposase binding sites") so that integration of the DNA can be achieved by supplying the transposase, e.g., by expressing it from the same or a different plasmid. In some embodiments the transposase is e.g., a member of the Sleeping Beauty family of transposases, the piggyBac family of transposases, or the Tol2 family of transposases (see Grabundzija, I., et al., Molecular Therapy, vol. 18 no. 6, 1200-1209 (2010) for review of transposon systems that utilize these transposases, and various uses thereof in genetic engineering). Examples of Sleeping Beauty transposases include SB10, SB11, and SB100X (see, e.g., Mates, L., et al., Nat Genet. (2009) 41(6):753-61; Jin, Z., et al. Gene Therapy (2011) 18, 849-856). In some embodiments the vector is suitable for use to genetically engineer cells, e.g., human cells, that are to be administered to a human subject. In some embodiments the vector has been used in at least one clinical trial in human subjects, results of which have been published, without reported clinically unacceptable adverse events attributable to the vector. In some embodiments the vector is a self-inactivating retroviral vector. Such vectors may be created by deletion of at least part of the U3 portion of the 3' LTR. Exemplary retroviral and lentiviral vectors are described in US Pat. Pub. No. 20050251872, US Pat. Pub. No. 20040259208, and various other references cited herein. In some embodiments a second or third generation lentiviral vector may be used.

DETAILED DESCRIPTION OF CERTAIN EMBODIMENTS

I. Sortagging Non-Genetically Engineered Eukaryotic Polypeptides and Cells

The present disclosure describes the unexpected discovery that non-genetically engineered mammalian cells can be effectively labeled using sortase, i.e., in a sortase-catalyzed transacylation. In some aspects, the invention provides methods of using sortase to conjugate agents to living mammalian cells that have not been genetically engineered to express a protein comprising a sortase recognition motif or a nucleophilic acceptor sequence. In some embodiments the mammalian cells have not been genetically engineered. Some aspects of this invention relate to the recognition that the sortase-catalyzed transacylation reaction allows for the conjugation of agents to one or more polypeptides that are endogenous to living mammalian cells, i.e., sortase can be used to conjugate agents to living mammalian cells that are not genetically engineered for sortagging. As used herein, a polypeptide is "not genetically engineered for sortagging" if the polypeptide is not genetically engineered in a way that allows it to serve as a sortase substrate or as a nucleophile in a sortase-catalyzed reaction, i.e., the polypeptide is not genetically engineered to comprise a sortase recognition motif in a region accessible to a sortase (e.g., at or near the C-terminus) and is not genetically engineered to comprise a nucleophilic acceptor sequence that can serve as a nucleophile in a sortase-catalyzed reaction, such as a sequence comprising one or more glycines, located at the N-terminus of the polypeptide or positioned such that cleavage of the polypeptide can result in the sequence being located at an N-terminus. In some embodiments the polypeptide is not genetically engineered. A cell is considered "not genetically engineered for sortagging" if the cell has not been genetically engineered to express a polypeptide that (either naturally or as a result of genetic engineering) is suitable to serve as a sortase substrate or as a nucleophile in a sortase-catalyzed reaction. In some embodiments the cell has not been genetically engineered to express a polypeptide comprising a sortase recognition motif or a nucleophilic acceptor sequence. In some embodiments the cell is not genetically engineered. In some embodiments the cell does not comprise a modification to its genome introduced by the hand of man. In some aspects, the invention relates to use of sortase to attach any of a wide variety of agents to the surface of non-genetically engineered mammalian cells. Unless otherwise indicated or clearly evident from the context, where the present disclosure refers to sortagging mammalian cells it is generally intended to mean mammalian cells that have not been genetically engineered for sortagging. In certain embodiments the animal cells are not genetically engineered.

As described in Examples 1 and 2, non-genetically engineered mouse splenocytes were effectively sortagged with a variety of sortase substrates at readily detectable levels. In other experiments, sortagging of non-genetically engineered cells of a human kidney cell line (HEK293T cells) and canine kidney cell line (MDCK cells) and variety of other non-genetically engineered eukaryotic cell types (fungal, protozoal) was also observed. Thus, sortase can be used for modification of mammalian cell surfaces and other eukaryotic cell surfaces without requiring that the cells be engineered to express polypeptides comprising a sortase recognition sequence or nucleophilic acceptor sequence. In accordance with certain embodiments of the present invention a non-genetically engineered mammalian cell expresses one or more endogenous polypeptides comprising a nucleophilic acceptor sequence, thus allowing it to serve as a nucleophile in a sortase-catalyzed transacylation. Such polypeptide(s) may comprise a sequence of one or more glycines exposed at the cell surface, e.g., in an N-terminal domain, available to act as a nucleophile in a reaction in which sortase is used to conjugate a sortase substrate to the polypeptide. In some embodiments the endogenous polypeptide may comprise an N-terminal glycine. In some embodiments the endogenous polypeptide may comprise a sequence of between 1-10 glycines at its N-terminus, e.g., 1, 2, 3, 4, or 5 glycines. In some embodiments the polypeptide may not have an N-terminal glycine when initially synthesized (e.g., the N-terminal amino acid may be methionine) but undergoes co-translational or post-translational processing (e.g., cleavage) or partial degradation so that a sequence of one or more glycines is present at the N-terminus. For example, a secretion signal sequence may be removed. Such processing or degradation may occur before exposure of at least a portion of the polypeptide at the cell surface (e.g., in the endoplasmic reticulum) or may occur following exposure of at least a portion of the polypeptide to the extracellular environment. It will thus be understood that aspects of the invention comprise sortagging eukaryotic cell surfaces, e.g., mammalian cell surfaces, without first modifying the cells so as to cause them to have a sortase recognition sequence or a moiety capable of serving as a nucleophile in a sortase-catalyzed reaction attached to their surface.

Aspects of the invention comprise sortagging an endogenous polypeptide expressed by a living eukaryotic cell, e.g., a mammalian cell, wherein the endogenous polypeptide comprises an extracellular domain that naturally comprises one or more amino acids capable of serving as a nucleophile in a sortase-catalyzed reaction. According to such aspects the natural DNA sequence encoding the extracellular domain of such polypeptide has not been modified by the hand of man to encode an amino acid capable of serving as a nucleophile in a sortase-catalyzed reaction, and the polypeptide has not been modified by the hand of man by adding such an amino acid to the extracellular domain. For example, the extracellular domain of the polypeptide has not been subjected to covalent or noncovalent linkage of a (G)n moiety, an (A)n moiety, or a moiety comprising a free amine capable of serving as a nucleophile in a sortase-catalyzed reaction. In certain embodiments of any aspect, cells are not subjected to chemical modification prior to sortagging.

In some aspects, the invention provides compositions useful for generating sortase-modified eukaryotic cells, e.g., sortase-modified mammalian cells. In some embodiments the compositions comprise a sortase and one or more living eukaryotic cells, e.g., mammalian cells, wherein the cell(s) do not express a polypeptide that has been genetically engineered to comprise a sortase recognition motif or nucleophilic acceptor sequence. In some embodiments the cell(s) are not genetically engineered. In some embodiments a composition further comprises a sortase substrate. In some embodiments the sortase substrate comprises any of a variety of agents, e.g., In some aspects, the invention provides compositions comprising sortase-modified eukaryotic cells, e.g., sortase-modified mammalian cells. In some embodiments the compositions comprise one or more sortase-modified eukaryotic cells, e.g., sortase-modified mammalian cells, wherein the cells are modified by conjugation of an agent to a polypeptide expressed by the cells, wherein the polypeptide has not been genetically engineered to comprise a sortase recognition motif or nucleophilic acceptor sequence. In some embodiments the eukaryotic cells, e.g., mammalian cells, are not genetically engineered.

In some aspects, the invention provides a eukaryotic cell, e.g., a mammalian cell, that comprises an agent conjugated via a sortase recognition motif to a non-genetically engineered endogenous polypeptide expressed by the cell. In some embodiments the cell is not genetically engineered. In some embodiments, two, three, four or more different non-genetically engineered endogenous polypeptides expressed by the cell have an agent conjugated thereto via a sortase recognition motif. The agents attached to different polypeptides may be the same or the cell may be sortagged with multiple different agents.

In some aspects, the invention provides methods of generating sortase-modified eukaryotic cells, e.g., mammalian cells. In some aspects, the invention provides methods that comprise conjugating an agent to a non-genetically engineered eukaryotic, e.g., mammalian, polypeptide using a sortase. In some aspects, the invention provides methods comprising conjugating an agent to a mammalian polypeptide using a sortase, wherein the polypeptide has not been engineered to comprise a sortase recognition motif or nucleophilic acceptor sequence. In some embodiments the polypeptide is expressed by a living mammalian cell, and the methods comprise contacting the cell with a sortase and a sortase substrate comprising the agent under conditions suitable for a sortase reaction to occur. In some embodiments the polypeptide comprises an extracellular domain, and the methods comprise conjugating the sortase substrate to the extracellular domain of the polypeptide. In some embodiments the extracellular domain comprises the N-terminus of the polypeptide. In some embodiments the mammalian polypeptide comprises an N-terminal nucleophilic acceptor sequence, e.g., a sequence comprising an N-terminal glycine, before conjugation of the sortase substrate thereto. In some embodiments a method comprises contacting one or more living mammalian cells with sortase and a sortase substrate under conditions and for a time suitable for a sortase-mediated transacylation reaction to occur, wherein the living mammalian cell(s) have not been genetically engineered to express a polypeptide that comprises a sortase recognition motif or nucleophilic acceptor sequence. In some embodiments the mammalian cell(s) have not been genetically engineered.

In some embodiments a method further comprises separating one or more of the living mammalian cell(s) from sortase and/or from sortase substrate that is not conjugated to the cells. The cells may be processed so as to achieve a selected degree of purity with respect to sortase, unconjugated sortase substrate, or both. For example, in some embodiments the amount of sortase and/or the amount of unconjugated sortase substrate may be reduced to below a selected concentration and/or a selected proportion of the sortase and/or unconjugated sortase substrate may be removed. For example, the concentration of sortase and/or unconjugated sortase substrate may be reduced by at least 80%, 85%, 90%, 95%, 96%, 97%, 98%, 99%, 99.5%, or more 99.9% relative to the initial concentration, or at least 80%, 85%, 90%, 95%, 96%, 97%, 98%, 99%, 99.5%, 99.9%, or more of the sortase and/or unconjugated sortase substrate that was present in the composition comprising one or more living mammalian cells and sortase may be removed. In some embodiments the concentration of sortase and/or unconjugated sortase substrate is reduced to no more than 0.01%, 0.05%, 0.1%, 0.5%, or 1.0% relative to the concentration used to sortag the mammalian cells. In some embodiments a sortase polypeptide and/or unconjugated sortase substrate is not detectable in the composition as measured by standard immunoblot using an antibody or other affinity agent that specifically binds to the polypeptide and/or agent. Various suitable methods for separating sortagged cells from sortase and/or from unconjugated sortase substrate are described herein, but other suitable methods may be used.

In some aspects, the invention provides living mammalian cells having an agent conjugated thereto via a sortase-mediated transacylation reaction ("sortagged cells"). In some embodiments the agent is conjugated to a polypeptide comprising a domain exposed at the cell surface. In some embodiments compositions comprising a plurality of such cells are provided. In some embodiments the polypeptide to which the agent is conjugated comprises, after such conjugation, a sortase recognition motif. In some embodiments a composition comprising a plurality of such sortagged cells has a reduced level of sortase, unconjugated sortase substrate, or both, as compared with a composition in which the cells were sortagged. In some embodiments the composition has a selected degree of purity with respect to sortase, unconjugated sortase substrate, or both. In some embodiments at least a selected percentage of the cells in a composition are modified, i.e., have an agent conjugated thereto by sortase. For example, in some embodiments at least 5%, 10%, 15%, 20%, 25%, 30%, 40%, 50%, 60%, 70%, 80%, 90%, 95%, 96%, 97%, 98%, 99%, or more of the cells have an agent conjugated thereto. In some embodiments a method may comprise separating cells that have an agent conjugated thereto from cells that do not.

In certain embodiments an endogenous mammalian polypeptide comprises one or more N-terminal glycines. A polypeptide comprising one or more N-terminal glycines may be represented as $G(G)n-B^1$, wherein G is glycine, $B^1$ represents an amino acid sequence, and n is a non-negative integer, e.g., between 0 and 10, or may equivalently be represented as follows:

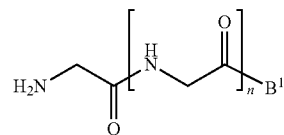

wherein $B^1$ represents an amino acid sequence, and n is a non-negative integer, e.g., between 0 and 10. In certain embodiments n is 0, 1, 2, 3, 4, or 5. In general, $B^1$ may be of any length and sequence, provided that, in certain embodiments, the polypeptide comprising $B^1$ has a sequence that is endogenous to a mammalian cell, so that a mammalian cell may express the polypeptide without having been genetically engineered to do so.

In some embodiments the invention provides a method comprising contacting a living mammalian cell that comprises a polypeptide of the following structure exposed at the cell surface:

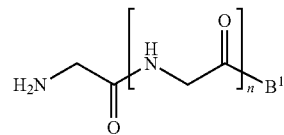

with a sortase substrate of the following structure:

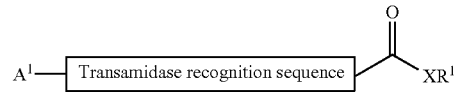

wherein the transamidase recognition sequence is an amino acid sequence motif recognized by a transamidase enzyme;

X is —O—, —NR—, or —S—; wherein R is hydrogen, substituted or unsubstituted aliphatic, or substituted or unsubstituted heteroaliphatic;

$A^1$ is acyl, substituted or unsubstituted aliphatic, substituted or unsubstituted heteroaliphatic, substituted or unsubstituted aryl, substituted or unsubstituted heteroaryl, an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle;

$R^1$ is acyl, substituted or unsubstituted aliphatic, substituted or unsubstituted heteroaliphatic, substituted or unsubstituted aryl, or substituted or unsubstituted heteroaryl; in the presence of a transamidase enzyme, for example, a sortase, under suitable conditions to form a compound of formula:

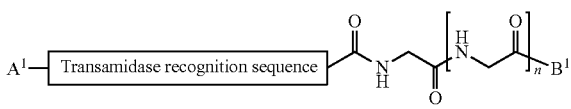

wherein n is between 0 and 10, and wherein $B^1$ represents an extracellular domain of a polypeptide expressed by a living mammalian cell.

The resulting sortase-modified cell may be represented as follows:

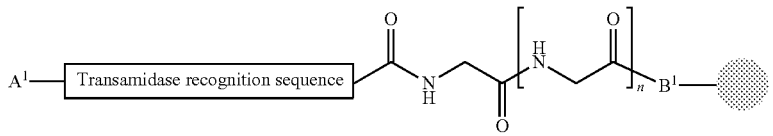

wherein the circle represents a cell and the short line between $B^1$ and the cell indicates that $B^1$ is attached to the cell (e.g., $B^1$ may be part of an integral membrane polypeptide or peripheral membrane polypeptide). The sortase substrate and agent $A^1$ may be said to be conjugated to the cell. It will be appreciated that the $XR^1$ moiety of the sortase substrate is released as a reaction byproduct.

In some embodiments X is —NR— and $XR^1$ represents glycine (G), alanine (A), or another amino acid that may be found at the C-terminus of a naturally occurring sortase recognition sequence. In some embodiments X is —NR— and $XR^1$ represents $(G)_j(Xaa)_m$, wherein each Xaa can be independently any amino acid, j is at least 1, and j+m is between 1 and 5, between 1 and 10, between 1 and 20, or between 1, 5, 10, or 20 and 100. In some embodiments j is 1. In some embodiments j is 2, 3, 4, or 5. In some embodiments j is 1. In some embodiments j is 2, 3, 4, or 5. In some embodiments $XR^1$ comprises a detectable label or epitope tag (e.g., $(Xaa)_m$ may comprise an epitope tag or may have a tag or label attached to a side chain), so that the reaction byproduct may be detected and/or isolated or separated from the cells.

In certain embodiments X is —O—, —NR—, or —S—; wherein R is hydrogen, substituted or unsubstituted aliphatic, or substituted or unsubstituted heteroaliphatic. In certain embodiments $R^1$ is acyl. In certain embodiments $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl. In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl. In certain embodiments $R^1$ comprises a label (e.g., a fluorophore) or affinity tag. In certain embodiments a label or affinity tag may be used, e.g., to detect and/or remove sortase substrate that does not participate in a sortase-mediated reaction, to detect and/or remove reaction byproduct comprising $XR^1$, to measure or monitor the progress of a sortase-mediated reaction or determine the extent to which sortase substrate has been consumed.

In certain embodiments, the C-terminal amino acid of a 5 amino acid transamidase recognition sequence, e.g., a transamidase recognition sequence that would ordinarily comprise a C-terminal glycine or alanine as a fifth amino acid, may be omitted. For example, an acyl group

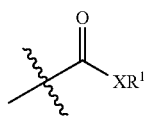

that is not a glycine, alanine, or other residue that may be found at the C-terminus of a naturally occurring transamidase recognition sequence may replace the C-terminal amino acid of a 5 amino acid transamidase recognition sequence. In some embodiments, $XR^1$ is selected to be a moiety that exhibits poor nucleophilicity once released from the transamidase, thereby providing for a more efficient ligation, e.g., as compared with the efficiency if $XR^1$ is a C-terminal amino acid of a naturally occurring transamidase recognition sequence, e.g., glycine. Any moiety exhibiting such poor nucleophilicity can be used in accordance with certain embodiments. In some embodiments, the acyl group

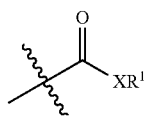

is not an amino acid or peptide. In some embodiments, the acyl group is

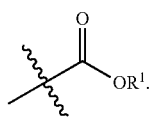

In some embodiments, the acyl group is

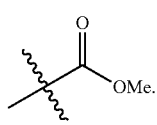

Some embodiments of the invention provide modified, non-genetically engineered mammalian proteins comprising a sortase recognition motif. Some embodiments provide modified, non-genetically engineered mammalian proteins comprising a sortase recognition motif having an agent conjugated thereto. Some embodiments provide mammalian cells comprising a modified, non-genetically engineered protein comprising a sortase recognition motif. Some embodiments provide mammalian cells comprising a modified, non-genetically engineered protein comprising a sortase recognition motif having an agent conjugated thereto.

Some embodiments provide a non-genetically engineered mammalian protein comprising an N-terminal modification installed by sortase, wherein the non-genetically engineered mammalian protein comprises a structure according to Formula (I):

[Xaa]$_y$-TRS-PRT  (I)

Some embodiments provide a non-genetically engineered mammalian protein comprising an N-terminal modification installed by sortase, wherein the non-genetically engineered mammalian protein comprises a structure according to Formula (II):

M-[Xaa]$_y$-TRS-PRT  (II)

In Formulas (I) and (II):

PRT is an amino acid sequence of at least three amino acids, wherein the sequence is endogenous to a mammalian cell, e.g., a polypeptide comprising $B^1$ as described above;

each instance of Xaa is independently any amino acid residue;

y is 0 or an integer between 1-2000

TRS is a transamidase recognition motif; and

M in Formula II is an agent attached to [Xaa]$_y$, or, if y is 0, M is a moiety directly attached to the TRS. In some embodiments M comprises an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a click chemistry handle, or a particle.

In some aspects, a mammalian cell comprises a modified protein according to Formula (I) or Formula (II). In some embodiments at least the portion of the protein comprising [Xaa]$_y$-TRS or comprising M-[Xaa]$_y$-TRS is exposed at the cell surface. In some embodiments the cell is not genetically engineered.

In some embodiments a polypeptide modified by sortase (e.g., a polypeptide comprising $B^1$ as described above) is an integral membrane protein (IMP) or a subunit of an IMP. An IMP is a protein that is naturally stably attached to the plasma membrane of a cell. A polypeptide may be attached to the cell in any of various ways by which mammalian polypeptides are naturally attached to cell plasma membranes. An IMP may comprise a transmembrane (TM) domain and, in some embodiments an intracellular domain. A polypeptide may have its C-terminal amino acid located within the plasma membrane or in the cytosol. A TM polypeptide may be a single pass TM polypeptide or multi-pass. In some embodiments a polypeptide is associated with the membrane from one side but does not span the lipid bilayer completely, may bind covalently to a membrane lipid, may have a glycophosphatidylinositol (GPI) anchor, and/or may be associated with membrane lipids via electrostatic or ionic interactions. In some embodiments a polypeptide modified by sortase is a peripheral membrane protein.

Sortase substrates may comprise any of a wide variety of agents, e.g., an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle, or a click chemistry handle. In certain embodiments an agent may comprise two or more such moieties. For example, a linker may have any of a wide variety of moieties attached thereto.

In some embodiments a sortase substrate to be used to conjugate an agent $A^1$ to a mammalian cell using sortase may be represented as follows:

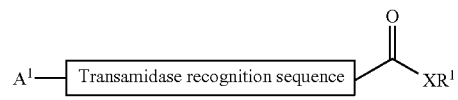

wherein X and $R^1$ are as described above.

In some embodiments $A^1$ comprises a protein. In some embodiments, $A^1$ comprises a peptide. In some embodiments, $A^1$ comprises an amino acid sequence comprising at least 3 amino acids. In some embodiments, $A^1$ comprises an antibody, an antibody chain, an antibody fragment, an antigen-binding antibody domain, a VHH domain, a single-domain antibody, a camelid antibody, a nanobody, an adnectin, an affibody, an anticalin, or an aptamer. In some embodiments, $A^1$ comprises a recombinant protein, a protein or peptide comprising one or more non-standard amino acids (e.g., D-amino acids), a branched protein or peptide, a therapeutic protein or peptide, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, or a glycosylated peptide or protein. In some embodiments, $A^1$ comprises an antigen or an epitope. In some embodiments $A^1$ comprises an enzyme, growth factor, cytokine, costimulator, or adjuvant. In some embodiments $A^1$ comprises a small molecule, a click chemistry handle, a fatty acid, a polynucleotide, a carbohydrate, a tag, a metal atom, a contrast agent, a peptide, a polypeptide, a non-polypeptide polymer, a recognition element, a lipid, a label, or a particle. In some embodiments $A^1$ comprises a binding moiety. In some embodiments $A^1$ comprises a targeting moiety. In some embodiments a moiety may be incorporated into $A^1$ in any manner and at any position that can be envisioned by those of ordinary skill in the art. For example, $A^1$ may comprise an amino acid, and a moiety may be attached, e.g., to the central carbon of the amino acid, the side chain of the amino acid, the carboxyl group of the amino acid, or the nitrogen. In some embodiments an agent comprises an amino acid having a side chain comprising a primary or secondary amine. Examples of suitable amino acids include, e.g., lysine, ε-aminocaproic acid, and various others known in the art. A sortase recognition motif may be extended to include such an amino acid, e.g., as K-LPXTG. Such amino acids may conveniently be used as a point of attachment of a moiety of interest through reaction with the amine group. In some embodiments $A^1$ comprises a biologically active moiety, i.e., a moiety that is capable of causing a biological effect when contacted with a cell or administered to a subject. In some embodiments $A^1$ comprises or is attached to the TRS via a linker. In some embodiments a linker comprises a cleavage site, thereby allowing release of at least a portion of $A^1$ when the cleavage site is cleaved, e.g., by a protease in vivo after administration of a sortagged cell to a subject. In some embodiment cleavage releases an agent that comprises both a therapeutically active or detectable moiety and a targeting moiety. The targeting moiety may target the released agent to a target cell or site in the body of a subject. Cleavage may occur over a selected time frame so that agent is released over a period of time, e.g., to maintain a therapeutically useful level of agent over a period of time. In some embodiments the period of time is between 12 and 24 hours, 24 and 48 hours, 2-6 days, or up to about 1, 2, 4, 6, 10, or 12 weeks, or more.

In some aspects, the invention provides methods of using living mammalian cells that have an agent conjugated thereto via a sortase-catalyzed transacylation reaction (sortagged living mammalian cells). Sortagged mammalian cells may be used in vitro, in vivo, in research, for detection, for diagnosis, or for therapy. Certain uses of interest are described further below but it should be understood that the invention is not limited in this respect. Exemplary therapeutic applications include treatment of infectious diseases, cancer, autoimmune diseases, inflammatory conditions, enzyme deficiencies, or immunodeficiencies. In some embodiments sortagged living mammalian cells are used in cell therapy, e.g., in regenerative medicine, adoptive immunotherapy, or as vaccine components. In some embodiments sortagged mammalian cells may be used as delivery vehicles e.g., for delivering detection agents or therapeutic agents to a subject. In some embodiments an agent conjugated to mammalian cells comprises a moiety that is useful in diagnosis, monitoring, or treatment of a disease. In some embodiments sortagged mammalian cells are administered to a subject, e.g., a subject in need of diagnosis, monitoring, or treatment of a disease. In some embodiments the cells originate from a subject to whom they are subsequently administered or originate from a donor who is histocompatible with the subject.

In some aspects, the invention provides a method of increasing the circulation time or plasma half-life of an agent in the body of a mammal, the method comprising: providing an agent; and conjugating the agent to a mammalian cell using sortase. In some embodiments the method further comprises administering the mammalian cell to the animal, e.g., directly into the circulatory system, e.g., intravenously. In some embodiments cells may be administered locally, e.g., into a tissue or organ at which an effect, e.g., a therapeutic effect, is desired. In some embodiments conjugating an agent to a cell, e.g., a hematologic cell, e.g., a red blood cell, lymphocyte, or red blood cell or lymphocyte precursor, may reduce clearance of the agent, e.g., by the kidneys and/or may reduce diffusion or transport of the agent out of the circulatory system as compared with the rate at which the unconjugated agent would be cleared by the kidneys or otherwise removed from the circulatory system. In some embodiments the mammalian cell or an ancestor thereof is obtained from a mammal to whom the sortase-modified cell is administered. In some embodiments the average circulation time or plasma half-life may be increased by at least a factor of 2, 3, 5, 10, 20, 50, or more. In some embodiments the average circulation time or plasma half-life may be at least 5, 10, 15, 20, 25, 50 days, or more, e.g., up to the average lifespan of the cell to which the agent is attached.

In some embodiments a therapeutic function may be provided by a therapeutic agent, e.g., an enzyme or therapeutic antibody or small molecule, conjugated to a mammalian cell. In some embodiments a therapeutic function may be provided by a moiety targeting a specific cell or cell type to a target site, attracting a specific cell or cell type to a target site, activating a specific cell or cell type, e.g., at a target site, stimulating or inhibiting one or more biological activities of a specific cell or cell type, e.g., at a target site, providing a catalytic activity, e.g., at a target site, or by a therapeutic agent acting on cells, e.g., at a target site. In some embodiments a protein or other agent conjugated to mammalian cells comprises a binding domain, e.g., an antigen binding domain, or antibody targeting a specific cell, cell type, tissue, or site, for example, in a subject. In some embodiments the binding domain or antibody is conjugated to a therapeutic agent, for example, a small molecule, or a therapeutic polypeptide. In some embodiments the binding domain or antibody is conjugated to a label. In some embodiments it is contemplated to attach any therapeutic agent to mammalian cells using sortase, e.g., any therapeutic agent known in the art.

In some embodiments a mammalian cell has an agent comprising a label conjugated thereto, e.g., a fluorophore, fluorescent polypeptide, quantum dot, metal-containing nanoparticle, or any other suitable label. The mammalian cell may be detected by detecting the label. In some embodiments the cell may be detected in vitro, e.g., in a cell culture system. In some embodiments the cell may be administered to a subject and detected in vivo. In some embodiments the cell may be administered to a subject and detected in a sample subsequently obtained from the subject. In some embodiments the cell has a targeting moiety conjugated thereto. The targeting moiety and label may be conjugated separately to the cell or may be part of a single agent conjugated to the cell. The cells may accumulate at a target site and may be detected in vivo by detecting the label. In some embodiments the cell may further have a therapeutic agent conjugated thereto or may provide a therapeutic function, e.g., a cytotoxic effect against tumor cells or infected cells.

In some embodiments a mammalian cell is sortagged with a bifunctional agent, e.g., a bifunctional protein. In some embodiments a bifunctional agent comprises a first domain that provides a first function and a second domain that provides a second function. The two domains and/or functions may be the same or different. In some embodiments at least one domain comprises a binding domain that targets the bifunctional agent to a target. A target may be, e.g., an organ, a cell or cell type (e.g., a diseased cell, such as a tumor cell or infected cell), a tissue, or a site of disease). In some embodiments at least one domain provides a therapeutic function or labeling function. Any of a wide variety of bifunctional agents may be used. In some embodiments a bifunctional agent comprises a bivalent agent, e.g., a bivalent antibody. A bivalent agent is capable of binding to two molecules or entities, which may be the same or different, depending on the agent.

In some embodiments a bifunctional agent is a bispecific agent, e.g., a bispecific protein, e.g., a bispecific antibody. In some embodiments, a bispecific agent targets a specific antigen, cell, cell type, or site in a cell population, tissue, organism, or subject. For example, in some embodiments, a bispecific protein comprises a first binding domain, e.g., an antigen binding domain, that targets the protein to a target site (e.g., an organ, a cell or cell type (e.g., a diseased cell, such as a tumor cell), a tissue, or a site of disease) and a second binding domain, e.g., a second antigen binding domain, that provides a function, e.g., a therapeutic function. In some embodiments, a protein or binding domain or binding agent binds to a target antigen, e.g., a tumor antigen or an antigen of a pathogen. In some embodiments a binding domain is conjugated to a therapeutic agent, for example, a small molecule, or a therapeutic polypeptide. In some embodiments such conjugation is performed using click chemistry. For example, sortase may be used to produce a bifunctional, bivalent, or bispecific agent by installing click chemistry handles on each of two polypeptides (e.g., scFvs and/or sdAbs) or other molecules, which are then conjugated to each other via a click chemistry reaction (e.g., as discussed further below). A sortase recognition motif may be included at or near a free C-terminus and/or a (G)n or (A)n sequence may be included at or near a free N-terminus to facilitate additional sortase-catalyzed conjugation of the agent.

In certain embodiments an agent is a trifunctional agent. A trifunctional agent may be a trivalent agent, e.g., a trispecific agent. Trivalent agents or agents of even higher valency may be produced as single polypeptides comprising three or more scFv, sdAb, or a combination thereof. By including scFv and/or or sdAb with different specificities in a single polypeptide chain, multispecific (e.g., bispecific, trispecific) agents are produced. Such agents may have multiple distinct functions conferred by binding to different molecules or entities. Sortase may be used to produce trifunctional agents as described for bifunctional agents. Other methods of producing abifunctional or trifunctional agent may also be used. For example, chemical conjugation may be performed using any of a variety of different approaches (see, e.g., Hermanson, G, cited above).

In some embodiments a particle is conjugated to mammalian cells using sortase. In some embodiments the particle comprises a detectable label or therapeutic agent. In some embodiments the particle is a polymeric particle. A detectable label or therapeutic agent may be encapsulated in, impregnated into, or coated on at least a portion of the surface of the particle or otherwise physically associated with the particle. In some embodiments the label or agent is released from particles over a period of time, e.g., to maintain a therapeutically useful level of agent over a period of time. In some embodiments the period of time is between 12 and 24 hours, 24 and 48 hours, 2-6 days, or up to about 1, 2, 4, 6, 10, or 12 weeks, or more.

In some embodiments the particle is an ultrasound microbubble or comprises a contrast agent. In some embodiments the particle has a diameter or average longest axis or length of at least 5 nm, up to about 100 nm, 500 nm, 1 µm, 2 µm, or 3 µm. In some embodiments sortagging may be used to attach a mammalian cell to a support. The support may have an agent comprising a TRS attached thereto, e.g., attached directly to the support or to a coating on all or part of the support. The support is contacted with mammalian cells and sortase under conditions such that the agent is conjugated to the cells, thereby attaching the cells to the support.

Those of ordinary skill in the art will understand that sortase substrates, sortagged mammalian polypeptides, and sortagged cells may comprise any agent, e.g., any binding agent, therapeutic agent, or detection agent, that either comprises or can be linked to a polypeptide comprising a sortase recognition sequence. In some aspects, the invention encompasses mammalian cells produced according to methods described herein, and compositions comprising such cells, wherein the cells may be of any cell type and may have any agent conjugated thereto using sortase. In some aspects, the invention encompasses methods of using such cells, e.g., for one or more purposes described herein.

In some embodiments a mammalian cell is sortagged with an agent that is capable of binding to one or more entities. Such a moiety may be referred to as a "binding moiety". In some embodiments an agent comprising a binding moiety is attached to a mammalian cell as described herein, and the mammalian cell is placed in an environment comprising one or more entities. The binding moiety causes the mammalian cell to become attached (bound) to at least one of the entities via interaction between the binding moiety and the entity. The entity may contain a specific domain, moiety, or binding site that physically interacts with the binding moiety. In general a binding moiety may be any moiety capable of specifically recognizing an entity of interest. It will be understood that a binding moiety may recognize only a portion of an entity, e.g., an epitope of a protein. In general, a binding moiety that binds to a particular entity may be any moiety capable of forming appropriate interactions with the entity. In some embodiments a binding moiety may be a protein, a peptide, an antibody, an antibody fragment, an engineered binding protein (e.g., an affibody, anticalin, or adnectin), a nucleic acid aptamer, a naturally occurring or artificial ligand, etc. In some embodiments a ligand is a small molecule. For example, a binding moiety may be a small molecule that binds to a receptor. In some embodiments a binding moiety may be a receptor, which may bind to an entity comprising a ligand of the receptor. In certain embodiments two, three, or more binding moieties with the same or different specificities may be combined (e.g., by chemical linkage, production as a fusion protein, or by sortase-catalyzed reactions) to form a multivalent agent, e.g., a bivalent or trivalent agent. In some embodiments an agent comprises a multimer or concatamer comprising 3-10, 10-25, 25-50, 50-100, 100-1000 binding moieties, or more. In some embodiments, a multivalent agent may have higher affinity or avidity for a target than does an agent comprising a single binding moiety.

In some embodiments a binding moiety is capable of targeting an agent to a target of interest. Such a binding moiety may be referred to as a "targeting moiety". In some embodiments an agent comprising a targeting moiety is attached to a mammalian cell and targets the mammalian cell to a target of interest. In general, any binding moiety may be used as a targeting moiety, provided that the binding moiety recognizes and binds to a target of interest. A target of interest may be any of a variety of different entities. In some embodiments a target of interest is associated with or comprises a cell, structure, or molecule. In some embodiments a target of interest is a normal cell. In some embodiments a target of interest is an abnormal cell, e.g., a diseased cell such as a cancer cell or infected cell. In some embodiments a targeting moiety binds to a polypeptide, lipid, or sugar exposed at the surface of a target cell, e.g., an extracellular domain of a polypeptide expressed by the target cell. In some embodiments a target of interest is or comprises a specific antigen, cell type, or site in tissue, organ, or subject. In some embodiments a targeting moiety binds to a marker on a cell of interest. In some embodiments a target or marker specific for a diseased cell or site of disease.

In some embodiments a population of mammalian cells is contacted with two or more different sortase substrates each comprising a sortase recognition motif and a different agent, to produce a composition comprising cells that are sortagged with at least two different agents. In some embodiments a population of mammalian cells is divided into multiple aliquots. The number of aliquots and number of cells per aliquot may be selected in any convenient manner. In some embodiments an aliquot comprises at least $10^3$, $10^4$, $10^5$, $10^6$, $10^7$, or $10^8$ cells. In some embodiments the number of aliquots is between 2 and 1,000. One or more aliquots may be stored for future use. In some embodiments two or more different sortase substrates each comprising a sortase recognition motif and a different agent conjugated to the sortase recognition motif, are conjugated to cells of two or more different aliquots, to produce two or more populations of mammalian cells having different agents conjugated thereto. The different aliquots, or portions thereof, may be subsequently combined. Different agents may be of the same or different compound classes (e.g., polypeptides, polynucleotides, small molecules). Different agents may or may not be related in sequence or structure or capable of binding to the same target.

In some embodiments two, three, or more sequential sortagging reactions are performed. In some embodiments, cells are contacted with a sortase and a first substrate comprising a sortase recognition sequence and a first agent, and the sortagging reaction is allowed to proceed for a time and under conditions appropriate to sortag the cells with the first agent. Cells are then separated from the first substrate, e.g., by removing the cells or the first substrate from the vessel. The sortagged cells are then contacted with a second substrate comprising a sortase recognition sequence and a second agent, and the sortagging reaction is allowed to proceed for a time and under conditions appropriate to sortag the cells with the second agent, resulting in cells that are sortagged with the first agent and with a second agent. In some embodiments, cells are contacted with a sortase and a first substrate comprising a sortase recognition sequence and a first agent, and the sortagging reaction is allowed to proceed for a time and under conditions appropriate to sortag the cells with the first agent. A second sortase substrate is then added to the reaction mixture without separating the first sortase substrate, and the reaction is allowed to proceed. Factors such as the time and conditions of each sortagging reaction, the order in which different substrates are added or used, etc., may be adjusted to achieve a desired proportion of first and second agents attached to the cells. In some embodiments in which two or more substrates have different molecular weights, a substrate having a higher molecular weight may be used before a substrate having a lower molecular weight. The process may be repeated one or more times. If desired, a time course may be conducted to monitor the extent of sortagging over time. For example, conditions that result in a reaction that goes a selected portion of the way to completion (maximum conjugation) may be determined (e.g., 25%, 50%, 75%, 90%, or more). Information obtained from the time course may be used to optimize the reactions to achieve desired ratio of different agents on the cell surface. Of course each sortagging reaction may be conducted using a mixture of sortase substrates together, thus potentially resulting in any number of different agents, e.g., 3, 4, 5, 6, or more, conjugated to the cells.

In some embodiments, the total number of molecules of agent(s) conjugated to a mammalian cell using sortase according to the present invention is between 10 and 100; between 100 and 1,000; between 1,000 and 10,000; between 10,000 and 50,000; between 50,000 and 100,000; between 100,000 and 500,000; between 500,000 and 1,000,000; between 1,000,000 and 2,500,000; between 2,500,000 and 5,000,000; between 5,000,000 and 10,000,000, or more. In some embodiments, the average number of agent molecules per cell conjugated to mammalian cells in a preparation of mammalian cells sortagged according to the present invention is between 10 and 100; between 100 and 1,000; between 1,000 and 10,000; between 10,000 and 50,000; between 50,000 and 100,000; between 100,000 and 500,000; between 500,000 and 1,000,000; between 1,000,000 and 2,500,000; between 2,500,000 and 5,000,000; between 5,000,000 and 10,000,000, or more. The number, or average number, of molecules per cell may be controlled, if desired, by appropriate selection of the reaction conditions, e.g., by controlling one or more factors such as the sortase used, the temperature, and/or the duration of the reaction. The number, or average number, of molecules per cell may also vary depending on the available surface area or cell type. In some embodiments the molecules of agent(s) conjugated to a non-mammalian cell using sortase according to the present invention is as mentioned for mammalian cells. In certain embodiments a cell preparation is characterized in that least 10%, 20%, 30%, 40%, 50%, 60%, 70%, 80%, 90%, or more of the cells in the cell preparation have a number of agent molecules within any of the afore-mentioned ranges conjugated to them.

Without wishing to be bound by any theory, sortase-mediated modification of mammalian cells that are not genetically engineered may have one or more advantages for a variety of purposes, e.g., for certain purposes in which the cells are administered to subjects. Use of non-genetically engineered cells may, for example, permit modification of cells that are refractory to genetic engineering, avoid the potentially time-consuming step of genetic engineering, and/or avoid safety concerns that may arise when genomic sequence is modified using, e.g., viral vectors such as retroviruses to insert a nucleic acid into the genome. Such concerns may include potential insertional mutagenesis, which may lead to activation of oncogenes or inactivation of tumor suppressor genes.

While use of non-genetically engineered cells may have certain advantages, unless otherwise indicated or clearly evident from the context, any of the methods of generating or using sortase-modified animal cells described herein may, in certain embodiments, use animal cells that have been genetically engineered to express a polypeptide that comprises a sortase recognition motif or nucleophilic acceptor sequence, so that the polypeptide is suitable for use as a sortase substrate or nucleophile in a sortase-mediated reaction. Similarly, unless otherwise indicated or clearly evident from the context, any of the compositions comprising sortase-modified animal cells or useful for generating or using such cells may, in certain embodiments, use cells that have been genetically engineered to express a polypeptide that comprises a sortase recognition motif or nucleophilic acceptor sequence so that the polypeptide is suitable for use as a sortase substrate or nucleophile in a sortase-mediated reaction.

In some embodiments, genetically engineered cells are modified by using sortase to attach a sortase substrate to a non-genetically engineered endogenous polypeptide of the cell. The cell may, for example, have been genetically engineered to express any of a wide variety of products, e.g., polypeptides or noncoding RNAs, may be genetically engineered to have a deletion of at least a portion of one or more genes, and/or may be genetically engineered to have one or more precise alterations in the sequence of one or more endogenous genes. In certain embodiments a non-engineered endogenous polypeptide of such genetically engineered cell is sortagged with any of the various agents described herein.

Although the invention is described herein mainly in regard to mammalian cells, the invention provides embodiments in which any eukaryotic cell, e.g., any animal cells, e.g., any vertebrate cells, e.g., avian cells, fish cells, amphibian cells, or reptilian cells, or invertebrate animal cells, e.g., insect cells, or fungal cells (e.g., yeast), or protozoal cells may be used, in any aspect described herein. Accordingly, where the disclosure refers to mammalian cells, it should be understood that analogous aspects and embodiments pertaining to other eukaryotic cell types, e.g., fungal, insect, protozoal, are provided unless otherwise indicated or evident from the context. In some embodiments polypeptides endogenous to such cells may be sortagged.

In certain embodiments, sortagging eukaryotic cells, e.g., animal cells, as described herein does not comprise and/or is not performed in connection with sortagging cells that have been genetically engineered for sortagging. For example, the method is not performed as a negative control in connection with sortagging cells that have been genetically engineered to comprise a protein comprising a sortase recognition sequence or nucleophilic acceptor sequence. In certain embodiments the method is performed in order that the sortagged animal cells that have not been engineered for sortagging may be used for one or more purposes of interest. In certain embodiments the sortagging occurs at a level above what would reasonably be expected as background level of nonspecific binding of a sortase substrate to an animal cell. In some embodiments the number of sortagged cells produced is sufficient to administer a therapeutically effective amount of an agent to a mammalian subject, e.g., a human.

II. Suitable Transamidase Enzymes and Transamidase Recognition Motifs

Enzymes identified as "sortases" have been isolated from a variety of Gram-positive bacteria. In nature, these enzymes catalyze a cell wall sorting reaction in which a surface protein with a sorting signal containing a sortase recognition motif is cleaved and the carboxyl end of the protein is covalently attached to a pentaglycine cross-bridge of peptidoglycan. Gram-positive bacteria include the following genera: *Actinomyces*, *Bacillus*, *Bifidobacterium*, *Cellulomonas*, *Clostridium*, *Corynebacterium*, *Micrococcus*, *Mycobacterium*, *Nocardia*, *Staphylococcus*, *Streptococcus*, and *Streptomyces*. In certain embodiments the transpeptidation reaction catalyzed by sortase results in the ligation of species containing a sortase recognition motif with species bearing one or more N-terminal glycine residues or an N-terminal alkylamine group. Sortases, sortase-mediated transacylation reactions, and their use in protein engineering are well known to those of ordinary skill in the art (see, e.g., Ploegh et al., International Patent Applications PCT/US2010/000274 (WO/2010/087994), and PCT/US2011/033303 (WO/2011/133704). Additional description of use of sortase, sortase preparation methods, sortases, sortase substrates, sortase recognition sequences, etc., may be found in Popp M W, Ploegh H L., Angew Chem Int Ed Engl, 2011; 50:5024-5032; Strijbis, K., et al., Traffic 2012; 13: 780-789; Witte M D, et al., Proc Natl Acad Sci USA. 2012; 109(30):11993-8; Hess G T, et al., Bioconjug Chem. 2012 Jul. 18; 23(7):1478-87, Witte M D et al. (2012) PNAS 109:11993-11998; Guimaraes C P et al. (2013) Site-specific C-terminal and internal loop labeling of proteins using sortase-mediated reactions. Nat Protoc 8:1787-1799, and references in any of these.

Sortases have been classified into 4 classes, designated A, B, C, and D, based on sequence alignment and phylogenetic analysis of 61 sortases from Gram positive bacterial genomes (Dramsi S, Trieu-Cuot P, Bierne H, Sorting sortases: a nomenclature proposal for the various sortases of Gram-positive bacteria. Res Microbiol. 156(3):289-97, 2005. These classes correspond to the following subfamilies, into which sortases have also been classified by Comfort and Clubb (Comfort D, Clubb R T. A comparative genome analysis identifies distinct sorting pathways in gram-positive bacteria. Infect Immun., 72(5):2710-22, 2004): Class A (Subfamily 1), Class B (Subfamily 2), Class C (Subfamily 3), Class D (Subfamilies 4 and 5). The aforementioned references disclose numerous sortases and recognition motifs. See also Pallen, M. J.; Lam, A. C.; Antonio, M.; Dunbar, K. TRENDS in Microbiology, 2001, 9(3), 97-101. Those skilled in the art will readily be able to assign a sortase to the correct class based on its sequence and/or other characteristics such as those described in Drami, et al., supra. The term "sortase A" is used herein to refer to a class A sortase, usually named SrtA in any particular bacterial species, e.g., SrtA from *S. aureus* or *S. pyogenes* Likewise "sortase B" is used herein to refer to a class B sortase, usually named SrtB in any particular bacterial species, e.g., SrtB from *S. aureus*. The present disclosure encompasses embodiments relating to any of the sortase classes known in the art (e.g., a sortase A from any bacterial species or strain, a sortase B from any bacterial species or strain, a class C sortase from any bacterial species or strain, and a class D sortase from any bacterial species or strain). In certain embodiments a sortase that utilizes a nucleophilic acceptor sequence having an N-terminal glycine, e.g., 1-5 N-terminal glycines, is used, such as SrtA from *S. aureus*. In some embodiments it is contemplated to use two or more sortases. In some embodiments the sortases may utilize different sortase recognition sequences and/or different nucleophilic acceptor sequences. For example, SrtA from *S. pyogenes* can utilize a nucleophilic acceptor sequence having one or more N-terminal alanines, e.g., 1-5 N-terminal alanines and/or may utilize a sortase recognition motif comprising LPXTA.

Amino acid sequences of Srt A and Srt B and the nucleotide sequences that encode them are known to those of skill in the art and are disclosed in a number of references cited herein, the entire contents of all of which are incorporated herein by reference. The amino acid sequences of *S. aureus* SrtA and SrtB are homologous, sharing, for example, 22% sequence identity and 37% sequence similarity. The amino acid sequence of a sortase-transamidase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the *S. pyogenes* open reading frame. There is about a 28% sequence identity with best alignment over the entire sequenced region of the *A. naeslundii* open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, or 30% or more sequence identity with the *S. aureus*, *S. pyogenes*, *A. naeslundii*, *S. mutans*, *E. faecalis* or *B. subtilis* open reading frame encoding a sortase can be screened, and enzymes having transamidase activity comparable to Srt A or Srt B from *S. aureus* can be utilized (e. g., comparable activity sometimes is 10% of Srt A or Srt B activity or more).

Thus in some embodiments of the invention the sortase is a sortase A (SrtA). SrtA recognizes the motif LPXTG, with common recognition motifs being, e.g., LPKTG, LPATG, LPNTG. In some embodiments LPETG is used. However, motifs falling outside this consensus may also be recognized. For example, in some embodiments the motif comprises an 'A' rather than a 'T' at position 4, e.g., LPXAG, e.g., LPNAG. In some embodiments the motif comprises an 'A' rather than a 'G' at position 5, e.g., LPXTA, e.g., LPNTA. In some embodiments the motif comprises a 'G' rather than 'P' at position 2, e.g., LGXTG, e.g., LGATG. In some embodiments the motif comprises an T rather than 'L' at position 1, e.g., IPXTG, e.g., IPNTG or IPETG.

In some embodiments, a variant of a naturally occurring sortase may be used. Such variants may be produced through processes such as directed evolution, site-specific modification, etc. Considerable structural information regarding sortase enzymes, e.g., sortase A enzymes, is available, including NMR or crystal structures of SrtA alone or bound to a sortase recognition sequence (see, e.g., Zong Y, et al. J. Biol Chem. 2004, 279, 31383-31389). Three dimensional structure information is also available for other sortases, e.g., *S. pyogenes* SrtA (Race, P R, et al., J Biol Chem. 2009, 284(11):6924-33). The active site and substrate binding pocket of *S. aureus* SrtA have been identified. One of ordinary skill in the art can generate functional variants by, for example, avoiding deletions or substitutions that would disrupt or substantially alter the active site or substrate binding pocket of a sortase. In some embodiments a functional variant of *S. aureus* SrtA comprises His at position 120, Cys at position 184, and Arg at position 197, wherein Cys at position 184 is located within a TLXTC motif. Functional variants of other SrtA proteins may have His, Cys, Arg, and TLXTC motifs at positions that correspond to the positions of these residues in *S. aureus* SrtA. In some embodiments, a sortase variant comprises a sequence at least 80%, 85%, 90%, 91%, 92%, 93%, 94%, 95%, 96%, 97%, 98%, or 99% identical to a wild type sortase A sequence or catalytic domain thereof, e.g., at least 80%, 85%, 90%, 91%, 92%, 93%, 94%, 95%, 96%, 97%, 98%, or 99% identical to amino acids 60-206 of SEQ ID NO: 1 or SEQ ID NO: 2, or at least 80%, 85%, 90%, 91%, 92%, 93%, 94%, 95%, 96%, 97%, 98%, or 99% identical to amino acids 26-206 of SEQ ID NO: 1 or SEQ ID NO: 2. In some embodiments, a sortase variant comprises 1, 2, 3, 4, 5, 6, 7, 8, 9, 10, 11, 12, 13, 14, or 15 amino acid substitutions relative to amino acids 60-206 of SEQ ID NO: 1 or relative to amino acids 26-206 of SEQ ID NO: 1 or SEQ ID NO: 2.

In some embodiments, a transamidase having higher transamidase activity than a naturally occurring sortase may be used. In some embodiments the activity of the transamidase is at least about 10, 15, 20, 40, 60, 80, 100, 120, 140, 160, 180, or 200 times as high as that of *S. aureus* sortase A. In some embodiments the activity is between about 10 and 50 times as high as that of *S. aureus* sortase A, e.g., between about 10 and 20 times as high, between about 20 and 30 times as high, between about 30 and 50 times as high. In some embodiments the activity is between about 50 and about 150 times as high as that of *S. aureus* sortase A, e.g., between about 50 and 75 times as high, between about 75 and 100 times as high, between about 100-125 times as high, or between about 125 and 150 times as high. For example, variants of *S. aureus* sortase A with up to a 140-fold increase in LPETG-coupling activity compared with the starting wild-type enzyme have been identified (Chen, I., et al., PNAS 108(28): 11399-11404, 2011). In some embodiments such a sortase variant is used in a composition or method of the invention. In some embodiments a sortase variant comprises any one or more of the following substitutions relative to a wild type *S. aureus* SrtA: P94S or P94R, D160N, D165A, K190E, and K196T mutations.

One of ordinary skill in the art will appreciate that the foregoing descriptions of substitutions utilize standard notation of the form $X_1NX_2$, in which $X_1$ and $X_2$, represent amino acids and N represents an amino acid position, $X_1$ represents an amino acid present in a first sequence (e.g., a wild type *S. aureus* SrtA sequence), and $X_2$ represents an amino acid that is substituted for $X_1$ at position N, resulting in a second sequence that has $X_2$ at position N instead of $X_1$. It should be understood that the present disclosure is not intended to be limited in any way by the identity of the original amino acid residue $X_1$ that is present at a particular position N in a wild type SrtA sequence used to generate a SrtA variant and is replaced by $X_2$ in the variant. Any substitution which results in the specified amino acid residue at a position specified herein is contemplated by the disclosure. Thus a substitution may be defined by the position and the identity of $X_2$, whereas $X_1$ may vary depending, e.g., on the particular bacterial species or strain from which a particular SrtA originates. Thus in some embodiments, a sortase A variant comprises any one or more of the following: an S residue at position 94 (S94) or an R residue at position 94 (R94), an N residue at position 160 (N160), an A residue at position 165 (A165), an E residue at position 190 (E190), a T residue at position 196 (T196) (numbered according to the numbering of a wild type SrtA, e.g., SEQ ID NO: 1). For example, in some embodiments a sortase A variant comprises two, three, four, or five of the aforementioned mutations relative to a wild type *S. aureus* SrtA (e.g., SEQ ID NO: 1). In some embodiments a sortase A variant comprises an S residue at position 94 (S94) or an R residue at position 94 (R94), and also an N residue at position 160 (N160), an A residue at position 165 (A165), and a T residue at position 196 (T196). For example, in some embodiments a sortase A variant comprises P94S or P94R, and also D160N, D165A, and K196T. In some embodiments a sortase A variant comprises an S residue at position 94 (S94) or an R residue at position 94 (R94) and also an N residue at position 160 (N160), A residue at position 165 (A165), a E residue at position 190, and a T residue at position 196. For example, in some embodiments a sortase A variant comprises P94S or P94R, and also D160N, D165A, K190E, and K196T. In some embodiments a sortase A variant comprises an R residue at position 94 (R94), an N residue at position 160 (N160), a A residue at position 165 (A165), E residue at position 190, and a T residue at position 196. In some embodiments a sortase comprises P94R, D160N, D165A, K190E, and K196T.

It is to be further understood that the disclosure contemplates variants of any wild-type sortase A. Those skilled in the art will appreciate that wild-type sequences of sortase A may vary, e.g., SrtA from various species may have gaps, insertions, and/or may vary in length relative to the amino acid sequence of exemplary wild-type *S. aureus* SrtA. Those skilled in the art will appreciate that the positions described herein in regard to substitutions or other alterations pertain to the sequence of exemplary wild type *S. aureus* SrtA, unless otherwise indicated, and that such positions may be adjusted when making corresponding substitutions in different bacterial SrtA sequences in order to account for such gaps, insertions, and/or length differences. For example, as noted above, certain sortase variants comprise a substitution at amino acid position 94 (e.g., the amino acid is changed to an S residue). However, the amino acid at position 94 in *S. aureus* SrtA may correspond to an amino acid at a different position (e.g., position Z) in SrtA from a second bacterial species when the sequences are aligned. When generating a variant of the SrtA of the second bacterial species comprising a substitution at "position 94" (based on the wild type *S. aureus* SrtA sequence numbering), it is the amino acid at position Z of the SrtA from the second bacterial species that should be changed (e.g., to S) rather than the amino acid at position 94. Those skilled in the art will understand how to align any original wild-type sortase A sequence to be used for generating a SrtA variant with an exemplary wild-type *S. aureus* sortase A sequence for purposes of determining the positions in the original wild-type sortase A sequence that correspond to the exemplary wild-type *S. aureus* sortase A sequence when taking into account gaps and/or insertions in the alignment of the two sequences.

In some embodiments, amino acids at position 94, 160, 165, 190, and/or 196 are altered in a variant as compared with the amino acids present at those positions in a wild type *S. aureus* SrtA, and the other amino acids of the variant are identical to those present at the corresponding positions in a wild type SrtA, e.g., a wild type *S. aureus* SrtA. In some embodiments, one or more of the other amino acids of a variant, e.g., 1, 2, 3, 4, 5, 6, 7, 8, 9, or 10 of the other amino acids differ from those present at corresponding position(s) in a wild type SrtA, e.g., a wild type *S. aureus* SrtA. In some embodiments a variant may have any of the properties or degrees of sequence identity specified in the definition of "variants" above.

An exemplary wild type *S. aureus* SrtA sequence (Gene ID: 1125243, NCBI RefSeq Acc. No. NP_375640.1) is shown below, with the afore-mentioned positions underlined:

```
                                          (SEQ ID NO: 1)
MKKWTNRLMTIAGVVLILVAAYLFAKPHIDNYLHDKDKDEKIEQYDKNVK

EQASKDNKQQAKPQIPKDKSKVAGYIEIPDADIKEPVYPGPATPEQLNRG

VSFAEENESLDDQNISIAGHTFIDRPNYQFTNLKAAKKGSMVYFKVGNET

RKYKMTSIRDVKPTDVEVLDEQKGKDKQLTLITCDDYNEKTGVWEKRKIF

VATEVK.
```

One of ordinary skill in the art will appreciate that different subspecies, strains, and isolates may differ in sequence at positions that do not significantly affect activity. For example, another exemplary wild type *S. aureus* SrtA sequence (Gene ID: 3238307, NCBI RefSeq Acc. No. YP_187332.1; GenBank Acc. No. AAD48437) has a K residue at position 57 and a G residue at position 167, as shown below in SEQ ID NO: 2:

```
                                          (SEQ ID NO: 2)
MKKWTNRLMTIAGVVLILVAAYLFAKPHIDNYLHDKDKDEKIEQYDKNVK

EQASKDKKQQAKPQIPKDKSKVAGYIEIPDADIKEPVYPGPATPEQLNRG

VSFAEENESLDDQNISIAGHTFIDRPNYQFTNLKAAKKGSMVYFKVGNET

RKYKMTSIRDVKPTDVGVLDEQKGKDKQLTLITCDDYNEKTGVWEKRKIF

VATEVK
```

Either or both of these amino acids (i.e., K57 and/or G167) may be present in or introduced into any SrtA sequence, e.g., any *S. aureus* SrtA sequence, whether naturally occurring or generated by man. Furthermore, as described herein, any sortase sequence may further comprise a tag (e.g., 6×His), a spacer, or both. For example, the N- or C-terminus may be extended to encompass a tag, optionally separated from the rest of the sequence by a spacer, In some embodiments a sortase variant comprising the following sequence may be used, in which amino acid substitutions relative to a wild type *S. aureus* SrtA of SEQ ID NO: 1 or SEQ ID NO: 2 are shown in underlined bold letters:

```
                                          (SEQ ID NO: 3)
MQAKPQIPKDKSKVAGYIEIPDADIKEPVYPGPATREQLNRGVSFAEENE

SLDDQNISIAGHTFIDRPNYQFTNLKAAKKGSMVYFKVGNETRKYKMTSI

RNVKPTAVEVLDEQKGKDKQLTLITCDDYNEETGVWETRKIFVATEVK.
```

As will be appreciated, amino acids 2-148 of the above sequence correspond to amino acids 60-206 of the full length *S. aureus* SrtA sequence (the catalytic domain). For example, the "R" residue at position 36 of SEQ ID NO: 3 corresponds to the "P" residue at position 94 in SEQ ID NO: 1 or 2. It is also contemplated in some embodiments to use sortase variants that have other substitutions at one or more of positions 94, 160, 165, 190, and 196 (numbered according to the numbering of SEQ ID NO: 1 or 2), e.g., wherein such substitutions utilize an amino acid that would be a conservative substitution at the relevant position as compared with the sequence of SEQ ID NO: 3.

In some embodiments a calcium-independent sortase, e.g., a calcium-independent sortase A, is used. In some embodiments a calcium-independent variant of *S. aureus* SrtA is used. As used herein "calcium-independent" refers to the ability of a sortase enzyme, e.g., a sortase A enzyme, to exhibit catalytic activity in a manner that is substantially independent of the absence, presence, or concentration of calcium, at least across a concentration range of about 0 mM-about 10 mM. For example, in some embodiments the activity of a calcium-independent sortase in an aqueous medium that comprises a calcium chelator such as EDTA or EGTA at a concentration sufficient to chelate substantially all calcium ions is equal to or at least approximately 80%, 85%, 90%, 95%, or more as great as its activity in the same medium in the absence of the calcium chelator. A calcium-independent sortase may exhibit calcium-independent activity at higher calcium concentrations as well, e.g., up to any concentration that is not detrimental to proper functioning of the enzyme. In some embodiments, a sortase can be assayed for ability to exhibit sortase catalytic activity in the presence of calcium concentrations that are lower than calcium concentrations which are required for calcium-dependent sortase to exhibit catalytic activity. As used herein, "calcium-dependent" in connection with a sortase means that the catalytic activity of the sortase relies or depends on the presence and concentration of calcium, such that in the absence of calcium or the absence of a sufficient amount of calcium, the calcium-dependent sortase will not exhibit sortase catalytic activity or has greatly reduced catalytic activity (e.g., less than about 5%, or less than about 10%, of the activity that it has when calcium is present in sufficient amounts (e.g., 5 mM-10 mM)). In some embodiments a calcium-dependent sortase, e.g., a wild type *S. aureus* SrtA or catalytic domain thereof, is used to sortag eukaryotic cells in a medium containing more than 0.5 mM calcium, e.g., at least 1.0 mM, at least 2.0 mM, at least 3.0 mM, at least 4.0 mM, or at least 5.0 mM calcium. For example, the concentration of calcium may be 1.0 mm-2.5 mM, 2.5 mM-5.0 mM, 5.0 mM-7.5 mM, 7.5 mM-10.0 mM, 10.0 mM-15 mM, 15 mM-20 mM. In some embodiments, a calcium-independent sortase may be used to sortag eukaryotic cells in a medium that lacks calcium or has a low calcium concentration (e.g., a calcium concentration below that at which the sortase exhibits maximum activity).

A sortase (e.g., a sortase having a naturally occurring sortase sequence or a sortase variant generated by man) can be assayed for ability to exhibit sortase catalytic activity in a calcium-independent manner by, for example, contacting a target protein comprising a C-terminal sortase recognition motif with a tagged N-terminal oligoglycine derivative in the absence of calcium in the presence of the sortase and determining whether the target protein is ligated to the tagged N-terminal oligoglycine derivative by the sortase. In some embodiments, catalytic activity may be measured by the yield of sortagged target protein after a selected time period, e.g., about 6, 12, or 18 hours of reaction. In some embodiments, catalytic activity may be measured by measuring $k_{cat}$, $K_m$, and/or $k_{cat}/K_m$. In some embodiments, one or more kinetic parameters of SrtA activity (e.g., $k_{cat}$, $k_{cat}/K_m$) may be determined as described in Ton-That et al., J Biol Chem. 2000; 275(13):9876-81. In some embodiments a calcium-independent sortase is a variant of a calcium-dependent sortase, wherein the variant comprises one or more amino acid substitutions relative to the calcium-dependent sortase. In some embodiments a calcium-independent variant has a $k_{cat}$ at least about 25%, 30%, 40%, 45%, 50%, 55%, 60%, or more as high as that of a calcium-dependent sortase of which it is a variant. In some embodiments a calcium-independent variant has a $k_{cat}/K_m$ at least about 25%, 30%, 40%, 45%, 50%, 55%, 60%, or more as high as that of a calcium-dependent sortase of which it is a variant.

In some embodiments a calcium-independent sortase is a naturally occurring sortase, e.g., SrtA from *S. pyogenes B. anthracis, E. faecalis, L. plantarum, L. lactis,* or *L. monocytogenes*. In some embodiments a calcium-independent sortase is a *S. aureus* SrtA variant. In some embodiments, the present invention contemplates use of any sortase A, e.g., any mutant of an *S. aureus* SrtA, described in co-pending US provisional patent application entitled "Calcium-Independent Sortase A Mutants", filed on even date herewith, which is hereby incorporated by reference. It should be noted that the term "mutant" is used interchangeably with "variant" and should not be considered to imply that any particular way of generating the mutant sequences is required or that any particular starting materials is required. The disclosure contemplates any suitable method of generating variants. Examples of suitable methods include, but are not limited to, introducing mutations into an appropriate wild-type coding sequence (e.g., using site-specific mutagenesis), synthesizing the sequences of the variants de novo, for example, utilizing solid phase peptide synthesis, and in vitro translation a synthetic mRNA, to name only a few. Calcium-independent sortases may be used in various embodiments of any method or composition described herein. In some embodiments, a calcium-independent *S. aureus* SrtA variant has a mutation at position 105 and position 108 as compared with a wild type *S. aureus* SrtA. For example, glutamine (E) residues at position 105 and position 108 in a wild type *S. aureus* SrtA sequence may be changed to a residue that is present at the corresponding position in a calcium-independent sortase (e.g., K or Q, respectively). In some embodiments, for example, a sortase variant comprises an E105K and an E108A substitution or an E105K and an E108Q substitution in a wild type *S. aureus* SrtA sequence or functional variant or fragment thereof.

In some embodiments, a calcium-independent sortase A variant comprises at least three amino acid substitutions relative to a wild-type sortase A, wherein the amino acid substitutions comprise a) a K residue at position 105; b) a Q or A residue at position 108; and c) at least one amino acid substitution selected from the group consisting of i) a R residue at position 94; ii) a S residue at position 94; iii) a N residue at position 160; iv) a A residue at position 165; v) a E residue at position 190; and vi) a T residue at position 196.

In some embodiments a calcium-independent sortase A variant comprises the following amino acid substitutions relative to a wild-type sortase A: a) a K residue at position 105; b) a Q or A residue at position 108; c) an S residue at position 94 or R residue at position 94; d) an N residue at position 160; e) an A residue at position 165, and a T residue at position 196. In some embodiments, a calcium-independent sortase A variant comprises the following amino acid substitutions relative to a wild-type sortase A: a) a K residue at position 105; b) a Q or A residue at position 108; c) a R or S residue at position 94; d) a N residue at position 160; e) a A residue at position 165; f) a E residue at position 190; and g) a T residue at position 196. In some embodiments a sortase comprises the following sequence, in which amino acids at positions 94, 105, 108, 160, 165, 190, and 196 relative to a full length *S. aureus* SrtA sequence are shown in bold:

(SEQ ID NO: 4)
MQAKPQIPKDKSKVAGYIEIPDADIKEPVYPGPATREQLNRGVSFAKENQ

SLDDQNISIAGHTFIDRPNYQFTNLKAAKKGSMVYFKVGNETRKYKMTSI

RNVKPTAVEVLDEQKGKDKQLTLITCDDYNEETGVWETRKIFVATEVK.

In some embodiments a transamidase that has an altered substrate selectivity as compared with a naturally occurring sortase may be used. For example, variants of *S. aureus* sortase A that accept aromatic amino acids (e.g., phenylalanine), as well as amino acids with small side chains such as Ala, Asp, Ser, Pro, and Gly, at position 1 of the sortase recognition motif (instead of L) have been identified (Piotukh K, et al., *J Am Chem Soc.,* 133(44):17536-9, 2011). In some embodiments such a sortase is used in a composition or method of the invention. A sortase with an altered substrate selectivity with regard to the sortase recognition motif may be generated by engineering one or more mutations in the sortase, e.g., in a region of the protein that is involved in recognition and/or binding of the sortase recognition motif, e.g., the putative substrate recognition loop (e.g., the loop connecting strands P6 and P7 (β6/β7 loop) in SrtA (Val161-Asp176). A crystal structure of *S. aureus* SrtA and a substrate, illustrating the loops, is described in Zong, Y., et al., J Biol Chem. 2004 Jul. 23; 279(30):31383-9.). In some embodiments, a phage-display, yeast display, or other screen of a mutant sortase library randomized in the substrate recognition loop may be performed, and variants with altered substrate specificity may be identified.

In some embodiments the sortase is a sortase B (SrtB), e.g., a sortase B of *S. aureus, B. anthracis,* or *L. monocytogenes*. Motifs recognized by sortases of the B class (SrtB) often fall within the consensus sequences NPXTX, e.g., NP[Q/K]-[T/sHN/G/s], such as NPQTN or NPKTG. For example, sortase B of *S. aureus* or *B. anthracis* cleaves the NPQTN or NPKTG motif of IsdC in the respective bacteria (see, e.g., Marraffini, L. and Schneewind, O., Journal of Bacteriology, 189(17), p. 6425-6436, 2007). Other recognition motifs found in putative substrates of class B sortases are NSKTA, NPQTG, NAKTN, and NPQSS. For example, SrtB from *L. monocytogenes* recognizes certain motifs lacking P at position 2 and/or lacking Q or K at position 3, such as NAKTN and NPQSS (Mariscotti J F, et al., The *Listeria monocytogenes* sortase-B recognizes varied amino acids at position two of the sorting motif. J Biol Chem. 2009 Jan. 7. [Epub ahead of print]).

In some embodiments, the sortase is a class C sortase. Class C sortases may utilize LPXTG as a recognition motif.

In some embodiments, the sortase is a class D sortase. Sortases in this class are predicted to recognize motifs with a consensus sequence NA-[E/A/S/H]-TG (Comfort D, supra). Class D sortases have been found, e.g., in *Streptomyces* spp., *Corynebacterium* spp., *Tropheryma whipplei*, *Thermobifida fusca*, and *Bifidobacterium longhum*. LPXTA or LAXTG may serve as a recognition sequence for class D sortases, e.g., of subfamilies 4 and 5, respectively subfamily-4 and subfamily-5 enzymes process the motifs LPXTA and LAXTG, respectively). For example, *B. anthracis* Sortase C, which is a class D sortase, has been shown to specifically cleave the LPNTA motif in *B. anthracis* BasI and BasH (Marrafini, supra).

See Barnett and Scott for description of a sortase from that recognizes QVPTGV motif (Barnett, T C and Scott, J R, Differential Recognition of Surface Proteins in *Streptococcus pyogenes* by Two Sortase Gene Homologs. Journal of Bacteriology, Vol. 184, No. 8, p. 2181-2191, 2002).

The invention contemplates use of sortases found in any gram positive organism, such as those mentioned herein and/or in the references (including databases) cited herein. The invention also contemplates use of sortases found in gram negative bacteria, e.g., *Colwellia psychrerythraea*, *Microbulbifer degradans*, *Bradyrhizobium japonicum*, *Shewanella oneidensis*, and *Shewanella putrefaciens*. They recognize sequence motifs LP[Q/K]T[A/S]T. In keeping with the variation tolerated at position 3 in sortases from gram positive organisms, a sequence motif LPXT[A/S], e.g., LPXTA or LPSTS may be used. Use of sortases from Archaea (e.g. *Methanobacterium thermoautotrophicum*) is contemplated in certain embodiments.

In some embodiments, the sortase, or transamidase, recognition sequence is LPXTG, wherein X is a standard or non-standard amino acid. In some embodiments, X is selected from D, E, A, N, Q, K, or R. In some embodiments, the recognition sequence is selected from LPXTG, SPXTG, LAXTG, LSXTG, NPXTG, VPXTG, IPXTG, and YPXRG, wherein X may be selected from D, E, A, N, Q, K, or R in certain embodiments. In some embodiments a C-terminal G is replaced by A. In some embodiments X is selected to match a naturally occurring transamidase recognition sequence.

In certain embodiments the C-terminal amino acid residue of a sortase recognition motif may be replaced with a moiety that exhibits poorer nucleophilicity once released from the sortase (PCT/US2010/000274; Antos, J., et al., J. Am. Chem. Soc., 2009, 131 (31), pp 10800-10801). For example, the G in LPXTG may be replaced by a moiety that exhibits poorer nucleophilicity than glycine once released from the sortase, such as an alkyl ester, e.g., a methyl ester. In some embodiments, the transamidase recognition sequence is selected from: LPKT, LPIT, LPDT, SPKT, LAET, LAAT, LAET, LAST, LAET, LPLT, LSRT, LPET, VPDT, IPQT, YPRR, LPMT, LPLT, LAFT, LPQT, NSKT, NPQT, NAKT, and NPQS. In certain embodiments any of the afore-mentioned TRSs having four amino acids may further comprise a moiety that exhibits a poorer nucleophilicity than glycine once released from the sortase.

In some embodiments, e.g., in certain embodiments in which sortase A is used, the transamidase recognition motif comprises the amino acid sequence $X_1PX_2X_3$ or $X_1PX_2X_3G$, where $X_1$ is leucine, isoleucine, valine or methionine; $X_2$ is any amino acid; $X_3$ is threonine, serine or alanine; P is proline and G is glycine. In specific embodiments, as noted above $X_1$, is leucine and $X_3$ is threonine. In certain embodiments, $X_2$ is aspartate, glutamate, alanine, glutamine, lysine or methionine. In certain embodiments, e.g., where sortase B is utilized, the recognition sequence often comprises the amino acid sequence $NPX_1TX_2$, where $X_1$ is glutamine or lysine; $X_2$ is asparagine or glycine; N is asparagine; P is proline and T is threonine. In some embodiments selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

The invention contemplates use of sortase recognition motifs from any of the experimentally verified or putative sortase substrates listed at http://bamics3.cmbi.kun.nl/jos/sortase_substrates/help.html, the contents of which are incorporated herein by reference, and/or in any of the above-mentioned references. In some embodiments the sortase recognition motif is selected from: LPKTG, LPITG, LPDTA, SPKTG, LAETG, LAATG, LAHTG, LASTG, LAETG, LPLTG, LSRTG, LPETG, VPDTG, IPQTG, YPRRG, LPMTG, LPLTG, LAFTG, LPQTS, it being understood that in various embodiments of the invention the $5^{th}$ residue is replaced, as described elsewhere herein. For example, the sequence used may be LPXT, LAXT, LPXA, LGXT, IPXT, NPXT, NPQS, LPST, NSKT, NPQT, NAKT, LPIT, LAET, or NPQS. The invention comprises embodiments in which 'X' in any sortase recognition motif disclosed herein or known in the art is any standard or non-standard amino acid. Each variation is disclosed. In some embodiments, X is selected from the 20 standard amino acids found most commonly in proteins found in living organisms. In some embodiments, e.g., where the recognition motif is LPXTG or LPXT, X is D, E, A, N, Q, K, or R. In some embodiments, X in a particular recognition motif is selected from those amino acids that occur naturally at position 3 in a naturally occurring sortase substrate. For example, in some embodiments X is selected from K, E, N, Q, A in an LPXTG or LPXT motif where the sortase is a sortase A. In some embodiments X is selected from K, S, E, L, A, N in an LPXTG or LPXT motif and a class C sortase is used. In some embodiments the first position of a sortase recognition motif is an aromatic amino acid (e.g., F or W) or an amino acid with a relatively small side chain such as A, D, S, P, and G, and a sortase variant capable of recognizing the resulting motif is used. For example, in some embodiments L in LPXT is replaced by A, D, S, P, G, F, or W.

In some embodiments, a recognition sequence further comprises one or more additional amino acids, e.g., at the N or C terminus. For example, one or more amino acids (e.g., up to 5 amino acids) having the identity of amino acids found immediately N-terminal to, or C-terminal to, a 5 amino acid recognition sequence in a naturally occurring sortase substrate may be incorporated. Such additional amino acids may provide context that improves the recognition of the recognition motif.

In some embodiments any of the sortase recognition sequences may further comprise one or more additional glycines or alanines at the C-terminus. It will be appreciated that a C-terminal amino acid of a polypeptide, e.g., a C-terminal amino acid of a polypeptide comprising a transamidase recognition sequence, may be amidated, i.e., a C-terminal amino acid may have a —$CONH_2$ group instead of a —COOH group at the C-terminus in certain embodiments.

The term "transamidase recognition sequence" may refer to a masked or unmasked transamidase recognition sequence. An unmasked transamidase recognition sequence can be recognized by a transamidase. An unmasked transamidase recognition sequence may have been previously masked, e.g., as described in WO2010087994. In some embodiments, a "masked transamidase recognition sequence" is a sequence that is not recognized by a transamidase but that can be readily modified ("unmasked") such that the resulting sequence is recognized by a transamidase. For example, in some embodiments at least one amino acid of a masked transamidase recognition sequence has a side chain that comprises a moiety that inhibits, e.g., substantially prevents, recognition of the sequence by a transamidase of interest, wherein removal of the moiety allows the transamidase to recognize the sequence. Masking may, for example, reduce recognition by at least 80%, 90%, 95%, or more (e.g., to undetectable levels) in certain embodiments. By way of example, in certain embodiments a threonine residue in a transamidase recognition sequence such as LPXTG is phosphorylated, thereby rendering it refractory to recognition and cleavage by SrtA. The masked recognition sequence can be unmasked by treatment with a phosphatase, thus allowing it to be used in a SrtA-catalyzed transamidation reaction.

It will be appreciated that transamidase fragments having transamidation activity can be utilized in the methods described herein. As described in PCT/US2010/000274, such fragments can be identified by producing transamidase fragments by known recombinant techniques or proteolytic techniques, for example, and determining the rate of protein or peptide ligation. The fragment sometimes consists of about 80% of the full-length transamidase amino acid sequence, and sometimes about 70%, about 60%, about 50%, about 40% or about 30% of the full-length transamidase amino acid sequence such as that of S. aureus Sortase A (GenBank Accession number AAD48437). In some embodiments, the fragment lacks an N-terminal portion of the full-length sequence, e.g., the fragment lacks the N-terminal portion extending to the end of the membrane anchor sequence (up to about amino acid 26). In some embodiments the fragment comprises the C-terminus of a full-length transamidase amino acid sequence. In some embodiments, a catalytic core region from a sortase is utilized, e.g., a region is from about position 60 to about position 206 of SrtA, e.g., S. aureus SrtA, or about from position 82 to about position 249 of SrtAstrep. Thus a sortase may comprise or consist of a catalytic domain of a full length sortase polypeptide. It will be appreciated that the polypeptide may also comprise an N-terminal methionine residue.

Transamidases from other organisms also can be utilized in the processes described herein. Such transamidases often are encoded by nucleotide sequences substantially identical or similar to the nucleotide sequences that encode Srt A and Srt B. A similar or substantially identical nucleotide sequence may include modifications to the native sequence, such as substitutions, deletions, or insertions of one or more nucleotides. Included are nucleotide sequences that sometimes are 55%, 60%, 65%, 70%, 75%, 80%, or 85% or more identical to a native nucleotide sequence, and often are 90% or 95% or more identical to the native nucleotide sequence (each identity percentage can include a 1%, 2%, 3% or 4% variance). One test for determining whether two nucleic acids are substantially identical is to determine the percentage of identical nucleotide sequences shared between the nucleic acids.

Calculations of sequence identity can be performed as follows. Sequences are aligned for optimal comparison purposes and gaps can be introduced in one or both of a first and a second nucleic acid sequence for optimal alignment. Also, non-homologous sequences can be disregarded for comparison purposes. The length of a reference sequence aligned for comparison purposes sometimes is 30% or more, 40% or more, 50% or more, often 60% or more, and more often 70%, 80%, 90%, 100% of the length of the reference sequence. The nucleotides at corresponding nucleotide positions then are compared among the two sequences. When a position in the first sequence is occupied by the same nucleotide as the corresponding position in the second sequence, the nucleotides are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two nucleotide sequences can be determined using the algorithm of Meyers & Miller, CABIOS 4: 11 17 (1989), which has been incorporated into the ALIGN program (version 2.0), using a PAM120 weight residue table, a gap length penalty of 12 and a gap penalty of 4. Percent identity between two nucleotide sequences can be determined using the GAP program in the GCG software package (available at www.gcg.com), using a NWSgapdna. CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frame shift gap penalty of 5.

III. Methods of Sortagging and Processing Sortagged Cells

"Sortagging process" refers to a process in which at least some entities (e.g., proteins, cells) become sortagged. In general, a sortagging process comprises contacting an entity to be sortagged, e.g., a eukaryotic cell, e.g., a mammalian cell, with a transamidase and a sortase substrate under conditions in which a sortase-catalyzed reaction can occur. In certain embodiments a sortase reaction is performed under physiological conditions. In general sortase-catalyzed conjugation may be performed by contacting a transamidase, acyl donor (sortase substrate), and nucleophilic acyl acceptor with one another under suitable conditions to effect conjugation of the acyl donor to the acyl acceptor. In embodiments of the present disclosure the nucleophilic acyl acceptor may be a protein expressed by a mammalian cell. Contacting the components with one another can be accomplished by adding them to one body of fluid and/or in one reaction vessel, for example, or otherwise placing the components in close proximity to one another and allowing them to collide. The components in the system may be mixed in a variety of manners, such as by oscillating a vessel, if desired. The components may be added in any order to the system. Conjugation may be performed in any convenient vessel (e.g., tubes such as microfuge tubes, flask, dish), microtiter plates (e.g., 96-well or 384-well plates), etc. The reaction mixture may be maintained at any convenient temperature at which the reaction can be performed. In some embodiments, the conjugation is performed at a temperature ranging from about 3 or 4 degrees C. to about 15 degrees C. In some embodiments, the conjugation is performed at a temperature ranging from about 15 degrees C. to about 50 degrees C. In some embodiments, the ligation is performed at a temperature ranging from about 23 degrees C. to about 37 degrees C. In certain embodiments, the temperature is room temperature (e.g., about 25 degrees C.). Any convenient volume and component ratio may be utilized to conjugate a sortase substrate to animal cells. In some embodiments, the acyl donor is present at a concentration ranging from about 5 µM to about 10 mM, about 10 µM to about 5 mM, about 1001 µM to about 5001 µM, about 2001 µM to about 1 mM. In some embodiments the concentration of acyl donor is at least 0.25 mM, at least 0.5 mM, or at least 1 mM. In certain embodiments, the transamidase is present at a concentration ranging from about 1 µM to about 500 µM, about 15 µM to about 150 µM, about 150 µM to about 250 µM, about 250 µM to about 5001 µM. In certain embodiments, the transamidase is present at a concentration greater than 101 µM, e.g., 111 µM to 201 µM, 201 µM to 301 µM, 301 µM to 501 µM, 501 µM to 100 µM. In some embodiments a transamidase is present at a concentration greater than 101 µM and is a wild type sortase, e.g., a wild type sortase A, e.g., a wild type S. aureus SrtA, or a variant thereof that has an activity between 0.5-fold and 5-fold that of wild type S. aureus SrtA. In certain embodiments, the transamidase is present at a concentration of about 10 µM to 1 mM, about 15 µM to about 1 mM, about 20 µM to about 1 mM, about 25 µM to about 1 mM, 30 µM to about 1 mM, about 50 µM to about 1 mM, about 100 µM to about 1 mM, or about 250 µM to about 1 mM. In certain embodiments, these concentrations apply to wild type sortase A in particular, e.g., a wild type S. aureus sortase A.

In certain embodiments conjugation is performed in a reaction mixture comprising an aqueous medium. Water with an appropriate buffer and/or salt content compatible with cell viability may be used. One of ordinary skill in the art will be familiar with a variety of buffers that could be used in accordance with the present invention. In some embodiments, the aqueous medium comprises calcium ions. For example, the aqueous medium may contain between about 1.0 mM and about 50 mM calcium ions, e.g., from about 2 mM to about 25 mM calcium ions, e.g., from about 5 mM to about 15 mM calcium ions, e.g., about 1, 2, 3, 4, 5, 6, 7, 8, 9, or 10 mM calcium ions. In certain embodiments, the aqueous medium contains between about 1 mM and about 5 mM calcium ions. In other embodiments, the aqueous medium contains greater than 0.5 mM or greater than 1 mM calcium ions. In certain embodiments, the aqueous medium does not contain substances that bind to, or sequester calcium ions or contains only trace amounts of such substances, which would have negligible effects on the concentration of free calcium ions. In certain embodiments, the aqueous medium does not contain substances that precipitate calcium ions. In some embodiments, the aqueous medium does not include phosphate ions. In some embodiments, the aqueous medium does not include carbonate ions. In some embodiments, the aqueous medium does not contain chelating agents. For example, in some embodiments the aqueous medium does not contain substances that chelate calcium ions, such as EDTA or EGTA or contains only trace amounts of such substances, which would have negligible effects on the concentration of free calcium ions. In some embodiments, if the medium contains a substance (other than a sortase) that binds to calcium ions, the concentration of such substance is not sufficient to result in a decrease in the catalytic activity of the sortase of more than 5%, 10%, 15%, 20%, or 25%. In some embodiments, the aqueous medium is prepared without addition of calcium ions. In some embodiments the concentration of calcium ions is below about 1.0 mM, e.g., below about 0.5 mM, 0.25 mM, 0.1 mM, 0.05 mM, or lower. In some embodiments, suitable ligation conditions comprise pH in the range of 6 to 8.5, 6 to 8, 6 to 7.5, 6.5 to 8.5, 7 to 8.5, 7.5 to 8.5, 7.0 to 8.5, 7.3 to 7.8. It will be understood that the afore-mentioned concentrations, ratios, and conditions are exemplary and non-limiting. Higher or lower concentrations and/or different conditions may be used in various embodiments.

When sortase substrates are conjugated to mammalian cells, reaction conditions that are compatible with cell viability and, in some embodiments, suitable to maintain normal cell function, are used. Appropriate conditions within the range of conditions described above may be used. For example, the temperature is within a suitable range for mammalian cells, e.g., typically not more than 39 or 40 degrees, although higher temperatures, e.g., up to 45 degrees, may be used in certain embodiments. In some embodiments a temperature between about 10 and 25 degrees C. may be used. In some embodiments a temperature between about 25 and 37 degrees C. may be used. In some embodiments a relatively low temperature, e.g., between about 4 and 10 degrees, may be used to reduce cellular metabolism and/or internalization of cell surface proteins. In embodiments in which non-mammalian cells are sortagged, reaction conditions that are compatible with cell viability and, in some embodiments, suitable to maintain normal cell function, are used. Appropriate conditions within the range of conditions described above may be used.

In some embodiments cells are at a concentration of between about $10^5$ cells/ml and about $10^{12}$ cells/ml, e.g., between about $10^6$ cells/ml and about $10^{11}$ cells/ml. A gentle means of mixing may be used if desired such as gentle rocking. In some embodiments mammalian cells are sortagged in a composition comprising culture medium suitable for culturing the mammalian cell(s). In some embodiments the culture medium is free or essentially free of serum, plasma, and/or animal tissue or organ extracts. In some embodiments the culture medium contains serum or plasma. In some embodiments serum or plasma, if present, is from the subject from whom the cells originated or to whom the cells are to be administered. In some embodiments the culture medium is chemically defined.

Parameters such as the concentration of sortase, concentration of sortase substrate, number and/or concentration of cells, ratio of sortase substrate and/or sortase to cells, aqueous medium, and length of time of the reaction may be selected based on a variety of factors, such as the activity of the particular sortase, the nature of the sortase substrate (e.g., how readily it serves as a substrate for sortase), the degree of conjugation desired, etc. In some embodiments the sortase reaction may be permitted to proceed for at least 15 minutes. In some embodiments the sortase reaction may be permitted to proceed for more than 15 minutes. In some embodiments the sortase reaction may be permitted to proceed for between about 30 minutes and about 24 hours, e.g., about 1-2, 2-4, 4-8, 8-12, 12-16, or 16-24 hours. In certain embodiments samples may be removed from a reaction vessel and tested for concentration of unconjugated sortase substrate or reaction byproduct and/or level of agent conjugated to cells. The reaction may be permitted to proceed until a desired endpoint is reached. In certain embodiments the number of cells is up to about $10^{14}$ cells, e.g., about $10^3$, $10^4$, $10^5$, $10^6$, $10^7$, $10^8$, $10^9$, $10^{10}$, $10^{11}$, $10^{12}$, $10^{13}$ or $10^{14}$ cells, or any intervening range, e.g., between about $10^5$ and about $10^{12}$ cells, between about $10^6$ and about $10^{11}$ cells, between about $10^7$ and about $10^{10}$ cells. In certain embodiments sortase-mediated modification of mammalian cells may be performed in 1-2 hours, or less (e.g., between 15 and 30 minutes, between 30 and 60 minutes). In some embodiments primary cells are obtained from a subject or from a donor, modified in vitro using sortase, and at least some of the modified cells are administered to the subject on the same day as the cells were obtained, or the following day. In some embodiments the complete procedure, from cell harvesting to administration of modified cells, may take between 4-12 hours, 12-24 hours, or 24-48 hours. In certain embodiments cells that have a poor survival rate or lose functional activity or alter their phenotype when maintained in culture may be sortagged and administered to a subject before losing viability or functional activity or exhibiting altered phenotype.

In some embodiments a composition comprising one or more living mammalian cells, sortase, and, in some embodiments, further comprising a sortase substrate, is characterized in that at least 80%, 85%, 90%, 95%, 97%, 98%, 99%, or more of the cell(s) remain viable in the composition for at least between 1-2 hours, 2-4 hours, 4-8 hours, 8-12 hours, or more, e.g., at least 12-24 hours. In certain embodiments living mammalian cells modified using sortase exhibit at most a 1%, 2%, 3%, 5%, 10%, 15%, 20%, or 25% reduction in viability as compared to a suitable control. In some embodiments, living mammalian cells modified using sortase retain substantial functional activity. For example, in some embodiments cells subjected to a sortagging process exhibit at most a 1%, 2%, 3%, 5%, 10%, 15%, 20%, or 25% reduction in at least one functional activity as compared to a suitable control. In some embodiments, living mammalian cells modified using sortase gain a new functional activity or have an increased functional activity as compared with a suitable control. For example, in some embodiments cells subjected to a sortagging process may exhibit an increase of at least 10%, 20%, 30%, 40%, 50%, 60%, 70%, 80%, 90%, or 100% in at least one functional activity as compared to a suitable control. In some embodiments cells subjected to a sortagging process may exhibit at least a 2-fold, 5-fold, 10-fold, 20-fold, or more increase in at least one functional activity as compared to a suitable control. In some embodiments a new or increased functional activity is conferred by or as a result of an agent conjugated to the cells. In some embodiments a functional activity may be measured in vitro. In some embodiments a functional activity or change in a functional activity may be measured after administration of cells to a subject. In some embodiments a functional activity is binding activity, cytokine secretion, cytotoxic activity, phagocytic activity, antigen presenting activity, or costimulation activity. In some embodiments, living mammalian cells modified using sortase may exhibit minimal or no detectable non-specific alteration (e.g., oxidation, denaturation, degradation) to cell surface proteins (other than those modified by sortase-mediated conjugation) as compared with a suitable control. In some embodiments a suitable control is cells of the same cell type or subtype that have not been contacted with sortase. In some embodiments a suitable control is cells of the same cell type or subtype that have been contacted with sortase in the absence of a sortase substrate. In some embodiments control cells may originate from the same culture, cell line, or subject as the cells with which they are compared. In some embodiments control cells not contacted with sortase have been maintained under standard culture conditions for that cell type or subtype (without sortase). In some embodiments a suitable control refers to a value (e.g., for viability or functional activity) measured for the cells prior to contacting them with sortase. In some embodiments control cells not modified using sortase have been incubated in a composition without sortase for about the same length of time and under substantially identical conditions as the sortase-modified cells with which they are compared.

In some embodiments a sortase substrate comprising an agent that has a functional activity is conjugated to living mammalian cells with sortase. In some embodiments the agent retains at least 20%, 30%, 40%, 50%, 60%, 70%, 80%, 90%, 95%, 99% or all of its functional activity as compared to that of an unconjugated agent. In some embodiments a functional activity is a catalytic activity, an inhibitory activity, a binding activity, or a cytotoxic activity. In some embodiments a functional activity is an ability to stimulate a cell to survive, proliferate, become activated, differentiate, migrate, produce or secrete one or more substances, exhibit a phenotypic characteristic (e.g., expression of one or more genes, cell surface marker phenotype), or attack a target cell. In some embodiments a functional activity is an ability to inhibit a cell from proliferating, becoming activated, differentiating, migrating, producing or secreting one or more substances, dying, altering a phenotypic characteristic (e.g., expression of one or more genes, cell surface marker phenotype), or attacking a target cell. In some embodiments an agent confers an ability to participate in a new cell-cell interaction. In some embodiments an agent conjugated to a mammalian cell exerts an autocrine effect. For example, the agent may bind to a cell surface receptor expressed by a cell to which the agent is conjugated and exert an effect on the cell. In some embodiments an agent exerts a paracrine effect. For example, the agent may bind to a cell surface receptor expressed by a cell located near the cell to which the agent is conjugated and exert an effect on the cell. Binding of an agent to a cell surface receptor may modulate a signaling pathway, cause the cell to survive, differentiate, divide, migrate, maintain or acquire a functional activity, etc.

In some embodiments mammalian cells are subjected to a sortagging process, and at least some sortagged cells are then separated from sortase, unconjugated sortase substrate, and/or reaction byproduct. Separation may be performed using a variety of different methods and may be based at least in part on size, charge, affinity, hydrophobicity, hydrophilicity, and/or other properties. In some embodiments sortase is immobilized by attaching it to a support before or after being contacted with mammalian cells. Immobilization may comprise contacting sortase or a composition containing sortase with an affinity reagent, e.g., an antibody, that binds to sortase, wherein the affinity reagent is attached to a support. In some embodiments the sortase is tagged, and the affinity reagent binds to the tag. In some embodiments the support is in a column, and a composition comprising cells and sortase is passed through the column. Sortase is retained by the column whereas cells pass through. Cells may pass through the column at a different rate to unconjugated agent, thereby achieving separation. In some embodiments the agent comprises a tag that is removed during sortagging as part of a reaction byproduct. Unconjugated sortase substrate and/or reaction byproduct can be removed by an affinity agent that binds to the tag. In some embodiments sortase is immobilized before being contacted with mammalian cells. For example, sortase may comprise a tag, e.g., a 6×-His tag, which may be used to immobilize the sortase to a metal-ion containing resin or substrate. Mammalian cells are incubated in the presence of the immobilized sortase and an agent to be conjugated thereto. Cells can readily be separated from the immobilized sortase. In some embodiments sortase is immobilized to magnetic particles. It will be understood that magnetic particles may be magnetisable and paramagnetic, e.g., superparamagnetic, i.e., they may only magnetic in a magnetic field.

In some embodiments at least 5%, 10%, 15%, 20%, 25%, 30%, 40%, 50%, 60%, 70%, 80%, 90%, 95%, 96%, 97%, 98%, 99% or more of the mammalian cells in a population of cells subjected to a sortagging process become conjugated with an agent. In some embodiments a population of cells is processed after sortagging to produce a composition in which at least 5%, 10%, 15%, 20%, 25%, 30%, 40%, 50%, 60%, 70%, 80%, 90%, 95%, 96%, 97%, 98%, 99% or more of the mammalian cells are conjugated with an agent. In some embodiments mammalian cells that have been subjected to sortagging may be separated into two, three, four, or more groups, e.g., between 2 and 10 groups, during or after being contacted with sortase or may be subjected to selection. In some embodiments separation or selection produces a population of cells that is enriched in cells having a property that is desired and/or that is at least partly depleted of cells having a property that is not desired, as compared with a starting population prior to separation.

In some embodiments cells that have been subjected to a sortagging process are separated into two or more groups based at least in part on the level of a moiety that has been conjugated thereto by sortase. In some embodiments at least some cells that have a moiety conjugated thereto at a level detectably greater than a suitable control level are separated from cells that do not. In some embodiments cells that exhibit at least a specified level of moiety at their surface may be separated from cells that exhibit a lower level or completely lack the moiety at their surface. Groups may be defined based on the level of moiety using any suitable classification system. In some embodiments cells are divided into groups that are considered to exhibit low, intermediate, or high levels. In some embodiments the 1%, 5%, 10%, 15%, 20%, 25%, 30%, 40%, 50%, 60%, 70%, 80%, or 90% of cells having the highest level of moiety conjugated thereto are separated from the rest of the cells in a population. A level may be an absolute amount, relative amount, surface density, volume density, or other suitable parameter. Suitable separation methods may be utilized so as to produce a composition in which a selected degree of conjugation is achieved. For example, in some embodiments a composition comprises cells that have on average a specified level or range of levels of moiety at their surface. A specified percentage may be a minimum percentage, e.g., at least 10%, or a range, e.g., between 10% and 50%, between 50% and 90%, etc.

Any suitable method may be used to detect or measure the level of an agent conjugated to cells or to separate cells into two or more populations if desired. One of ordinary skill in the art will be able to select an appropriate method taking into consideration factors such as, for example, one or more physical, chemical, or biological properties of the agent such as affinity (e.g., binding affinity), charge, fluorescence, color, magnetic properties, mass, enzymatic activity. In some embodiments a method utilizes fluorescence, affinity, or both. For example, in some embodiments an agent to be conjugated to cells comprises a fluorescent moiety. Cells having the fluorescent moiety conjugated thereto may be detected or measured using, e.g., flow cytometry or immunofluorescence microscopy, and the level of agent may be measured, if desired. Cells may be separated using fluorescence activated cell sorting (FACS). In some embodiments an agent is capable of binding to or being bound by a reagent (e.g. an antibody) comprising a fluorescent label, and cells are contacted with such a reagent under conditions suitable for binding to occur, optionally followed by washing to remove non-specifically associated reagent. Cells are then subjected to fluorescence activated cell sorting. In some embodiments an affinity-based method is used. For example, in some embodiments an agent to be conjugated to cells comprises a tag. The tag may be detected using a suitable reagent.

IV. Cells and Cell Culture

In general, any type of cells may be sortagged as described herein or used as a source of cells to be sortagged. In some embodiments cells comprise or consist of mammalian cells. In some embodiments mammalian cells are primate cells (human cells or non-human primate cells), rodent cells (e.g., mouse, rat, rabbit, hamster cells), canine, feline, bovine, porcine, or other mammalian cells. In some embodiments cells are avian cells. In some embodiments cells are invertebrate animal cells. In some embodiments cells are fungal (e.g., yeast or mold) or protozoal cells.

A cell may be a primary cell, non-immortalized cell, immortalized cell, normal cell, abnormal cell, tumor cell, non-tumor cell, etc., in various embodiments. A cell may originate from a particular tissue or organ of interest or may be of a particular cell type. In some embodiments primary cells may be freshly isolated from a subject. In some embodiments, cells are maintained in culture and may be passaged or allowed to double once or more following their isolation from a subject (e.g., between 1-5, 5-10, 10-20, 20-50, 50-80 passages or population doublings times) prior to use in a method disclosed herein. In some embodiments, cells have been passaged or permitted to double no more than 1, 2, 5, 10, 20, or 50 times following isolation from a subject before use in a method described herein. Cells "obtained from a subject" may comprise originally isolated cells and/or descendants thereof that arise during culture of the originally isolated cells. In some embodiments cells are obtained from any tissue or organ of interest. In some embodiments cells are obtained from a fluid such as blood, sputum, lymph, mucus, saliva, urine, blood, or lymph, from bone marrow, or lymphoid tissue (e.g., lymph node, spleen). In some embodiments cells are obtained from connective tissue, muscle tissue, adipose tissue, epithelial tissue. In some embodiments cells are obtained from a tumor, site of infection, site of inflammation or immune-mediated tissue damage, or lymphoid tissue that receives lymph from such a site (e.g., nearest draining lymph nodes).

In some embodiments a cell is a member of a cell line. In some embodiments, a cell line is capable of indefinite proliferation in culture (immortal; immortalized). An immortalized cell line has acquired an essentially unlimited life span, i.e., the cell line appears to be capable of proliferating essentially indefinitely. For purposes hereof, a cell line that has undergone or is capable of undergoing at least 100 population doublings in culture may be considered immortal. Numerous cell lines are known in the art and may be used in various methods described herein. Cell lines can be generated using methods known in the art or obtained, e.g., from depositories or cell banks such as the American Type Culture Collection (ATCC), Coriell Cell Repositories, Deutsche Sammlung von Mikroorganismen and Zellkulturen (German Collection of Microorganisms and Cell Cultures; DSMZ), European Collection of Cell Cultures (ECACC), Japanese Collection of Research Bioresources (JCRB), RIKEN, Cell Bank Australia, etc. The paper and online catalogs of the afore-mentioned depositories and cell banks are incorporated herein by reference.

In some embodiments a cell line, cell population, or cell culture is derived from a single cell. In some embodiments, a cell line, cell population, or cell culture is derived from multiple cells. In some embodiments, cells of a cell line, cell population, or cell culture are descended from a cell or cells originating from a single sample (e.g., a sample obtained from a tumor) or individual. If desired, cells may be tested to confirm whether they are derived from an individual or a particular cell line by any of a variety of methods known in the art such as DNA fingerprinting (e.g., short tandem repeat (STR) analysis), single nucleotide polymorphism (SNP) analysis (which may be performed using, e.g., SNP arrays (e.g., SNP chips) or sequencing), isoenzyme analysis, human lymphocyte antigen (HLA) typing, chromosomal analysis, karyotyping, morphology, etc.

An appropriate cell donor, cell source, or cell line may be selected based on a variety of factors, such as the intended use of the cells, number of cells desired, availability, etc. In some embodiments, cells are obtained from an individual who is healthy or is reasonably presumed to be healthy at the time the cells are obtained. In some embodiments, cells are obtained from an individual who does not have or is reasonably presumed not to have one or more particular diseases, e.g., cancer, infection, autoimmune disease, at the time the cells are obtained. In some embodiments cells are obtained from an individual who does not have a history of having a particular disease. In some embodiments cells are obtained from an individual who has or has had a particular disease. In some embodiments the disease is cancer, a disease caused by a pathogen, or an autoimmune disease. In some embodiments the subject exhibits resistance to a disease, e.g., a disease caused by a pathogen. In some embodiments the subject is recovering or has recovered from a disease. In some embodiments the subject is in need of treatment of a disease, e.g., cancer, a disease caused by a pathogen, an autoimmune disease, or a disease for which a transplant is indicated. In some embodiments cells are obtained from an individual who is histocompatible with a subject in need of treatment of such a disease.

Cells used in a method described herein may have been procured directly from a subject or procured indirectly, e.g., by receiving the cells (or ancestors of the cells) through a chain of one or more persons originating with a person who procured the cells (or ancestors of the cells) directly from the subject, e.g., by performing a biopsy, blood draw, surgery, or other procedure on the subject. In some embodiments at least some of the originally isolated cells may undergo one or more rounds of cell division. In some embodiments cells are obtained from a tissue biopsy such as an excisional biopsy, incisional biopy, or core biopsy; a fine needle aspiration biopsy; a brushing; or a lavage. In some embodiments cells are obtained from surgical or cellular samples from a subject (e.g., tissue or cellular material harvested for purposes of obtaining tissue or cells, excess or discarded tissue or cellular material, etc.). A surgical sample may be obtained from an organ or part of an organ that has been removed from a subject, e.g., because it is diseased or injured or enlarged. Methods of obtaining samples and isolating cells from samples are well known in the art. In some embodiments cells are obtained from a tissue sample. In some embodiments cells are isolated from a tissue sample, by dissociation, e.g., mechanical or enzymatic dissociation and may be collected, e.g., by centrifugation, and washed, if desired. Cells can be subjected to a variety of procedures to select or enrich for cells of a desired cell type or having desired properties. In some embodiments enrichment is performed at least in part based on expression (which may be lack of expression) of one or more cell surface markers using, e.g., FACS or affinity reagents. One can select for against cells that express particular markers. In some embodiments enrichment is performed at least in part by exposing cells to an agent or combination of agents (e.g., cytokines) that promote differentiation and/or expansion of one or more cell types. In some embodiments a composition comprises at least 10%, 20%, 30%, 40%, 50%, 60%, 70%, 80%, 90%, or more cells of a particular type and/or expressing a particular marker or combination of markers. In some embodiments at least some cells obtained from a subject and/or descendants of such cells are stored, e.g., cryopreserved. Aliquots may subsequently be thawed and used in one or more methods or compositions described herein. In some embodiments cells may be expanded in vitro prior to storage, after storage, or both.

In some embodiments cells may originate from any of the three germ layers: ectoderm, mesoderm, and endoderm. In some embodiments cells may originate from any biological tissue of the four general classes of biological tissues: epithelial, muscular, connective, and nervous tissues. In some embodiments cells comprise epithelial cells. "Epithelium" refers to layers of cells that line the cavities and surfaces of numerous structures in the body and is the type of tissue from which many glands are at least partly formed. Epithelial tissues include, for example, tissues found in the gastrointestinal tract (e.g., esophagus, stomach, small intestine, colon, rectum), liver, biliary tract, pancreas, respiratory tract (e.g., nasal passages, pharynx, larynx, trachea, bronchioles, bronchi, lungs, alveoli), oral cavity, skin, kidneys, ovaries, breast, prostate, cervix, uterus, bladder, ureter, testes, exocrine glands, endocrine glands, eye (e.g., retinal pigment epithelium, corneal epithelium, conjunctiva), blood vessels (vascular endothelium), lymph vessels (lymphatic endothelium), etc. In some embodiments cells comprise or consist of muscle cells, e.g., skeletal, smooth, or cardiac myocytes or myoblasts. In some embodiments cells comprise or consist of connective tissue cells, e.g., fibroblasts, adipocytes, cartilage cells (e.g., chondrocytes, chondroblasts), bone cells (e.g., osteoblasts, osteoclasts). In some embodiments cells comprise or consist of nervous system cells, e.g., neural cells (e.g., neurons), glial cells (e.g., astrocytes, oligodendrocytes, Schwann cells). In certain embodiments cells comprise or consist of pancreatic beta cells, hepatocytes, keratinocytes, or melanocytes.

In some embodiments cells comprise hematopoietic cells. Hematopoietic cells include hematopoietic stem cells (HSCs), the blood cells that give rise to all other blood cells, and cells of the myeloid (e.g., monocytes and macrophages, neutrophils, basophils, eosinophils, erythrocytes, megakaryocytes/platelets, dendritic cells) and lymphoid (T cells, B cells, NK cells) lineages. In some embodiments hematopoietic cells are obtained from peripheral blood, e.g., by venipuncture. In some embodiments hematopoietic cells are obtained by apheresis, a technique in which the blood of an individual is passed through an apparatus that separates one or more constituents and returns the remainder to the circulation. For example, erythrocytapheresis may be used to obtain red blood cells, leukapheresis may be used to obtain leukocytes (white blood cells), plateletpheresis (also called thrombapheresis, thrombocytapheresis) may be used to obtain platelets. Separation may employ, e.g., centrifugation, elutriation, adsorbtion onto resin (e.g., beads) with appropriate affinity, filtration, etc. In some embodiments cells are obtained peripheral blood after mobilization of such cells or their precursors, e.g., from bone marrow. For example, in some embodiments bone marrow hematopoietic stem cells (HSCs) are mobilized by, e.g., injections of granulocyte-colony stimulating factor (G-CSF). In some embodiments cells, e.g., HSCs or other hematopoietic cells, are isolated from blood, e.g., peripheral blood or umbilical cord blood. In some embodiments hematopoietic cells, e.g., HCSc, are isolated from mobilized peripheral blood. HSCs may be expanded ex vivo and/or may be differentiated ex vivo to yield lymphoid and/or myeloid cells of one or more types.

In some embodiments cells comprise erythrocytes (red blood cells) and/or committed progenitors thereof. Red blood cells (RBCs) are typically abundant and readily accessible. In certain embodiments RBCs may be of particular interest as vehicles for delivery of therapeutic agents. In some embodiments, for example, RBCs are sortagged with a therapeutic agent, e.g., a protein, a chemotherapy drug, an anti-infective agent, etc., and administered into the vascular system, e.g., intravenously.

In some embodiments cells comprise immune system cells. In some embodiments an immune system cell is a lymphocyte, monocyte, dendritic cell, macrophage, neutrophil, mast cell, eosinophil, basophil, natural killer (NK) cell, or mast cell. In some embodiments a lymphocyte is a cell of the B cell lineage or T cell lineage. In some embodiments a B lymphocyte has rearranged its heavy (H) chain gene. In some embodiments a B lymphocyte expresses a membrane-bound antibody. In some embodiments a T cell expresses an alpha beta ($\alpha\beta$) T cell receptor (TCR). In some embodiments a T cell expresses a gamma delta ($\gamma\delta$) TCR. In some embodiments a T cell is a member of a T cell subset, e.g., a cytotoxic T cell (also called killer T cell) or a helper T cell. Cytotoxic T cells are typically positive for the cell surface marker CD8. Helper T cells are typically positive for the cell surface marker CD4. In some embodiments a cell is a CD4+CD8− T cell. In some embodiments a cytotoxic cell is a CD4+ T cell, e.g., a CD4+CD8− T cell. In some embodiments a cell is a CD4−CD8+ T cell. In some embodiments a cell is a CD4−CD8− T cell. In some embodiments a cell is a CD4+CD8+ T cell. In some embodiments a T cell is a natural killer T (NKT) cell, e.g., an invariant NKT (iNKT) cell. Natural killer T (NKT) cells are a subset of T cells that display markers characteristic of both natural killer (NK) cells and T cells. NKT cells recognize lipid or lipid-containing antigens (e.g., glycolipids, lipopeptides) in the context of CD1 molecules. NKT cells express an invariant TCR$\alpha$ chain rearrangement: V$\alpha$14J$\alpha$18 in mice and V$\alpha$24J$\alpha$18 in humans, which is associated with V$\beta$ chains of limited diversity, and are sometimes referred to as canonical or invariant NKT (iNKT) cells. Similar to conventional T cells, NKT cells develop from CD4−CD8− thymic precursor T cells following the appropriate signaling by CD1d. Human NKT cells can be stimulated and expanded ex vivo by contacting them with $\alpha$-galactosylceramide ($\alpha$-GalCer) and a variety of cytokines.

In some embodiments a T cell is a regulatory T cell (Treg), e.g., a FoxP3+ regulatory T cell. In some embodiments a regulatory T cell is a type 1 regulatory (Tr1) cell, which does not express FoxP3. Tr1 cells typically secrete interleukin 10 (IL-10) and transforming growth factor-$\beta$ (TGF-$\beta$), e.g., in response to antigenic stimulation. Tr1 cells are capable of dampening autoimmunity and tissue inflammation partly through their secretion of IL-10. In some embodiments a T cell is a follicular helper T cell (T$_{FH}$). T$_{FH}$ are antigen-experienced CD4+ T cells found in the B cell follicles of secondary lymphoid organs such as lymph nodes, spleens and Peyer's patches and may be identified by their constitutive expression of the B cell follicle homing receptor CXCR5. In some embodiments a T cell expresses and, in some embodiments secretes, one or more cytokine(s) and/or has a characteristic cell surface marker expression profile. For example, in some embodiments a T cell has a T helper 1 (Th1), T helper 2 (Th2), or T helper 17 (Th17) cytokine secretion profile and/or cell surface marker profile. Th1 cells are typically characterized by production of interferon-$\gamma$ and TGF-beta. Th2 cells may characteristically produce IL-4, IL-5, IL-6, IL-10, and IL-13. Th17 cells are typically characterized by production of interleukin-17.

In some embodiments a lymphocyte is a naïve cell (i.e., a cell that has not encountered an antigen to which its B cell receptor (BCR) or TCR binds and is not descended from a lymphocyte that has encountered an antigen to which its BCR or TCR binds). In some embodiments an immune system cell has encountered, in culture or in vivo, an antigen to which its BCR or TCR binds, or is descended from such a cell. In some embodiments an immune system cell has been activated, in culture or in vivo. In some embodiments an immune system cell is activated by exposure to an antigen presenting cell (APC) that displays an antigen to which the cell's TCR or BCR binds and/or by exposure to one or more cytokines. In some embodiments an immune system cell having characteristics of any of the afore-mentioned cell types may be generated at least in part in vitro, e.g., by differentiation from a less differentiated or naïve cell. Protocols and reagents useful for generating such cells are known in the art. Further information on various immune cell types may be found in, e.g., Zhu, J., et al., Differentiation of effector CD4 T cell populations. Annu. Rev. Immunol., 28 (2010), pp. 445-489; S. Crotty, Follicular helper CD4 T cells (TFH), Annu. Rev. Immunol., 29 (2011), pp. 621-663.

In some embodiments a cell is a lymphokine-activated killer cell (LAK). LAKs are a heterogeneous population of cells consisting primarily of NK, NKT and T cells, which are generated in vitro by culture of peripheral blood mononuclear cells (PBMCs) in IL-2 (see, e.g., West, E J, et al., British Journal of Cancer (2011) 105, 787-795 and references therein, e.g., Grimm E A, et al. J Exp Med 155(6): 1823-1841). The predominant effector cells within LAKs are believed to be NK cells, but LAKs may be more cytotoxic against tumour cells, including otherwise NK-resistant targets, than typical peripheral blood NK cells (Grimm et al, 1982). In some embodiments LAKs or other immune system cells may be sortagged with an agent comprising IL-2 or another cytokine or growth factor that may exert an autocrine effect on the cells. Sortagging the cells may provide an alternative to separately administering the cytokine or growth factor (e.g., systemically), which may reduce unwanted side effects that might otherwise be associated with such administration.

In some embodiments a cell is an antigen presenting cell (APC). An antigen-presenting cell (APC) is a cell that can process and display foreign antigens in association with major histocompatibility complex (MHC) molecules on its surface. T-cells may recognize these complexes using their T-cell receptors (TCRs). APCs may also display other molecules (costimulatory proteins) that are required for activating naïve T cells. In some embodiments APCs express MHC class II molecules. Such APCs include dendritic cells, macrophages, and B cells. In some embodiments APCs are capable of stimulating CD4+ and CD8+ T cells. In some embodiments APCs comprise professional APCs. In some embodiments professional APCs are dendritic cells or macrophages. Dendritic cells (DCs) are a class of white blood cells that occur in most tissues of the body, particularly those in contact with the exterior such as the skin (which contains a specialized dendritic cell type termed a Langerhans cell)

and mucosal surfaces, as well as in the blood. During certain developmental stages DCs grow membranous projections known as dendrites, from which the cell type gets its name. DCs serve as a link between peripheral tissues and lymphoid organs and play important roles in modulating the activity of other immune system cells. Immature DCs sample the surrounding environment for pathogens such as viruses and bacteria through pattern recognition receptors (PRRs) such as toll-like receptors (TLRs). In response to stimuli such as pathogen components or other danger signals, inflammatory cytokines, and/or antigen-activated T cells, they undergo maturation and migrate to the T cell area of lymph nodes or spleen, where they display fragments of previously phagocytosed and processed antigens at their cell surface using MHCII complexes. As part of the maturation process, DCs upregulate cell-surface receptors that act as co-receptors in T cell activation, such as CD80 (B7-1), CD86 (B7-2), and/or CD40. DCs activate helper T cells (Th cells) by presenting them with antigens derived from the pathogen in the context of MHCII complexes, together with non-antigen specific costimulators. Binding of CD4+ expressed at the surface of Th cells to a non-polymorphic region of MHCII enhances the physical interaction between DC and Th cells, allowing potent stimulation of helper T cells that express TCR molecules capable of binding the peptide. In addition, DCs have the capacity to directly activate cytotoxic T cells and B-cells through presentation of MHCII-peptide complexes and costimulators and are also able to activate the innate arm of anti-tumor immunity, e.g., NK and NKT effector cells. DC stimulation promotes Th cell proliferation, activation, and differentiation into effector Th cells, memory Th cells, and regulatory Th cells. Effector Th cells provide "help" to cytotoxic T cells, B cells, and macrophages by, e.g., secreting cytokines that exert a variety of stimulatory effects on these cell types. Th help promotes proliferation and activation of cytotoxic T cells, stimulates B-cell proliferation, induces B-cell antibody class switching, and stimulates antibody production. Th stimulation also enhances the killing ability of macrophages. Memory T cells play an important role in promoting the rapid mounting of a specific, strong adaptive immune response upon encountering an antigen to which a subject has previously been exposed. Regulatory Th cells are believed to play an important role in the self-limiting nature of the immune response. In some embodiments, DCs capable of presenting a particular peptide stimulate both the cell-mediated and humoral branches of the adaptive immune response towards targets containing that peptide as well as enhancing activity of the innate immune system. In some embodiments DCs comprise immature DCs, which lack one or more characteristics found in mature DCs present in tissues. For example, immature DCs may lack dendrites and/or lack one or more markers of mature DCs. In some embodiments immature DCs, e.g., immature human DCs, express and/or lack expression of CD83. In some embodiments DCs, e.g., human DCs, comprise myeloid DCs. In some embodiments DCs, e.g., human DCs, comprise plasmacytoid DCs. In some embodiments DCs comprise plasmacytoid CD303+ DCs, myeloid CD1c+ DCs, and/or myeloid CD141+ DCs. In some embodiments DCs, e.g., immature DCs, are obtained from the blood or generated in vitro from peripheral blood mononuclear cells (PBMCs). See, e.g., Tuyaerts, S., Cancer Immunol Immunother (2007) 56:1513-1537, for discussion of DC generation, antigen loading methods and immunomonitoring approaches that may be used.

In some embodiments immune system cells are generated or expanded in vitro from, e.g., HSCs or myeloid lineage progenitor cells.

In some embodiments a population of cells comprises immune system cells of two or more types or subtypes, e.g., lymphocytes and DCs, CD4+ T cells and CD8+ T cells, lymphocytes and NK cells, etc. Any combination is encompassed. Two or more populations may be individually isolated and subsequently combined. One or more of the populations, or the combined population, may be sortagged.

In some embodiments cells comprise peripheral blood mononuclear cells (PBMCs). As known in the art, PBMCs are peripheral blood cells that have a round nucleus, such as lymphocytes, monocytes, and NK cells. In some embodiments PBMCs are sortagged as a mixed population comprising two or more distinct cell types or subtypes distinguishable by size, morphology, cell surface markers, and/or functional characteristics. In some embodiments PBMCs are separated from other cells in a blood sample, so that at at least 80%, 85%, 90%, 95%, 96%, 97%, 98%, 99%, or more of the cells are PBMCs. In some embodiments PBMCs are sortagged without first separating the PBMCs into two or more types distinguishable by size, morphology, cell surface markers, and/or functional characteristics. In some embodiments PBMCs may be separated into two or more distinct populations, wherein one or more of the populations is enriched for one or more types of PBMC or is depleted of one or more PBMC types. In some embodiments the PBMCs are obtained from a subject to whom at least some of the PBMCs or their descendants are to be administered after such cells are sortagged ex vivo. PBMCs can be isolated using standard methods known in the art, such as using Ficoll density gradient centrifugation, which separates blood into a top layer containing plasma and platelets, followed by a layer containing PBMCs, and a bottom fraction containing polymorphonuclear cells (such as neutrophils and eosinophils) and erythrocytes. The PBMC layer can be removed, e.g., using a pipette, and sortagged. In some embodiments a preparation containing PBMCs isolated from blood may be further purified to remove residual red blood cells, e.g., prior to sortagging or after sortagging. Red blood cell depletion from blood or from a preparation containing PBMCs isolated from blood may be performed by a variety of methods known in the art, such as osmotic shock, filtration, density gradients such as ficoll-hypaque, percoll and hydroxyethyl starch and immunoaffinity with monoclonal antibodies such as CD34 coupled to magnetic beads. In some embodiments, T cells may be isolated from PBMC. In some embodiments a T cell subtype such as CD4+ or CD8+ T cells are isolated from PBMC. In some embodiments, NK cells may be isolated from PBMC. In some embodiments PBMCs are depleted of one or more of cell such types. In some embodiments, memory T cells, e.g., central memory T cells, are isolated from PBMC.

In some embodiments a cell is an artificial APC (aAPC). Cellular aAPC may be derived, e.g., from primary or transformed human or xenogeneic cells, e.g., fibroblasts or leukemia cells. In some embodiments non-mammalian cells, such as insect (e.g., *D. melanogaster*) cells may be used. Such cells may be engineered, e.g., using retroviral or lentiviral transduction or other approaches such as transposon systems, to cause them to express molecules that provide TCR interaction, costimulatory, and adhesion events involved in immune synapse formation, allowing them to behave like naturally occurring APCs. Certain aAPCs are reviewed in Kim, et al., Nature Biotechnology, 22(4): 403-410. In some embodiments, such aAPCs maybe used or sortagged in accordance with embodiments of the present invention. In some embodiments cells are engineered to coexpress any one or more of the following: a low affinity Fc receptor (e.g., CD32), a high affinity Fc receptor (e.g., CD64), CD40, CD40L, CD70, CD80, CD83, CD86 (B7-2), ICOSL, GITRL, CD137L (4-1BBL), CD252 (OX40L), B7-H3, ICAM-1, LFA-3, and/or CD1. Some examples of genetically engineered aAPCs and methods of making and using them are described in Maus, M. V. et al. Ex vivo expansion of polyclonal and antigen-specific cytotoxic T lymphocytes by artificial APCs expressing ligands for the T-cell receptor, CD28 and 4-1BB. Nat. Biotechnol. 20, 143-148 (2002); Thomas, A. K., et al. A cell-based artificial antigen-presenting cell coated with anti-CD3 and CD28 antibodies enables rapid expansion and long-term growth of CD4 T lymphocytes. Clin. Immunol. 105, 259-272 (2002). In some embodiments, cells may naturally express one or more of the afore-mentioned molecules and, optionally, are genetically engineered to express one or more additional afore-mentioned molecules. In some embodiments cells express at least two or all of the following: CD64, B7-2 (CD86), and CD137 ligand (CD137L). In some embodiments cells express one or more cytokines, e.g., IL-2, IL-12, or IL-15. In some embodiments, cells express one or more membrane-bound cytokines, e.g., membrane-bound IL-15.

In some aspects, the present disclosure contemplates use of sortagging to modify an aAPC or cell to be used as an aAPC by conjugating any of a variety of agents to the cell surface. In some embodiments, cells are sortagged with (CD137L), membrane-bound IL-15, and/or other protein(s) that are normally expressed on the cell surface and may act as ligands or interaction partners for receptors or other molecules expressed on other cells, e.g., cells to which an antigen is to be presented. Sortagging may be used in some embodiments to attach one or more proteins to the cell surface instead of or in addition to causing the cells to express such proteins through use of genetic engineering. Sortagging may be used in some embodiments to attach moieties that cannot be genetically encoded, such as lipids or small molecules, optionally complexed or attached to MHC proteins, CD1, or other proteins that normally present antigens. Such moieties may be presented as antigens or used for other purposes such as detection in vitro or in vivo.

In some embodiments, cells to be used as aAPC are sortagged with an antigen of interest, resulting in aAPC that have an antigen of interest attached to their cell surface. In some embodiments, cells to be used as aAPC are genetically engineered to express an antigen of interest at their cell surface, resulting in aAPC that have an antigen of interest exposed at least in part on their surface. The antigen of interest may be modified to include a secretion signal sequence and transmembrane domain to cause it to be expressed as a cell surface protein. In some embodiments, the cells to be used as aAPC do not express HLA class I and/or HLA class II molecules on their cell surface or at least do not express HLA-A, HLA-B, HLA-DQ, and HLA-DR. In some aspects, a lack of such major histocompatibility (MHC) antigens prevents immune responses that may otherwise be directed against an aAPC that expresses such MHC antigens if the aAPC is cultured with non-allogeneic immune cells and/or introduced into a non-allogeneic subject. In some embodiments cells to be used as aAPCs are engineered to express an HLA class I molecule, HLA class II molecule, or both. In some embodiments the cells do not otherwise express HLA class I, HLA class II, or both. In some embodiments, cells to be used as aAPC are contacted with a soluble antigen, e.g., in vitro. In some embodiments, the cells take up, process, and display the antigen or fragments thereof (e.g., peptides) on their surface in association with an HLA class I and/or class II molecule. In some embodiments, cells to be used as aAPC are sortagged with an antigen presenting molecule (APM). For example, cells may be sortagged with a molecule comprising at least a portion of an MHC protein that is capable of binding to an antigen. In some embodiments the antigen presenting molecule has been contacted or is contacted (e.g., in vitro) with a peptide or other antigen such that the peptide or other antigen is bound to the APM. In some embodiments an APM comprises at least a portion of an MHC protein that is capable of binding to an antigen, e.g., an MHC multimer or an HLA-Ig fusion protein (Oelke, 2003, full citation below).

aAPCs may be used for a variety of purposes, e.g., in the stimulation (activation and/or expansion) and/or positive and negative modulation of cellular immune responses, e.g., of lymphocytes (T and/or B cells), NK cells, or other cells. aAPCs may be used in vitro, e.g., to activate and expand immune cells that are normally stimulated by or require antigen presentation (e.g., engagement of the TCR by antigen in an appropriate context, e.g., with provision of costimulatory signals by other cells) for maturation, proliferation, or acquisition of effector functions. aAPCs may be used, for example, for the in vitro stimulation of immune system cells that are to be administered to a subject. In some embodiments a composition comprises aAPC and immune cells to be stimulated. In some embodiments the composition further comprises at least one cytokine (e.g., IL-2, IL-7, IL-12, IL-15, IL-21), anti-CD3 monoclonal antibody such as OKT3, and/or anti-CD28 monoclonal antibody. In some embodiments the composition does not comprise anti-CD3 and/or anti-CD28 antibodies. In some embodiments, aAPCs are cultured in the presence of anti-CD3 monoclonal antibody such as OKT3, and/or anti-CD28 monoclonal antibody prior to contacting them with immune cells to be stimulated and are subsequently cultured in the presence of cells to be stimulated, optionally in the absence of anti-CD3 and/or anti-CD28 antibodies. In some embodiments, the culture does not comprise further comprise feeder cells (other than the aAPCs and/or such cells as may be incidentally present in a population of cells to be stimulated by the aAPCs and may act as feeder cells, i.e., cells are not added specifically to act as feeder cells). In some embodiments, aAPC that express an antigen to which a BCR, TCR, or CAR binds is used to stimulate the cells to cause them to proliferate and/or become activated in vitro. In some embodiments aAPC are used in vivo. For example, in some embodiments aAPC are administered to a subject, e.g., to stimulate endogenous immune system cells or immune system cells administered to the subject (or their descendants).

In some embodiments cells comprise phagocytic cells. Phagocytic cells may be professional or non-professional phagocytes. Professional phagocytes include macrophages, monocytes, dendritic cells, mast cells, and neutrophils.

In some embodiments cells comprise adult stem cells. Adult stem cells are undifferentiated cells that exist in post-natal, e.g., adult, organisms and are capable of giving rise to multiple different cell types. Adult stem cells may be characterized by self-renewal (the ability to go through numerous cycles of cell division giving rise to daughter cells at least one of which maintains an undifferentiated state) and multipotency or multidifferentiation potential, i.e., the ability to give rise to descendants of multiple distinct cell types. An adult stem cell may have multilineage potential and/or may be capable of generating all the cell types of the organ or tissue from which it originates, potentially regenerating an entire organ from a few cells. Adult stem cells may undergo symmetric division, which gives rise to two identical daughter cells, both endowed with stem cell properties or asymmetric division, which produces one stem cell and a progenitor cell with more limited self-renewal potential. Progenitor cells can go through at least one round of cell division, typically several rounds of cell division, before differentiating into a mature cell. Examples of adult stem cells include, e.g., hematopoietic stem cells, neural stem cells, endothelial stem cells, intestinal stem cells, mammary stem cells, mesenchymal stem cells, neural crest stem cells. Adult stem cells may be further differentiated using appropriate protocols known in the art. In some embodiments cells comprise or consist of gametes (egg or sperm cells) or germ cells. In some embodiments cells comprise pluripotent cells, e.g., embryonic stem cells. In some embodiments mesenchymal stem cells (MSCs) comprise adherent non-hematopoietic bone marrow-derived stem cells. In some embodiments MSC may be characterized by: plastic adherence, maintenance of tri-lineage (osteogenic, adipocytic, and chondroblastic differentiation potential after in vitro propagation), and lack of the hematopoietic markers CD45, CD34, CD14, CD11b, CD79-a, CD19, and HLA-DR, and simultaneous expression of the surface molecules CD73, CD90, and CD105 on at least 95% of the population (Dominici M et al., (2006) Minimal criteria for defining multipotent mesenchymal stromal cells. The International Society for Cellular Therapy position statement. Cytotherapy 8:315-317).

In some embodiments cells may be generated in vitro by reprogramming a somatic cell to a less differentiated state or by reprogramming a somatic cell from a first differentiated state to a second differentiated state (sometimes termed "transdifferentiation"). In some embodiments reprogramming comprises reprogramming a cell to a multipotent or pluripotent state. In some embodiments a reprogrammed cell is an induced pluripotent stem (iPS) cell. In some embodiments an iPS cell may be generated by causing the cell to express or contain one or more genetic factors ("reprogramming factors"). Suitable combinations of reprogramming factors are known in the art. In some embodiments reprogramming factors include one or more factor selected from Oct4, Sox2, Klf4, Nanog, Lin28, and c-Myc. Examples of suitable combinations include, e.g., (1) Oct4, Klf4, Sox2, and optionally c-Myc; (2) Oct4, Sox2, Nanog and Lin28; (3) Oct4, Esrrb, Nanog; (4) Sox2, Sal14, Nanog; (5) Lin28, Sal14, Esrrb, Nanog; (6) Lin28, Sal14, Esrrb, Nanog. Nanog may be replaced by Dppa2. A variety of small molecules that enhance reprogramming and/or substitute for or induce expression of one or more reprogramming factors are known and may be used in various embodiments. Such molecules may, e.g., activate or inhibit one or more signaling pathways or may cause alterations in chromatin structure. In some embodiments a somatic cell to be reprogrammed is a fibroblast, keratinocyte, or hematopoietic cell. In some embodiments a somatic cell is reprogrammed using Oct4 and at least one small molecule. In some embodiments nucleic acid(s) encoding one or more reprogramming factors operably linked to regulatory elements capable of directing transcription is introduced into cells using a viral vector, e.g., a retroviral vector. A copy of the coding sequence(s) may integrate into the genome. In some embodiments such nucleic acid is subsequently at least partially excised from reprogrammed cells. In some embodiments reprogramming is performed using a method that does not involve altering the genome of a cell. For example, translatable RNA encoding one or more reprogramming factors may be introduced into the cell and/or a cell may be contacted with one or more small molecules that promote reprogramming. In some embodiments translatable RNA may be synthetic modified RNA. Methods that may be used for reprogramming using synthetic modified RNA are described, e.g., in PCT/US2011/032679 (WO2011130624) and/or in Mandal P K, Rossi D J. Reprogramming human fibroblasts to pluripotency using modified mRNA. Nat Protoc. 2013; 8(3):568-82. In some embodiments, reprogramming mammalian somatic cells may comprise stressing the cells by, e.g., transient exposure to chemical or physical stimuli such as low-pH conditions (e.g., about pH 5.7). The cells may thereby be stimulated to undergo stimulus-triggered acquisition of pluripotency (STAP), and cell lines comprising pluripotent cells may be derived under appropriate conditions (see, e.g., Obokata, H., et al., Stimulus-triggered fate conversion of somatic cells into pluripotency. Nature, 2014; 505 (7485): 641-647; and Obokata, H., et al., Bidirectional developmental potential in reprogrammed cells with acquired pluripotency. Nature, 2014; 505 (7485): 676-680). In some embodiments lymphocytes are reprogrammed via STAP. In some embodiments the reprogramming does not entail introducing exogenous nucleic acids or proteins into the cells. In some embodiments a cell that has been reprogrammed to a less differentiated state, e.g., to pluripotency is induced to differentiate into one or more selected cell types or along one or more selected cell lineages. For example, a pluripotent cell may be induced to have properties of an adult stem cell. Such cells may be further differentiated using appropriate protocols known in the art. Adult stem cells or cells differentiated therefrom may be sortagged as described herein. In some embodiments, for example, pluripotent cells generated from somatic cells may be reprogrammed to hematopoietic cells, e.g., immune system cells, e.g., T cells, B cells, NK cells.

Cells may be cultured in any suitable cell culture vessel or using any suitable cell culture system. In some embodiments plates (e.g., multiwell plates) or flasks, e.g., conventional tissue culture plasticware, may be used. A cell culture system may comprise means for regulating oxygen and/or carbon dioxide concentration, pH, or other cell culture relevant parameters. In some embodiments a cell culture system, sometimes termed a cell bioreactor, that provides mechanical rocking or stirring or pumping (e.g., sparging) to perfuse media with gas or that provides continuous or intermittent media flow or exchange may be used. The use of such systems may enhance cell expansion, which may result in higher cell densities than typically attained using conventional plasticware. A variety of cell culture systems (e.g., hollow fiber bioreactors, stirred tank bioreactors, bags, etc.) useful for culturing cells are known in the art. In some embodiments a gas-permeable bag or vessel comprising a gas-permeable membrane, e.g., a silicone membrane, may be used. In some embodiments Vuelife™ bags (Cellgenix, Freiburg, Germany), a WAVE Bioreactor™ system (GE Health, Uppsala, Sweden), BIOSTAT® CultiBag RM system (Sartorius Stedim Biotech, Göttingen, Germany), or G-Rex system (Wilson Wolf Manufacturing, New Brighton, Minn.), or system employing similar technology, may be used. In some embodiments, for example, a cell culture system may comprise a cell culture vessel comprising a gas-permeable cultureware flask in which $O_2$ and $CO_2$ are exchanged across a gas-permeable membrane at the base of the flask. In some embodiments a cell culture vessel may have a volume or recommended media volume of, e.g., up to 5 ml, 10 ml, 15 ml, 20 ml, 25 ml, 30 ml, 40 ml, 50 ml, 75 ml, 100 ml, 200 ml, 300 ml, 400 ml, 500 ml, 750 ml, or 1,000 ml. In some embodiments a cell culture vessel may have a volume or recommended media volume of more 1 liter (l), e.g., up to 1.5, 2.0, 2.5, 3.0, 4.5, 5.0 liters, or more. In some embodiments a selected number of cells may be cultured produced in a single culture vessel or system or in some embodiments using multiple culture vessels or systems. In some embodiments a selected number of cells may be cultured produced without need for stirring. In some embodiments a selected number of cells may be cultured produced without need for medium change, or with only 1, 2, 3 medium changes. In some embodiments a selected number of cells may be, e.g., up to about $10^{14}$ cells, e.g., about $10^3$, $10^4$, $10^5$, $10^6$, $10^7$, $10^8$, $10^9$, $10^{10}$, $10^{11}$, $10^{12}$, $10^{13}$ or $10^{14}$ cells, or any intervening range, e.g., between about $10^5$ and about $10^{12}$ cells, between about $10^6$ and about $10^{11}$ cells, between about $10^7$ and about $10^{10}$ cells. In some embodiments between about $10^5$-$10^8$ cells and about $10^{11}$-$10^{13}$ cells are cultured or produced. In some embodiments a system allows for medium changes without removing a lid. In some embodiments cell culture is performed under aseptic conditions. In some embodiments cells may be cultured on microcarriers.

In some embodiments cells are obtained, e.g., from a subject, and expanded in vitro. Cell "expansion" refers to an increase in the number of cells. In some embodiments cells are cultured for between about 48 hours and about 12 weeks, e.g., between 2 and 6 weeks. In some embodiments the number of cells is increased by a factor of at least 2, e.g., between 2 and 100, between 100 and 500, between 500 and 1,000, between 1,000 and 5,000, between 5,000 and 10,000, between 10,000 and 50,000, between 50,000 and 100,000, or more, relative to the number of cells in an initial sample or culture. In some embodiments expanded cells substantially retain or exhibit a particular phenotype, functional activity, or cell surface marker profile of interest. In some embodiments an expanded culture may be subjected to sorting or separating or selection to enrich for cells having a selected phenotype, functional activity, or cell surface marker profile. In some embodiments an expanded culture may be characterized for a selected phenotype, functional activity, or cell surface marker profile.

Protocols and useful reagents and culture systems suitable for culturing and/or expanding a wide variety of cell types are known in the art. In some embodiments a cell culture medium, cell culture system, sortase preparation, sortase substrate, cell culture process, or sortagging process complies with Good Manufacturing Practices (GMP). In some embodiments a sortase preparation that is free or substantially free or essentially free of endotoxin may be used. In some aspects, the present disclosure provides GMP-compliant compositions comprising one or more cells that have an agent conjugated by sortase to a non-genetically engineered endogenous polypeptide expressed by the cell. In some embodiments cell culture, sortagging, or both, are performed under conditions appropriate to permit subsequent introduction of the sortagged cells into a human subject. In some embodiments a cell composition may be subjected to any one or more tests used in the art to assess suitability for administration to humans and/or for veterinary purposes. In some embodiments a cell composition satisfies any one or more criteria used in the art to assess suitability for administration to humans and/or for veterinary purposes. In some embodiments culture conditions include use of culture medium that is free or essentially free of serum, plasma, and/or cell and tissue-derived substances extracts. In some embodiments culture conditions may include absence of feeder cells. In some embodiments, if one or more such substance(s) or feeder cells is used, they have been appropriately tested to confirm that they are free of human pathogens and/or substances that would render them potentially unsafe or unsuitable for administration to human subjects. In some embodiments, if one or more such substance(s) or feeder cells is used, it is obtained from the same subject as that from which the cells are obtained or a subject to whom the cells are to be administered. In some embodiments one or more recombinantly produced proteins may be used. In some embodiments the composition comprises a chemically defined culture medium. Suitable culture medium may be obtained from a variety of commercial suppliers, e.g., Stemcell Technologies Inc. (Vancouver, BC, Canada), Life Technologies, Inc. (Carlsbad, Calif.), Lonza (Basel, Switzerland). For example, in some embodiments StemSpan medium may be used, e.g., to culture hematopoietic cells. In some embodiments AIM V® Medium may be used, e.g., to culture immune system cells such as lymphocytes, monocytes, dendritic cells, natural killer cells, PBMC, macrophages, etc. In some embodiments GIBCO OpTmizer™ CTS™ T-Cell Expansion Serum Free Medium (Life Technologies) is used, e.g., for culture of human T lymphocytes. In some embodiments X-VIVO™ medium (Lonza), e.g., X-VIVO™ 10, X-VIVO™ 15, or X-VIVO™ 20 is used, e.g., to culture immune system cells such as lymphocytes, monocytes, dendritic cells, natural killer cells, PBMC, macrophages, etc. In some embodiments RPMI, DME, or DMEM may be used. One of ordinary skill in the art will be aware of suitable culture media for cell types of interest.

As used herein, a composition may be considered "free" of a particular material or substance if the material or substance is not deliberately added to or known to be present in the composition and/or is undetectable using standard methods used in the art for detection of such material or substance and/or if the composition has been prepared under conditions accepted in the art as sufficient to achieve absence of the material or substance. In some embodiments a composition may be substantially free or essentially free of any one or more materials or substances. In some embodiments "essentially free" refers to a concentration of no more than 0.1%. 0.05%, 0.01%, 0.005%, 0.001%, 0.0005% of such material or substance by weight (e.g., dry weight), volume, or by moles. In some embodiments "substantially free" refers to 1% or less, e.g., 0.5% or less, e.g., 0.2% or less of such material or substance by weight (e.g., dry weight), volume, or by moles. In some embodiments a composition is considered substantially free of a material or substance, e.g., an adjuvant, if the component or substance is not detectable using a standard detection method used in the art for detecting such material or substance. In some embodiments a composition is prepared without deliberately including a substance, e.g., an adjuvant. In some embodiments a composition is prepared without deliberately including an adjuvant in an amount that would be effective to enhance an immune response when the composition is contacted with cells in vitro or in vivo.

In some embodiments cells cultured or sortagged in the composition satisfy regulatory requirements for administration to a human subject. In some embodiments cells cultured or sortagged in the composition satisfy regulatory requirements of a government agency such as the US Food and Drug Administration, European Medicines Evaluation Agency, or a similar agency responsible for evaluating the safety of therapeutic agents prior to their administration to humans or being placed on the market for administration to humans. In some embodiments cells are washed or otherwise processed to remove media components after sortagging, e.g., prior to administration to a subject. In some embodiments a composition is tested and determined to be free of pathogens that may infect humans. In some embodiments a test may utilize PCR or a biological assay for presence of a particular pathogen.

Methods for culturing, expanding, and, in some embodiments, activating, cells of various types are known in the art. For example, T cells may be expanded and activated using antibodies that bind to CD3 (e.g., Muromonab-CD, also known as Orthoclone OKT3, "OKT3"), optionally in combination with one or more cytokines such as IL-2. In some embodiments immune system cells may be exposed to costimulatory signals provided by soluble, surface-bound, or cell-bound (e.g., APC-bound) costimulatory molecules, such as CD28, for example. In some embodiments immune system cells may be contacted in vitro with an antigen or epitope, optionally in association with an MHC protein. Hematopoietic stem cells may be culturing and/or expanded as described, e.g., in US Pat. Pub. Nos. 20110117061; 20110136230; and/or 20110196343. Such cells may be differentiated along various hematopoietic lineages if desired.

Examples of systems and/or protocols that may in various embodiments be used to culture, and, in some embodiments, expand and/or activate, cells are described in PCT/US2002/028161 (WO/2003/024989); PCT/US2004/001349 (WO/2004/065590); PCT/US2008/062687 (WO/2009/136907); PCT/US2009/049944 (WO/2010/006055); PCT/US2010/046505 (WO/2011/028531); PCT/NL2006/000319 (WO/2007/001173); PCT/US2010/061706 (WO/2011/079165); PCT/EP2012/063034 (WO/2013/007574); PCT/SE2010/050333 (WO/2010/110734); Digiusto, D L and Cooper, L J N, Cytotherapy. 2007; 9(7):613-29; Sutlu, T., et al., Cytotherapy. 2010 December; 12(8):1044-55; Spanholtz J, et al., PLoS One. 2011; 6(6):e20740. doi: 10.1371/journal.pone.0020740, Levine, B. et al., J Hematother. (1998) 7(5): 437-48; Tumaini, Cytotherapy. 2013; 15(11):1406-15, and references in any of the foregoing).

In some embodiments cells are separated into two or more groups prior to sortagging, and only one or some (but not all) of the groups are subjected to a sortagging process. For example, in some embodiments cells of a particular cell type may be selected for sortagging from a starting population comprising cells of multiple types. Cells of other types that may be present in the starting population may, for example, be used for other purposes, stored (e.g., cryopreserved), discarded, or subsequently combined with sortagged cells. Cells may be selected based on any one or more properties. A property may be any phenotypic characteristic of a cell, cell type, or cell state, e.g., any characteristic that may be observed or detected, or any combination of such characteristics. Examples include, e.g., morphologic characteristics; physical, biochemical, or physiological properties; biological behavior, the presence, absence, or level of gene expression products such as RNA or proteins. In some embodiments a phenotypic characteristic is quantifiable. In some embodiments cells may be separated based on size, light scattering, density, binding affinity for one or more substances, expression of at least one gene as assessed, e.g., by the level of a gene product of the gene.

Any suitable separation method(s) may be used. Multiple steps of selection or separation may be used. In some embodiments selection comprises at least one positive selection, wherein desired cells are retained or enriched for based on one or more properties of the cells of interest (wanted cells; desired cells), e.g., using a binding agent that binds to cells of interest. In some embodiments selection may comprise at least one negative selection, wherein cells that are not of interest (unwanted cells; undesired cells) are removed or depleted based on one or more properties of the unwanted cells (e.g., using a binding agent that binds to unwanted cells). Examples of useful separation methods include centrifugation, elutriation, contacting with an affinity resin (e.g., beads) that retains or removes unwanted cells, flow cytometry, fluorescence activated cell sorting (e.g., after contacting the cells with appropriately labeled reagents that bind to cell surface markers characteristic of cells whose removal or retention is desired).

In some embodiments cells having a particular cell surface marker expression profile are selected or removed. A cell surface marker expression profile may comprise presence, absence, and/or level of any one or more cell surface markers. Cell surface marker expression profiles characteristic of many different cell types or cell subsets having various functional characteristics of interest are known in the art. In some embodiments a cell surface marker comprises a cluster of differentiation (CD) molecule. In some embodiments an antibody-based enrichment procedure is used, which may be combined with columns, magnet-based separation, and/or centrifugation. In some embodiments magnetic particles (particles, whether or not magnetic, are sometimes termed "beads") may be used. Examples of such particles include those known as Dyabeads (Life Technologies, Carlsbad, Calif.), MACS microbeads (Miltenyi Biotech, Auburn, Calif.). In some embodiments, cells in a single-cell suspension are magnetically labeled with beads that have an appropriate binding agent (e.g., an antibody) attached thereto. The sample is applied to a column placed in a magnetic separator. The unlabeled cells pass through while the magnetically labeled cells are retained within the column. The flow-through can be collected as the unlabeled cell fraction. The column may be washed and removed from the separator, and the magnetically labeled cells eluted from the column. Thus both labeled and unlabeled cells can be isolated if desired. In some embodiments beads may have any appropriate dimensions, e.g., diameter, volume. In some embodiments desired cells are obtained without using columns, without using magnets, and/or without labeling desired cells with a binding reagent such as an antibody. For example, whole blood may be contacted with antibody complexes that comprise two or more antibodies to antigen(s) expressed at the surface of red blood cells but not expressed at the surface of desired cells and one or more antibodies to antigen(s) expressed at the surface of cells to be removed. In some embodiments a tetrameric antibody complex may be used. The antibody complexes crosslink undesired cells to red blood cells present in the whole blood, resulting in complexes (sometimes termed immunorosettes) that can be removed by centrifugation, e.g., over an appropriate density medium (e.g., Ficoll™). Centrifugation may be used to pellet the immunorosettes, thereby removing the unwanted cells along with red blood cells and leaving desired cells. The purified cells are present as an enriched population at the interface between the plasma and the buoyant density medium. Reagents suitable for performing such separation are commercially available. For example, RosetteSep® reagents or kits may be used (Stemcell Technologies) may be used. This technology utilizes tetrameric antibody complexes that crosslink unwanted cells to multiple red blood cells already present in the sample, forming immunorosettes. When centrifuged over the appropriate density medium (e.g. Ficoll), the unwanted (rosetted) cells pellet along with the red blood cells, leaving the desired cells untouched and highly enriched at the density medium:

plasma interface. RosetteSep™ may be used on its own with standard density gradient centrifugation or with a specialized cell processing tube (SepMate™). Suitable RBC antigens include, e.g., glycophorin, e.g., glycophorin A. In some embodiments isolation of desired cells from a mixed sample is performed using a procedure that takes no more than 30 minutes or no more than 60 minutes. In some embodiments separation may be performed at least in part using an automated system. For example, RoboSep™ (Stemcell Technologies) is an instrument that provides for automation of immunomagnetic cell separation performing the steps necessary to magnetically label and separate virtually cells of a selected cell type by positive or negative selection. In some embodiments a selection procedure may comprise culturing cells under selective conditions, wherein the selective conditions kill or inhibit proliferation of cells having certain characteristics that are not desired. In some embodiments selective conditions comprise culturing a cell population comprising multiple cell types in the absence of one or more factors required for survival or proliferation of unwanted cells.

In some embodiments mammalian cells may be assessed for immunocompatibility with a subject to whom they are to be administered. Cells may be deemed immunocompatible if they are unlikely to provoke a significant immune response in a subject to whom they are administered, e.g., an immune response that would materially reduce the viability and/or functional activity of the cells or produce excessive symptoms in a subject. In some embodiments immunocompatibility comprises histocompatibility. Histocompatibility may be assessed using any suitable method known in the art. In some embodiments histocompatibility testing comprises determining whether a potential recipient has antibodies to HLA antigens expressed by cells to be administered and/or whether a potential recipient has an HLA genotype that differs from that of the cells to a sufficient extent as to be deemed incompatible (e.g., likely to be or at risk of being subject to attack by the recipient's immune system) as reasonably determined by one of ordinary skill in the art. In some embodiments cells to be administered to a human subject are tested to determine their HLA-A, HLA-B, HLA-C, HLA-DP, HLA-DQ, and/or HLA-DR genotype and/or a sample from a subject is tested to determine whether it contains antibodies to MHC Class I and/or MHC Class II antigens of cells to be administered to the subject. In some embodiments cells are deemed histocompatible for administration to a subject if they have at least the same HLA-A, HLA-B, and HLA-DR alleles as the subject's cells and/or if the subject's blood does not harbor antibodies to MHC molecules expressed by the cells. Methods of testing for histocompatibility include, e.g., screening for preformed alloreactive antibodies using complement-dependent cytotoxicity assays (CDC) which detects complement-activating IgG1/3 and IgM antibodies using a panel of HLA-typed lymphocytes to identify reactive antibodies, solid-phase methods such as ELISA, and flow cytometry-based techniques (using classical flow cytometry or Luminex). For example, Luminex-based antibody screening technology uses purified HLA antigens immobilized on a panel of microbeads. These HLA molecules on the microbeads are targets for HLA-specific antibodies in a given sample. Anti-HLA antibodies of the IgG isotypes which are bound to the microbeads are detected by a secondary IgG-specific antibody which may conjugated with a label such as R-phycoerythrin (PE). Nucleic acid-based (e.g., DNA-based) tissue typing may be performed using, e.g., sequence-specific primers and/or sequence-specific probes (see, e.g., Dunckley H. HLA typing by SSO and SSP methods. Methods Mol Biol. 2012; 882:9-25). Primers may be used to amplify relevant sequences, e.g., using PCR. Probes may be attached to oligonucleotide arrays or beads. In some embodiments sequencing, e.g., high throughput sequencing, may be used for genotyping. In some embodiments techniques generating low-resolution (i.e. 2-digits HLA nomenclature) results or high-resolution (i.e. at least 4-digits HLA nomenclature) results may be used. Intermediate HLA resolution comprises a 2-digits HLA nomenclature with supplemental characters to define groups of HLA alleles. In general, an HLA typing resolution and/or degree of HLA matching at a level relevant for different clinical applications may be used.

In some embodiments immunocompatible red blood cells are of the same blood group as an individual to whom such cells are to be administered (e.g., at least with respect to the ABO blood type system and, in some embodiments, with respect to the D blood group system) or may be of a compatible blood group. For example, in some embodiments type O Rh D negative blood may be administered to an individual of any ABO blood group (i.e., A, B, O or AB), and persons with type O RhD negative blood may be considered "universal donors". Methods for determining blood groups are well known in the art. In some embodiments red blood cells are cross-matched with a potential recipient of the cells. Cross-matching may comprise mixing a sample of the recipient's serum, plasma, or blood with a sample of the red blood cells to potentially be administered and checking if the mixture agglutinates. If agglutination is not observed, the RBCs may be considered to match the recipient.

In some embodiments a eukaryotic cell that comprises a sortagged, endogenous, non-genetically engineered polypeptide is a genetically engineered cell. In some embodiments the cell has not been genetically engineered for sortagging. In some embodiments the cell has been genetically engineered before being sortagged. In general, the cell may be any genetically engineered eukaryotic cell. The cell may be a mammalian cell, fungal cell, insect cell, protozoal cell, or other eukaryotic cell. The cell may be of any cell type, e.g., any cell type described herein. For example, in some embodiments the genetically engineered cell is an immune system cell, e.g., a T cell, B cell, NK cell, dendritic cell, monocyte, or macrophage. In general the cell may be genetically engineered for any purpose, in any way, and using any method known in the art. A genetically engineered cell may comprise multiple genetic alterations of any one or more type(s), e.g., one or more insertions into genomic DNA, one or more deletions of genomic DNA, or both. A polypeptide or noncoding RNA encoded at least in part by exogenous DNA integrated into the genome of a cell or encoded by an endogenous gene whose sequence has been modified by genetic engineering may be referred to as a "recombinant gene product".

In general, genetic engineering comprises introducing one or more exogenous nucleic acids into a cell. Nucleic acids can be introduced into cells using transfection (e.g., using any of a variety of transfection reagents), electroporation, virus-mediated nucleic acid transfer, etc. One of ordinary skill in the art will select appropriate methods, vectors, expression control elements, etc., to achieve desired alterations in the genome of a cell and/or to achieve expression of desired proteins and/or RNAs. For example, if a virus is used as a vector, an appropriate method may comprise contacting a mammalian cell with the virus under conditions appropriate for the virus to enter the cell. It will be understood that, depending on factors such as the vector and the particular method, a nucleic acid introduced into a cell may be at least in part copied or reverse transcribed, and such copy or a portion thereof may be inserted into the genome. It will also be understood that use of the term "inserted" is not intended to imply or require any particular mechanism and encompasses processes mediated by retroviral integrase, homologous or non-homologous recombination, creation of breaks in genomic DNA that are repaired by endogenous DNA repair mechanisms, or any other process that results in addition of one or more nucleotides to the genome of a cell or substitution of one or more nucleotides by a different nucleotide in the genome of a cell.

In some embodiments, a cell is genetically modified using a nuclease that is targeted to one or more selected DNA sequences. Such methods may be used to induce precise cleavage at selected sites in endogenous genomic loci. Genetic engineering in which DNA is inserted, replaced, or removed from a genome, e.g., at a defined location of interest, using targetable nucleases, may be referred to as "genome editing". Examples of such nucleases include zinc-finger nucleases (ZFNs), Transcription activator-like effector nuclease (TALENs), engineered meganuclease homing endonucleases, and RNA directed nucleases such as CRISPR (clustered regularly interspaced short palindromic repeats)-associated (Cas) nucleases, e.g., derived from type II bacterial CRISPR/Cas systems (e.g., Cas9).

In some embodiments the nuclease comprises a DNA cleavage domain and a DNA binding domain (DBD) that targets the nuclease to a particular DNA sequence, thereby allowing the nuclease to be used to engineer genomic alterations in a sequence-specific manner. The DNA cleavage domain may create a double-stranded break (DSB) or nick at or near the sequence to which it is targeted. ZFNs comprise DBDs selected or designed based on DBDs of zinc finger (ZF) proteins. DBDs of ZF proteins bind DNA in a sequence-specific manner through one or more zinc fingers, which are regions of amino acid sequence whose structure is stabilized through coordination of a zinc ion. TALENs comprise DBDs selected or designed based on DBDs of transcription activator-like (TAL) effectors (TALEs) of *Xanthomonas* spp. ZFN or TALEN dimers induce targeted DNA DSBs that stimulate DNA damage response pathways. The binding specificity of the designed zinc-finger domain directs the ZFN to a specific genomic site. TALEs contain multiple 33-35-amino-acid repeat domains, each of which recognizes a single base pair. Like ZFNs, TALENs induce targeted DSBs that activate DNA damage response pathways and enable custom alterations. The DNA cleavage domain of an engineered site-specific nuclease may comprise a catalytic domain from a naturally occurring endonuclease such as the Fok1 endonuclease or a variant thereof. In some embodiments FokI cleavage domain variants with mutations designed to improve cleavage specificity and/or cleavage activity may be used (see, e.g., Guo, J., et al. (2010) Journal of Molecular Biology 400 (1): 96-107; Doyon, Y., et al., (2011) Nature Methods 8: 74-79. Meganucleases are sequence-specific endonucleases characterized by a large recognition site (double-stranded DNA sequences of 12 to about 40 base pairs). The site generally occurs no more than once in a given genome. The specificity of a meganuclease can be changed by introducing changes sequence of the nuclease (e.g., in the DNA binding domain) and then selecting functional enzymes capable of cleaving variants of the natural recognition site or by associating or fusing protein domains from different nucleases.

In some embodiments, an RNA directed nuclease may be used to perform genome editing. For example, the use of CRISPR/Cas-based systems is contemplated. In some embodiments a Cas nuclease, such as Cas9 (e.g., Cas9 of *Streptococcus pyogenes, Streptococcus thermophiles*, or *Neisseria meningiditis*, or a variant thereof), is introduced into cells along with a guide RNA comprising a sequence complementary to a sequence of interest (the RNA is sometimes termed a single guide RNA). The region of complementarity may be, e.g., about 20 nucleotides long. The Cas nuclease, e.g., Cas9, is guided to a particular DNA sequence of interest by the guide RNA. The guide RNA may be engineered to have complementarity to a target sequence of interest in the genome, e.g., a sequence in any gene or intergenic region of interest. The nuclease activity of the Cas protein, e.g., Cas9, cleaves the DNA, which can disable the gene, or cut it apart, allowing a different DNA sequence to be inserted. In some embodiments multiple sgRNAs comprising sequences complementary to different genes, e.g., 2, 3, 4, 5, or more genes, are introduced into the same cell sequentially or together. In some embodiments alterations in multiple genes may thereby be generated in the same step.

In general, use of nuclease-based systems for genetic engineering, e.g., genome editing, entails introducing a nuclease into cells and maintaining the cells under conditions and for a time appropriate for the nuclease to cleave the cell's DNA. In the case of CRISP/Cas systems, a guide RNA is also introduced. The nuclease is typically introduced into the cell by introducing a nucleic acid encoding the nuclease. The nucleic acid may be operably linked to a promoter capable of directing expression in the cell and may be introduced into the cell in a plasmid or other vector. In some embodiments mRNA encoding the nuclease may be introduced. In some embodiments the nuclease itself may be introduced. sgRNA may be introduced directly (by methods such as transfection) or by expressing it from a nucleic acid construct such as an expression vector. In some embodiments a sgRNA and Cas protein are expressed from a single expression vector that has been introduced into the cell or, in some embodiments, from different expression vectors. In some embodiments multiple sgRNAs comprising sequences complementary to different genes, e.g., 2, 3, 4, 5, or more genes, are introduced into the same cell individually or together as RNA or by introducing one or more nucleic acid constructs encoding the sgRNAs into the cell for intracellular transcription.

Upon cleavage by a nuclease, a target locus (e.g., in the genome of a cell) may undergo one of two major pathways for DNA damage repair, namely non-homologous end joining (NHEJ) or homology-directed repair (HDR). In the absence of a suitable repair template comprising sufficient homology to the sequences flanking the cleavage site to stimulate HDR (see discussion below), DSBs are re-ligated through NHEJ, which can result in an insertion or deletion. NHEJ can be used, for example, to engineer gene knockouts or generate proteins with altered activity. For example, an insertion or deletion in an exon can lead to a frameshift mutation or premature stop codon. Two or more DSBs can be generated in order to produce larger deletions in the genome.

In some embodiments a nucleic acid (e.g., a plasmid or linear DNA) comprising a sequence of interest to be inserted into the genome at the location of cleavage is introduced into a cell in addition to a nuclease. In some embodiments a sequence of interest is inserted into a gene. The sequence of interest may at least in part replace the gene. In some embodiments the nucleic acid comprises sequences that are homologous to the sequences flanking the cleavage site, so that homology-directed repair is stimulated. In some embodiments the nucleic acid contains a desired alteration as compared to a sequence present in the cell's genome at or near the site of cleavage. A nucleic acid comprising a sequence to be at least in part introduced into the genome, e.g., a nucleic acid sequence comprising homologous sequence(s) and a desired alteration may be referred to as a "donor sequence". The donor sequence may become at least in part physically into integrated the genome at the site of a break or may be used as a template for repair of the break, resulting in the introduction of all or part of the nucleotide sequence present in the donor into the genome of the cell. Thus, a sequence in a cell's genome can be altered and, in certain embodiments, can be converted into a sequence present in a donor nucleic acid. In some embodiments the donor sequence may be contained in a circular DNA (e.g. a plasmid), a linear double-stranded DNA (e.g., a linearized plasmid or a PCR product), or single-stranded DNA, e.g., a single-stranded oligonucleotide. In some embodiments the donor sequence has between about 10-25 bp and about 50-100 bp of homology to either side or each side of the target site in the genome. In some embodiments a longer homologous sequence may be used, e.g., between about 100-500 bp up to about 1-2 kB, or more. In some embodiments an alteration is introduced into one allele of a gene. In some embodiments a first alteration is introduced into one allele of a gene, and a different alteration is introduced into the other allele. In some embodiments the same alteration is introduced into both alleles. In some embodiments two alleles or target sites (or more) may be genetically modified in a single step. In some embodiments two alleles or target sites (or more) may be genetically modified in separate steps.

Methods of designing, generating and using ZFNs and/or TALENs are described in, e.g., WO2011097036; Urnov, F D, et al., Nature Reviews Genetics (2010), 11: 636-646; Miller J C, et al., Nat Biotechnol. (2011) 29(2):143-8; Cermak, T., et al. Nucleic Acids Research (2011) 39 (12): e82, Sanjana, N. E. et al. A transcription activator-like effector toolbox for genome engineering. Nat Protoc 7, 171-192 (2012) and references in any of the foregoing. ZFN, TALEN, and CRISPR/Cas-based methods for genome engineering are reviewed in Gaj, T., et al., Trends Biotechnol. 2013 July; 31(7):397-405. Epub 2013 May 9. Use of CRISPR/Cas systems in genome engineering is described in, e.g., Cong L, et al. Multiplex genome engineering using CRISPR/Cas systems. Science. 2013; 339(6121):819-23; Mali P, et al., RNA-guided human genome engineering via Cas9. Science. 2013; 339(6121):823-6; Wang, H. et al. One-step generation of mice carrying mutations in multiple genes by CRISPR/Cas-mediated genome engineering. Cell 153, 910-918 (2013); Ran, F. A. et al. Double Nicking by RNA-Guided CRISPR Cas9 for Enhanced Genome Editing Specificity. Cell 154, 1380-1389 (2013); Mali, P., et al., Nat Methods. 2013; 10(10):957-63; Ran, F A, Nat Protoc. 2013; 8(11):2281-308). In some embodiments a nuclease that cleaves only one strand of dsDNA (a nickase) may be used to stimulate HDR without activating the NHEJ repair pathway. Nickases may be created by inactivating the catalytic activity of one nuclease monomer in the ZFN or TALEN dimer required for double stranded cleavage or inactivating a catalytic domain of a Cas protein. For example, mutations of one of the catalytic residues (D10 in the RuvC nuclease domain and H840 in the HNH nuclease domain), e.g., to alanines (D10A, H840A) convert Cas9 into DNA nickases.

In some embodiments, a CRISP/Cas based system may be used to modulate gene expression. For example, coexpression of a guide RNA with a catalytically inactive Cas9 lacking endonuclease activity generates a DNA recognition complex that can specifically interfere with transcriptional elongation, RNA polymerase binding, or transcription factor binding. This system, sometimes referred to CRISPR interference (CRISPRi), can efficiently repress expression of targeted genes in mammalian cells (Qi, S., et al., Cell. 2013; 152(5):1173-83; Larson, M H, et al., Nat Protoc. 2013; 8(10:2180-96). By attaching any of a variety of effector domains to a catalytically inactive Cas9 one can create a chimeric Cas9 protein that can be used to achieve sequence-specific control over gene expression and/or DNA modification. Suitable effector domains include, e.g., a transcriptional activation domain (such as those comprising the VP16 transactivation domain, e.g., VP64), a transcriptional coactivation domain, a transcriptional inhibitory or co-inhibitory domain, a protein-protein interaction domain, an enzymatic domain, etc. A guide RNA guides the chimeric Cas9 protein to a site of interest in the genome (e.g., in or near an expression control element such as a promoter), whereby the effector domain exerts an effect such as activating or inhibiting transcriptional activity (see, e.g., Gilbert L A, et al., Cell. 2013; 154(2):442-51; Maeder M L, et al., Nat Methods. 2013; 10(10):977-9). Appropriate effector domains may be any of those present in naturally occurring proteins that are capable of performing the function of interest (e.g., inhibiting or activating transcription).

Cells that have been subjected to a genetic engineering process may be selected or analyzed to identify or isolate those that express a desired recombinant gene product or lack expression of an endogenous gene that has been disabled via genetic engineering or have any desired genetic alteration. For example, in some embodiments the donor sequence or vector used to deliver the donor sequence may comprise a selectable marker, which may be used to select cells that have incorporated at least a portion of the donor sequence comprising the selectable marker into their genome. In some embodiments selection is not used. In some embodiments cells may be screened, e.g., by Southern blot to identify those cells or clones that have a desired genetic alteration. If desired, cells may be tested for expression level or activity of a recombinant gene product or endogenous gene product or for one or more functional properties associated with or conferred by a recombinant or endogenous gene product, or any other criteria of interest. Suitable methods of analysis are known to those of ordinary skill in the art and include, e.g., Western blot, flow cytometry, FACS, immunofluorescence microscopy, ELISA assays, affinity-based methods in which cells are contacted with an agent capable of binding to a protein of interest that labels or retains cells that express the protein, etc. Functional assays may be selected based on the identity of the recombinant gene product, endogenous gene product, and/or function or property of interest. For example, a functional property may be ability to bind to an antigen of interest or ability to exert cytotoxicity towards target cells that express an antigen of interest. Cells may be analyzed, e.g., by PCR, Southern blotting, or sequencing, to determine the number of inserted DNA sequences, their location, and/or to determine whether desired genomic alterations have occurred. One or more cells that have desired alteration(s), expression level, and/or functional properties may be identified, propagated, expanded. The cells or their descendants may be used to generate a cell line, subjected to sortagging, and/or stored for future use.

In some embodiments, a genetically engineered cell comprises an exogenous DNA inserted into its genome. In some embodiments the exogenous DNA comprises a sequence that encodes a polypeptide or noncoding RNA. In some embodiments the DNA comprises a cDNA. An inserted exogenous DNA may encode one or more RNAs or polypeptides. In some embodiments, the genome comprises a single copy of an exogenous DNA. In some embodiments the genome comprises no more than 2, 3, or 4 copies. A cell may have 1, 2, 3, 4 or more distinct DNA sequences inserted into its genome. A sequence that encodes an RNA or polypeptide may be operably linked to appropriate expression control elements, e.g., at least a promoter, capable of directing transcription of the sequence. The expression control elements are typically part of the exogenous DNA integrated into the genome. Expression of a recombinant gene product may be constitutive or conditional (e.g., inducible, repressible, cell-type specific). A recombinant gene product may be any protein or RNA described herein. In some embodiments the protein is a secreted protein, a transmembrane protein, or an intracellular protein. In some embodiments a cell a recombinant gene product comprises a selectable marker (e.g., an optically detectable protein such as a fluorescent or luminescent protein or a protein that confers resistance to a drug), a therapeutic protein, a cytokine, a chemokine, a costimulator, a coinhibitor, a growth factor, a receptor, or an adhesion molecule. In certain embodiments the receptor is a chimeric antigen receptor, a T cell receptor, a B cell receptor, a cytokine receptor, a chemokine receptor, a costimulator, receptor, an adhesion molecule, or a fusion protein comprising two or more of the foregoing. In some embodiments a cell is genetically engineered to produce one, more than one, or all subunits of a multisubunit protein, e.g., a multisubunit cytokine or receptor. In some embodiments a cell is genetically engineered to express a noncoding RNA. A noncoding RNA may be, e.g., a short hairpin RNA (which may be processed intracellularly to produce siRNA), a siRNA, a microRNA precursor (which may be processed intracellularly to produce miRNA), a miRNA, or a long noncoding RNA. In some embodiments the noncoding RNA regulates expression of one or more genes, e.g., by affecting transcription, processing, stability, and/or translation of one or more pre-mRNAs or mRNAs. In some embodiments the noncoding RNA inhibits gene expression by the RNA interference (RNAi) pathway. By expressing an RNAi agent targeted towards a particular gene in a cell, expression of the gene can be stably inhibited. One of ordinary skill in the art will be able to select appropriate sequences for an RNAi agent in order to inhibit expression of a gene of interest.

The sequence of a recombinant gene product may be a naturally occurring sequence or may be at least in part created by man (non-naturally occurring) in various embodiments. In some embodiments, the sequence comprises or consists of a full length naturally occurring sequence (e.g., a polypeptide or RNA encoded in a eukaryotic genome) or a functional variant or fragment thereof. In some embodiments, the sequence comprises or consists of one or more functional domains of a naturally occurring eukaryotic polypeptide. In some embodiments the exogenous DNA comprises a chimeric protein. For example, in some embodiments, the sequence comprises or consists of multiple functional domains of different naturally occurring eukaryotic polypeptides. In some embodiments, the recombinant gene product comprises a sortase recognition sequence or a sequence capable of serving as a nucleophilic acceptor sequence in a sortase-catalyzed reaction. In some embodiments the recombinant gene product does not comprise a sortase recognition sequence or a sequence capable of serving as a nucleophilic acceptor sequence in a sortase-catalyzed reaction. In some embodiments, if a sortase recognition sequence or a sequence capable of serving as a nucleophilic acceptor sequence in a sortase-catalyzed reaction is present in a recombinant gene product, it is located in an intracellular or transmembrane domain or is otherwise not accessible to a sortase located outside the cell.

In some embodiments exogenous DNA is integrated into the genome of a mammalian cell, e.g., a human cell, at a "safe harbor" locus. A "safe harbor" locus is an intragenic or extragenic region of the genome (e.g., the human genome) that is generally able to accommodate the insertion of DNA without causing a significant detectable effect on the phenotype of host cell (other than the effect, if any, caused by expression of a recombinant gene product encoded by the inserted DNA) and that permits the transcription of inserted DNA comprising suitable expression control elements (e.g., a promoter). In some embodiments, a significant effect is a statistically significant change in the viability or proliferative capacity of the cell or the ability of the cell to perform a normal biological function. In some embodiments a safe harbor locus is the AAVSV1 (the natural integration site for the wild-type AAV on chromosome 19), ROSA26, or CCR5 locus. The locations of these loci are well known in the art. The AAVS1 site is in chromosome 19 (position 19q13.42) and integration in the AAVS1 locus may disrupt the gene phosphatase 1 regulatory subunit 12C (PPP1R12C). The human ROSA26 locus is in chromosome 3 (position 3p25.3). The human CCR5 gene is located on chromosome 3 (position 3p21.31). See US Pat. Pub, 20110239319 for a description of additional sites that may be used as safe harbor loci, methods of identifying safe harbor loci, and methods of inserting DNA into safe harbor loci. In some embodiments exogenous DNA is integrated into a site located at least 100 kB away from any known proto-oncogene or tumor suppressor gene.

In some embodiments a cell is genetically engineered to alter the expression or sequence of an endogenous gene. For example, in some embodiments a gene whose expression is not desired is disabled in the cell. As used herein, a gene is "disabled" in a cell if its expression is reduced to a level below that which is necessary for the cell to exhibit normal levels of one or more biological activities of the gene product or if the sequence of the encoded gene product is altered in a way that reduces the activity of the gene product to a level below that which is necessary for the cell to exhibit normal levels of one or more biological activities of the gene product. A gene may be disabled by at least partly deleting the gene, by introducing an insertion into the gene in an appropriate location, or by altering the gene so that the encoded gene product has reduced activity, e.g., by deleting or changing an active site residue or other functionally important residue. In some embodiments, precise alterations that introduce one or more substitutions, insertions, or deletions at a desired location are made. Such alterations may, for example change the sequence of an allele that causes or contributes to a disease to one that is not associated with the disease or may change the specificity of a receptor. Expression control elements may be inserted or modified to increase or decrease expression of a selected endogenous gene. In some embodiments the endogenous gene encodes a receptor, a transmembrane protein, a secreted protein, a costimulator, a coinhibitor, a cytokine, a chemokine, a growth factor, or an adhesion molecule. In some embodiments an endogenous gene that is disabled may encode a gene product that mediates immunosuppressive extracellular signals (e.g., receptors for cytokines that may exert immunosuppressive effects, such as IL-10 or TGF-beta) or contributes to T cell exhaustion. T cell exhaustion is a state of T cell dysfunction that arises during many chronic infections and cancer. It is defined by poor effector function, sustained expression of inhibitory receptors and a transcriptional state distinct from that of functional effector or memory T cells (reviewed in Wherry, E J, Nature Immunology, 2011; 12(6): 492-9). T cell exhaustion can be promoted by a variety of cell surface inhibitory receptors such as PD-1, LAG-3, CD244 (2B4), CD160, TIM-3, and/or CTLA-4. In some embodiments inhibiting one or more such receptors, e.g., by disabling one or more genes that encode such receptors, may reduce the likelihood that a T cell will become exhausted. In some embodiments an endogenous gene that is disabled may encode a gene product that mediates effects of a toxic substance such as a pro-apoptotic agent, a cytolytic agent, a cytotoxic drug, or a toxin. For example, the endogenous gene may encode a receptor for the toxic substance. Disabling the endogenous gene may reduce the susceptibility of the cell to the substance relative to a cell in which the endogenous gene is expressed or functional.

As discussed herein, certain embodiments relate to sortagged mammalian immune system cells that are capable of mounting an immune response towards target cells that are recognized by the sortagged immune system cells. For example, certain embodiments relate to sortagged mammalian immune system cells that comprise a binding moiety that binds to an antigen expressed by target cells. In some embodiments, such sortagged immune system cells have cytotoxic activity towards target cells. The cells may, for example, be CD8+ T cells or NK cells. In some embodiments such cells are not genetically engineered.

In some embodiments immune system cells are genetically modified to express a recombinant gene product that binds to an antigen of interest, e.g., an antigen expressed by target cells. For example, in some embodiments a recombinant gene product comprises a chimeric antigen receptor that binds to a particular antigen of interest. The cells may, in addition, be sortagged with any of the various agents described herein. In some embodiments a recombinant gene product comprises a TCR chain that binds to a particular antigen of interest. The TCR chain(s) may originate from a T cell with high affinity for a selected antigen. The T cell may originate from a human or from a non-human mammal (e.g., following immunization with the antigen or a portion thereof). The non-human mammal may be genetically engineered to express human TCR genes (e.g., at least a TCR alpha and/or beta chain). T cells that bind to an antigen of interest may be identified, and their TCR genes may be isolated and, optionally, may be sequenced at least in part. Human TCR genes with a desired affinity to a selected antigen may alternately or additionally be identified using display technologies such as phage display. In some embodiments, an endogenous gene that encodes a TCR chain may be modified by introducing one or more alterations that cause the binding specificity of the endogenous TCR to be directed to an antigen of interest. For example, at least a portion of the variable domain of an endogenous TCR gene may be modified. In some embodiments one or more CDRs may be modified. Introducing genes encoding TCRalpha and TCRbeta chains that have affinity for a selected target antigen into the genome of a T cell or modifying endogenous TCR chains to confer or increase affinity for a selected target antigen creates a redirected T cell that is capable of recognizing and responding to the target antigen. In some embodiments one or more chains of an endogenous TCR gene may be disabled. Disabling an endogenous TCR may be useful, e.g., when a cell is engineered to express a CAR or when a gene encoding an exogenous TCR chain is introduced into a site other than the site of the corresponding endogenous TCR chain. Similar methods may be applied to TCR delta and gamma chains and/or BCR chains. Certain methods and compositions useful for introducing desired TCR genes into a known chromosomal locus (e.g., a safe harbor locus), altering endogenous TCR genes, and/or inactivating TCR genes using zinc finger nucleases (ZFNs) are described in U.S. Publication No. 20110158957.

A recombinant gene product may serve any one or more purposes described herein. For example, a recombinant gene product may serve as a binding moiety, targeting moiety, therapeutic agent, detectable agent, or agent that alters one or more properties of the cell. In some embodiments, an agent conjugated to the cell using sortase comprises a targeting moiety, and the recombinant gene product comprises a chimeric antigen receptor. In some embodiments, an agent conjugated to the cell using sortase comprises a targeting moiety, and the recombinant gene product comprises a protein or RNA that alters one or more properties of the cell. Altering one or more properties of the cell may comprise stimulating or inhibiting proliferation or activity of the cell, inhibiting or enhancing activity of a cell surface receptor, conferring responsiveness to an extracellular ligand. The recombinant gene product may increase or inhibit expression of one or more genes, bind to an intracellular domain of a receptor, increase or inhibit an intracellular protein-protein interaction, increase or inhibit an intracellular protein translocation. In some embodiments, an agent conjugated to the cell using sortase comprises a targeting moiety, and the recombinant gene product comprises a different targeting moiety. The first and second targeting moieties may be the same or different. If different, they may bind to the same antigen (e.g., to different epitopes thereof) or to different antigens. For example, the first and second targeting agents may bind to different tumor antigens, which may both be present in a tumor. In some embodiments, an agent conjugated to the cell using sortase comprises a targeting moiety, and the recombinant gene product comprises a therapeutic protein. In some embodiments the targeting moiety targets the cell to a desired site of activity in the body.

In some embodiments, immune system cells that are to be administered to a subject or contacted with other cells ex vivo may be processed to reduce the likelihood that they will mount an immune response against non-target cells and/or to reduce the likelihood that a subject's immune system cells will mount an immune response towards administered cells. In some embodiments, T cells are rendered nonreactive to antigens that are present on normal cells of a subject (alloantigens) by coculturing them with allogeneic cells in the presence of one or more agents that inhibit costimulation of the T cells. The nonreactive cells may be referred to as "anergized cells". The allogeneic cells may be obtained from a subject to whom the anergized cells are to be administered. In some embodiments the allogeneic cells are allogeneic PBMC. Costimulation can be inhibited by, e.g., inhibiting the receipt of costimulatory signals. This may be achieved by blocking the binding of B7 family members (e.g., B7-1 and/or B7-2) to their receptors on T cells using agents such as anti-B7-1 and/or anti-B7-2 monoclonal antibodies. The anergized cells preferably retain ability to recognize and kill target cells but have reduced or absent ability to kill non-target cells. In some embodiments.

In some embodiments, expression or activity of an endogenous TCR is eliminated or inhibited, which may be achieved, for example, by engineering a disruption or insertion in a gene encoding TCR α, TCR β, CD3zeta, and/or CD3epsilon. In some embodiments, the cell may also be genetically engineered to express a TCR or a CAR. In some embodiments, immune system cells in which endogenous TRC expression or activity is eliminated or inhibited lack ability to respond to TCR-mediated stimulation but retain ability to be stimulated by contact with an antigen to which a TCR or CAR has specificity. (See Torikai, H., et al., Blood (2012), 119(24): 5697-5705 for description of irreversible disruption of endogenous TCR expression in CAR T cells using zinc finger nucleases targeting the constant regions of TCR α or TCR β genes. The CAR T cells expressed a CAR comprising a moiety that binds to CD19. The TCRnegCAR+ T cells did not respond to TCR-mediated stimulation by cross-linking CD3 with OKT3, but retained CD19 specificity, were activated and stimulated to proliferate by contact with CD19, and induced cytotoxicity in CD19+ leukemic cells.) Such an approach may be used, e.g., to generate allogeneic antigen-specific T cells from one donor that may be administered to multiple different recipients. In some embodiments cells are engineered to express one or more nucleic acids encoding shRNA, siRNA, and/or miRNA molecules to down-regulate expression of an endogenous gene encoding TCR α, TCR β, CD3zeta, and/or CD3epsilon. In some embodiments, immune system cells in which endogenous TRC expression or activity is eliminated or inhibited may be administered to subjects who express different major and/or minor histocompatibility antigens than do the administered cells, with reduced likelihood of resulting in graft-versus-host-disease (GVHD) as compared with administration of control cells that express a functional endogenous TCR.

In some embodiments cells, e.g., cells to be administered to a subject, are engineered to eliminate or inhibit expression of one or more HLA class I and/or II genes, e.g., genes encoding HLA-A, HLA-B, HLA-C, or encoding an alpha or beta chain of HLA-DR, HLA-DP, or HLA-DQ. In some embodiments, this is achieved by engineering a disruption or insertion in the gene or by engineering cells to express one or more nucleic acids encoding shRNA, siRNA, and/or miRNA molecules that inhibit expression of the gene. In some embodiments, eliminating or inhibiting expression or activity of HLA class I and/or II genes of cells to be administered to a subject may reduce the likelihood that endogenous immune system cells of a subject will mount an immune response against the administered cells.

In some embodiments, cells that are engineered to lack expression of one or more endogenous cell-surface proteins may be contacted with one more agents (e.g., antibodies) that binds to the extracellular portion of such proteins in order to remove remaining cells (if any) that express the protein at their surface. The binding agent may be attached to a support, such as magnetic beads, which retains any cells that express the endogenous protein at their surface For example, cells engineered to lack expression of the TCR may be contacted with anti-CD3 antibodies to remove remaining cells that express a TCR at their cell surface.

In some embodiments a cell is genetically engineered to comprise a gene that encodes an inducible suicide gene. A suicide gene is a gene that encodes a gene product that causes a cell that contains the suicide gene to die following induction of expression of the gene or induction of activity of the gene product encoded by the gene. In certain embodiments at least 50%, 60%, 70%, 80%, 90%, 95%, 97%, 98%, 99%, or more of the cells have died within a defined time period following induction of expression or activity of the gene or induction of activity of the gene product, The defined time period may be, e.g., about 24-72 hours. In some embodiments, the inducible suicide gene is expressed only in the presence of an inducer, which may be contacted with the cells ex vivo or administered to a subject to whom cells comprising the suicide gene have been administered. In some embodiments, the inducible suicide gene may be expressed in the absence of an inducer, but the resulting gene product is inactive in the absence of the inducer. Administration of the inducer to a subject comprising cells that harbor an inducible suicide gene causes induction of the suicide gene, resulting in death or at least reduced proliferation of cells that harbor the suicide gene. In some embodiments the protein encoded by the suicide gene has one, more than one, or all of the following properties: non-immunogenic (at least in humans or other mammalian subjects to whom a cell expressing the suicide gene may be administered), non-cell-cycle dependent (the transcription of the gene and activity of the gene product are not restricted to particular phases of the cell cycle or limited to dividing cells or inactive in quiescent cells), clinically compatible (neither the gene product nor the inducing agent produce unacceptable toxicity in vivo), inducible by an inducing agent that has wide biodistribution so that the inducing agent, when administered to a subject, will reach a high percentage of cells harboring the gene. In some embodiments, a gene that encodes at least a portion of a human protein may be used. In some embodiments an inducible suicide gene exploits chemical inducers of dimerization (CID) (see, e.g., Amara J F, Proc Natl Acad Sci USA. 1997; 94(20):10618-23; Clackson T, et al., Proc Natl Acad Sci USA. 1998, 95:10437-10442; Rollins C T, et al. Proc Natl Acad Sci USA. 2000; 97(13):7096-7101). According to this approach, a proapototic molecule or other inducer of cell death is modified to comprise one or more binding sites for a CID. Binding of the CID to its target(s) causes their oligomerization, resulting in activation of the apoptotic pathway or other cell death-inducing pathway. In some embodiments the binding site for a CID comprises a mutated FK506-binding protein (FKBP12) that mediates dimerization upon binding of a small molecule ligand (e.g., a CID such as AP1510 or AP1903). In some embodiments the CID is a dimeric analog of the immunosuppressive agent FK506. In some embodiments the analog of FK506 lacks the immunosuppressive activity of FK506. In some embodiments the CID is biologically inert at concentrations at which it is used. Fusing one or more FKBPs, e.g., FKBP12 or a mutant thereof to a pro-apoptotic domain or other cell death inducing domain, results in a protein whose activity (pro-apoptotic activity or other cell death inducing activity) can be stimulated by a CID. If the protein is expressed by a cell, activity of the protein can be stimulated by contacting the cell with a CID, e.g., by culturing the cell in the presence of a CID or administering the CID to a subject comprising the cell. Examples of useful suicide genes include genes that encode pro-apoptotic proteins, which can be modified to render their activity inducible. For example, inducible suicide genes based on caspases 1, 3, 8, or 9 (Straathof K C, et al. Blood. 2005; 105(11):4247-4254), the death receptor Fas (Thomis D C, et al., Blood. 2001; 97(5):1249-1257) or FADD may be used. One such gene, designated iC9, encodes a fusion protein that links a truncated human caspase 9 lacking the endogenous caspase recruitment domain (CARD) with a mutated FK506-binding protein (FKBP12). In the presence of an appropriate CID, e.g., AP1903, functional active caspase 9 is generated, leading to apoptosis (see, e.g., Fan L, et al., (1999) Hum Gene Ther 10: 2273-2285; see also 20110286980). In general, an inducible suicide gene may be introduced into cells using standard methods of genetic engineering. For example, a nucleic acid encoding the gene product operably linked to a promoter may be introduced in a vector, e.g., a viral vector or plasmid, which is then introduced into a cell. In the case of a cell that is genetically engineered to express a CAR, the nucleic acid encoding the inducible suicide gene product may in some embodiments be included in the same construct or vector, optionally further including a sequence encoding a cytokine such as IL-15. Examples of cells that genetically engineered to express a CAR, an inducible suicide gene, and a cytokine are described in U.S. Pat. Pub. No. 20130071414.

In some embodiments, two or more nucleic acid sequences that encode different proteins, different noncoding RNAs, or at least one protein and at least one noncoding RNA, are included in a single nucleic acid construct, which may further include one or more operably linked expression control elements. Without wishing to be bound by any theory, may be advantageous as it allows coexpression of multiple gene products from a single exogenous DNA. In some embodiments, transcription of each nucleic acid sequence may be directed by a promoter operably linked thereto, resulting in two or more separate RNAs. In some embodiments, a bidirectional promoter may be used to direct transcription of two separate RNAs. In some embodiments, a single promoter directs expression of an RNA that encodes multiple (e.g., two, three, four, or more) polypeptides. Translation of multiple polypeptides from one RNA can be achieved by using self-cleaving peptides or internal ribosome entry sites (IRESs). The sequences that encode the polypeptides may have an internal ribosome entry site (IRES) located between them or a sequence that encodes a "self-cleaving peptide" such as a 2A peptide. When IRES elements are included between multiple open reading frames (ORFs), the first ORF is translated by the typical cap-dependent mechanism, while the rest are translated through a cap-independent mechanism (Martinez-Salas, E. Curr Opin Biotechnol. 1999; 10: 458-464; Hellen C U, Sarnow P, Genes & Development, 2001; 15: 1593-1612). Since the genes are translated independently, the relative expression of different genes can be adjusted, if desired, by varying the strength of the IRES located upstream of each ORF. IRESs are found in a variety of different viral (e.g., picornavirus) and eukaryotic mRNAs. For example, IRESes are found in entero- and rhinoviruses, cardio- and aphthoviruses, and hepatitis A virus. The encephalomyocarditis virus (EMCV) IRES is among the most widely used IRES elements for multiple gene expression in mammalian cells. An exemplary IRES sequence comprises about the region from 260 to 848 in the EMCV-R genome (Genbank: M81861). Other IRES sequences useful for expressing multiple open reading frames encoding different polypeptides from a single promoter are described in Sasaki Y, J Biotechnol. 2008; 136(3-4):103-12. IRES sequences may be identical to those found in nature or may be modified to increase or decrease their efficiency and thereby alter the absolute and/or relative amount of the linked ORFs. Self-cleaving 2A peptides mediate 'ribosomal skipping' between the proline and glycine residues and inhibit peptide bond formation without affecting downstream translation. These peptides allow multiple proteins to be encoded as polyproteins, which dissociate into component proteins upon translation. Sequences linked by 2A peptides are expressed in a single open reading frame (ORF) and "self-cleavage" occurs co-translationally to produce separate polypeptides. Use of the term "self-cleaving" in reference to 2A peptides is common in the art and is not intended to imply a proteolytic cleavage reaction. Multicistronic vectors comprising 2A peptides between sequences that encode proteins are reviewed in Szymczak A L, et al. 2005; 5:627-638). Self-cleaving peptides are found in members of the Picornaviridae virus family, including aphthoviruses such as foot-and-mouth disease virus (FMDV), equine rhinitis A virus (ERAV), Thosea asigna virus (TaV) and porcine teschovirus-1 (PTV-1) and cardioviruses such as Theilovirus (e.g., Theiler's murine encephalomyelitis) and encephalomyocarditis viruses (Donnelly, M L, et al., J. Gen. Virol., 2001; 82: 1027-1041; Ryan, M D, et al., J. Gen. Virol., 2001; 72: 2727-2732; DeFelipe, P., et al., Trends Biotechnol. 2006; 24(2):68-75). The 2A peptides derived from FMDV, ERAV, PTV-1, and TaV are sometimes referred to as "F2A", "E2A", "P2A", and "T2A", respectively. Aphthovirus 2A polypeptides contain a Dx1Ex2NPG sequence (SEQ ID NO: 5), where x1 is often valine or isoleucine. An exemplary 2A sequence is VKQTLNFDLLKLAGDVESNPGP (SEQ ID NO: 6) from FMDV, where underlined residues are conserved in many 2A peptides. In some embodiments a spacer sequence such as GSG or SGSG may be included ahead of a 2A sequence. In some embodiments a protease cleavage site may additionally be included, such as a cleavage site for furin (RAKR). A cell may be genetically engineered to express any two or more recombinant gene products using any of the above approaches. In some embodiments two or more subunits of a multisubunit protein are expressed. In some embodiments, any two or more of the following recombinant gene products are expressed: a receptor, a cytokine, a costimulator, a coinhibitor, a suicide protein. The receptor may be an antigen receptor (e.g., a chimeric antigen receptor), a cytokine receptor, a costimulatory or coinhibitory receptor. All different combinations of products to be expressed and methods of achieving expression of multiple products are encompassed. In some embodiments, for example, a CAR and a suicide protein, a CAR and a cytokine, or a CAR, a cytokine, and a suicide protein may be translated from a single RNA encoded by an exogenous DNA inserted into the genome of a cell.

V. Click Chemistry

In some embodiments an agent conjugated or to be conjugated to a eukaryotic cell, e.g., a mammalian cell, may comprise a click chemistry handle. For example, $A^1$ in a sortase substrate described above may comprise a click chemistry handle. Click chemistry is a chemical philosophy introduced by Sharpless in 2001 and describes chemistry tailored to generate substances quickly and reliably by joining small units together (see, e.g., Kolb, Finn and Sharpless *Angewandte Chemie International Edition* (2001) 40: 2004-2021; Evans, *Australian Journal of Chemistry* (2007) 60: 384-395). Additional exemplary click chemistry handles, reaction conditions, and associated methods useful according to aspects of this invention are described in Joerg Lahann, *Click Chemistry for Biotechnology and Materials Science,* 2009, John Wiley & Sons Ltd, ISBN 978-0-470-69970-6. In some embodiments, a click chemistry handle is described in any of the references herein and/or in Table 1 or Table 2. For example, a click chemistry handle may comprise or consist of a terminal alkyne, azide, strained alkyne, diene, dieneophile, alkoxyamine, carbonyl, phosphine, hydrazide, thiol, or alkene moiety.

Two entities, e.g., two proteins, each comprising a click chemistry handle (e.g., a first protein comprising a click chemistry handle providing a nucleophilic (Nu) group and a second protein comprising an electrophilic (E) group that can react with the Nu group of the first click chemistry handle) can be covalently conjugated under click chemistry reaction conditions. The installation of a click chemistry handle on a protein confers click chemistry reactivity to the protein. In some embodiments a sortase-mediated conjugation is used to install a first click chemistry handle on a polypeptide expressed by a mammalian cell, and a click chemistry reaction is then used to conjugate an entity comprising a second click chemistry handle to the first click chemistry handle, thereby conjugating the entity to the polypeptide and thus attaching it to the cell. In general, the second click chemistry handle may be located at any position of the entity. In some embodiments the entity comprising the second click chemistry handle is a polypeptide. In some embodiments the second click chemistry handle may be at the C-terminus or the N-terminus of the polypeptide or may be attached to a side chain at or near the C-terminus or N-terminus. The second click chemistry handle may be incorporated into the entity, e.g., polypeptide using sortase or other methods. Methods of installing click chemistry handles on polypeptides are described in PCT/US2012/044584. In some embodiments the use of click chemistry allows two proteins to be conjugated at their respective N-termini, generating an N—N conjugated chimeric protein. For example, the N-terminus of a non-genetically engineered polypeptide expressed by a mammalian cell may be modified using sortase to install a first click chemistry handle, as described herein. A polypeptide having a compatible click chemistry handle installed at or near its N-terminus may then be conjugated via click chemistry to the first click chemistry handle.

Click chemistry should be modular, wide in scope, give high chemical yields, generate inoffensive byproducts, be stereospecific, be physiologically stable, exhibit a large thermodynamic driving force (e.g., >84 kJ/mol to favor a reaction with a single reaction product), and/or have high atom economy. Several reactions have been identified which fit this concept:

(1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer;

(2) Other cycloaddition reactions, such as the Diels-Alder reaction;

(3) Nucleophilic addition to small strained rings like epoxides and aziridines;

(4) Nucleophilic addition to activated carbonyl groups; and (5) Addition reactions to carbon-carbon double or triple bonds.

For two proteins to be conjugated via click chemistry, the click chemistry handles of the proteins have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to those described in Table I:

TABLE 1

Exemplary click chemistry handles and reactions.

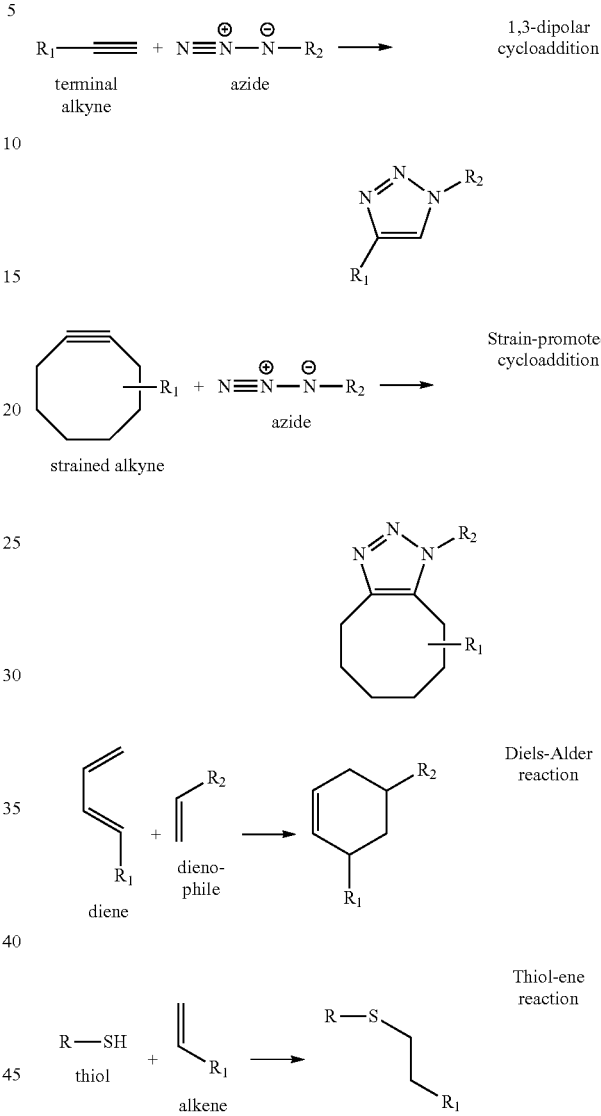

In some embodiments R, $R_1$ or $R_2$ in click chemistry handles and reactions above is a non-genetically engineered polypeptide -$[Xaa]_y$-TRS-PRT according to Formula I above expressed by a living mammalian cell, wherein the polypeptide has been modified by sortase-catalyzed conjugation of a click chemistry handle thereto, and the other of R, $R_1$ or $R_2$ is a moiety to be conjugated to the click chemistry handle of the modified polypeptide.

In some embodiments, click chemistry handles are used that can react to form covalent bonds in the absence of a metal catalyst. Such click chemistry handles are well known to those of skill in the art and include the click chemistry handles described in Becer, Hoogenboom, and Schubert, *Click Chemistry beyond Metal-Catalyzed Cycloaddition*, Angewandte Chemie International Edition (2009) 48: 4900-4908.

TABLE 2 exemplary click chemistry handles and reactions.

| Reagent A | Reagent B | Mechanism | Notes on reaction[a] | Reference |
|---|---|---|---|---|
| 0 azide | alkyne | Cu-catalyzed [3 + 2] azide-alkyne cycloaddition (CuAAC) | 2 h at 60° C. in $H_2O$ | [9] |
| 1 azide | cyclooctyne | strain-promoted [3 + 2] azide-alkyne cycloaddition (SPAAC) | 1 h at RT | [6-8, 10, 11] |
| 2 azide | activated alkyne | [3 + 2] Huisgen cycloaddition | 4 h at 50° C. | [12] |
| 3 azide | electron-deficient alkyne | [3 + 2] cycloaddittion | 12 h at RT in $H_2O$ | [13] |
| 4 azide | aryne | [3 + 2] cycloaddition | 4 h at RT in THF with crown ether or 24 h at RT in $CH_3CN$ | [14, 15] |
| 5 tetrazine | alkene | Diels-Alder retro-[4 + 2] cycloaddition | 40 min at 25° C. (100% yield) $N_2$ is the only by-product | [36-38] |
| 6 tetrazole | alkene | 1,3-dipolar cycloaddition (photoclick) | few min UV irradiation and then overnight at 4° C. | [39, 40] |
| 7 dithioester | diene | hetero-Diels-Alder cycloaddition | 10 min at RT | [43] |
| 8 anthracene | maleimide | [4 + 2] Diels-Alder | 2 days at reflux in toluene | [41] |
| 9 thiol | alkene | reaction radical addition (thio click) | 30 min UV (quantitative conv.) or 24 h UV irradiation (>96%) | [19-23] |
| 10 thiol | enone | Michael addition | 24 h at RT in $CH_3CN$ | [27] |
| 11 thiol | maleimide | Michael addition | 1 h at 40° C. in THF or 16 h at RT in dioxane | [24-26] |
| 12 thiol | para-fluoro | nucleophilic substitution | overnight at RT in DMF or 60 min at 40° C. in DMF | [32] |
| 13 amine | para-fluoro | nucleophilic substitution | 20 min MW at 95° C. in NMP as solvent | [30] |

[a]RT= room temperature, DMF = N,N-dimethylformamide, NMP = N,N-methylpyrolidone, THF = tetrahydrofuran, $CH_3CN$ = acetonitrile.
From Becer, Hoogenboom, and Schubert, *click Chemistry beyond Metal-Catalyzed Cycloaddition*, Angewandte Chemie International Edition (2009) 48: 4900-4908.

Additional click chemistry handles suitable for use in methods of conjugation described herein are well known to those of skill in the art, and such click chemistry handles include, but are not limited to, the click chemistry reaction partners, groups, and handles described in PCT/US2012/044584 and references therein, which references are incorporated herein by reference for click chemistry handles and methodology.

In some embodiments eukaryotic cells, e.g., mammalian cells are modified by using sortase to conjugate a moiety comprising a first click chemistry handle to a polypeptide expressed by the cells, wherein the polypeptide is not genetically engineered to comprise an extracellular sortase recognition motif or extracellular glycine, e.g., non-genetically engineered eukaryotic, e.g., mammalian, cells. Once a click chemistry handle has been installed using sortase, the cells may be further modified by click chemistry mediated attachment of any available entity comprising a compatible click chemistry handle, without need to modify the entity to incorporate a sortase recognition motif. This approach may facilitate rapid conjugation of diverse entities onto cells. In some embodiments a population of cells that have been modified by using sortase to conjugate a moiety comprising a first click chemistry handle to a polypeptide expressed by the cells may be divided into two or more aliquots. The number of aliquots and number of cells per aliquot may be selected in any convenient manner. In some embodiments aliquots comprise at least $10^3$, $10^4$, $10^5$, $10^6$, or $10^7$ cells. In some embodiments the number of aliquots is between 2 and 1,000. One or more aliquots may be stored for future use. In some embodiments two or more different moieties, each comprising a second click chemistry handle that is compatible with the first click chemistry handle are conjugated to cells of two or more different aliquots, to produce two or more populations of modified mammalian cells having the different moieties conjugated thereto. Cells of different aliquots, or portions thereof, having different entities conjugated thereto, may be subsequently combined.

VI. Sortagged Mammalian Cells and Uses Thereof

Without limiting the invention, this section discusses certain proteins, nucleic acids, lipids, small molecules, and other entities of interest in the context of the present disclosure, certain methods of preparing or using sortagged mammalian cells, and related compositions. Entities described herein may be used for various purposes. For example, in various embodiments proteins, nucleic acids, lipids, small molecules, and sugars may be conjugated to mammalian cells using sortase, conjugated to each other using sortase, used in cell culture (e.g., to expand, stimulate, or differentiate cells), and/or administered to a subject.

In some embodiments a first protein is conjugated to a second protein using sortase. In some embodiments the second protein is expressed by a living mammalian cell. For example, $A^1$ in sortase substrate A described above may comprise any protein. In general, any protein or polypeptide that comprises or is modified to comprise an appropriately positioned sortase recognition motif can be conjugated to a living mammalian cell. In some embodiments a protein is modified by conjugating an agent to it using sortase, and the resulting protein is conjugated to a mammalian cell using sortase. In some embodiments two or more polypeptides are conjugated using sortase, and the resulting protein is conjugated to a mammalian cell using sortase. In some embodiments a polypeptide may be extended to include a sortase recognition motif at or near its C-terminus and/or to include one or more N-terminal glycines or other appropriate nucleophilic acceptor sequence to allow it to participate in a sortase-catalyzed reaction.

In some embodiments a protein is an enzyme, e.g., an enzyme that plays a role in metabolism or other physiological processes in a mammal. In some embodiments a protein, is characterized in that deficiency of the protein underlies a disease that affects a mammal. In some embodiments a protein is an enzyme that plays a role in carbohydrate metabolism, amino acid metabolism, organic acid metabolism, porphyrin metabolism, purine or pyrimidine metabolism, and/or lysosomal storage. Deficiencies of enzymes or other proteins can lead to a variety of diseases, e.g., diseases associated with defects in carbohydrate metabolism, amino acid metabolism, organic acid metabolism, purine or pyrimidine metabolism, lysosomal storage disorders, and blood clotting, among others. Examples include the following (name of deficient enzyme or other protein is indicated in parentheses if not part of name of disease): glucose-6-phosphate dehydrogenase deficiency, alpha-1 antitrypsin deficiency, phenylketonuria (deficiency in phenylalanine hydroxylase), Fabry disease (alpha galactosidase A deficiency), Gaucher disease (glucocerebrosidase deficiency), Pompe disease (acid alpha-glucosidase deficiency), adenosine deaminase deficiency, mucopolysaccharidoses such as MPSI (alpha-L-iduronidase deficiency), MPSII (iduronate-2-sulfatase deficiency), MPSIIIA (heparan sulfamidase deficiency), MPSVI (N-acetylgalactosamine-4-sulfatase deficiency), hemophilia (various coagulation factors), hereditary angioedema (C1 esterase inhibitor deficiency); hypophosphatasia (tissue-nonspecific isozyme of alkaline phosphatase (TNSALP). In some embodiments the enzyme is one wherein exogenous administration of the enzyme at least in part alleviates the disease. In some embodiments the enzyme is one that is normally present in the blood. In some embodiments the enzyme may normally be produced by cells in the liver or kidneys and secreted into the blood. In some embodiments the enzyme acts on a substrate whose increased presence or accumulation in the blood may contribute to a disease or which may be transported by the blood to a site in the body where it contributes to a diseases. In some embodiments a deficiency is due to an inherited mutation. In some embodiments a deficiency may be transient, e.g., it may be due at least in part to excessive consumption, degradation, or loss of the enzyme (e.g., due to bleeding), or due at least in part to toxicity (e.g., exposure to a toxin that inactivates the enzyme or increases requirement for the enzyme). In some embodiments a disease, e.g., an enzyme deficiency disease, is a rare disease or orphan disease as defined in the US or as defined in the relevant jurisdiction where a patient is treated.

In some embodiments an enzyme conjugated to mammalian cells is catalytically active. In some embodiments the enzyme is in a catalytically inactive form (e.g., a zymogen) and is cleaved in vivo (after administration of the cells to a subject) to generate an active form. Such cleavage may be catalyzed by an endogenous protease. In some embodiments the enzyme may be released from cells in vivo. Such release may occur via a proteolytic cleavage that, in some embodiments, also activates the enzyme. It will be understood that an enzyme used to treat an enzyme deficiency need not be the same as the deficient enzyme so long as it provides the required enzymatic activity, e.g., at least the enzymatic activity necessary to treat the disease.

In some embodiments an agent comprises both (i) a therapeutically active domain, e.g., an enzyme, small molecule, therapeutic protein, therapeutic antibody, and (ii) a targeting domain, wherein the targeting domain targets the cells and/or agent to a site in the body where the therapeutic activity is desired. The targeting domain binds to a target present at such site. Any targeting domain may be used, e.g., an antibody. In some embodiments the agent may be released from cell surfaces after administration and the released agent, comprising both a targeting domain and a therapeutic domain, accumulates at a site of disease. The site may be any organ or tissue, e.g., any organ or tissue where the disease causes destruction, degradation, or symptoms. For example, an agent may be targeted to respiratory tract (e.g., lung), bone, kidney, liver, pancreas, skin, cardiovascular system (e.g., heart), smooth or skeletal muscle, gastrointestinal tract, eye, blood vessel surfaces, etc.

In some embodiments an agent conjugated to mammalian cells, e.g., hematopoietic cells, e.g., red blood cells, comprises a moiety that modulates blood coagulation or breakdown of blood clots (fibrinolysis). In some embodiments the moiety promotes blood coagulation, e.g., the moiety may be a protein that participates in the coagulation pathway, e.g., a coagulation factor (e.g., factor VII, VIIa, VIII or IX). In some embodiments, mammalian cells conjugated with a moiety that promotes blood coagulation, such as a coagulation factor, may be administered to a subject to speed blood clotting in order to promote cessation of blood loss from a damaged vessel (e.g., a subject who has experienced a physical injury). In some embodiments cells conjugated with an agent that promotes blood coagulation may be administered prophylactically, e.g., to a subject with a defect in blood coagulation (e.g., hemophilia) with an aim of preventing excessive blood loss in case the subject is injured, to a subject who is to undergo surgery that presents a risk of significant blood loss, or to a subject who has received an excessive amount of an anticoagulant. In some embodiments the moiety inhibits coagulation and/or promotes fibrinolysis, e.g., the moiety may comprise a coagulation pathway regulator, heparin, plasmin, tissue plasminogen activator, streptokinase, urokinase, or a variant of any of these. In some embodiments cells conjugated with a moiety that inhibits coagulation and/or promotes fibrinolysis may be administered to a subject at risk of blood clot formation. For example, the subject may have an arrhythmia such as atrial fibrillation and/or a history of pathologic coagulation (e.g., embolism, thrombophlebitis, ischemic stroke), etc. The moiety that inhibits coagulation and/or promotes fibrinolysis may comprise Protein C, antithrombin, tissue factor pathway inhibitor, or plasmin.

In some embodiments, a protein comprises a receptor or receptor fragment (e.g., at least a portion of an extracellular domain). In some embodiments the receptor is a cytokine receptor, growth factor receptor, interleukin receptor, or chemokine receptor. In certain embodiments a growth factor receptor is a TNFα receptor (e.g., Type I TNF-α receptor), VEGF receptor, EGF receptor, PDGF receptor, IGF receptor, NGF receptor, or FGF receptor. In some embodiments the protein comprises at least a sufficient portion of a receptor to bind to a natural ligand of the receptor. In some embodiments the protein is capable of acting as a decoy receptor, i.e., a receptor that binds a ligand and thereby inhibits the ligand from binding to its normal receptor. In some embodiments cells conjugated with a decoy receptor that binds to a natural ligand are administered to a subject in order to inhibit activity of the natural ligand. In some embodiments cells conjugated with a decoy receptor that binds to a natural ligand are administered to a subject suffering from a disease that can be effectively treated by administration of a decoy receptor or other inhibitor of the ligand and/or by administration of an inhibitor of a natural receptor for the ligand, e.g., a disease that is at least in part caused or exacerbated by a natural ligand of the receptor. For example, a protein comprising a soluble TNF receptor, e.g., etanercept may be used in treatment of a variety of inflammatory and autoimmune diseases such as rheumatoid arthritis, psoriasis, ankylosing spondylitis, and Behcet's disease.

In certain embodiments, a protein comprises urate oxidase. Urate oxidase can be formulated as a protein drug (rasburicase) for the treatment of acute hyperuricemia, e.g., in patients receiving chemotherapy. In some embodiments cells having urate oxidase conjugated thereto may be administered to a subject in need of treatment of acute hyperuricemia, e.g., a patient receiving chemotherapy). Acute hyperuricemia may occur as a feature of tumor lysis syndrome in patients receiving chemotherapy, e.g., for hematologic cancers such as leukemias and lymphomas. In some embodiments cells having urate oxidase conjugated thereto may be administered to a subject in need of treatment of chronic hyperuricemia, e.g., a patient with gout, e.g., gout that is refractory to other treatments.

In some embodiments a protein is a cytokine. In some embodiments a cytokine is an interleukin (IL) e.g., any of IL-1-IL-38. In some embodiments a protein is a four-helix bundle protein, e.g., a four-helix bundle cytokine. In some embodiments a four-helix bundle cytokine is a member of the IL-2 subfamily, the interferon (IFN) subfamily, or the IL-10 subfamily. Exemplary four-helix bundle cytokines include, e.g., certain interferons (e.g., a type I interferon, e.g., IFN-α), interleukins (e.g., IL-2, IL-3, IL-4, IL-5, IL-6, IL-7, IL-12), and colony stimulating factors (e.g., G-CSF, GM-CSF, M-CSF). The IFN can be, e.g., interferon alpha 2a or interferon alpha 2b. See, e.g., Mott H R and Campbell I D., Curr Opin Struct Biol. 1995, 5(1):114-21; Chaiken I M, Williams W V, Trends Biotechnol. 1996, 14(10):369-75; Klaus W, et al., J Mol Biol., 274(4):661-75, 1997, for further discussion of certain of these cytokines. In some embodiments, the cytokine has a similar structure to one or more of the afore-mentioned cytokines. For example, the cytokine can be an IL-6 class cytokine such as leukemia inhibitory factor (LIF) or oncostatin M. In some embodiments, the cytokine is one that in nature binds to a receptor that comprises a GP130 signal transducing subunit. Other four-helix bundle proteins include growth hormone (GH) and prolactin (PRL). In some embodiments, the protein is an erythropoiesis stimulating agent, e.g., erythropoietin (EPO), which is also a four-helix bundle cytokine. In some embodiments, an erythropoiesis stimulating agent is an EPO variant, e.g., darbepoetin alfa, also termed novel erythropoiesis stimulating protein (NESP), which is engineered to contain five N-linked carbohydrate chains (two more than recombinant HuEPO). In some embodiments the cytokine is one that stimulates differentiation, activation, survival, and/or proliferation of one or more types or subtypes of immune system cells, e.g., T cells (e.g., CD4+ helper T cells, CD8+ cytotoxic T cells, Tregs), NK cells, B cells, DCs, monocytes, macrophages, or precursors of any of the foregoing.

In some embodiments, the protein comprises five helices. For example, the protein can be an interferon beta, e.g., interferon beta-la or interferon beta-1b, which (as will be appreciated) is often classified as a four-helix bundle cytokine.

In some embodiments a cytokine is an IL-12 family member. IL-12 family members are heterodimeric cytokines and include, e.g., IL-12, IL-23, IL-27 and IL-35. IL-12 and IL-23 have mainly proinflammatory properties, whereas IL-27 and IL-35 have mainly anti-inflammatory properties. IL-12 and IL-23 share the β-chain p40 (IL-12(3), whereas IL-27 and IL-35 share the β-chain Epstein-Barr virus-induced gene 3 (EBI3). IL-12 and IL-35 share the α-chain p35, whereas IL-23 and IL-27 have unique α-chains. IL-12 and IL-23 are disulfide-linked heterodimers whereas IL-27 and IL-35 lack a disulfide linkage. IL-35 is produced mainly by Treg cells. IL-12, IL-23 and IL-27 are secreted by myeloid cells such as macrophages and DCs, e.g., after stimulation by contact with specific pathogen-associated molecular patterns. IL-12 is composed of IL-12A (p35) and IL-12B (p40) subunits. IL-12 is involved in the differentiation of naive T cells into Th1 cells and plays an important role in enhancing the activities of natural killer cells and T lymphocytes. IL-23 is a composed of p40, which is also a component of IL-12, and p19, which is considered the IL-23 alpha subunit. IL-23 has several proinflammatory effects including the capacity to stimulate naive CD4+ T cells to differentiate into Th17 cells. IL-27 consists of two subunits p28 and EBI3. It acts as a differentiation factor in the generation of Tr1 cells and inhibits Th17 cells. IL-35 heterodimers are composed of EBI3 and the IL-12p35 subunit. See, e.g., Hunter, C A, Nature Reviews Immunology 5: 521-531, 2005, for discussion of certain IL-12 family members.

In some embodiments a cytokine is IL-17. In some embodiments a cytokine is IL-9, IL-10, IL-11, IL-13, IL-14, or IL-15.

In some embodiments, a protein comprises a biologically active portion of a cytokine, e.g., IL-2, IL-7, IL-12, IL-15, or IL-21. In some embodiments, a multi-subunit cytokine such as IL-12 is produced as a single polypeptide. In some embodiments the polypeptide preserves the N-terminus of the p40 subunit of IL-12 in a sequential p40-p35 fusion. In some embodiments the polypeptide comprises a p35-p40 fusion. In some embodiments the subunits are joined by a spacer, e.g. a polypeptide linker, in a fusion protein. Examples of bioactive fusion proteins comprising the p35 and p40 subunits of IL-12, nucleic acids and vectors encoding such proteins, and methods of producing the proteins are described in U.S. Pat. No. 5,891,680. In some embodiments the p35 and p40 are expressed as parts of separate polypeptides that permit heterodimerization of the p35 and p40 subunits may be used.

In some embodiments, a protein comprises a biologically active variant or fragment of a co-stimulatory molecule or cell adhesion molecule, wherein the biologically variant or fragment is capable of binding to a naturally occurring receptor, ligand, or interaction partner of such molecule.

In some embodiments a protein is a subunit of a multi-subunit protein, e.g., a multisubunit cytokine or multisubunit cytokine receptor. In some embodiments a subunit is unique to a particular cytokine or cytokine receptor. In some embodiments a subunit is found in multiple different cytokines or cytokine receptors. In some embodiments, two or more subunits of a multisubunit protein may be linked to form a single molecule. The two or more subunits may be linked to form a single polypeptide, e.g., as a fusion protein, or may be linked by any suitable linker. In some embodiments the two or more subunits may be linked using click chemistry. The two or more subunits may be separated from each other by a spacer, e.g., a polypeptide spacer, which may facilitate assembly of the subunits to form the normal quaternary structure of the protein. In some embodiments, two or more subunits of a multisubunit protein may be individually attached to a cell or expressed by a cell.

In some embodiments a protein promotes survival, proliferation and/or differentiation of one or more cell types. A protein may provide an extracellular signal that is necessary or promotes survival, e.g., by inhibiting apoptosis. One of ordinary skill in the art will be aware of certain proteins that act as survival factors for particular cell types. Such proteins include, e.g., growth factors, cytokines, chemokines, and others.

In some embodiments, a protein comprises a growth factor for one or more cell types. Growth factors include, e.g., members of the vascular endothelial growth factor (VEGF, e.g., VEGF-A, VEGF-B, VEGF-C, VEGF-D), epidermal growth factor (EGF), insulin-like growth factor (IGF; IGF-1, IGF-2), fibroblast growth factor (FGF, e.g., FGF1-FGF22), platelet derived growth factor (PDGF), or nerve growth factor (NGF) families. It will be understood that the afore-mentioned protein families comprise multiple members. Any member may be used in certain embodiments. In some embodiments a growth factor promotes survival, proliferation and/or differentiation of one or more hematopoietic cell types. For example, a growth factor may be CSF1 (macrophage colony-stimulating factor), CSF2 (granulocyte macrophage colony-stimulating factor, GM-CSF), or CSF3 (granulocyte colony-stimulating factors, G-CSF), stem cell factor (SCF), thrombopoietin (TPO), or Flt-3 ligand. In some embodiments, mammalian cells that have a growth factor or growth factor receptor agonist conjugated thereto may be contacted with cells in vitro or administered to a subject in order to promote proliferation of cells whose proliferation is stimulated by such moieties.

In some embodiments a protein is a chemokine. Chemokines are a family of small cytokines that have the ability to induce directed chemotaxis in responsive cells, i.e., they are chemotactic cytokines. Proteins may be classified as chemokines according to shared structural characteristics such as small size (approximately 8-10 kilodaltons in size), and the presence of at least two cysteine residues, e.g., four cysteine residues, in conserved locations that play an important role in their 3-dimensional structure (some chemokines contain one or more additional cysteines). The chemokine family may be divided into four subfamilies depending on the spacing of their first two cysteine residues: CXC, CX3C, C (or XC), and CX3C chemokines. A chemokine may be CCL1-CCL28, CXCL1-CXCL17, XCL1 or XCL2, or CXC3L1. Chemokine receptors are G protein-coupled receptors containing 7 transmembrane domains. Chemokine receptors may be divided into four families depending on the type of chemokine they bind; CXCR that bind CXC chemokines, CCR that bind CC chemokines, CX3CR1 that binds the CX3C chemokine (CX3CL1), and XCR1 that binds the two XC chemokines (XCL1 and XCL2). In some embodiments, mammalian cells that have a chemokine or chemokine receptor agonist conjugated thereto may be contacted with cells in vitro or administered to a subject in order to promote migration of cells whose migration is stimulated by such moieties.

In some embodiments, a protein is a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, in some embodiments, the protein is a factor that promotes neurite outgrowth. In some embodiments, the protein is ciliary neurotrophic factor (CNTF; a four-helix bundle protein) or an analog thereof such as Axokine, which is a modified version of human ciliary neurotrophic factor with a 15 amino acid truncation of the C terminus and two amino acid substitutions, which is three to five times more potent than CNTF in in vitro and in vivo assays and has improved stability properties. In some embodiments, mammalian cells that have a neutrophic factor or neurotrophic factor receptor agonist conjugated thereto may be contacted with cells in vitro or administered to a subject in order to promote survival, development, and/or function of cells whose survival, development, and/or function is stimulated by such moieties.

In some embodiments a protein comprises a constant domain of an antibody (e.g., an Fc domain) that recruits Fc receptor-bearing cells, e.g., monocytes, dendritic cells, and natural killer cells. Upon administration of the sortagged cells to a subject, Fc receptor-bearing cells are recruited to a location to which the sortagged cell is present (e.g., a site of target cells in a tumor or site of infection). The Fc receptor-bearing cells may further promote an immune response mounted by the sortagged cells, may promote an immune response by endogenous immune system cells of the subject, or may mount their own immune response against target cells. In some embodiments a protein comprises a constant domain of an antibody (e.g., an Fc domain) that has been modified to alter (e.g., increase or decrease) one or more activities that such Fc domain would otherwise have. The modification may, for example, alter the ability of the Fc domain to recruit Fc receptor-bearing cells and/or fix complement. In some embodiments a protein does not comprise an Fc domain or such domain is modified so that it does not bind to an Fc receptor and/or fix complement.

In some embodiments a protein comprises or consists of a polypeptide that is identical in sequence to or is a variant of a naturally occurring protein or polypeptide, e.g., a variant that is at least 80%, 85%, 90%, 95%, 96%, 97%, 98%, 99%, 99.5%, or 100% identical to a naturally occurring protein or polypeptide or fragment thereof. In some embodiments a protein has no more than 1, 2, 3, 4, 5, 6, 7, 8, 9, or 10 amino acid differences relative to a naturally occurring sequence. In some embodiments a naturally occurring protein is a mammalian protein, e.g., of human origin. In some embodiments a protein is an antibody, an antibody fragment, or protein comprising an antigen-binding domain.

In some embodiments a protein is a chimeric protein comprising two or more different polypeptides that are not found joined together in nature. For example, a chimeric protein may comprise two or more different targeting moieties or may comprise a targeting moiety and a therapeutic agent. In some embodiments the two or more polypeptides are joined directly to each other, e.g., via peptide bond(s). In some embodiments the two or more polypeptides are joined to each other via one or more linkers, which may comprise or consist of one or more amino acid(s), e.g., a polypeptide. In some embodiments the two or more polypeptides are joined in a single polypeptide chain. In some embodiments the polypeptide chain comprises one or more amino acids, e.g., a polypeptide linker, between any two portions of the polypeptide. If the polypeptide comprises multiple polypeptide linkers, they may be the same or different in sequence. Any polypeptide can be extended, e.g., to comprise one or more additional amino acids, e.g., a polypeptide linker. In some embodiments at least two of the polypeptides are subunits of the same protein, e.g., the same cytokine or cytokine receptor. In some embodiments a chimeric protein may be generated by producing a nucleic acid that encodes the chimeric protein and expressing the nucleic acid in a suitable expression system using standard methods. In some embodiments sortase may be used to generate a chimeric protein.

In some embodiments a protein is one that forms homodimers or heterodimers, (or homo- or heterooligomers comprising more than two subunits, such as tetramers). In certain embodiments the homodimer, heterodimer, or oligomer structure is such that a terminus of a first subunit is in close proximity to a terminus of a second subunit. For example, an N-terminus of a first subunit is in close proximity to a C-terminus of a second subunit. In certain embodiments the homodimer, heterodimer, or oligomer structure is such that a terminus of a first subunit and a terminus of a second subunit are not involved in interaction with a receptor, so that the termini can be joined via, e.g., a non-genetically encoded peptide element, without significantly affecting biological activity. In some embodiments, termini of two subunits of a homodimer, heterodimer, or oligomer are conjugated via click chemistry using a method described herein, thereby producing a dimer (or oligomer) in which at least two subunits are covalently joined. For example, the neurotrophins nerve growth factor (NGF); brain-derived neurotrophic factor (BDNF); neurotrophin 3 (NT3); and neurotrophin 4 (NT4) are dimeric molecules which share approximately 50% sequence identity and exist in dimeric forms. See, e.g., Robinson R C, et al., Biochemistry. 34(13): 4139-46, 1995; Robinson R C, et al., Protein Sci. 8(12): 2589-97, 1999, and references therein. In some embodiments, the dimeric protein is a cytokine, e.g., an interleukin.

In some embodiments a protein is a member of the immunoglobulin superfamily (IgSF). The IgSF is a group of cell surface and soluble proteins that are involved in a variety of cell processes, such as recognition, binding, and/or adhesion. Proteins are classified as members of the IgSF based on characteristic shared structural features with immunoglobulins (antibodies), i.e., they possess a domain known as an immunoglobulin domain or fold which is found in antibodies. Members of the IgSF include, e.g., antibodies, cell surface antigen receptors, co-receptors and costimulatory molecules of the immune system, molecules involved in antigen presentation to lymphocytes, cell adhesion molecules, certain cytokine receptors, and various intracellular muscle proteins. Ig domains contain about 70-110 amino acids and may be further categorized according to their size and function. Ig domains possess a characteristic fold formed by two sheets of antiparallel beta strands. The sheets are held together by a disulfide bond. Cell surface antigen receptors include (i) the T cell receptor (TCR), which comprises two chains, either the TCR-alpha and -beta chains or the TCR-delta and gamma chains, associated with a CD3 complex; (ii) the B cell receptor (BCR), which comprises cell surface immunoglobulin associated with antigen-non-specific signaling molecules termed Ig alpha and Ig beta. Major histocompatibility complex (MHC) proteins are ligands for TCRs. MHC class I proteins form a dimer with beta-2 microglobulin ($\beta2M$) and interact with the TCR on cytotoxic T cells. MHC class II proteins have two chains (alpha and beta) that interact with the TCR on helper T cells. MHC class I, MHC class II and $\beta2M$ proteins all possess Ig domains and therefore are members of the IgSF. MHC class I, MHC class II, and beta-2 microglobulin function as antigen presenting molecules (APMs). Co-receptors include a variety of proteins that function together with primary receptors to mediate a cellular event. Certain co-receptors are expressed on the surfaces of lymphocytes and interact with MHC molecules during TCR or BCR engagement. The co-receptor CD4 is found on helper T cells and the co-receptor CD8 is found on cytotoxic T cells. A co-receptor complex including the proteins CD19, CD21, and CD89 is used by the BCR. Certain co-receptors regulate T cell function positively (e.g., CD28) or negatively (e.g., cytotoxic T lymphocyte antigen 4 (CTLA-4)) by interacting with distinct cell-surface receptors. Costimulatory or inhibitory molecules include a variety of signaling receptors and ligands that regulate the activation, expansion and effector functions of immune system cells. A major group of IgSF co-receptors are molecules of the CD28 family, e.g., CD28, CTLA-4, programmed cell death-1 (PD-1), the B- and T-lymphocyte attenuator (BTLA, CD272, also referred to as B and T cell associated), and the inducible T-cell costimulator (ICOS, CD278). IgSF ligands of these molecules include members of the B7 family, e.g., CD80 (B7-1), CD86 (B7-2), ICOS ligand, PD-L1 (B7-H1), PD-L2 (B7-DC), B7-H3, and B7-H4. The leukocyte immunoglobulin-like receptors (LILR) are members of the IgSF. They are also known as CD85, ILTs and LIR families, and can exert immunomodulatory effects on a wide range of immune cells.

In some embodiments, a protein is one that participates in cell-cell or cell-substrate physical interactions. For example, the protein may mediate binding of cells to each other or to the extracellular matrix (ECM). A physical interaction between cells may be between cells of the same type or between cells of different types. In some embodiments a physical interaction between cells or between cells and ECM may be relatively stable, such as those cell involved in establishing or maintaining the structure or organization of tissues. Examples of proteins that participate in cell-cell or cell-substrate physical interactions include, e.g., cell adhesion molecules (CAMs). Most CAMs belong to any of four protein families: immunoglobulin (Ig) superfamily (IgSF) CAMs, integrins, the cadherin superfamily, and the selectins. Many CAMs are transmembrane proteins composed of three domains: an intracellular domain that interacts with the cytoskeleton, a transmembrane domain, and an extracellular domain that interacts with other CAMs or CAM ligands. Members of all CAM superfamilies can mediate cell-cell interactions, whereas integrins can also mediate cell-matrix interactions. CAMs bind to either the exact same protein, known as homophilic binding, or different proteins, called heterophilic binding. IgSF CAMs include, e.g., synaptic cell adhesion molecules, neural cell adhesion molecules (NCAMs), intercellular cell adhesion molecule (ICAM-1), vascular cell adhesion molecule (VCAM-1), platelet-endothelial cell adhesion molecule (PECAM-1). The cadherin superfamily is composed of proteins that include extracellular cadherin domains (ECD). Such proteins include cadherins, protocadherins, desmogleins, and desmocollins, and others (see, e.g., Hulpiau P, van Roy F (2009), "Molecular evolution of the cadherin superfamily". Int. J. Biochem. Cell Biol. 41 (2): 349-69). Cadherins are Ca2+-dependent glycoproteins. Different cadherins typically exhibit different patterns of tissue distribution, and many of these proteins are named according to tissue in which they are typically found, such as epithelial (E-cadherins), placental (P-cadherins), neural (N-cadherins), retinal (R-cadherins), brain (B-cadherins and T-cadherins) and muscle (M-cadherins). Many cell types express multiple cadherin types.

Integrins mediate cell interactions with a variety of ligands on other cells or in the ECM such as collagen, fibrinogen, fibronectin, laminin, and vitronectin. Integrins are heterodimers, consisting of an alpha and beta subunit. There are at least 18 alpha subunits and at least 8 beta subunits in mammals, which combine to make up at least 24 different integrin proteins. Many integrins bind to ligands containing an RGD or LDV tripeptide.

In some embodiments a CAM or CAM ligand is conjugated to mammalian cells using sortase. A CAM or CAM ligand may be used as a targeting moiety. A mammalian cell that has a CAM or CAM ligand conjugated to it may have increased ability to physically associate with cells or ECM that comprise a compatible CAM or CAM ligand, as compared with control cells. This property may be useful, e.g., if cells are used in regenerative medicine or if it is desired that the cells integrate into an organ or tissue. An appropriate CAM or CAM ligand may be selected based on the site at which it is desired that the cells associate or integrate. For example, a CAM or CAM ligand known to bind to a CAM or CAM ligand present at the site may be selected.

Selectins are a family of heterophilic CAMs that bind fucosylated carbohydrates. Selectins are involved in a variety of processes including constitutive lymphocyte homing and in chronic and acute inflammation. The three selectin family members are E-selectin (endothelial), L-selectin (leukocyte), and P-selectin (platelet). Selectin ligands include P-selectin glycoprotein ligand-1 (PSGL-1), which is a mucin-type glycoprotein expressed on white blood cells. Selectin ligands include sialyl Lewis X (SLex) (NeuAcα2-3Galβ1-4(Fucα1-3)G1cNAc) and sialyl Lewis A (sLe(a)) tetrasaccharides and a variety of structurally similar carbohydrate moieties, typically in the context of more extensive binding determinants. Among other things, interaction between selectin ligands present on endothelial cell surfaces and selectins on leukocyte cell surfaces mediates rolling and attachment of leukocytes to vessel walls and facilitates their extravasation into tissues, e.g., at sites of inflammation. Selectin binding to sLe(x) and sLe(a) present on various cancer cell types, e.g., colon, gastric, bladder, pancreatic, breast, and prostate carcinomas, is implicated in enhancing metastasis. In some embodiments a selectin or selectin ligand is conjugated to mammalian cells using sortase. In some embodiments a selectin ligand serves as a target or targeting moiety. For example, a selectin ligand may be conjugated to mammalian cells, e.g., immune systems cells, using sortase. The cells may be administered to a subject, e.g., intravascularly. The selectin may target the mammalian cells to sites of inflammation, where endothelial cells express the cognate selectin ligand. In some embodiments, e.g., if the inflammation is unwanted, e.g., associated with autoimmune disease or causing excessive symptoms, tissue damage or cytokine release, mammalian cells that have immunosuppressive activity (e.g., Tregs or cells that have been stimulated to express an immunosuppressive cytokine or other immunosuppressive molecule or modified to have an immunosuppressive cytokine or other immunosuppressive molecule at their surface) may be targeted to the site. In some embodiments, e.g., if the inflammation is in response to an infection or other condition in which it may be beneficial to stimulate an immune response, mammalian cells that have or may stimulate appropriate effector responses may be targeted to the site. In some embodiments mammalian cells that have a therapeutic agent conjugated thereto may be targeted to the site. In some embodiments a selectin serves as a target or targeting moiety. For example, a selectin may be conjugated to mammalian cells, e.g., immune systems cells, using sortase. The selectin may target the mammalian cells to tumor cells that express the cognate selectin ligand. The mammalian cells may be immune system cells that have anti-tumor activity and/or may have a therapeutic agent, e.g., a cytotoxic agent, at their surface.

The invention encompasses application of the inventive methods to any of the proteins described herein and any proteins known to those of skill in the art. Without limitation, sequences of certain proteins of interest are found in, e.g., U.S. Ser. Nos. 10/773,530; 11/531,531; U.S. Ser. Nos. 11/707,014; 11/429,276; 11/365,008, and/or in Table T and/ or under the NCBI accession numbers listed in Table T or encoded by genes identified by Gene ID and/or NCBI RefSeq accession number in Table T, described by Official Symbol (assigned by the HUGO Gene Nomenclature Committee in the case of human genes), and/or described by name or otherwise herein. It is noted that where multiple isoforms of a particular protein exist, the dominant isoform, longest isoform, isoform 1, or isoform having a particular biological activity of interest may be selected. In some embodiments a cell-bound isoform may be selected. In some embodiments a secreted isoform may be selected.

In some embodiments, modified versions of any protein, wherein the modified version comprises (i) one or more nucleophilic residues such as glycine at the N-terminus (e.g., between 1 and 10 residues) and, optionally, a cleavage recognition sequence, e.g., a protease cleavage recognition sequence that masks the nucleophilic residue(s); or (ii) a sortase recognition motif at or near the C-terminus may be used in a composition or method described herein, e.g., attachment of the modified version to a mammalian cell. In some embodiments, the protein comprises both (i) and (ii). In some aspects, the present disclosure provides proteins comprising any protein described herein, e.g., any antibody, antibody fragment, antibody chain, antibody domain, scFv, VHH, affibody, adnectin, anticalin, cytokine, cytokine chain, Ig superfamily protein, pro-apoptotic domain, or antigen, or a biologically active fragment or variant of any of the foregoing; and a sequence comprising a sortase recognition motif. In some embodiments the sortase recognition motif is located at or near a C-terminus of the protein.

One of skill in the art will be aware that certain proteins, e.g., secreted eukaryotic (e.g., mammalian) proteins, often undergo intracellular processing (e.g., cleavage of a secretion signal prior to secretion and/or removal of other portion(s) that are not required for biological activity), to generate a mature form. Such mature, biologically active versions of proteins are used in certain embodiments of the invention.

TABLE T

Selected Protein Sequences and Selected Gene IDs and Accession Numbers

| | |
|---|---|
| Tissue plasminogen activator (1rtf) | Chain A: TTCCGLRQY (SEQ ID NO: 5)<br>Chain B:<br>IKGGLFADIASHPWQAAIFAKHHRRGGERFLCGGILISSCWILSAA<br>HCFQQQQQEEEEERRRRRFFFFFPPPPPPHHLTVILGRTYRVVPGE<br>EEQKFEVEKYIVHKEFDDDTYDNDIALLQLKSSSSSDDDDDSSSSS<br>SSSSSRRRRRCAQESSVVRTVCLPPADLQLPDWTECELSGYGKHE<br>ALSPFYSERLKEAHVRLYPSSRCTTTSSSQQQHLLNRTVTDNMLC<br>AGDTTTRRRSSSNNNLHDACQGDSGGPLVCLNDGRMTLVGIISW<br>GLGCGGQQKDVPGVYTKVTNYLDWIRDNMRP (SEQ ID NO: XX) |
| Factor IX | Chain A:<br>VVGGEDAKPGQFPWQVVLNGKVDAFCGGSIVNEKWIVTAAHCV<br>EETTGVKITVVAGEHNIEETEHTEQKRNVIRIIPHHNYNNNAAAA<br>AAINKYNHDIALLELDEPLVLNSYVTPICIADKEYTTTNNNIIIFLK |

TABLE T-continued

Selected Protein Sequences and Selected Gene IDs and Accession Numbers

| | |
|---|---|
| | FGSGYVSGWGRVFHKGRSALVLQYLRVPLVDRATCLRSTKFTIY<br>NNMFCAGGFFHEGGGRRDSCQGDSGGPHVTEVEGTSFLTGIISW<br>GEECAAMMKGKYGIYTKVSRYVNWIKEKTKLT (SEQ ID NO: 6)<br>Chain B:<br>MTCNIKNGRCEQFCKNSADNKVVCSCTEGYRLAENQKSCEPAVP<br>FPCGRVSVSQTSK (SEQ ID NO: 7) |
| Glucocerebrosidase | EFARPCIPKSFGYSSVVCVCNATYCDSFDPPALGTFSRYESTRSGR<br>RMELSMGPIQANHTGTGLLLTLQPEQKFQKVKGFGGAMTDAAA<br>LNILALSPPAQNLLLKSYFSEEGIGYNIIRVPMASCDFSIRTYTYAD<br>TPDDFQLHNFSLPEEDTKLKIPLIHRALQLAQRPVSLLASPWTSPT<br>WLKTNGAVNGKGSLKGQPGDIYHQTWARYFVKFLDAYAEHKL<br>QFWAVTAENEPSAGLLSGYPFQCLGFTPEHQRDFIARDLGPTLAN<br>STHHNVRLLMLDDQRLLLPHWAKVVLTDPEAAKYVHGIAVHW<br>YLDFLAPAKATLGETHRLFPNTMLFASEACVGSKFWEQSVRLGS<br>WDRGMQYSHSIITNLLYHVVGWTDWNLALNPEGGPNWVRNFV<br>DSPIIVDITKDTFYKQPMFYHLGHFSKFIPEGSQRVGLVASQKNDL<br>DAVALMHPDGSAVVVVLNRSSKDVPLTIKDPAVGFLETISPGYSI<br>HTYLWHRQ (SEQ ID NO: 8) |
| alpha galactosidase A | LDNGLARTPTMGWLHWERFMCNLDCQEEPDSCISEKLFMEMAE<br>LMVSEGWKDAGYEYLCIDDCWMAPQRDSEGRLQADPQRFPHGI<br>RQLANYVHSKGLKLGIYADVGNKTCAGFPGSFGYYDIDAQTFAD<br>WGVDLLKFDGCYCDSLENLADGYKHMSLALNRTGRSIVYSCEW<br>PLYMWPFQKPNYTEIRQYCNHWRNFADIDDSWKSIKSILDWTSF<br>NQERIVDVAGPGGWNDPDMLVIGNFGLSWNQQVTQMALWAIM<br>AAPLFMSNDLRHISPQAKALLQDKDVIAINQDPLGKQGYQLRQG<br>DNFEVWERPLSGLAWAVAMINRQEIGGPRSYTIAVASLGKGVAC<br>NPACFITQLLPVKRKLGFYEWTSRLRSHINPTGTVLLQLENTM<br>(SEQ ID NO: 9) |
| arylsulfatase-A (iduronidase, α-L-) | RPPNIVLIFADDLGYGDLGCYGHPSSTTPNLDQLAAGGLRFTDFY<br>VPVSLPSRAALLTGRLPVRMGMYPGVLVPSSRGGLPLEEVTVAE<br>VLAARGYLTGMAGKWHLGVGPEGAFLPPHQGFHRFLGIPYSHD<br>QGPCQNLTCFPPATPCDGGCDQGLVPIPLLANLSVEAQPPWLPGL<br>EARYMAFAHDLMADAQRQDRPFFLYYASHHTHYPQFSGQSFAE<br>RSGRGPFGDSLMELDAAVGTLMTAIGDLGLLEETLVIFTADNGPE<br>TMRMSRGGCSGLLRCGKGTTYEGGVREPALAFWPGHIAPGVTHE<br>LASSSLDLLPTLAALAGAPLPNVTLDGFDLSPLLLGTGKSPRQSLFF<br>YPSYPDEVRGVFAVRTGKYKAHFFTQGSAHSDTTADPACHASSS<br>LTAHEPPLLYDLSKDPGENYNLLGATPEVLQALKQLQLLKAQLD<br>AAVTFGPSQVARGEDPALQICCHPGCTPRPACCHCP (SEQ ID NO:<br>10) |
| arylsulfatase B (N-acetylgalactos-amine-<br>4-sulfatase) (1fsu) | SRPPHLVFLLADDLGWNDVGFHGSRIRTPHLDALAAGGVLLDNY<br>YTQPLTPSRSQLLTGRYQIRTGLQHQIIWPCQPSCVPLDEKLLPQL<br>LKEAGYTTHMVGKWHLGMYRKECLPTRRGFDTYFGYLLGSEDY<br>YSHERCTLIDALNVTRCALDFRDGEEVATGYKNMYSTNIFTKRAI<br>ALITNHPPEKPLFLYLALQSVHEPLQVPEEYLKPYDFIQDKNRHH<br>YAGMVSLMDEAVGNVTAALKSSGLWNNTVFIFSTDNGGQTLAG<br>GNNWPLRGRKWSLWEGGVRGVGFVASPLLKQKGVKNRELIHIS<br>DWLPTLVKLARGHTNGTKPLDGFDVWKTISEGSPSPRIELLHNID<br>PNFVDSSPCSAFNTSVHAAIRHGNWKLLTGYPGCGYWFPPPSQY<br>NVSEIPSSDPPTKTLWLFDIDRDPEERHDLSREYPHIVTKLLSRLQF<br>YHKHSVPVYFPAQDPRCDPKATGVWGPWM (SEQ ID NO: 11) |
| beta-hexosaminidase A (2gjx) | LWPWPQNFQTSDQRYVLYPNNFQFQYDVSSAAQPGCSVLDEAF<br>QRYRDLLFGTLEKNVLVVSVVTPGCNQLPTLESVENYTLTINDDQ<br>CLLLSETVWGALRGLETFSQLVWKSAEGTFFINKTEIEDFPRFPHR<br>GLLLDTSRHYLPLSSILDTLDVMAYNKLNVFHWHLVDDPSFPYES<br>FTFPPELMRKGSYNPVTHIYTAQDVKEVIEYARLRGIRVLAEFDTP<br>GHTLSWGPGIPGLLTPCYSGSEPSGTFGPVNPSLNNTYEFMSTFFL<br>EVSSVFPDFYLHLGGDEVDFTCWKSNPEIQDFMRKKGFGEDFKQ<br>LESFYIQTLLDIVSSYGKGYVVWQEVFDNKVKIQPDTIIQVWREDI<br>PVNYMKELELVTKAGFRALLSAPWYLNRISYGPDWKDFYVVEPL<br>AFEGTPEQKALVIGGEACMWGEYVDNTNLVPRLWPRAGAVAER<br>LWSNKLTSDLTFAYERLSHFRCELLRRGVQAQPLNVGFCEQEFLQ<br>(SEQ ID NO: 12) |
| Hexosaminidase A and B (2gjx) | CHAIN A:<br>LWPWPQNFQTSDQRYVLYPNNFQFQYDVSSAAQPGCSVLDEAF<br>QRYRDLLFGTLEKNVLVVSVVTPGCNQLPTLESVENYTLTINDDQ<br>CLLLSETVWGALRGLETFSQLVWKSAEGTFFINKTEIEDFPRFPHR<br>GLLLDTSRHYLPLSSILDTLDVMAYNKLNVFHWHLVDDPSFPYES<br>FTFPPELMRKGSYNPVTHIYTAQDVKEVIEYARLRGIRVLAEFDTP<br>GHTLSWGPGIPGLLTPCYSGSEPSGTFGPVNPSLNNTYEFMSTEFL<br>EVSSVFPDFYLHLGGDEVDFTCWKSNPEIQDFMRKKGFGEDFKQ<br>LESFYIQTLLDIVSSYGKGYVVWQEVFDNKVKIQPDTIIQVWREDI |

TABLE T-continued

Selected Protein Sequences and Selected Gene IDs and Accession Numbers

| | |
|---|---|
| | PVNYMKELELVTKAGFRALLSAPWYLNRISYGPDWKDFYVVEPL<br>AFEGTPEQKALVIGGEACMWGEYVDNTNLVPRLWPRAGAVAER<br>LWSNKLTSDLTFAYERLSHFRCELLRRGVQAQPLNVGFCEQEFLQ<br>(SEQ ID NO: 13)<br>Chain B:<br>PALWPLPLSVKMTPNLLHLAPENFYISHSPNSTAGPSCTLLEEAFR<br>RYHGYIFGTQVQQLLVSITLQSECDAFPNISSDESYTLLVKEPVAV<br>LKANRVWGALRGLETFSQLVYQDSYGTFTINESTIIDSPRFSHRGI<br>LIDTSRHYLPVKIILKTLDAMAFNKFNVLHWHIVDDQSFPYQSITF<br>PELSNKGSYSLSHVYTPNDVRMVIEYARLRGIRVLPEFDTPGHTLS<br>WGKGQKDLLTPCYSDSFGPINPTLNTTYSFLTTFFKEISEVFPDQFI<br>HLGGDEVEFKCWESNPKIQDFMRQKGFGTDFKKLESFYIQKVLDI<br>IATINKGSIVWQEVFDDKAKLAPGTIVEVWKDSAYPEELSRVTAS<br>GFPVILSAPWYLDLISYGQDWRKYYKVEPLDFGGTQKQKQLFIG<br>GEACLWGEYVDATNLTPRLWPRASAVGERLWSSKDVRDMDDA<br>YDRLTRHRCRMVERGIAAQPLYAGYCN (SEQ ID NO: 14)<br>Chain C:<br>PALWPLPLSVKMTPNLLHLAPENFYISHSPNSTAGPSCTLLEEAFR<br>RYHGYIFGTQVQQLLVSITLQSECDAFPNISSDESYTLLVKEPVAV<br>LKANRVWGALRGLETFSQLVYQDSYGTFTINESTIIDSPRFSHRGI<br>LIDTSRHYLPVKIILKTLDAMAFNKFNVLHWHIVDDQSFPYQSITF<br>PELSNKGSYSLSHVYTPNDVRMVIEYARLRGIRVLPEFDTPGHTLS<br>WGKGQKDLLTPCYSLDSFGPINPTLNTTYSFLTTFFKEISEVFPDQ<br>FIHLGGDEVEFKCWESNPKIQDFMRQKGFGTDFKKLESFYIQKVL<br>DIIATINKGSIVWQEVFDDKAKLAPGTIVEVWKDSAYPEELSRVT<br>ASGFPVILSAPWYLDLISYGQDWRKYYKVEPLDFGGTQKQKQLFI<br>GGEACLWGEYVDATNLTPRLWPRASAVGERLWSSKDVRDMDD<br>AYDRLTRHRCRMVERGIAAQPLYAGYCN (SEQ ID NO: 15)<br>Chain D:<br>LWPWPQNFQTSDQRYVLYPNNFQFQYDVSSAAQPGCSVLDEAF<br>QRYRDLLFGTLEKNVLVVSVVTPGCNQLPTLESVENYTLTINDDQ<br>CLLLSETVWGALRGLETFSQLVWKSAEGTFFINKTEIEDFPRFPHR<br>GLLLDTSRHYLPLSSILDTLDVMAYNKLNVFHWHLVDDPSFPYES<br>FTFPELMRKGSYNPVTHIYTAQDVKEVIEYARLRGIRVLAEFDTP<br>GHTLSWGPGIPGLLTPCYSGSEPSGTFGPVNPSLNNTYEFMSTEFL<br>EVSSVFPDFYLHLGGDEVDFTCWKSNPEIQDFMRKKGFGEDFKQ<br>LESFYIQTLLDIVSSYGKGYVVWQEVFDNKVKIQPDTIIQVWREDI<br>PVNYMKELELVTKAGFRALLSAPWYLNRISYGPDWKDFYVVEPL<br>AFEGTPEQKALVIGGEACMWGEYVDNTNLVPRLWPRAGAVAER<br>LWSNKLTSDLTFAYERLSHFRCELLRRGVQAQPLNVGFCEQEFLQ<br>(SEQ ID NO: 16) |
| phenylalanine hydroxylase (PAH) (1j8u) | VPWFPRTIQELDRFANQILSYGAELDADHPGFKDPVYRARRKQFA<br>DIAYNYRHGQPIPRVEYMEEEKKTWGTVFKTLKSLYKTHACYEY<br>NHIFPLLEKYCGFHEDNIPQLEDVSQFLQTCTGFRLRPVAGLLSSR<br>DFLGGLAFRVFHCTQYIRHGSKPMYTPEPDICHELLGHVPLFSDRS<br>FAQFSQEIGLASLGAPDEYIEKLATIYWFTVEFGLCKQGDSIKAYG<br>AGLLSSFGELQYCLSEKPKLLPLELEKTAIQNYTVTEFQPLYYVAE<br>SFNDAKEKVRNFAATIPRPFSVRYDPYTQRIEVL (SEQ ID NO: 17) |
| Cathepsin A | APDQDEIQRLPGLAKQPSFRQYSGYLKSSGSKHLHYWFVESQKD<br>PENSPVVLWLNGGPGCSSLDGLLTEHGPFLVQPDGVTLEYNPYS<br>WNLIANVLYLESPAGVGFSYSDDKFYATNDTEVAQSNFEALQDF<br>FRLFPEYKNNKLFLTGESYAGIYIPTLAVLVMQDPSMNLQGLAVG<br>NGLSSYEQNDNSLVYFAYYHGLLGNRLWSSLQTHCCSQNKCNF<br>YDNKDLECVTNLQEVARIVGNSGLNIYNLYAPCAGGVPSHFRYE<br>KDTVVVQDLGNIFTRLPLKRMWHQALLRSGDKVRMDPPCTNTT<br>AASTYLNNPYVRKALNIPEQLPQWDMCNFLVNLQYRRLYRSMN<br>SQYLKLLSSQKYQILLYNGDVDMACNFMGDEWFVDSLNQKMEV<br>QRRPWLVKYGDSGEQIAGFVKEFSHIAFLTIKGAGHMVPTDKPLA<br>AFTMFSRFLNKQPY (SEQ ID NO: 18) |
| G-CSF | LPQSFLLKCLEQVRKIQGDGAALQEKLCATYKLCHPEELVLLGHS<br>LGIPWAPLLAGCLSQLHSGLFLYQGLLQALEGISPELGPTLDTLQL<br>DVADFATTIWQQMEELGMMPAFASAFQRRAGGVLVASHLQSFL<br>EVSYRVLRHLA (SEQ ID NO: 19) |
| GM-CSF | EHVNAIQEARRLLNLSRDTAAEMNETVEVISEMFDLQEPTCLQTR<br>LELYKQGLRGSLTKLKGPLTMMASHYKQHCPPTPETSCATQIITF<br>ESFKENLKDFLLVIP (SEQ ID NO: 20) |
| Interferon alfa-2 | CDLPQTHSLGSRRTLMLLAQMRKISLFSCLKDRHDFGFPQEEFGN<br>QFQKAETIPVLHEMIQQIFNLFSTKDSSAAWDETLLDKFYTELYQ<br>QLNDLEACVIQGVGVTETPLMKEDSILAVRKYFQRITLYLKEKKY<br>SPCAWEVVRAEIMRSFSLSTNLQESLRSKE (SEQ ID NO: 21) |
| Interferon beta-1 | MSYNLLGFLQRSSNFQCQKLLWQLNGRLEYCLKDRMNFDIPEEI<br>KQLQQFQKEDAALTIYEMLQNIFAIFRQDSSSTGWNETIVENLLA |

TABLE T-continued

Selected Protein Sequences and Selected Gene IDs and Accession Numbers

| | |
|---|---|
| | NVYHQINHLKTVLEEKLEKEDFTRGKLMSSLHLKRYYGRILHYL<br>KAKEYSHCAWTIVRVEILRNFYFINRLTGYLRN (SEQ ID NO: 22) |
| Interferon gamma-1b | MQDPYVKEAENLKKYFNAGHSDVADNGTLFLGILKNWKEESDR<br>KIMQSQIVSFYFKLFKNFKDDQSIQKSVETIKEDMNVKFFNSNKK<br>KRDDFEKLTNYSVTDLNVQRKAIDELIQVMAELGANVSGEFVKE<br>AENLKKYFNDNGTLFLGILKNWKEESDRKIMQSQIVSFYFKLFKN<br>FKDDQSIQKSVETIKEDMNVKFFNSNKKKRDDFEKLTNYSVTDL<br>NVQRKAIHELIQVMAELSPAA (SEQ ID NO: 23) |
| IL-2 (1M47) | STKKTQLQLEHLLLDLQMILNGINNYKNPKLTRMLTFKFYMPKK<br>ATELKHLQCLEEELKPLEEVLNLAQNFHLRPRDLISNINVIVLELK<br>GFMCEYADETATIVEFLNRWITFCQSIISTLT (SEQ ID NO: 24) |
| IL-1 (2nvh) | APVRSLNCTLRDSQQKSLVMSGPYELKALHLQGQDMEQQVVFS<br>MSFVQGEESNDKIPVALGLKEKNLYLSCVLKDDKPTLQLESVDP<br>KNYPKKKMEKRFVFNKIEINNKLEFESAQFPNWYISTSQAENMPV<br>FLGGTKGGQDITDFTMQFVS (SEQ ID NO: 25) |
| TNF-alpha (4tsv) | DKPVAHVVANPQAEGQLQWSNRRANALLANGVELRDNQLVVPI<br>EGLFLIYSQVLFKGQGCPSTHVLLTHTISRIAVSYQTKVNLLSAIKS<br>PCQRETPEGAEAKPWYEPIYLGGVFQLEKGDRLSAEINRPDYLDF<br>AESGQVYFGIIAL (SEQ ID NO: 26) |
| TNF-beta (lymphotoxin) (1tnr) | KPAAHLIGDPSKQNSLLWRANTDRAFLQDGFSLSNNSLLVPTSGI<br>YFVYSQVVFSGKAYSPKATSSPLYLAHEVQLFSSQYPFHVPLLSS<br>QKMVYPGLQEPWLHSMYHGAAFQLTQGDQLSTHTDGIPHLVLSP<br>STVFFGAFAL (SEQ ID NO: 27) |
| Erythropoietin | APPRLICDSRVLERYLLEAKEAEKITTGCAEHCSLNEKITVPDTKV<br>NFYAWKRMEVGQQAVEVWQGLALLSEAVLRGQALLVKSSQPW<br>EPLQLHVDKAVSGLRSLTTLLRALGAQKEAISNSDAASAAPLRTI<br>TADTFRKLFRVYSNFLRGKLKLYTGEACRTGDR (SEQ ID NO: 28) |
| Insulin | Chain A: GIVEQCCTSICSLYQLENYCN (SEQ ID NO: 29)<br>Chain B: FVNQHLCGSHLVEALYLVCGERGFFYTPK (SEQ ID NO: 30) |
| Growth hormone (GH) (Somatotropin) (1huw) | FPTIPLSRLADNAWLRADRLNQLAFDTYQEFEEAYIPKEQIHSFW<br>WNPQTSLCPSESIPTPSNKEETQQKSNLELLRISLLLIQSWLEPVQF<br>LRSVFANSLVYGASDSNVYDLLKDLEEGIQTLMGRLEALLKNYG<br>LLYCFNKDMSKVSTYLRTVQCRSVEGSCGF (SEQ ID NO: 31) |
| Follicle-stimulating hormone (FSH) | CHHRICHCSNRVFLCQESKVTEIPSDLPRNAIELRFVLTKLRVIQK<br>GAFSGFGDLEKIEISQNDVLEVIEADVFSNLPKLHEIRIEKANNLLY<br>INPEAFQNLPNLQYLLISNTGIKHLPDVHKIHSLQKVLLDIQDNINI<br>HTIERNSFVGLSFESVILWLNKNGIQEIHNCAFNGTQLDELNLSDN<br>NNLEELPNDVFHGASGPVILDISRTRIHSLPSYGLENLKKLRARST<br>YNLKKLPTLE (SEQ ID NO: 32) |
| Leptin (1ax8) | IQKVQDDTKTLIKTIVTRINDILDFIPGLHPILTLSKMDQTLAVYQQ<br>ILTSMPSRNVIQISNDLENLRDLLHVLAFSKSCHLPEASGLETLDSL<br>GGVLEASGYSTEVVALSRLQGSLQDMLWQLDLSPGC (SEQ ID NO: 33) |
| Insulin-like growth factor (or somatomedin) (1wqj) | PETLCGAELVDALQFVCGDRGFYFNKPTGYGSSSRRAPQTGIVDE<br>CCFRSCDLRRLEMYCAP (SEQ ID NO: 34) |
| Adiponectin (1c28) | Chain A:<br>MYRSAFSVGLETRVTVPNVPIRFTKIFYNQQNHYDGSTGKFYCNI<br>PGLYYFSYHITVYMKDVKVSLFKKDKAVLFTYDQYQENVDQAS<br>GSVLLHLEVGDQVWLQVYYADNVNDSTFTGFLLYHDT (SEQ ID NO: 35)<br>Chain B:<br>MYRSAFSVGLPNVPIRFTKIFYNQQNHYDGSTGKFYCNIPGLYYF<br>SYHITVYMKDVKVSLFKKDKVLFTYDQYQEKVDQASGSVLLHL<br>EVGDQVWLQVYDSTFTGFLLYHD (SEQ ID NO: 36)<br>Chain C:<br>MYRSAFSVGLETRVTVPIRFTKIFYNQQNHYDGSTGKFYCNIPGL<br>YYFSYHITVDVKVSLFKKDKAVLFTQASGSVLLHLEVGDQVWLQ<br>NDSTFTGFLLYHD (SEQ ID NO: 37) |
| Factor VIII (aka antihemophilic factor) (2r7e) | Chain A:<br>ATRRYYLGAVELSWDYMQSDLGELPVDARFPPRVPKSFPFNTSV<br>VYKKTLFVEFTDHLFNIAKPRPPWMGLLGPTIQAEVYDTVVITLK<br>NMASHPVSLHAVGVSYWKASEGAEYDDQTSQREKEDDKVFPGG<br>SHTYVWQVLKENGPMASDPLCLTYSYLSHVDLVKDLNSGLIGAL<br>LVCREGSLAKEKTQTLHKFILLFAVFDEGKSWHSETKNAASARA |

TABLE T-continued

Selected Protein Sequences and Selected Gene IDs and Accession Numbers

| | |
|---|---|
| | WPKMHTVNGYVNRSLPGLIGCHRKSVYWHVIGMGTTPEVHSIFL<br>EGHTFLVRNHRQASLEISPITFLTAQTLLMDLGQFLLFCHISSHQH<br>DGMEAYVKVDSCPEEPQFDDDNSPSFIQIRSVAKKHPKTWVHYIA<br>AEEEDWDYAPLVLAPDDRSYKSQYLNNGPQRIGRKYKKVRFMA<br>YTDETFKTREAIQHESGILGPLLYGEVGDTLLIIFKNQASRPYNIYP<br>HGITDVRPLYSRRLPKGVKHLKDFPILPGEIFKYKWTVTVEDGPT<br>KSDPRCLTRYYSSFVNMERDLASGLIGPLLICYKESVDQRGNQIM<br>SDKRNVILFSVFDENRSWYLTENIQRFLPNPAGVQLEDPEFQASNI<br>MHSINGYVFDSLQLSVCLHEVAYWYILSIGAQTDFLSVFFSGYTF<br>KHKMVYEDTLTLFPFSGETVFMSMENPGLWILGCHNSDFRNRGM<br>TALLKVSSCDKNTGDYYEDSYED (SEQ ID NO: 38)<br>Chain B:<br>RSFQKKTRHYFIAAVERLWDYGMSSSPHVLRNRAQSGSVPQFKK<br>VVFQEFTDGSFTQPLYRGELNEHLGLLGPYIRAEVEDNIMVTFRN<br>QASRPYSFYSSLISYEEDQRQGAEPRKNFVKPNETKTYFWKVQH<br>HMAPTKDEFDCKAWAYSSDVDLEKDVHSGLIGPLLVCHTNTLNP<br>AHGRQVTVQEFALFFTIFDETKSWYFTENMERNCRAPCNIQMED<br>PTFKENYRFHAINGYIMDTLPGLVMAQDQRIRWYLLSMGSNENI<br>HSIHFSGHVFTVRKKEEYKMALYNLYPGVFETVEMLPSKAGIWR<br>VECLIGEHLHAGMSTLFLVYSNKCQTPLGMASGHIRDFQITASGQ<br>YGQWAPKLARLHYSGSINAWSTKEPFSWIKVDLLAPMIIHGIKTQ<br>GARQKFSSLYISQFIIMYSLDGKKWQTYRGNSTGTLMVFFGNVDS<br>SGIKHNIFNPPIIARYIRLHPTHYSIRSTLRMELMGCDLNSCSMPLG<br>MESKAISDAQITASSYFTNMFATWSPSKARLHLQGRSNAWRPQV<br>NNPKEWLQVDFQKTMKVTGVTTQGVKSLLTSMYVKEFLISSSQD<br>GHQWTLFFQNGKVKVFQGNQDSFTPVVNSLDPPLLTRYLRIHPQS<br>WVHQIALRMEVLGCEAQDLY (SEQ ID NO: 39) |
| Human serum albumin (1ao6) | Chain A:<br>SEVAHRFKDLGEENFKALVLIAFAQYLQQCPFEDHVKLVNEVTEF<br>AKTCVADESAENCDKSLHTLFGDKLCTVATLRETYGEMADCCA<br>KQEPERNECFLQHKDDNPNLPRLVRPEVDVMCTAFHDNEETFLK<br>KYLYEIARRHPYFYAPELLFFAKRYKAAFTECCQAADKAACLLP<br>KLDELRDEGKASSAKQRLKCASLQKFGERAFKAWAVARLSQRFP<br>KAEFAEVSKLVTDLTKVHTECCHGDLLECADDRADLAKYICENQ<br>DSISSKLKECCEKPLLEKSHCIAEVENDEMPADLPSLAADFVESKD<br>VCKNYAEAKDVFLGMFLYEYARRHPDYSVVLLLRLAKTYETTLE<br>KCCAAADPHECYAKVFDEFKPLVEEPQNLIKQNCELFEQLGEYKF<br>QNALLVRYTKKVPQVSTPTLVEVSRNLGKVGSKCCKHPEAKRMP<br>CAEDYLSVVLNQLCVLHEKTPVSDRVTKCCTESLVNRRPCFSALE<br>VDETYVPKEFNAETFTFHADICTLSEKERQIKKQTALVELVKHKP<br>KATKEQLKAVMDDFAAFVEKCCKADDKETCFAEEGKKLVAASQ<br>AA (SEQ ID NO: 40)<br>Chain B:<br>SEVAHRFKDLGEENFKALVLIAFAQYLQQCPEEDHVKLVNEVTEF<br>AKTCVADESAENCDKSLHTLFGDKLCTVATLRETYGEMADCCA<br>KQEPERNECFLQHKDDNPNLPRLVRPEVDVMCTAFHDNEETFLK<br>KYLYEIARRHPYFYAPELLEFFAKRYKAAFTECCQAADKAACLLP<br>KLDELRDEGKASSAKQRLKCASLQKFGERAFKAWAVARLSQRFP<br>KAEFAEVSKLVTDLTKVHTECCHGDLLECADDRADLAKYICENQ<br>DSISSKLKECCEKPLLEKSHCIAEVENDEMPADLPSLAADFVESKD<br>VCKNYAEAKDVFLGMFLYEYARRHPDYSVVLLLRLAKTYETTLE<br>KCCAAADPHECYAKVFDEFKPLVEEPQNLIKQNCELFEQLGEYKF<br>QNALLVRYTKKVPQVSTPTLVEVSRNLGKVGSKCCKHPEAKRMP<br>CAEDYLSVVLNQLCVLHEKTPVSDRVTKCCTESLVNRRPCFSALE<br>VDETYVPKEFNAETFTFHADICTLSEKERQIKKQTALVELVKHKP<br>KATKEQLKAVMDDFAAFVEKCCKADDKETCFAEEGKKLVAASQ<br>AA (SEQ ID NO: 42) |
| Hemoglobin (1bz0) | Chain A:<br>VLSPADKTNVKAAWGKVGAHAGEYGAEALERMFLSFPTTKTYF<br>PHFDLSHGSAQVKGHGKKVADALTNAVAHVDDMPNALSALSDL<br>HAHKLRVDPVNFKLLSHCLLVTLAAHLPAEFTPAVHASLDKFLA<br>SVSTVLTSKYR (SEQ ID NO: 43)<br>Chain B:<br>VHLTPEEKSAVTALWGKVNVDEVGGEALGRLLVVYPWTQRFFE<br>SFGDLSTPDAVMGNPKVKAHGKKVLGAFSDGLAHLDNLKGTFA<br>TLSELHCDKLHVDPENFRLLGNVLVCVLAHHFGKEFTPPVQAAY<br>QKVVAGVANALAHKYH (SEQ ID NO: 44) |
| Trail (TNFSF10) | Gene ID: 8743; NP_003801.1 (isoform 1);<br>NP_003801.1 (isoform 2);<br>NP_001177872.1 (isoform 3) |
| E-selectin (SELE) | Gene ID: 6401; NP_000441.2 |
| CD3 epsilon (CD3E) | Gene ID: 916; NP_000724.1 |

TABLE T-continued

Selected Protein Sequences and Selected Gene IDs and Accession Numbers

| | |
|---|---|
| CD3 zeta (CD247) | Gene ID: 919; NP_932170.1 (isoform 1); NP_000725.1 (isoform 2) |
| CD3 delta (CD3D) | Gene ID: 915; NP_000723.1 (isoform A); NP_001035741.1 (isoform B) |
| CD3 gamma (CD3G) | Gene ID: 917; NP_000064.1 |
| CD28 | Gene ID: NP_006130.1 (isoform 1); NP_001230006.1 (isoform 2); NP_001230007.1 (isoform 3) |
| Programmed cell death 1 (PD-1) (PDCD1) | Gene ID: 5133; NP_005009.2 |
| PD-L1 (CD274) | Gene ID: 29126NP_054862.1 (isoform a); NP_001254635.1 (isoform b); |
| PD-L2 (PDCD1LG2) | Gene ID: 80380; NP_079515.2 |
| CTLA-4 | Gene ID: 1493; NP_005205.2 (isoform CLTA4-TM); NP_001032720.1 (isoform CTLA4delTM) |
| BCMA (TNFRSF17) | Gene ID: 608; NP_001183.2 |
| CD137L (TNFSF9) | Gene ID: 8744; NP_003802.1 |

It will be appreciated that considerable structure/function information is available regarding many of the afore-mentioned proteins, as well as sequences from different mammalian species, that can be used to design variants of the naturally occurring sequence that retain significant biological activity (e.g., at least 25%, 75%, 90%, 95%, 98%, 99%, or more of the activity of the naturally occurring protein, or greater activity than the naturally occurring protein). For example, crystal structures or NMR structures of a number of proteins, in some instances in a complex with the corresponding receptor, are available. It will be understood that a naturally occurring sequence can be extended, e.g., at or near its C-terminus, e.g., with a flexible peptide spacer (e.g., any of the polypeptide linkers mentioned herein), which may allow the polypeptide more freedom to fold and/or interact or associate with free or cell-bound molecules or structures in the extracellular environment after it is conjugated to mammalian cells than would otherwise be the case. In addition, it will be understood that, if the naturally occurring N- and C-termini are not located in close proximity to each other in the native structure, a naturally occurring sequence can be extended at the N- and/or C-termini, e.g., with a flexible peptide spacer so that the termini can come into close proximity, which may be desirable, for example, if the polypeptide is to be circularized.

In some embodiments, a protein has been tested in one or more human clinical trials and, in some embodiments, demonstrated acceptable safety in at least a Phase I trial. In some embodiments, a protein is approved by the US Food & Drug Administration (or an equivalent regulatory authority such as the European Medicines Evaluation Agency) for use in treating a disease or disorder in humans. In some embodiments a protein is a PEGylated version of the protein.

In some embodiments an agent conjugated to a living mammalian cell using sortase comprises an antigen or a binding moiety that binds to an antigen. In some embodiments an antigen is any molecule or complex comprising at least one epitope recognized by a B cell, e.g., a mammalian or avian B cell and/or by a T cell, e.g., a mammalian or avian T cell. An antigen may comprise a polypeptide, a polysaccharide, a carbohydrate, a lipid, a nucleic acid, or combination thereof. In some embodiments an antigen comprises a protein, e.g., a polypeptide encoded or expressed by an organism. A polypeptide antigen may comprise or consist of a full length polypeptide or a portion thereof, such as a peptide at least about 6, 7, 8, 9, 10, 11, 12, 13, 14, or 15 amino acids long. In some embodiments an antigen comprises a lipid or glycolipid such as α-galactosylceramide (α-GalCer), which is recognized by iNKT cells. An antigen may be naturally occurring or synthetic. In some embodiments, an antigen is naturally produced by and/or is genetically encoded by a pathogen, an infected cell, or a neoplastic cell (e.g., a cancer cell). In some embodiments, an antigen is an autoantigen ("self antigen"), or an agent that has the capacity to initiate or enhance an autoimmune response. In some embodiments, an antigen is a graft-associated antigen. In some embodiments, an antigen is produced or genetically encoded by a virus, bacteria, fungus, or parasite which, in some embodiments, is a pathogenic agent. In some embodiments, an agent (e.g., virus, bacterium, fungus, parasite) infects and, in some embodiments, causes disease in, at least one mammalian or avian species, e.g., human, non-human primate, bovine, ovine, equine, caprine, and/or porcine species. In some embodiments, a pathogen is intracellular during at least part of its life cycle. In some embodiments, a pathogen is extracellular. In some embodiments an antigen comprises a molecule that is produced by an infected cell as a result of infection by a pathogen. In some embodiments, an antigen is an envelope protein, capsid protein, secreted protein, structural protein, cell wall protein or polysaccharide, capsule protein or polysaccharide, or enzyme. In some embodiments an antigen is a toxin, e.g., a bacterial toxin.

In some embodiments mammalian cells, e.g., hematopoietic cells, e.g., immune system cells or red blood cells, that have an epitope, antigen or portion thereof conjugated thereto by sortase may be used as vaccine components. As used herein, "vaccine" refers to a product or composition that may be administered to a subject to modulate the subject's immune system or immune response towards one or more entit(ies) of interest. A vaccine often contains an agent that resembles at least a portion of an entity against which an immune response is desired, e.g., a disease-causing microorganism, parasite, or toxin, or an agent that resembles an entity against which an immune response is not desired, e.g., a self antigen or environmental allergen. In some embodiments an agent stimulates the body's immune system to recognize an entity as foreign, destroy it, and "remember" it (e.g., by inducing formation of memory T and/or B cells), so that the immune system can more easily recognize and destroy such an entity that it subsequently encounters. In some embodiments an agent stimulates the body's immune system to recognize an entity as "self" or not to recognize the entity, so that the immune system does not mount a response against the entity. For example, it may be desirable to inhibit an immune response towards self antigens or graft-associated antigens. A vaccine may be prophylactic (e.g., to prevent or reduce the severity of a future infection by a pathogen or exposure to an allergen), or therapeutic (e.g., vaccines against cancer or to treat autoimmune disease or an existing allergy). In some embodiments a vaccine modulates the adaptive immune system or a component thereof. In some embodiments a vaccine is designed to modulate the immune response towards a single antigen, microorganism, or other entity. In some embodiments a vaccine is designed to modulate the immune response towards two or more strains of the same microorganism or entity, two or more microorganisms or entities, or two or more distinct antigens of a tumor, graft, or self cell or structure. Sortagged cells used as a vaccine or vaccine component may be used to deliver an epitope, antigen or portion thereof to a subject in order to modulate an immune response of the subject towards an entity that comprises the epitope or antigen. In some embodiments an antigen conjugated to animal cells using sortase may be any antigen used in a conventional vaccine known in the art.

One of ordinary skill in the art will be aware of numerous microbes (e.g., viruses, bacteria, fungi, protozoa) and multicellular parasites from which antigens or epitopes may be derived, e.g., microbes and parasites capable of causing disease in mammals. In some embodiments an antigen is a surface protein or polysaccharide of, e.g., a viral capsid, envelope, or coat, or bacterial, fungal, protozoal, or parasite cell. In some embodiments an antigen is a toxin, e.g., a toxin produced by a bacterium. A toxin may be provided in an inactivated form, e.g., as a toxoid. An antigen or epitope may be modified, e.g., by chemical treatment (e.g., formaldehyde) or physical treatment (e.g., heat) and/or by conjugation with a second agent. It will be understood that an antigen, e.g., a protein, "derived from" a particular microbe or parasite can be produced using any suitable method, e.g., using recombinant DNA technology in yeast, bacteria, or cell cultures. In some embodiments a variant antigen may be used. For example, a native sequence may be modified to render it more immunogenic. In some embodiments an antigen or epitope is sufficiently similar to a naturally occurring antigen or epitope such that it binds with at least about 10%, 20%, 30%, least 50%, 60%, 70%, 80%, 90%, 95%, or the same affinity to an antigen receptor or antibody that binds to the naturally occurring antigen or epitope. In some embodiments an antigen or epitope is sufficiently similar to a naturally occurring antigen or epitope to elicit a desired response.

Exemplary viruses include, e.g., Retroviridae (e.g., lentiviruses such as human immunodeficiency viruses, such as HIV-I); Caliciviridae (e.g. strains that cause gastroenteritis); Togaviridae (e.g. equine encephalitis viruses, rubella viruses); Flaviridae (e.g. dengue viruses, encephalitis viruses, yellow fever viruses, hepatitis C virus); Coronaviridae (e.g. coronaviruses); Rhabdoviridae (e.g. vesicular stomatitis viruses, rabies viruses); Filoviridae (e.g. Ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunga viruses, phleboviruses and Nairo viruses); Arenaviridae (hemorrhagic fever viruses); Reoviridae (erg., reoviruses, orbiviurses and rotaviruses); Birnaviridae; Hepadnaviridae (Hepatitis B or C virus); Parvoviridae (parvoviruses); Papovaviridae (papilloma viruses, polyoma viruses); Adenoviridae; Herpesviridae (herpes simplex virus (HSV) 1 and 2, varicella zoster virus, cytomegalovirus (CMV), EBV, KSV); Poxviridae (variola viruses, vaccinia viruses, pox viruses); and Picornaviridae (e.g. polio viruses, hepatitis A virus; enteroviruses, human coxsackie viruses, rhinoviruses, echoviruses).

Bacteria include, e.g., gram positive, gram negative, and acid-fast bacteria. Bacteria may be cocci, rod-shaped, spirochetes. Exemplary bacteria include, e.g., *Helicobacter pylori, Borellia* (e.g., *B. burgdorferi, B. afzelii, B. garinii*), *Legionella pneumophilia, Mycobacteria* (e.g., *M. tuberculosis, M. avium, M. intracellulare, M. kansasii, M. gordonae*), *Staphylococcus* (e.g., *Staphylococcus aureus*), *Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae, Campylobacter* sp., *Enterococcus* sp., *Chlamydia* sp., *Haemophilus influenzae, Bordetella* (e.g., *B. pertussis, B. parapertussis, B. bronchiseptica*), *Bacillus anthracis, Corynebacterium diphtheriae, Erysipelothrix rhusiopathiae, Clostridia* (e.g., *Clostridium perfringens, Clostridium tetani, Clostridium difficile*), *Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Actinomyces israelii* and *Francisella tularensis, E. coli* (e.g., pathogenic *E. coli*).

In some embodiments a fungus is a member of the phylum Ascomycota, Basidiomycota, Chytridiomycota, Glomeromycota, or Zygomycota. The fungus may be a member of a genus selected from the group consisting of *Aspergillus, Blastomyces, Candida, Coccidioides, Cryptococcus, Epidermophytum, Exserohilum, Fusarium, Histoplasma, Malassezia, Microsporum, Mucor, Paracoccidioides, Penicillium, Pichia, Pneumocystis, Pseudallescheria, Rhizopus, Rhodotorula, Scedosporium, Schizophyllum, Sporothrix, Stachybotrys, Saccharomyces, Trichophyton, Trichosporon, Bipolaris, Exserohilum, Curvularia, Alternaria,* or *Cladophialophora*. Exemplary fungi include, e.g., *Aspergillus*, such as *Aspergillus flavus, Aspergillus fumigatus, Aspergillus niger, Aspergillus clavatus, Blastomyces*, such as *Blastomyces dermatitidis, Candida*, such as *Candida albicans, Candida glabrata, Candida guilliermondii, Candida krusei, Candida parapsilosis, Candida tropicalis, Coccidioides*, such as *Coccidioides immitis, Cryptococcus*, such as *Cryptococcus neoformans, Epidermophyton, Fusarium, Histoplasma*, such as *Histoplasma capsulatum, Malassezia*, such as *Malassezia furfur, Microsporum, Mucor, Paracoccidioides*, such as *Paracoccidioides brasiliensis, Penicillium*, such as *Penicillium marneffei, Pichia*, such as *Pichia anomala, Pichia guilliermondii, Pneumocystis*, such as *Pneumocystis carinii, Pseudallescheria*, such as *Pseudallescheria boydii, Rhizopus*, such as *Rhizopus oryzae, Rhodotorula*, such as *Rhodotorula rubra, Scedosporium,* such as *Scedosporium apiospermum*, *Schizophyllum*, such as *Schizophyllum commune*, *Sporothrix*, such as *Sporothrix schenckii*, *Trichophyton*, such as *Trichophyton mentagrophytes*, *Trichophyton rubrum*, *Trichophyton verrucosum*, *Trichophyton violaceutn*, *Trichosporon*, such as *Trichosporon asahii*, *Trichosporon cutaneum*, *Trichosporon inkin*, and *Trichosporon mucoides*. In some embodiments a fungus is *Coccidioides immitis*, *Coccidioides posadasii*. *Cryptococcus neoformans*, *C. gattii*, *C. albidus*, *C. laurentii*, *C. uniguttulas*, *E. floccosum*, *Fusarium graminearum*, *Fusarium oxysporum* f.sp. *cubense*, a member of the *Fusarium solani* complex, *Fusarium oxysporum*, *Fusarium verticillioides*, *Fusarium proliferatum*, *Malassezia furfur*, *Mucor circinelloides*, *Paracoccidioides brasiliensis*, *Penicillium marneffei*, *Pichia anomala*, *Pichia guilliermondi*, *Pneumocystis carinii*, *Pneumocystis jirovecii*, *Pseudallescheria boydii*, *Rhizopus oryzae*, *Rhodotorula rubra*, *Scedosporium apiospermum*, *Schizophyllum commune*, *Sporothrix schenckii*, *Trichophyton mentagrophytes*, *Trichophyton rubrum*, *Trichophyton verrucosum*, *Trichophyton tonsurans*, or *Trichophyton violaceum*, *Trichosporon asahii*, *Trichosporon cutaneum*, *Trichosporon inkin*, *Trichosporon mucoides*, *Exserohilum rostratum E. meginnisii*, or *E. longirostratum*.

In some embodiments a parasite is a protozoan. In some embodiments the parasite belongs to the phylum *Apicomplexa*. Exemplary parasites include, e.g., parasites of the genus *Plasmodium* (*Plasmodium falciparum*, *Plasmodium vivax*, *Plasmodium ovale curtisi*, *Plasmodium ovale wallikeri*, *Plasmodium malariae*, or *Plasmodium knowlesi*), *Trypanosoma*, *Toxoplasma* (e.g., *Toxoplasma gondii*), *Leishmania* (e.g., *Leishmania major*), *Isospora*, *Schistosoma*, or *Cryptosporidium*. In some embodiments a member of the genus *Cryptosporidium* is *C. parvum*, *C. hominis*, *C. canis*, *C. felis*, *C. meleagridis*, or *C. muris*. In some embodiments a member of the genus *Isospora* is *Isospora belli*. In some embodiments a member of the genus *Babesia* is *Babesia microti* or *Babesia divergens*.

In some embodiments a protozoan is a member of a genus of amoebae. In some embodiments a protozoan is a member of the genus *Entamoeba*. In some embodiments a member of the genus *Entamoeba* is *Entamoeba histolytica*, *Entamoeba dispar*, or *Entamoeba moshkovskii*. In some embodiments a protozoan is a member of the genus *Naegleria*, e.g., *Naegleria fowleri*. In some embodiments a protozoan is a member of the genus *Balamuthia*, e.g., *Balamuthia mandriallaris*. In some embodiments a protozoan is a member of the genus Acanthameba. In some embodiments a member of the genus *Giardia* is *Giardia lamblia*. In certain embodiments a protozoon is a member of genus *Sarcocystis*, e.g., *Sarcocystis bovohominis*, *Sarcocystis suihominis* or *Sarcocystis bovicanis*. In certain embodiments, a protozoon is a member of genus *Cyclospora*, e.g., *Cyclospora cayetanensis*. In certain embodiments, a protozoan is a member of genus *Neospora*, e.g., *Neospora caninum*. In certain embodiments, a protozoan is a member of genus *Theileria* e.g., *Theileria parva*. In certain embodiments, a protozoan is a member of genus *Trichomonas*, e.g., *Trichomonas vaginalis*. In some embodiments a protozoan is a kinetoplastid. In some embodiments a kinetoplastid is a trypanosomatid, e.g., a member of the genus *Leishmania*, e.g., *L. donovani*, *L. major*, *L. tropica*, or *L. braziliensis*, or a member of the genus *Trypanosoma*, e.g., *T. brucii*, *T. cruzii*, *T. congolense*, or *T. equiperdum*.

In some embodiments a parasite resides extracellularly during at least part of its life cycle. Examples include nematodes, trematodes (flukes), and cestodes. In some embodiments an antigen may be from a nematode such as *Ascaris*, *Enterobius*, *Thichuris*, and/or cestodes such as *Taenia*, *Hymenolepis*, and *Echinococcus*, a cestode such as *Taenia*, *Hymenolepis*, *Echinococcus*, or *Fasciola*, a trematode such as *Schistosoma*. In some embodiments an antigen is from *Trichinella*, *Diphyllobothrium*, *Clonorchis*, *Paragonimus*, *Ancylostoma*, *Necator*, *Strongyloides*, *Wuchereria*, *Onchocerca*, or *Dracunculus*. In some embodiments an antigen is from an intestinal helminth. In various embodiments an antigen can originate from any component of the parasite or can be derived from parasites at any stage of their life cycle of the parasite, e.g., any stage that occurs within an infected organism such as a mammalian or avian organism. In some embodiments an antigen is derived from eggs of the parasite, cysts, or substances secreted by the parasite.

A graft-associated antigen may be any antigen expressed by or present in a transplanted tissue, organ, or cells. In some embodiments a graft-associated antigen is at least in part exposed at the surface of transplanted cells. For example, a graft-associated antigen may be a cell-surface protein expressed by transplanted cells. In some embodiments a graft-associated antigen is present in transplanted tissue, organ, or cells, but is absent or substantially absent (e.g., not detectable using standard detection methods) in a subject (recipient) that receives the transplanted tissue, organ, or cells. In some embodiments a graft-associated antigen is expressed by transplanted cells but is not expressed at a detectable level by recipient cells of the same cell type as the transplanted cells or, in some embodiments. In some embodiments a graft is from a donor of a different species to the recipient (i.e., the graft is a xenograft), in which case many proteins expressed by the transplanted cells may be graft-associated antigens. In some embodiments a graft-associated antigen is a polypeptide that is polymorphic within the particular species to which the subject belongs. For example, human leukocyte antigens (HLA) antigens, e.g., major histocompatibility antigens class I (MHC I) and class II (MHCII) are highly polymorphic.

In some embodiments an antigen is a tumor antigen (TA). In general, a tumor antigen can be any antigenic substance produced by cells in a tumor, e.g., tumor cells or in some embodiments tumor stromal cells (e.g., tumor-associated cells such as cancer-associated fibroblasts or tumor-associated vasculature). In many embodiments, a TA is a molecule (or portion thereof) that is differentially expressed by tumor cells as compared with non-tumor cells. A TA may be expressed by a subset of tumors of a particular type and/or by a subset of cells in a tumor. A TA may at least in part exposed at the cell surface of tumor cells or tumor stromal cells. In some embodiments a TA comprises an abnormally modified protein, lipid, glycoprotein, or glycolipid. Tumor antigens may include, e.g., proteins that are normally produced in very small quantities and are expressed in larger quantities by tumor cells, proteins that are normally produced only in certain stages of development, proteins whose structure (e.g., sequence or post-translational modification(s)) is modified due to mutation in tumor cells, or normal proteins that are (under normal conditions) sequestered from the immune system. In some embodiments, a TA is an expression product of a mutated gene, e.g., an oncogene or mutated tumor suppressor gene, an overexpressed or aberrantly expressed cellular protein, an antigen encoded by an oncogenic virus (e.g., HBV; HCV; herpesvirus family members such as EBV, KSV; papilloma virus, etc.), or an oncofetal antigen. Oncofetal antigens are normally produced in the early stages of embryonic development and largely or completely disappear by the time the immune system is fully developed. Examples are alphafetoprotein (AFP, found, e.g., in germ cell tumors and hepatocellular carcinoma) and carcinoembryonic antigen (CEA, found, e.g., in bowel cancers and occasionally lung or breast cancer). Tyrosinase is an example of a protein normally produced in very low quantities but whose production is greatly increased in certain tumor cells (e.g., melanoma cells). Other exemplary TAs include, e.g., CA-125 (found, e.g., in ovarian cancer); MUC-1 (found, e.g., in breast cancer, ovarian cancer, and others); HER-2/neu (found, e.g., in breast cancer); melanoma-associated antigen (MAGE; found, e.g., in malignant melanoma); prostatic acid phosphatase (PAP, found in prostate cancer), Wilms' tumor 1 protein (WT1, a transcription factor overexpressed in malignant mesothelioma, leukemias, and other solid tumors); C017-1A (found, e.g., in colon cancer), GD2 (a disialoganglioside expressed on tumors of neuroectodermal origin, including human neuroblastoma and melanoma), epithelial cell adhesion molecule (Epcam; epithelial tumors). In some embodiments a TA is a cancer/testis (CT) antigen. CT antigens are a family of proteins that are frequently expressed in a large variety of malignancies but are generally absent from healthy tissue, except for the testis and placenta. CT antigens include NY-ESO-1 and LAGE-1. In some embodiments a tumor antigen comprises human telomerase reverse transcriptase (hTERT). hTERT is a protein of 1132 amino acid residues and is broadly expressed in cancers but exhibits little or no expression in most normal somatic cells. In some embodiments a TA is an NKG2D ligand such as MICA, MICB, or ULBP1-6.

In some embodiments an antigen may be a protein that is found on normal B cells and plasma cells such as CD19 or CD20. These proteins may be useful as a target in subjects with hematologic malignancies involving such cells, such as various B cell malignancies, e.g., B cell lymphomas, acute lymphoblastic leukemia (ALL), chronic lymphocytic leukemia (CLL), hairy cell leukemias (HCL), acute myelogenous leukemia (AML), and multiple myeloma (MM). Other useful protein targets in hematologic malignancies include CD22 in, e.g., HCL and ALL (e.g., B-ALL), CD30 in, e.g., Hodgkins lymphoma and anaplastic large cell lymphoma, CD37 in, e.g., CLL, and CD38 in, e.g., MM.

In some embodiments a tumor antigen is mesothelin (Gene ID: 10232 (MSLN; the gene encodes a precursor protein that is cleaved into two products, megakaryocyte potentiating factor and mesothelin); NP_001170826.1 (isoform 1); NP_037536.2 (isoform 2). Mesothelin is a glycosylphosphatidylinositol (GPI) anchored cell surface protein that is highly expressed in a variety of cancer such as mesothelioma, ovarian cancer, pancreatic cancer, and is also expressed in lung adenocarcinoma, uterine serous carcinoma, cholangiocarcinoma, squamous cell carcinoma, and acute myeloid leukemia (Tang, Z, et al., Anticancer Agents Med Chem. 2013 Feb. 1; 13(2): 276-280, and references therein). Mesothelin can bind to MUC16 (also known as CA-125), to mediate heterotypic cell adhesion. A variety of agents that bind to mesothelin are known in the art. Such agents, or others, may be used as binding moieties or targeting moieties. For example, MORAb-009 (amatuximab), is a chimeric monoclonal antibody containing a single chain murine variable region (scFv) (murine anti-mesothelin scFv SS1) and human IgGγ1 and k constant regions. A human mAb, m912 that specifically binds to cell surface associated mesothelin was isolated from a human Fab library (Feng Y, et al. Mol. Cancer Ther. 2009; 8:1113-1118). A high-affinity human mAb named HN1 was identified based on a scFv isolated by phage display technology (Ho M, et al. Int. J. Cancer. 2011; 128:2020-2030). In some embodiments mesothelin or a fragment or variant thereof that binds to CA-125 may be used as a binding moiety, e.g., to target cells to tumor cells that express CA-125. In some embodiments the fragment of mesothelin comprises at least amino acids 296-359, consisting of 64 amino acids at the N-terminal of cell surface mesothelin.

In some embodiments a tumor antigen is a glypican, e.g., glypican 3 (GPC3). Glypicans are GPI-anchored proteins expressed by a variety of different cell types. Humans have six glypican proteins; GPC1-GPC6. Glypican 3 (GPC3) is expressed at high levels in certain tumors of various types, including hepatocellular carcinoma, colorectal cancer, ovarian clear cell carcinoma (CCC), and melanoma. Glypican 1 (GPC1) is expressed at high levels in a number of tumor types, including certain breast cancers and pancreatic cancer (e.g., pancreatic ductal adenocarcinoma). A variety of agents that bind to glypicans are known in the art. Such agents, or others, may be used as targeting moieties. For example. In some embodiments a subject with a tumor that has increased GPC3 expression has an elevated level of a soluble GPC3 fragment in their blood as compared with a normal level, as a result of cleavage of cell surface GPC3. In some embodiments the binding moiety binds to an epitope that comprises a portion of the extracellular portion of the C-terminal domain of GPC3 (e.g., within the C-terminal ~30 kD up to about amino acid 560) so as to bind to GPC3 molecules that remain attached to the cell surface. A variety of antibodies that bind to GPC3 are known in the art. Examples include monoclonal antibodies 1G12 (Capurro M, et al. Gastroenterology. 2003; 125:89-97) and YP6, YP7, YP8, YP9 and YP9.1 (Phung, Y., et al., MAbs. 2012 Sep. 1; 4(5): 592-599) A humanized and stabilized version of the murine anti-GCP3 monoclonal antibody GC33 has been described (Nakano, K., et al, Anticancer Drugs. 2010; 21:907-16). HN3 is a human heavy-chain variable domain antibody with high affinity (Kd=0.6 nM) for cell-surface-associated GPC3 molecules that recognizes a conformational epitope that requires both the amino and carboxy terminal domains of GPC3 (Feng, M., et al., Proc Natl Acad Sci USA. 2013; 110(12): E1083-91).

In some embodiments an antigen is chondroitin sulfate proteoglycan-4 (CSPG4). CSPG4 is highly expressed in melanoma, breast cancer (including triple negative breast cancer), head and neck squamous cell carcinoma, mesothelioma, glioblastoma, clear cell renal carcinoma, and sarcomas (Wang X, et al. Curr Mol Med. 2010 June; 10(4):419-29). A CSPG4-specific fully human single-chain antibody termed scFv-FcC21 has been described (Wang, X., et al., Cancer Res. (2011), 71(24):7410-22). scFv-FcC21 or its antigen-binding domain may be used to target cells to tumors.

In some embodiments an antigen may be a signaling lymphocyte activation molecule (SLAM) family receptor, such as SLAM or SLAMf7 (also known as CS1 and CD319).

In some embodiments an antigen is B cell maturation factor (BCMA), also known as B cell maturation antigen (BCMA, also known as CD269 and TNFRSF17). BCMA is a tumor necrosis family receptor (TNFR) member that is expressed in cells of the B cell lineage, such as terminally differentiated B cells and plasma cells. BCMA delivers pro-survival cell signals upon binding of its ligands, B cell activator of the TNF family (BAFF) and a proliferation inducing ligand (APRIL). Among other things, BCMA has functional activity in mediating the survival of B lineage cells such as plasma cells that maintain long-term humoral immunity. The expression of BCMA has also been linked to a number of cancers, autoimmune disorders, and infectious diseases. In some embodiments, cells are conjugated with a binding moiety that binds to BCMA. In some embodiments, cells conjugated with a binding moiety that binds to BCMA are used to deplete or inhibit a biological activity of cells that express BCMA. An exemplary binding moiety is SG1, an antibody that binds to BCMA and inhibits its activity (Ryan, M C, Mol Cancer Ther. 2007; 6(11):3009-18). In some embodiments, cells that are conjugated with a moiety that binds to BCMA are cytotoxic immune cells, e.g., cytotoxic T cells or NK cells and/or may have a cytotoxic moiety, e.g., a pro-apoptotic moiety such as TRAIL, attached thereto. The moiety that binds to BCMA, the cytotoxic moiety, or both, may be attached to the cell, e.g., to a non-genetically engineered endogenous polypeptide expressed by the cell, using sortase. In some embodiments the cells that express BCMA are abnormally reactive and/or autoantibody-secreting plasma cells and/or B cells. Depletion or inhibition of such cells may be useful in the treatment of a wide variety of autoimmune diseases, such as systemic lupus erythematosus (SLE), rheumatoid arthritis (RA), Sjogren's syndrome, or other autoimmune diseases. In some embodiments, cells conjugated with a moiety that binds to BCMA are used to deplete cancer cells that express BCMA. BCMA is expressed on a number of cancers, including a variety of hematologic malignancies such as Hodgkin's and non-Hodgkin's lymphomas and multiple myeloma, and its biological relevance in maintaining the viability and proliferation of various malignant cells has been demonstrated (see, e.g., Chiu, A, et al., Blood. 2007 Jan. 15; 109(2):729-39). BCMA expression has also been found on a variety of other tumor types such as glioblastoma, leukemia, Waldenstrom macroglobulinemia, and glioblastomas.

In some embodiments, an antigen is CD19. In some embodiments, cells are conjugated with a moiety that binds to CD19. In some embodiments, the binding moiety comprises an antibody that binds to CD19. Examples of such antibodies include XmAb5603 or XmAb5574 (Xenocor, Inc., Monrovia, Calif. and Morphosys, AG, Martinsried, Germany), which are IgG1, humanized MAbs (Horton H M, et al, Cancer Res 2008; 68(19):8049-8057). In some embodiments the murine monoclonal antibody FMC63 or a humanized version thereof is used as a binding moiety that binds to CD19. In certain embodiments anti-CD19 monoclonal antibodies described in U.S. Pat. Pub. No. 20110104150 may be used.

In some embodiments a TA is expressed by tumor-associated stromal cells (e.g., tumor-associated fibroblasts or tumor-associated macrophages) or by tumor-associated vasculature. In some embodiments a TA is a component of the modified subendothelial tumor extracellular matrix. Such component(s) may be secreted by tumor cells or tumor-associated cells. Examples include certain splice isoforms of fibronectin or of tenascin-C. Fibronectin is a large glycoprotein found in the extracellular matrix of mammalian tissues and plasma. Under tissue remodeling conditions, alternative splicing can lead to the insertion of EDB, an extra 91-amino-acid type III homology domain, into fibronectin. EDB is typically undetectable in healthy individuals, but in many aggressive solid tumors EDB is highly expressed around tumor vasculature. L19 is an antibody that recognizes EDB with high affinity and has been shown to localize to tumor blood vessels in animal models and cancer patients. Tenascins are glycoproteins found in the extracellular matrix of vertebrates. Isoforms of tenascin can arise in tumors through alternative splicing at sites of neo-angiogenesis. The C domain of tenascin is undetectable in normal adult tissue but strongly expressed in a perivascular pattern in brain and lung tumors. The F16 antibody recognizes the extra-domain A1 of tenascin and has shown selective accumulation at tumors and sites of inflammation in inflammatory disorders in animals and humans (see List, T. and Neri, D. Clinical Pharmacology: Advances and Applications 2013:5 (Suppl 1) 29-45, and references therein, for discussion of these and other antibodies that bind to the same antigens or other antigens of interest).

In some embodiments, an antigen is a molecular component (eg, histones or DNA) that may be released at sites of cell death, such as necrotic areas in tumors. Binding moieties, e.g., antibodies, that bind to such antigens may be used to target cells to a tumor. For example, human NHS76 is a phage display derived human monoclonal antibody that recognizes nucleic acids exposed by necrotic tumor cells as well as metastases (Sharifi J, et al. Hybrid Hybridomics. 2001; 20(5-6):305-312).

In some embodiments an antigen comprises a peptide. In some embodiments the peptide is at least 6, 7, 8, 9, 10, 11, 12, 13, 14, or 15 amino acids long. In some embodiments the peptide is between 20 and 50 amino acids long. In some embodiments the peptide is between 8 and 30, between 15 and 25, between 20 and 30, between 25 and 35, or between 35 and 50 amino acids long. Peptides may bind directly to MHC molecules expressed on cell surfaces, may be ingested and processed by APC and displayed on APC cell surfaces in association with MHC molecules, and/or may bind to purified MHC proteins (e.g., MHC oligomers). In some embodiments a peptide contains at least one epitope capable of binding to an appropriate MHC class I protein and/or at least one epitope capable of binding to an appropriate MHC class II protein. In some embodiments a peptide comprises a CTL epitope (e.g., the peptide can be recognized by CTLs when bound to an appropriate MHC class I protein). In some embodiments a peptide comprises a Th epitope (e.g., the peptide can be recognized by Th cells when bound to an appropriate MHC class II protein). In some embodiments the sequence of a peptide comprises or consists of the sequence of a portion of a longer polypeptide that is naturally encoded by a pathogen or a neoplastic cell or is produced by an infected cell as a result of the infection. In some embodiments an antigen is an artificial polypeptide whose sequence comprises multiple distinct sequences from different distinct polypeptides. For example, sequence of peptides that would be found as portions of distinct antigens in nature may be combined to produce a composite antigen comprising epitopes originating from such distinct antigens. For example, an antigen may comprise a polypeptide represented as X1-X2 . . . -Xn, where X1, X2 . . . Xn represent peptides found in distinct proteins, and in which n may range, e.g., from 2 to 5, 10, 20, or more. It will be understood that X1, X2, etc., may be directly adjacent to each other or joined by intervening linker(s). The resulting composite antigen may be capable of stimulating an immune response to multiple distinct antigens, e.g., each of the distinct antigens. In some embodiments multiple epitopes, e.g., multiple immunodominant epitopes, are combined to generate a composite antigen. In some embodiments the sequence of an antigen comprises multiple distinct variants of a polypeptide, wherein such variants are found in different strains, serotypes, or subtypes of a pathogen. For example, an antigen may comprise peptides or polysaccharides obtained from at least 2, 5, 10, 20, or more strains, serotypes, or subtypes (e.g., clades) of a pathogen. In some embodiments the sequence of an antigen comprises multiple distinct variants of a polypeptide, wherein such variants are found in different pathogenic strains or different pathogenic species belonging to a particular genus. In some embodiments at least some of the different polypeptides are naturally encoded by the same pathogen. In some embodiments the different polypeptides are naturally encoded by different pathogens. In some embodiments the different pathogens are viruses, bacteria, fungi, or parasites. In some embodiments the sequence of an antigen comprises multiple distinct sequences from different distinct tumor antigens. In some embodiments an antigen is any antigen known or used in the art as a vaccine or vaccine component. In some embodiments an epitope or antigen is a synthetic compound whose sequence or structure resembles that of a naturally occurring epitope antigen. For example, in some embodiments the sequence of a naturally occurring epitope or antigen may be altered by addition, deletion, or substitution of one or more amino acids. In some embodiments an epitope or antigen comprises a portion at least 80%, 85%, 90%, 95%, 96%, 96%, 97%, 98%, 99%, or more identical in sequence to at least a portion of a naturally occurring polypeptide, wherein the portion of the naturally occurring polypeptide is at least 10; 20; 30; 40; 50; 100; 200; 500; 1,000; 2,000; 3,000, or more amino acids long.

In some embodiments epitopes may be provided as a pool of peptides, which may be derived from one or more proteins. The protein(s) may include one or more proteins that are known to be target(s) of cell-mediated and/or humural immunity in at least some individuals. In some embodiments a mixture of peptides may contain at least one epitope capable of binding to MHC class I proteins and at least one epitope capable of binding to MHC class II proteins. In some embodiments a mixture of peptides may contain at least one CTL epitope and at least one Th epitope. A peptide pool may comprise multiple epitopes that can bind to different MHC alleles. Peptides in the pool may bind to MHC alleles from individuals of diverse genetic backgrounds and may be capable of stimulating T and/or B cells from individuals of diverse genetic backgrounds. The peptides may be from 8 to 30 amino acids (aa) long, e.g., 9 to 15 aa long, 15 to 25 aa long. In some embodiments the peptides may be generated by chemical and/or enzymatic partial hydrolysis of longer protein(s). In some embodiments the peptides comprise a mixture of overlapping synthetic peptides. Overlapping synthetic peptides typically represent sequential stretches of amino acids, wherein a given peptide within the pool overlaps with neighboring peptides by at least one aa up to n−1 aa, wherein n is the length of the peptides. The first aa of a given peptide may be offset from the first aa of its neighboring peptides by from 1 aa up to n−1, wherein n is the length of the peptides. In some embodiments the offset is 2, 3, 4, or 5 amino acids. For example, individual peptides may be 15 aa in length (15 mer) and overlap with their neighboring peptides by 11 aa (offset=4). Starting at position 1 of a 30 amino acid polypeptide, such a peptide pool would contain peptides extending from aa 1-15, aa 5-20, aa 10-25, and aa 15-30. As another example, peptides may be 20 aa in length, with 10 aa overlaps between sequential peptides (offset=10). Peptides in a pool may be, but need not be, the same length. A peptide pool may include some peptides that fall completely within the sequence of other peptides. The peptides may cover all or part of the full length of a polypeptide. In some embodiments a peptide pool comprises peptides that collectively encompass at least 50%, 60%, 70%, 80%, 90%, 95%, or all 9 peptide sequences of a particular protein or proteins. The number of different peptides in a peptide pool may range from 2 up to about 300, up to about 500, up to about 1,000, or more. In some embodiments the number of different peptides is at least 10, 20, 30, 40, 50, e.g., between 20 and 100, 100 and 200, 200 and 300, 300 and 400, or 400 and 500. The peptides may be synthesized using standard solid phase peptide synthesis methods.

In general, an antigen or epitope that originates from a particular source may, in various embodiments, be isolated from such source or may be produced using any appropriate means, e.g., using recombinant nucleic acid technology or chemical synthesis, or combinations thereof. An antigen or epitope may be modified, e.g., by conjugation to another molecule or entity (e.g., an adjuvant), chemical or physical denaturation, etc. In certain embodiments an antigen or antigen composition comprises or is derived at least in part from cells or tissues. For example, a tumor or tumor sample may be removed from a subject and used to isolate or identify one or more antigens present in the tumor or tumor sample. Such antigens may be used, e.g., to stimulate immune cells ex vivo, to generate or select binding agents (e.g., antibodies) that bind to the antigen(s).

Antigens may be useful for a variety of purposes. It will be understood that epitopes derived from a particular antigen may be used for any such purpose in certain embodiments. For example, an antigen may be used to identify, generate, test, or use an antibody or other agent that binds to the antigen or may be conjugated to another entity, e.g., to a polypeptide or cell. Antigens may be used in vitro to load or stimulate cells of the immune system. For example, antigens may be contacted with APCs to cause such APCs to take up, process, and display epitopes at the cell surface. The APCs may be administered to a subject or may be used in vitro to stimulate cells of the adaptive immune system (e.g., naïve T and/or B cells), which may subsequently be administered to a subject.

Pathogen-derived antigens may be useful in, e.g., identifying or detecting pathogens or pathogen-infected cells (e.g., for purposes of diagnosis of an infection, for purposes of monitoring subjects who have received treatment for an infection e.g., to test for recurrence), for purposes of targeting various agents (e.g., therapeutic agents) to pathogens or pathogen-infected cells, and/or for purposes of modulating (e.g., directing or enhancing) an immune response towards pathogens or pathogen-infected cells. Tumor antigens may be useful in, e.g., identifying or detecting tumor cells or tumor-associated cells (e.g., for purposes of diagnosis, for purposes of monitoring subjects who have received treatment for a tumor, e.g., to test for recurrence), for purposes of targeting, e.g., targeting therapeutic agents or cells, to tumor cells or tumor-associated cells, and/or for purposes of modulating (e.g., directing or enhancing) an immune response towards tumor cells or tumor-associated cells.

Self antigens may be useful in, e.g., identifying or detecting antibodies or immune system cells that may contribute to an autoimmune disease (e.g., for purposes of diagnosis of an autoimmune disease, for purposes of monitoring subjects who have received treatment for an autoimmune disease, e.g., to test for recurrence), identifying or detecting self cells or substances towards which an inappropriate, e.g., harmful or potentially harmful, immune response is directed in an autoimmune disease (e.g., for purposes of diagnosis or treatment selection), for purposes of targeting various agents (e.g., therapeutic agents) to self cells or substances towards which an inappropriate, e.g., harmful or potentially harmful, immune response is directed in an autoimmune disease, and/or for purposes of modulating (e.g., inhibiting) an immune response towards cells or substances towards which an inappropriate, e.g., harmful or potentially harmful, immune response is directed in an autoimmune disease.

Graft-associated antigens may be useful in, e.g., identifying or detecting antibodies or immune system cells that may contribute to graft rejection (e.g., for purposes of diagnosis of graft rejection, for purposes of monitoring subjects who have received a graft), identifying or detecting grafted cells towards which a harmful or potentially harmful immune response is directed in a subject who has received a graft (e.g., for purposes of diagnosis or treatment selection), for purposes of targeting various agents (e.g., therapeutic agents) to grafted cells towards which a harmful or potentially harmful immune response is directed in in a subject who has received a graft, and/or for purposes of modulating (e.g., inhibiting) an immune response towards grafted cells in a subject who has received a graft.

In some embodiments an antigen is a target for a targeting moiety that targets an entity, e.g., a cell, detection agent, or therapeutic agent, to a pathogen, pathogen-infected cell, tumor cell, or tumor associated cell. In some embodiments an antigen is a target for a targeting moiety that targets an entity, e.g., a cell, detection agent or therapeutic agent, towards a cell or substance comprising a self antigen or other antigen towards which tolerance is desired, such as a graft-associated antigen. In some embodiments an agent conjugated to a living mammalian cell using sortase comprises a moiety that binds to an antigen, such as an antibody or antibody fragment.

In some embodiments a protein comprises an antibody, antibody fragment, or antibody domain. In some embodiments a protein comprising an antibody, antibody fragment, or antibody domain is conjugated to living mammalian cells using sortase. The cells may be used as a delivery vehicle for the protein and/or the protein may serve as a targeting moiety to target the cells to a target to which the antibody, antibody fragment, or antibody domain binds. In some embodiments a protein is a therapeutic antibody. Exemplary therapeutic antibodies that are useful in various embodiments provided herein include, but are not limited to, the following antibodies (target of the antibody is listed in parentheses together with exemplary non-limiting therapeutic indications): Abciximab (glycoprotein IIb/IIIa; cardiovascular disease), Adalimumab (TNF-α, various auto-immune disorders, e.g., rheumatoid arthritis), Alemtuzumab (CD52; chronic lymphocytic leukemia), Basiliximab (IL-2Rα receptor (CD25); transplant rejection), Bevacizumab (vascular endothelial growth factor A; various cancers, e.g., colorectal cancer, non-small cell lung cancer, glioblastoma, kidney cancer; wet age-related macular degeneration), Blinatumomab (anti-CD3/anti-CD19; various hematologic malignancies), Brentuximab (CD30; various hematologic malignancies); Catumaxomab (CD3 and EpCAM; malignant ascites), Cetuximab (EGF receptor, various cancers, e.g., colorectal cancer, head and neck cancer), Certolizumab (e.g., Certolizumab pegol) (TNF alpha; Crohn's disease, rheumatoid arthritis), Daclizumab (IL-2Rα receptor (CD25); transplant rejection), Eculizumab (complement protein C5; paroxysmal nocturnal hemoglobinuria), Efalizumab (CD11a; psoriasis), Elotuzumab (CD1 (also known as SLAMF7 and as CD319, multiple myeloma); Epratuzumab (CD22; Non-Hodgkin's lymphoma; lupus; ALL); Gemtuzumab (CD33; acute myelogenous leukemia (e.g., with calicheamicin)), Ibritumomab tiuxetan (CD20; Non-Hodgkin lymphoma (e.g., with yttrium-90 or indium-111)), Infliximab (TNF alpha; various autoimmune disorders, e.g., rheumatoid arthritis), (Ipilimumab; CTLA-4, melanoma, prostate cancer), Milatuzumab (CD74; CD74-positive hematologic malignancies and solid tumors); Muromonab-CD3 (T Cell CD3 receptor; transplant rejection), Natalizumab (alpha-4 (a4) integrin; multiple sclerosis, Crohn's disease), Nivolumab (PD-1; cancer, e.g., non-small-cell lung cancer, melanoma, and renal-cell cancer); Omalizumab (IgE; allergy-related asthma); Ofatumumuab (CD20; Non-Hodgkin lymphoma, chronic lymphocytic leukemia); Obinutuzumab (CD20; Non-Hodgkin lymphoma, chronic lymphocytic leukemia); Palivizumab (epitope of RSV F protein; Respiratory Syncytial Virus infection), Panitumumab (EGF receptor; cancer, e.g., colorectal cancer), Ranibizumab (vascular endothelial growth factor A; wet age-related macular degeneration), Rituximab (CD20; Non-Hodgkin lymphoma), Tositumomab (CD20; Non-Hodgkin lymphoma), Trastuzumab (ErbB2; breast cancer); Tremelimumab (CTLA-4, melanoma); Veltuzumab (CD20; Non-Hodgkin lymphoma, chronic lymphocytic leukemia), and any antigen-binding fragment thereof. In some embodiments an antibody or other binding agent binds to the same target as any of the afore-mentioned antibodies. In some embodiments an antibody or other binding agent competes with any of the afore-mentioned antibodies for binding to its target. It will be understood that antigen binding domains of any of the afore-mentioned antibodies or others described may be used. For example, Fab fragments or single chain variable fragments (scFv) may be used.

In some embodiments a binding moiety, e.g., an antibody, binds to an extracellular domain of a mammalian receptor. In some embodiments the receptor is overexpressed in a tumor cell as compared with a normal cell, e.g., a normal cell of the same cell type, and/or has increased activity in a tumor cell as compared with a normal cell, e.g., a normal cell of the same cell type. In some embodiments the receptor is encoded by a gene that is mutated, is a fusion gene that results from a chromosomal translocation, and/or is amplified in a tumor cell. In some embodiments the receptor is a protein kinase, e.g., a tyrosine kinase or a serine/threonine kinase. In some embodiments the receptor is an oncogenic protein kinase.

In some embodiments, a therapeutic monoclonal antibody and a second agent useful for treating the same disease or comprising a targeting moiety are conjugated to mammalian cells using sortase. In some embodiments, the second agent comprises a polypeptide, peptide, small molecule, or second antibody.

In some embodiments, a monoclonal antibody and a cytokine, e.g., an interferon, e.g., interferon alpha, are conjugated to mammalian cells using sortase. Optionally, the monoclonal antibody and cytokine are both useful for treating the same disease.

In some embodiments one or more subunits (e.g., separate polypeptide chains) of a multisubunit protein (which term is used interchangeably with multichain protein) is conjugated to mammalian cells using sortase. In some embodiments, a multisubunit protein is a receptor (e.g., a cell surface receptor). In some embodiments, a multisubunit protein is an enzyme. In some embodiments, a multisubunit protein is a cytokine. In some embodiments, a multisubunit protein is a channel or transporter. In some embodiments at least one subunit of a multisubunit protein comprises a sortase recognition motif, which may be used to conjugate the subunit to mammalian cells or to conjugate a moiety to the polypeptide. Various multisubunit polypeptides and methods of modifying them using sortase are described in WO/2011/133704. In some embodiments a sortase recognition motif is located in a flexible loop, which may be cleaved by a protease so as to position the sortase recognition motif at or near the C-terminus of a resulting cleavage product. In some embodiments a first subunit of a multisubunit protein is conjugated to mammalian cells. In some embodiments one of more additional subunits may subsequently associate with the first subunit, e.g., to form a complete multi-subunit protein. In some embodiments such association may occur in vitro. The one or more additional subunits may be added to a culture vessel or may be produced by cells in the vessel. In some embodiments association occurs in vivo after administration of the cells to a subject. In some embodiments the one or more additional subunits may be produced by the administered cells, by other cells in the body of the subject, or may be administered to the subject. In some embodiments two or more subunits, at least one of which comprises a sortase recognition motif, assemble to form a multi-subunit protein before conjugation to mammalian cells. In some embodiments two or more subunits are covalently linked to each other directly or via a linker before the protein is conjugated to mammalian cells. In some embodiments, such linkage facilitates proper folding of the multi-subunit protein (e.g., accelerates folding or increases proportion of correctly folded functional proteins). In some embodiments a subunit of a multi-subunit protein may be modified using sortase before the subunit or a different subunit of the protein is conjugated to mammalian cells. For example, a label may be conjugated to a first subunit using sortase, and a second subunit may be conjugated to cells. The various conjugation and/or association steps may occur in any order in various embodiments.

In some embodiments a protein comprises a peptide that binds to a target. In some embodiments the peptide is selected using a display technology, e.g., phage display, yeast display, ribosome display, bacterial display, or directed evolution. In some embodiments the peptide is selected from a peptide library. In some embodiments a protein may comprise any of a variety of polypeptide scaffolds known in the art including, e.g., those based on or incorporating one or more protein folds or domains from, e.g., protein Z, fibronectin, ankyrin repeat proteins; cysteine-knot miniproteins, Armadillo repeat proteins, lipocalins, or stefin A. In some embodiments a protein comprises an affibody, adnectin, DARPin, knottin, anticalins, or steffin. The protein, e.g., affibody, adnectin, DARPin, knottin, anticalins, or steffin, may be designed or selected to bind to a target of interest. Such engineered binding proteins may in some embodiments have a specificity and/or affinity comparable to or in some embodiments superior to that of typical antibodies. In some embodiments a peptide that binds to a target is inserted into a polypeptide scaffold. See, e.g., Hoffmann, T., et al. Protein Eng Des Sel., 23(5):403-13, 2010, and references therein, for discussion of various proteins and polypeptide scaffolds. In some embodiments any such protein or scaffold is used, e.g., as a binding moiety, targeting moiety, immunomodulator, or therapeutic agent.

In some embodiments a binding agent or moiety, e.g., an antibody, binds to a target antigen, target entity, or binding partner with a $K_D$ of less than about $10^{-6}$M, less than about $10^{-7}$M, less than about $10^{-8}$M less than about $10^{-9}$M, less than about $10^{-10}$ M, less than about $10^{-11}$M, less than about $10^{-12}$M, or less than about $10^{-13}$M. In certain embodiments a binding agent or moiety binds to a target antigen or target entity or binding partner with a $K_D$ of between about $10^{-6}$M and about $10^{-13}$M, e.g., between about $10^{-6}$M and about $10^{-7}$M, between about $10^{-7}$M and about $10^{-8}$M, between about $10^{-8}$M and about $10^{-9}$M, between about $10^{-9}$M and about $10^{-10}$ M, between about $10^{-10}$ M and about $10^{-11}$M, or between about $10^{-11}$M and about $10^{-12}$ M or between about $10^{-12}$M and about $10^{-13}$M. In some embodiments a binding interaction may have a $K_D$ of between about $10^{-16}$M and about $10^{-12}$M.

In certain embodiments nucleic acids, e.g., short interfering RNAs, antisense oligonucleotides, or aptamers, may be conjugated to mammalian cells using sortase or used in vitro, e.g., to promote or inhibit expansion, activation, or differentiation of cells. In some embodiments nucleic acid aptamers are of interest, e.g., as binding moieties, targeting moieties, immunomodulators, therapeutic agents, ligands. An aptamer comprises an oligonucleotide that binds specifically and with high affinity to its target (e.g., a protein target). In some embodiments the oligonucleotide is single-stranded (although it may in some embodiments form regions of double-stranded secondary structure through intramolecular complementarity). An aptamer may be identified through a selection process using, e.g., systematic evolution of ligands by exponential enrichment (SELEX), phage display, or various directed evolution techniques. See, e.g., Turek, C. and Gold, L., Science 249: 505-10, 1990; Brody E N and Gold L J, Biotechnol. J, 74(1):5-13, 2000; L. Cerchia and V. de Franciscis, Trends Biotechnol., 28: 517-525, 2010; Keefe, A. Nat. Rev. Drug Discov. 9: 537-550, 2010. Aptamers can be generated using DNA or RNA backbones, either of which may comprise any of a variety of modifications such as substitution of ribonucleotides with 2'-amino, 2'-fluoro, or 2'-O-alkyl nucleotides. Aptamers can be generated against most targets and can inhibit the function of the proteins to which they bind or may act as agonists to activate a receptor to which they bind. Aptamers may be, e.g., about 25 to 80 nt long and can be synthesized chemically.

In some embodiments small molecules may be used, e.g., as targeting moieties, immunomodulators, detection agents, therapeutic agents, or as ligands to activate or inhibit a receptor.

In some embodiments an agent to be conjugated to mammalian cells comprises an anti-cancer agent (also termed a "chemotherapy drug"). In certain embodiments cells are conjugated both with an anti-cancer agent and a targeting moiety, wherein the targeting moiety targets the cell to a cancer, which in some embodiments is a cancer of a type that is typically treated with the anti-cancer agent. In certain embodiments cells conjugated with an anti-cancer agent and/or with a targeting moiety that targets the cells to a cancer are administered to a subject who is in need of treatment for cancer. Any anti-cancer agent may be used in various embodiments. In some embodiments an anti-cancer agent is a protein, e.g., a monoclonal antibody. In some embodiments an anti-cancer agent is an enzyme, e.g., asparaginase. Non-limiting examples of chemotherapy drugs that may be used include, e.g., alkylating and alkylating-like agents such as nitrogen mustards (e.g., chlorambucil, chlormethine, cyclophosphamide, ifosfamide, and melphalan), nitrosoureas (e.g., carmustine, fotemustine, lomustine, streptozocin); platinum agents (e.g., alkylating-like agents such as carboplatin, cisplatin, oxaliplatin, BBR3464, satraplatin), busulfan, dacarbazine, procarbazine, temozolomide, thioTEPA, treosulfan, and uramustine; anti-metabolites such as folic acids (e.g., aminopterin, methotrexate, pemetrexed, raltitrexed); purines such as cladribine, clofarabine, fludarabine, mercaptopurine, pentostatin, thioguanine; pyrimidines such as capecitabine, cytarabine, fluorouracil, floxuridine, gemcitabine; spindle poisons/mitotic inhibitors such as taxanes (e.g., docetaxel, paclitaxel), vincas (e.g., vinblastine, vincristine, vindesine, and vinorelbine), epothilones; cytotoxic/anti-tumor antibiotics such anthracyclines (e.g., daunorubicin, doxorubicin, epirubicin, idarubicin, mitoxantrone, pixantrone, and valrubicin), compounds naturally produced by various species of *Streptomyces* (e.g., actinomycin, bleomycin, mitomycin, plicamycin) and hydroxyurea; topoisomerase inhibitors such as camptotheca (e.g., camptothecin, topotecan, irinotecan) and podophyllums (e.g., etoposide, teniposide); monoclonal antibodies for cancer therapy such as anti-receptor tyrosine kinases (e.g., cetuximab, panitumumab, trastuzumab), anti-CD20 (e.g., rituximab and tositumomab), and others for example alemtuzumab, aevacizumab, gemtuzumab; photosensitizers such as aminolevulinic acid, methyl aminolevulinate, porfimer sodium, and verteporfin; tyrosine and/or serine/threonine kinase inhibitors, e.g., inhibitors of Abl, Kit, insulin receptor family member(s), VEGF receptor family member(s), EGF receptor family member(s), PDGF receptor family member(s), FGF receptor family member(s), mTOR, Raf kinase family, phosphatidyl inositol (PI) kinases such as PI3 kinase, PI kinase-like kinase family members, cyclin dependent kinase (CDK) family members, Aurora kinase family members (e.g., kinase inhibitors that are on the market or have shown efficacy in at least one phase III trial in tumors, such as cediranib, crizotinib, dasatinib, erlotinib, gefitinib, imatinib, lapatinib, nilotinib, sorafenib, sunitinib, vandetanib), growth factor receptor antagonists, and others such as retinoids (e.g., alitretinoin and tretinoin), altretamine, amsacrine, anagrelide, arsenic trioxide, asparaginase (e.g., pegasparagase), bexarotene, bortezomib, denileukin diftitox, estramustine, ixabepilone, masoprocol, mitotane, and testolactone, Hsp90 inhibitors, proteasome inhibitors (e.g., bortezomib), angiogenesis inhibitors, e.g., anti-vascular endothelial growth factor agents such as bevacizumab (Avastin) or VEGF receptor antagonists or soluble VEGF receptor domain (e.g., VEGF-Trap), matrix metalloproteinase inhibitors, various pro-apoptotic agents (e.g., apoptosis inducers), Ras inhibitors, anti-inflammatory agents, cancer vaccines, or other immunomodulating therapies, RNAi agents targeted to oncogenes, etc. It will be understood that the preceding classification is non-limiting. A number of anti-tumor agents have multiple activities or mechanisms of action and could be classified in multiple categories or classes or have additional mechanisms of action or targets.

In some embodiments an agent to be conjugated to mammalian cells comprises an anti-microbial agent. As used herein, anti-microbial agents include compounds that inhibit proliferation or activity of, weaken, destroy, or kill bacteria, viruses, fungi, parasites (e.g., protozoa, helminths (whether or not microscopic) compounds that inhibit invasion of cells by viruses, bacteria, or parasites; compounds that inhibit one or more steps of a viral, bacterial, fungal, or parasite life cycle. In certain embodiments cells are conjugated with an anti-microbial agent suitable for use against a bacteria, virus, fungi, or parasite and with a targeting moiety, wherein the targeting moiety targets the cell to the bacteria, virus, fungi, or parasite or targets the cell to a cell infected by the bacteria, virus, fungi, or parasite.

One of skill in the art will be aware of or can readily obtain the sequences of proteins described herein or other proteins of interest. Naturally occurring sequences, e.g., genomic, mRNA, and polypeptide sequences, from a wide variety of species, including human, are known in the art and are available in publicly accessible databases such as those available at the National Center for Biotechnology Information (www.ncbi.nih.gov) or Universal Protein Resource (www.uniprot.org). Databases include, e.g., GenBank, RefSeq, Gene, UniProtKB/SwissProt, UniProtKB/Trembl, and the like. In general, sequences, e.g., nucleic acid (e.g., mRNA) and polypeptide sequences, in the NCBI Reference Sequence database may be used as reference sequences. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (dbSNP), available at the NCBI website at www.ncbi.nlm.nih.gov/projects/SNP/. (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). Multiple isoforms of certain proteins may exist, e.g., as a result of alternative RNA splicing or editing. In general, where aspects of this disclosure pertain to a gene or gene product, embodiments pertaining to allelic variants or isoforms are encompassed unless indicated otherwise. Certain embodiments may be directed to particular sequence(s), e.g., particular allele(s) or isoform(s). It will be understood that a polypeptide may be encoded by any of numerous different nucleic acid sequences due to the degeneracy of the genetic code. If a polypeptide is produced recombinantly, a nucleic acid sequence encoding the polypeptide may be selected or codon optimized for expression in a particular species, if desired. It should be understood that wherever reference is made herein to a protein or polypeptide, e.g., a naturally occurring protein or polypeptide, the invention provides embodiments in which a variant or fragment, e.g., a functional variant or fragment, may be used. (See discussion of variants and fragments above). For example, it will be understood that an enzyme conjugated to mammalian cells for purposes of supplementing or replacing an enzyme that is lacking or present in insufficient amounts need not be identical in sequence to a naturally occurring enzyme that is lacking or insufficient, so long as it provides the appropriate catalytic activity.

In some embodiments a protein or other moiety conjugated to mammalian cells is PEGylated. In some embodiments PEGylation is may be accomplished using sortase, e.g., before the protein or other moiety is conjugated to mammalian cells. For example, a protein may be PEGylated at its N-terminus and then conjugated to mammalian cells via its C-terminus. In some embodiments sortase is used to conjugate a moiety comprising PEG to mammalian cells.

Sortagged cells, e.g., sortagged mammalian cells, described herein have a number of uses. Some of these uses are described herein, but the invention is not limited to uses described herein. In some embodiments sortagged mammalian cells may be used in cell therapy. As used herein, the terms "cell therapy", "cell-based therapy", or "cellular therapy" are used interchangeably to refer to administration of eukaryotic cells, e.g., mammalian cells, to a subject for therapeutic purposes. In some embodiments cell therapy comprises cell-based immunotherapy, which refers to administration of cells to a subject in order to modulate or augment the subject's immune system or immune response for therapeutic purposes. Cell-based immunotherapy encompasses administering immune system cells to a subject, wherein the administered cells or their descendants, through their own effector mechanisms and/or through interactions with cells or substances of the subject's immune system, may provide a therapeutic benefit to the subject. It will be understood that where the present disclosure refers to the effects of administered cells, such effects encompass the effects of the administered cells and their descendants that are generated in vivo. In some embodiments cell therapy is administered for treatment of cancer, infections, autoimmune diseases, or enzyme deficiencies. In certain embodiments administered cells may originate from the individual to whom they are administered (autologous), may originate from different genetically identical individual(s) of the same species (isogeneic), may originate from different non-genetically identical individual(s) of the same species (allogeneic), or may originate from individual(s) of a different species. In certain embodiments allogeneic cells may originate from an individual who is immunocompatible with the subject to whom the cells are administered.

In some embodiments living mammalian cells modified by sortase-mediated conjugation of an agent thereto are used as delivery vehicles for the agent. For example, living mammalian cells that have a protein conjugated to their surface may serve as delivery vehicles for the protein. Such cells may be administered to a subject suffering from a deficiency of the protein or who may benefit from increased levels of the protein. In some embodiments the cells are administered to the circulatory system, e.g., by infusion. In some embodiments the cells are administered intravenously. For example, hematopoietic cells, e.g., RBCs, WBCs, platelets, may be administered to the circulatory system. In some embodiments the cells are administered to the lymphatic system, e.g., by infusion. In some embodiments the protein is one that is normally present in the blood, e.g., a protein produced by the liver or by hematopoietic cells or endothelial cells. In some embodiments the protein is an enzyme. The enzyme may be catalytically active or may become catalytically active after administration. In some embodiments the enzyme may act on a substrate in the blood. In some embodiments at least a portion of the protein attached to sortagged may be released from the cells in vivo. Release may occur via cleavage that, in some embodiments, also activates the protein. For example, a protein may be attached as an inactive enzyme precursor (zymogen). In some embodiments sortase-modified cells are administered locally, e.g., to a tissue or organ in which a protein or a substrate of the protein is normally produced or active. Examples of various diseases associated with deficiency of various proteins, e.g., enzymes, are provided above.

In certain embodiments mammalian cells conjugated with an anti-microbial agent and/or with a targeting moiety that targets the cells to a microbe or parasite may be administered to a subject who is at risk of infection or is infected by the microbe or parasite, e.g., a subject who has been recently exposed to the microbe or parasite, has been determined to harbor detectable levels of the microbe or parasite (e.g., in the blood), or is clinically ill with an infection caused by the microbe or parasite. The cells may be administered to the circulatory system or locally at or near a site of infection.

In certain embodiments mammalian cells conjugated with an agent that inhibits a toxic or harmful substance maybe administered to a subject who has been exposed to the toxic or harmful substance and is at risk of toxicity or damage from the substance, a subject who exhibits symptoms of exposure, or a subject who is at risk of exposure. For example, a subject who is infected by or has been exposed to a toxin-producing pathogen that may be treated with cells that have been conjugated with an agent that inhibits the toxin.

In some aspects, sortase is used to modify mammalian cells that may be used in a cell based immunotherapy. For example, in some embodiments one or more epitopes or antigens (e.g., epitopes or antigens of pathogens or tumors) may be conjugated to mammalian cells using sortase. In some embodiments the mammalian cells are hematopoietic cells, e.g., RBCs. In some embodiments the mammalian cells are fibroblasts. In some embodiments, the sortase-modified cells may be administered to a subject in order to induce or enhance an immune response against the antigen or cells comprising the antigen(s), e.g., pathogens, pathogen-infected cells, tumor cells, toxic substances, etc. In some embodiments, the sortase-modified cells may be used ex vivo, e.g., to stimulate or activate other cells, e.g., immune system cells such as T cells, antigen-presenting cells (e.g., dendritic cells, macrophages), B cells, NK cells, or precursors of any such cells. In some aspects, the present disclosure provides methods of producing or modifying a cellular artificial APC. For example, in some embodiments, a cell is sortagged with one or more moieties (e.g., antigens, TCR-engaging molecules, costimulatory molecules) that allows it to serve as an aAPC or improves its ability to serve as an aAPC, e.g., to provide costimulation. In some embodiments cells that have been stimulated ex vivo by contact with a sortase-modified cell are administered to a subject, e.g., to induce or enhance an immune response directed to a pathogen, pathogen-infected cells, tumor, toxic substance, etc.

In some embodiments, sortase-modified mammalian immune system cells are used in adoptive immunotherapy. "Adoptive immunotherapy", also called "adoptive cell transfer" (ACT) refers to administration (transfer) of immune system cells to a subject, e.g., for therapeutic purposes. In some embodiments administered immune system cells exert an immune response against a tumor, pathogen, or pathogen-infected cells. For example, cytotoxic T cells (e.g., CD8+ T cells), NK cells, or phagocytes (e.g., neutrophils, macrophages) may exert direct cytotoxic effects on target cells. In some embodiments target cells may be tumor cells, tumor-associated cells, pathogens, pathogen-infected cells, or other unwanted cells. In some embodiments target cells may be immune system cells that exert an abnormal or damaging effect on self cells or tissues. For example, target cells may be autoreactive T cell clones, plasma cells that produce autoantibodies, etc.

In certain embodiments immune system cells (e.g., cytotoxic T cells, NK cells, CD4+ T cells, DCs, neutrophils, macrophages) are sortagged with a targeting moiety that targets the cells to a tumor cell, tumor-associated cell, pathogen, pathogen-infected cell, or other unwanted target. The targeting moiety may be any moiety that binds to the target. The targeting moiety may, for example, comprise an antibody, antibody fragment, engineered polypeptide, aptamer, or ligand (e.g., small molecule ligand). In some embodiments the targeting moiety binds to a tumor antigen. The targeting moiety targets the cell to tumor cells that express the tumor antigen. Binding agents (e.g., monoclonal antibodies) that specifically bind to a variety of different tumor antigens are known in the art, and additional binding agents can be identified using methods known in the art. For example, trastuzumab binds to Her2/Neu and may be used as a targeting moiety to target tumors that express Her2/Neu (e.g., certain breast cancers). Rituximab binds to CD20 and may be used as a targeting moiety to target malignancies that express CD20 (e.g., non-Hodgkin's lymphoma (e.g., follicular lymphoma), diffuse large B cell lymphoma, mantle cell lymphoma). In certain embodiments the sortagged cells mount an immune response or promote an endogenous immune response against tumor cells, tumor-associated cells, pathogens, pathogen-infected cells, or other unwanted cells or substances to which they are targeted. The immune response may comprise cell-mediated cytotoxicity, antibody production, release of cytokines or other agents that damage the target cells, etc. In some embodiments the administered cells may have been exposed in vitro to one or more antigens expressed by a tumor cell, tumor-associated cell, pathogen, or pathogen-infected cell. The cells may be exposed prior to or after sortagging. In some embodiments the cells may have been exposed ex vivo to APCs that present an epitope of an antigen expressed by a tumor cell, tumor-associated cell, pathogen, or pathogen-infected cell. In some embodiments the cells are exposed in vitro to agents that stimulate the cells to proliferate, differentiate, or become activated, such as anti-CD3 antibodies, costimulators, etc. In some embodiments, targeting APCs, e.g., DCs, to a tumor, pathogen, pathogen-infected cell, or other target results in increased presentation of target-associated antigens by the APCs, which may enhance an immune response mounted by endogenous or administered immune system cells. In some embodiments, targeting CD4+ T cells to a tumor, pathogen, pathogen-infected cell, or other target results in increased provision of "helper" functions by such cells, which may enhance an immune response mounted by endogenous or administered immune system cells that receive such help.

In some embodiments mammalian cells are sortagged with an agent comprising a substance that is capable of exerting toxic effects on a target cell, e.g., a tumor cell, tumor-associated cell, pathogen, or pathogen-infected cell. In some embodiments the cells are administered to a subject and deliver the toxic substance to a target such as a tumor. In some embodiments the toxic substance comprises a pro-apoptotic agent, a cytolytic agent, a cytotoxic drug, or a toxin. In some embodiments the target cells are relatively susceptible to the toxic effect of the toxic substance as compared with the sortagged cells. For example, a sortagged cell may on average remain viable when sortagged with the toxic substance and able to deliver the toxic substance to a target cell in an amount that is lethal to the target cell. The target cells may differ from the sortagged cells in one or more ways that renders the target cells more susceptible to effects of the toxic substance. Differences in tumor cell metabolism, proliferation rate, or oncogene expression, as compared with most non-tumor cells may be exploited to select agents that are selectively toxic to tumor cells. In some embodiments the sortagged cells may either naturally or as a result of engineering lack a receptor for the toxic substance or may lack a molecular target or functional biological pathway by which the toxic substance acts or otherwise be rendered relatively less susceptible to effects of the toxic substance.

In some embodiments mammalian cells, e.g., immune system cells, may be sortagged with an agent comprising a cytolytic domain. For example, cells may be sortagged with a perforin, granzyme, granulysin or biologically active domain thereof. Such a cytolytic domain may increase the cytotoxic activity of the cells (e.g., if the cells are cytotoxic cells) or may confer cytotoxic activity on cells that would otherwise lack it. In some embodiments a cytolytic domain comprises or is derived from a cytolytic agent that is naturally found in a subject, e.g., one that is normally used by immune system cells of the subject to lyse cells. In some embodiments a cytolytic domain comprises or is derived from a cytolytic agent that is not naturally found in a subject. For example, a variety of cytolytic toxins, e.g., cytolysins produced by various microbes, are known (see, e.g., discussion below). An agent may further comprise a targeting moiety that targets the cells to target cells to be lysed, e.g., tumor cells, infected cells, pathogens. In some embodiments a targeting moiety is separately conjugated to the cells.

In some embodiments mammalian cells, e.g., immune system cells, may be sortagged with a pro-apoptotic agent. In some embodiments a pro-apoptotic agent is an agent comprising a domain that promotes apoptosis (pro-apoptotic domain). In some embodiments a pro-apoptotic agent is an agent that can initiate or enhance an apoptotic pathway if introduced into or activated in a cell. As known in the art, apoptosis is a process of programmed cell death that occurs in multicellular organisms, e.g., mammals. A pro-apoptotic domain may be any domain that can deliver an extracellular signal that initiates or enhances an apoptotic pathway. In some embodiments an apoptotic pathway leads to activation of caspases, e.g., initiator caspases, which in turn activate effector caspases. Effector caspases proteolytically degrade a variety of intracellular proteins to carry out the cell death program. Pro-apoptotic domains include, e.g., ligands that bind to TNF alpha receptors (e.g., TNF-R1) or Fas in mammalian cells. In some embodiments a pro-apoptotic domain may comprise any moiety that can activate TNF-R1 or Fas. In some embodiments a pro-apoptotic domain comprises FasL, Trail, Tweak, Lymphotoxin, TNF alpha, or a biologically active domain thereof. A pro-apoptotic domain or other pro-apoptotic agent may increase the cytotoxic activity of the cells (e.g., if the cells are cytotoxic cells) or may confer cytotoxic activity on cells that would otherwise lack it. In some embodiments a pro-apoptotic domain or other pro-apoptotic agent comprises or is derived from a protein that is naturally found in a subject, e.g., one that is normally used by immune system cells of the subject or during development or other physiological processes that involve apoptosis. In some embodiments a pro-apoptotic domain or other pro-apoptotic agent comprises or is derived from a substance that is not naturally found in a subject. In some embodiments a pro-apoptotic agent comprises a TRAIL receptor agonist. TRAIL receptors include TRAIL-R1 (also known as death receptor 4 (DR4) and TRAIL-R2 (also known as death receptor 5 (DR5)). TRAIL receptor agonists include the natural ligand TRAIL and other agents that bind to a TRAIL receptor and mimic the effect of TRAIL. In some embodiments the TRAIL receptor agonist is a monoclonal antibody that binds to TRAIL-R1 and/or TRAIL-R2, such as Mapatumumab (human anti-DR4 mAb), Tigatuzumab (humanized anti-DR5 mAb), Lexatumumab (human anti-DR5 mAb), Conatumumab (human anti-DR5 mAb), Apomab (human anti-DR5 mAb). In some embodiments TRAIL or a TRAIL receptor agonist is useful in treatment of breast, colon, lung, pancreatic, prostate, renal carcinoma, thyroid carcinoma, glioma, multiple myeloma or leukemia. In some embodiments a pro-apoptotic agent induces apoptosis by inhibiting an anti-apoptotic protein such as Bcl-2, Bcl-xL, and Bcl-w or by activating a pro-apoptotic protein such as BAX, BID, BAK, or BAD inside a cell. For example, a pro-apoptotic agent may be a member of the BH3-only family of proteins or a biologically active domain thereof. BH3-only proteins inhibit antiapoptotic members of the Bcl-2 family. Examples of such proteins include NOXA or a biologically active fragment thereof (e.g., the BH3 domain or the mitochondrial targeting domain). In some embodiments the pro-apoptotic agent comprises a small molecule BH3 mimetic such as ABT-737, ABT-263 (navitoclax) or ABT-199 (Vandenberg C J and Cory, S., Blood. 2013; 121(12):2285-8 and references therein). In some embodiments, a pro-apoptotic domain is useful to treat a cancer that has increased expression or activity of an anti-apoptotic protein as compared with non-cancer cells. In some embodiments, a pro-apoptotic domain is useful to treat a cancer that has become resistant to cytotoxic chemotherapy or to inhibit emergence of such resistance. A pro-apoptotic agent may further comprise a targeting moiety that targets the cells to target cells whose apoptosis is desired e.g., tumor cells, infected cells. In some embodiments a targeting moiety is separately conjugated to the cells.

In certain embodiments mammalian cells, e.g., immune system cells, are sortagged with an immunomodulator. In some embodiments the immunomodulator promotes survival, proliferation, differentiation and/or one or more activities of at least some of the administered cells. In some embodiments the immunomodulator comprises a stimulatory cytokine, costimulatory molecule (e.g., OX40, OX40L, CD137L), or adjuvant (e.g., a CD40 ligand, anti-CD40 antibody, TLR ligand). In certain embodiments immune system cells are sortagged with a targeting moiety and an immunomodulator. A targeting moiety and an immunomodulator may be provided as individual agents or may be part of a bifunctional agent.

In some embodiments administered immune system cells may modulate immune system cells that are co-administered to the subject or already present in the subject. For example, administered immune system cells may stimulate or inhibit proliferation, activation, differentiation, migration, and/or maturation of immune system cells present in the subject. Stimulation or inhibition may result at least in part from secretion of cytokine(s) by the transferred cells and/or from cell-cell interactions (e.g., display of costimulatory molecules or inhibitory molecules such as CD28/CTLA-4 family members (e.g., CTLA-4 or PD-1 ligand) by the transferred cells). In some embodiments a moiety conjugated to immune system cells may comprise a costimulator. Such cells may provide costimulation at a tumor site or site of infection, which may, for example, enhance the ability of tumor-specific or pathogen-specific T cells to eliminate tumor cells or infected cells. Whether transferred cells stimulate or inhibit the immune system of the subject may depend on a variety of factors, such as the properties of the particular cell type transferred and/or the identity and/or amount of the agent conjugated to the transferred cells. Such factors may be selected according to the desired effect of the cells. Transferred CD4+ T cells may provide "help" to endogenous or co-administered cytotoxic cells, which may expand and/or augment the ability of cytotoxic cells to eliminate target cells. Transferred Treg cells may suppress immune responses of endogenous immune system cells that may otherwise exert unwanted or deleterious activity against the subject's own cells or tissues or against transplanted cells or tissues. Such suppression may be useful to treat autoimmune diseases or reduce the likelihood of rejection of a transplant.

In some embodiments immune system cells comprise a polyclonal population, in that the population comprises multiple subpopulations of cells that express TCRs or BCRs that are specific for a variety of different targets, antigens, or epitopes. For example, a polyclonal population may comprise T and/or B cells that collectively express at least $10^3$, $10^4$, $10^5$, or more distinct TCRs or BCRs. A polyclonal population of lymphocytes may be obtained, e.g., from peripheral blood. In some embodiments immune system cells comprise a monoclonal population of T or B cells in that cells in the population carry TCRs or BCRs that are specific for a particular epitope, which may be an epitope present in or on a target such as a tumor cell, tumor-associated cell, pathogen, pathogen-infected cell, or other unwanted cell. In some embodiments two or more monoclonal populations may be combined, e.g., populations having TCRs or BCRs specific for different epitopes of a target antigen or different antigens of a target entity.

In some embodiments autologous or allogeneic T cells with anti-tumor activity are obtained, optionally expanded and/or activated in vitro, and sortagged, (e.g., with a targeting moiety, biologically active moiety, or both). In some embodiments the sortagged T cells are introduced into a subject in need of treatment for cancer. In some embodiments T cells comprise autologous tumor-infiltrating lymphocytes (TILs). Autologous TILs may be obtained using methods known in the art from a tumor following biopsy or removal of the tumor from the subject. In some embodiments allogeneic T cells are a T cell line, e.g., the NK-92 cell line or a derivative thereof.

In some embodiments autologous or allogeneic NK cells with anti-tumor activity are obtained, optionally expanded and/or activated in vitro, and sortagged, (e.g., with a targeting moiety, biologically active moiety, or both). In some embodiments the sortagged NK cells are introduced into a subject in need of treatment for cancer. In some embodiments allogeneic NK cells are an NK cell line, e.g., the NK-92 cell line or a derivative thereof.

In some embodiments immune system cells may be contacted in vitro with one or more epitopes, e.g., in order to activate cells that recognize such epitope(s). In some embodiments immune system cells may be contacted in vitro with microbes or parasites, tumor cells, tumor tissue, pathogen-infected cells, cells of a tumor cell line, material (e.g., proteins, RNA, membrane fraction, lysate) derived from such cells or tissue, or partly purified or synthetic antigens or epitopes (e.g., a peptide pool). In some embodiments immune system cells (e.g., T cells) that bind to or proliferate in response to such cells or substances may be isolated. The immune system cells (e.g., T cells) may be sortagged, e.g., with a targeting moiety that targets them to a tumor or pathogen, and administered to a subject who is in need of treatment of a tumor or who is infected or at risk of infection by the pathogen. In some embodiments the cells or substances used to stimulate or isolate the immune system cells are derived from a particular patient's tumor or comprise TA(s) or TA epitopes found in a particular patient's tumor (or typically found in tumors of that type), and the sortagged immune system cells are administered to the patient.

In some embodiments a method may comprise isolating or determining the identity of one or more antigens or epitopes expressed by tumor cells or tumor-associated cells obtained or originating from a subject and conjugating a targeting moiety that binds to at least one of the antigens or epitopes to mammalian cells in vitro. The antigens or epitopes may be identified or isolated using any of a variety of methods used in the art. RNA (e.g., mRNA) or proteins from tumors, tumor cells, or tumor tissue samples can be analyzed using standard methods for RNA or protein detection and quantification. For example, proteins may be analyzed using immunological methods such as immunohistochemistry or ELISA. In some embodiments the cells comprise immune system cells, e.g., cytotoxic cells, e.g., cytotoxic T cells or NK cells. In some embodiments a cytotoxic cell releases proteins (e.g., cytolytic proteins) that induce lysis of a target cell. In some embodiments a cytotoxic cell is able to induce apoptosis in a target cell. In some embodiments the cells comprise T helper cells. The method may further comprise administering the cells to the subject. In some embodiments a method may comprise isolating or determining the identity of one or more antigens expressed by tumor cells or tumor-associated cells obtained or originating from a subject, and conjugating a targeting moiety that binds to at least one of the antigen(s) to immune system cells ex vivo. The method may further comprise administering the cells to the subject.

In some embodiments, a tumor sample is analyzed to identify one or more TAs expressed by the tumor, to which therapeutic cells are to be targeted. The tumor sample may be from a tumor removed at surgery, from a biopsy, blood sample (e.g., cells of a hematologic malignancy or circulating tumor cells from a solid tumor). A panel of antibodies or other binding agents may be used to identify cell surface TAs. In some embodiments, a patient who has been treated for a tumor or is suspected of having a tumor or tumor recurrence may be monitored by performing periodic blood tests to detect a soluble tumor antigen or circulating tumor cells. If test results show an increase or abnormally high level of the soluble TA or presence of circulating tumor cells, a therapeutic cell composition of the present invention, comprising cells targeted to a TA, may be administered. For example, a patient who has been or is being treated for a tumor that expresses CA-125 may be monitored to detect increased blood levels of CA-125. If such increased levels are detected, a therapeutic cell composition comprising cells targeted to CA-125 and/or targeted to a different TA expressed by the tumor may be administered.

In some embodiments, cells are conjugated to a first targeting moiety that binds to a first tumor antigen and a second targeting moiety that binds to a second tumor antigen, wherein the first and second tumor antigens are expressed by cells of the same tumor (tumor cells and/or tumor associated cells). The first and second TAs may be expressed by different cell populations in the tumor or may be expressed on at least some of the same cells of the tumor. The targeting moieties may be part of the same agent, e.g., a bispecific antibody, or may be two separate agents. In some embodiments, two cell populations are administered to a subject in need of treatment for a tumor: a first cell population targeted to a first TA and a second cell population targeted to a second TA. For example, as noted above, certain tumors express CA125 and mesothelin. Cells to be administered to a subject in need of treatment for a tumor may be conjugated to a first targeting moiety that binds to CA125 and a second targeting moiety that binds to mesothelin or a first cell population targeted to mesothelin and a second cell population targeted to CA125 may be administered. In some embodiments, administration of a cell targeted to two or more different tumor antigens may have an additive or greater than additive effect. In some embodiments, administration of two cell populations, each targeted to a different tumor antigen, may have an additive or greater than additive effect.

In some embodiments, cells, e.g., immune system cells, are sortagged with an agent comprising a targeting moiety that targets the cells to circulating tumor cells (CTCs). CTCs are cells from a tumor (e.g., a solid tumor) that intravasate into the circulation (vascular system and/or lymphatic system). CTCs may extravasate at sites to which they are carried by the circulation, where they may survive and form metastases. CTCs can interact with receptors on endothelial cell walls in a way that resembles leukocyte extravasation in inflammation and lymphocyte homing. CTCs from many types of primary tumors express sialylated carbohydrate ligands similar to those of leukocytes, which mediate interactions with selectins on the endothelium. In some embodiments a selectin is used as a targeting moiety to target cells, e.g., immune system cells, to circulating tumor cells (CTCs). In some embodiments the cells are sortagged both with a selectin and with one or more additional agents. In some embodiments the one or more additional agents comprise a cytotoxic moiety, a detectable moiety, a second targeting moiety (e.g., a targeting moiety that binds to a TA expressed by the tumor), or any combination thereof. In some embodiments the cytotoxic moiety comprises a pro-apoptotic agent, e.g., a pro-apoptotic protein such as TRAIL or a biologically active portion thereof or a TRAIL receptor agonist.

In some embodiments cells sortagged with a detectable moiety and targeted to CTCs may be useful to detect the presence of CTCs in a sample (e.g., a blood sample) obtained from a subject or in vivo. The subject may be suspected of having cancer or may have been treated for cancer. Without wishing to be bound by any theory, the fact that a cell may be sortagged with numerous individual molecules of a detectable moiety may facilitate detection of CTCs, e.g., by making detection more reliable (e.g., fewer false positive and/or false negative results) and/or by permitting detection of smaller numbers of CTCs than with various other methods.

Cancer stem cells (CSCs) are cancer cells found within tumors or hematological cancers that possess characteristics analogous to characteristics associated with normal stem cells. CSCs have the capacity to initiate tumors, self-renew, and differentiate into phenotypically diverse cancer cells. CSCs are often relatively resistant to chemotherapy drugs and radiation and are proposed to persist and cause relapse and metastasis by giving rise to new tumors. CSCs may express a variety of cell surface markers at levels that differentiate them from non-CSC cancer cells and/or most normal cells. For example, CD133, CD44, and EpCAM have been identified as CSC markers in a variety of epithelial cancers. In some embodiments a binding moiety, e.g., an antibody, that binds to a CSC marker is used as a targeting moiety to target cells, e.g., immune system cells, to CSCs. In some embodiments the cells are sortagged both with a CSC marker and with one or more additional agents. In some embodiments the one or more additional agents comprise a cytotoxic moiety, a detectable moiety, a second targeting moiety (e.g., a targeting moiety that binds to a TA expressed by non-CSC tumor cells or tumor-associated cells), or any combination thereof. In some embodiments the cytotoxic moiety comprises a pro-apoptotic agent, e.g., a pro-apoptotic protein such as TRAIL or a biologically active portion thereof or a TRAIL receptor agonist.

In some embodiments APCs are contacted in vitro with tumor cells, tumor tissue, pathogen-infected cells, material (e.g., proteins, RNA, membrane fraction, lysate) derived from such cells or tissue, or partly purified or synthetic antigens or epitopes (e.g., a peptide pool) and are then used to stimulate lymphocytes in vitro. In some embodiments the stimulated lymphocytes may be sortagged (e.g., with a targeting moiety that targets them to a tumor, with a chemotherapeutic agent potentially active against the tumor, and/or with an immunomodulator) and may be administered to a subject who is in need of treatment of a tumor or is at risk of developing a tumor or of tumor recurrence. In some embodiments the stimulated lymphocytes may be sortagged (e.g., with a targeting moiety that targets them to a pathogen or pathogen-infected cell, with an antimicrobial agent potentially active against the pathogen, and/or with an immunomodulator) and may be administered to a subject who is in need of treatment of an infection or is at risk of infection by the pathogen.

Protocols for T cell activation and/or expansion may include, e.g., culturing the cells in medium containing appropriate cytokines such as interleukin-2 (IL-2) and/or appropriate co-stimulatory molecules. In some embodiments an expansion protocol using IL-2 and CD3 ligation via an anti-CD3 antibody may be used (so-called "rapid expansion method", e.g., as described in Dudley M E, et al., Generation of tumor-infiltrating lymphocyte cultures for use in adoptive transfer therapy for melanoma patients. J Immunother 2003, 26:332-342). The cytokine(s) may be provided as isolated proteins or by co-culture with cells that secrete them either naturally or as a result of genetic manipulation. In some embodiments cells are cultured in the presence of anti-CD3 antibodies and anti-CD28 antibodies. In some embodiments, the antibodies are attached to beads (e.g., paramagnetic beads) or another support, such as the interior sides and bottom of a cell culture vessel. In some embodiments, a mixture of anti-CD3 and anti-CD28 antibodies is attached to the beads (coimmobilization) (see, e.g., Levine, B., et al., Tumaini, B., et al. (both cited above), and various other references cited herein. In some embodiments, cells are co-cultured with PBMCs, which comprise cells that provide one or more molecules that promote activation and/or expansion. In some embodiments cells are cultured with PBMC and anti-CD28 antibodies (e.g., attached to a support such as beads). In some embodiments the PBMCs are immunocompatible with the T cells. In some embodiments both the T cells and PBMCs are derived from a subject to whom the T cells are to be introduced. In some embodiments a ratio of beads to cells between 100:1 and 1:100 is used. In some embodiments, a ratio of beads to cells between 10:1 and 1:10, between 5:1 and 1:5, between 3:1 and 1:3, or about 1:1 is used.

In some embodiments lymphocytes are activated in vitro by contacting them with APCs. In some embodiments artificial APCs may be used. A variety of cellular aAPCs are known in the art. For example, K562 cells (available from the ATCC, Manassas, Va.) can serve as artificial APC. Such cells have been engineered to express a variety of co-stimulatory molecules and used for ex vivo expansion of polyclonal and antigen-specific cytotoxic T lymphocytes, natural killer cells, and antigen-experienced tumor-infiltrating lymphocytes (Maus M V, et al. Nat Biotechnol 2002, 20:143-148; Suhoski M M, et al. Mol Ther 2007, 15:981-988; Fujisaki, H., Cancer Res 2009; 69: 4010-4017; Ye Q, et al., J Transl Med 2011, 9:131; Butler, M O, et al., Clin Cancer Res Mar. 15, 2007 13; 1857). Cellular aAPC (e.g., a cellular aAPC that has been genetically engineered and/or has been or is to be sortagged) may be irradiated (e.g., with gamma radiation, e.g., about 100 Gy in certain embodiments) or otherwise rendered unable to proliferate. In some embodiments noncellular aAPCs may be used. Noncellular aAPCs may be particles that have antigen presenting molecules (APMs) attached thereto. Such particles may be contacted with antigen or antigen fragment (e.g., peptides) to allow them to serve as aAPCs. In some embodiments, noncellular APCs may be particles such as liposomes, beads (e.g., paramagnetic beads), particles comprised at least in part of organic polymers, quantum dots, etc. Such particles may have any of a variety of different molecules attached to their cell surface, e.g., any of the molecules discussed above in reference to cellular aAPC. Noncellular aAPCs may be generated as described in Oelke M, et al., Ex vivo induction and expansion of antigen-specific cytotoxic T cells by HLA-Ig-coated artificial antigen-presenting cells. Nat Med. 2003, 9:619-625; Webb, T, et. al., J Immunol Methods, 2009, 346(1-2): 38-44; Oelke M. and Schneck, J P, Immunol Res (2010); 47:248-256; East, J E, J Vis Exp. Artificial antigen presenting cell (aAPC) mediated activation and expansion of natural killer T cells. 2012 Dec. 29; (70). pii: 4333. doi: 10.3791/4333. In some embodiments APMs may be conjugated to a support, e.g., beads (e.g., magnetic beads), inner surface of a vessel such as a well or plate, etc. APCs may be loaded with antigen prior to or after being conjugated to a support. Cells to which the antigen is to be presented are contacted with the support to permit antigen presentation to occur. In some embodiments an APM may be conjugated or fused to an IgG domain or other moiety that may serve as a linker to attach the APM to a support.

In some embodiments lymphocytes, e.g., T cells, are stimulated in vitro by coculturing them with APCs, e.g., DCs or aAPCs. In some embodiments the APCs display at least one epitope that stimulates proliferation and/or effector activity of T cells that bind to it. In some embodiments an agent comprising one or more epitopes is conjugated to the APCs, e.g., using sortase. In some embodiments an agent comprising one or more epitopes is noncovalently bound to a cell surface molecule or complex expressed by APCs. In some embodiments the cell-surface molecule or complex is Dec-205, a C type lectin such as DC-SIGN, or MHC class II (MHCII) protein. In some embodiments the cells have been sortagged or the cells and/or descendants thereof are subsequently sortagged according to methods described herein. In some embodiments sortagged mammalian cells are administered to a subject.

In some embodiments a moiety conjugated to immune system cells using sortase may inhibit or overcome mechanisms that may exist in a subject that may otherwise limit the therapeutic efficacy of cellular immunotherapy or may limit the effectiveness of the subject's endogenous immune system. In the case of therapy for cancer, such mechanisms may include immune evasion mediated by the secretion of immunosuppressive substances such as transforming growth factor β (TGFβ) in the microenvironment of a tumor and/or mediated by the accumulation of regulatory T cells, both of which can, for example, dampen the in vivo activation, expansion, and tumor homing of transferred tumor-reactive CD8+ T cells. In the case of therapy for diseases caused by pathogens, such mechanisms may include any of various immunoevasive or immunosuppressive agents produced or encoded or induced by pathogens. A moiety conjugated to cells may inhibit the effect of an immunoevasive or immunosuppressive substance by, for example, binding to the substance, acting as an antagonist or competitor at a receptor for the substance, or antagonizing a pathway activated by the substance. In some embodiments a moiety conjugated to cells may inhibit development or activity of Tregs that would otherwise dampen an immune response against a tumor, pathogen, or pathogen-infected cell.

"Immune checkpoint pathways" or "immune checkpoints" are naturally existing inhibitory pathways of the immune system that play important roles in maintaining self-tolerance and modulating the duration and level of effector output (e.g., in the case of T the levels of cytokine production, proliferation or target killing potential) of physiological immune responses in order to minimize damage to the tissues of the individual mounting the immune response. Such pathways may, for example, downmodulate T cell activity or enhance regulatory T cell immunosuppressive activity. Examples of immune checkpoint pathways include, e.g., the PD-1 pathway and the CTLA-4 pathway, discussed further below. Tumors frequently co-opt certain immune-checkpoint pathways as a major mechanism of immune resistance, e.g., against T cells that are specific for tumor antigens. Certain aspects of the invention utilize sortase-modified cells to inhibit immune checkpoint mechanisms. In some aspects, the invention provides mammalian cells conjugated using sortase to a moiety comprising an immune checkpoint modulator. In some embodiments the immune checkpoint modulator is an immune checkpoint inhibitor. "Immune checkpoint inhibitor" refers to any agent that inhibits (suppresses, reduces activity of) an immune checkpoint pathway. In some embodiments the immune checkpoint modulator is an immune checkpoint activator. "Immune checkpoint activator" refers to any agent that activates (stimulates, increases activity. of) an immune checkpoint pathway. In some embodiments the cells are non-genetically modified cells. In some embodiments the cells are derived from a subject in need of treatment for cancer or an immunocompatible donor. In some embodiments the cells comprise PBMCs or RBCs. In some embodiments the cells comprise lymphocytes. "Immune checkpoint protein" refers to those proteins that are components of immune checkpoint pathways, and include membrane-bound, soluble (e.g., secreted), and intracellular proteins. Many immune checkpoint pathways are initiated by interactions between membrane-bound receptors and soluble or membrane-bound ligands. In some embodiments an immune checkpoint inhibitor is an agent that binds to receptor or ligand that is a component of an immune checkpoint pathway. Binding of the agent to the receptor or ligand blocks the ligand-receptor interaction, thus inhibiting the immune checkpoint pathway. For example, in some embodiments a moiety inhibits an interaction between PD-1 and a PD-1 ligand, e.g., by binding to either PD-1 or PD-1 ligand.

In some embodiments an agent comprises a modulator of the PD-1 pathway. PD-1 is an inhibitory surface receptor expressed by a variety of cells, including activated T cells, B cells, natural killer T cells, monocytes, and dendritic cells (DC). PD-1 has two naturally occurring ligands, programmed cell death ligand 1 (PD-L1) and programmed cell death ligand 2 (PD-L2), also called B7-H1 and B7-DC, respectively. The term "PD-L" refers to either or both PD-L1 and PD-L2. Where the term "PD-L" is used herein, certain embodiments pertain to PD-L1, certain embodiments pertain to PD-L2, and certain embodiments pertain to both PD-L1 and PD-L2. The term "PD-1 pathway" refers to the biological processes that occur in a cell, e.g., an immune system cell, upon binding of PD-L to PD-1 expressed by the cell. Binding of PD-L to PD-1 on immune system cells, e.g., helper or cytotoxic T cells, typically has inhibitory effects on their proliferation and/or activity, particularly in the context of stimulation by antigen, and may contribute to T cell exhaustion. However, the PD-1 pathway can promote the development and activity of T regulatory cells, which may suppress the activity of other immune system cells (e.g., helper and/or cytotoxic T cells) that would otherwise mount an immune response, e.g., against a tumor, infected cell, pathogen, or a self antigen (e.g., in a subject with an autoimmune disease). Tumors can use the PD-1 pathway to inhibit immune system cells that may otherwise mount an immune response against the tumor. Certain tumors express PD-L1, and its expression has been correlated with tumor aggressiveness and inversely correlated with survival of patients, possibly because natural antitumor immunity against such tumors is inhibited. The PD-1 pathway has also been shown to impair immune function in various infections such as influenza virus infection, HIV infection, HCV infection, and Mycobacterial infection. In some embodiments, inhibiting the PD-1 pathway is of use in treatment of conditions in which the PD-1 pathway inhibits the immune response of administered immune system cells (or their descendants) or endogenous immune system cells against a tumor, pathogen, or infected cell and/or in which activity of the PD-1 pathway is abnormally or inappropriately high or in which there is an abnormally or inappropriately high number and/or activity of Tregs. In some embodiments, activating the PD-1 pathway is of use in treatment of conditions in which activity of the PD-1 pathway is abnormally or inappropriately low, conditions in which there is an abnormally low number and/or activity of Tregs, and/or conditions in which increased number or activity of Tregs may be beneficial, e.g., in subjects at risk of or suffering from an autoimmune diseases, GVHD, and/or transplant rejection. A number of cells or level of activity may be abnormally or inappropriately high or low in absolute terms or relative to the number or activity of immune systems cells of one or more other types or subtype, e.g., Th1, Th2, Th17, cytotoxic T cells, helper T cells. In some embodiments, a modulator of the PD-1 pathway is of use to restore an appropriate balance between Tregs and other immune system cells.

In some embodiments a modulator of the PD-1 pathway is an inhibitor of the PD-1 pathway. An inhibitor of the PD-1 pathway reduces activity of the PD-1 pathway as compared to the activity of the pathway in the absence of the inhibitor. It will be understood that the effect of an inhibitor may be observable only in the presence of a ligand that would (in the absence of the inhibitor) bind to PD-1 and activate it. An inhibitor of the PD-1 pathway may be referred to as a PD-1 antagonist. In some embodiments a PD-1 antagonist binds to PD-1 or PD-L and blocks the interaction between PD-1 and PD-L. In some embodiments a PD-1 antagonist comprises a nucleic acid (e.g., a nucleic acid aptamer), protein, peptide, or small molecule that binds to PD-1, PD-L1, or PD-L2, wherein if the PD-1 antagonist binds to PD-1, it does not significantly stimulate PD-1 signaling. In some embodiments, an anti-PD-1, anti-PD-L1, or anti-PD-L2 antibody may be used as a PD-1 antagonist. Nivolumab (a fully human IgG4 monoclonal antibody), CT-011 (a humanized IgG1 monoclonal antibody), and lambrolizumab (also known as MK-3475, a humanized IgG4 monoclonal antibody) are examples of anti-PD-1 antibodies. BMS-936559 (a fully human IgG4 monoclonal antibody), MPDL3280A (human monoclonal, Genentech), and MEDI4736 (Medimmune) are anti-PD-L1 antibodies.

In some embodiments, a PD-1 antagonist comprises at least a portion of the extracellular domain of PD-1 or a variant or fragment thereof that binds to PD-L. If a cell is genetically engineered to express a variant or fragment of PD-1, a variant or fragment that substantially lacks the ability to inhibit cells that express it may be used. For example, the variant or fragment may have a mutation or at least partial deletion of its intracellular signaling domain. The variant or fragment may comprise the transmembrane domain and, optionally, at least a portion of the intracellular domain or may comprise a transmembrane domain from a different protein or a synthetic transmembrane domain to cause it to remain attached to the cell surface rather than secreted as a soluble protein. The extracellular domain of PD-1 or a variant or fragment thereof may serve as a targeting moiety to target cells, e.g., T cells or NK cells, to a tumor comprising cells that express PD-L (e.g., PD-L1).

By binding to PD-L at the surface of tumor cells or tumor-associated cells or infected cells that express PD-L, PD-1 extracellular domain may alternately or additionally serve to block the effect of PD-L on immune system cells that express PD-1. Thus, the immune suppressive effects of PD-L, e.g., PD-L1, expressed in tumors or infected cells, may be reduced. A variety of PD-1 antagonists, e.g., antibodies that bind to PD-1, PD-L1, or PD-L2 are described in U.S. Pat. Pub. No. 20040213795, 20110195068, 20120039906, 20120114649, 20130095098, 20130108651, 20130109843, 20130237580, and 20130291136, among others.

In some embodiments a modulator of the PD-1 pathway increases activity of the PD-1 pathway, e.g., by binding to and activating PD-1. A modulator of the PD-1 pathway that binds to and activates PD-1 may be referred to as a PD-1 agonist. A PD-1 agonist may comprise a biologically active fragment or variant of the extracellular domain of PD-L1 or PD-L2 or may mimic the effect induced by binding of PD-L1 or PD-L2 to PD-1. Cells that are sortagged with a PD-1 agonist may be useful in conditions in which it is desired to inhibit the immune response.

An agent that binds to PD-1 or PD-L may serve as a targeting moiety. For example, an agent that binds to PD-L may target cells that express or are sortagged with the agent to cells that express PD-1. The agent may also serve as a PD-1 agonist or antagonist in various embodiments. An agent that binds to PD-1 may target cells that express or are sortagged with the agent to cells that express PD-L. The agent may also serve as a PD-1 agonist or antagonist in various embodiments.

In some embodiments an agent comprises a modulator of a T cell co-inhibitory receptor, such as the anti-inflammatory receptor cytotoxic T lymphocyte antigen-4 (CTLA-4). CTLA-4 is an important negative regulator of T cell activation. In some embodiments a modulator of CTLA-4 inhibits CTLA-4 activity and may be referred to as a "CTLA-1 antagonist". Inhibiting negative regulation mediated by CTLA-4 has been shown to promote stimulation of adaptive immunity and potentiation of T cell activation. Binding of a CTLA-4 ligand (e.g., B7-1 or B7-2) to CTLA-4 can reduce T cell proliferation and functional activity and promote tolerance, which may reduce the ability of administered immune system cells and/or endogenous immune system cells of a subject to mount an immune response against a tumor, pathogen, or infected cells. Accordingly, in some embodiments a CTLA-4 antagonist is useful to limit or prevent negative regulation by CTLA-4. In some embodiments, a CTLA-4 antagonist comprises an agent that binds to CTLA-4 and blocks CTLA-4 ligands from binding to CTLA-4. For example, anti-CTLA-4 antibodies, such as ipilimumab or tremelimumab, may be used. In some embodiments a CTLA-4 antagonist comprises an antibody that binds to a CTLA-4 ligand. In addition to CTLA-4, other T cell co-inhibitory receptors including B7 family members B7-H3, B7-H4, T cell immunoglobulin and mucin domain-containing protein 3 (Tim-3), and lymphocyte activation gene-3 (LAG-3), interact with their cognate ligands on various cells types, including APCs, regulatory T cells (Tregs), and nonhematopoietic cells, resulting in reduced T cell proliferation and functional activity. BTLA is an inhibitory receptor on T cells. Its ligand is herpesvirus entry mediator (HVEM), which is expressed on certain tumor cell types such as melanoma and on tumor-associated endothelial cells.

In some embodiments, an agent inhibits production or immunosuppressive effect of adenosine. Such an agent may be referred to as an anti-adenosine agent. Adenosine is produced in the extracellular compartment by two ecto-nucleotidases: CD39, which hydrolyzes ATP and ADP into AMP, and CD73, which converts AMP into adenosine. Adenosine may also be released from dying cells, e.g., dying cells in a tumor. CD73 is expressed on tumor cells and host immune system cells, including Tregs and myeloid-derived suppressor cells, and is known to inhibit T-cell proliferation and reduce cytokine production and cytotoxicity of activated T-cells via A2a receptor (A2aR) subtype activation, protecting the tumour from immune-mediated destruction. Adenosine A2a receptor (A2aR), the ligand of which is adenosine (which may be released from dying cells in a tumor), inhibits T cell responses in part by driving CD4+ T cells to develop into Treg cells. In some embodiments an anti-adenosine agent is an inhibitor of CD73 or CD39. In some embodiments an anti-adenosine agent comprises an antibody or other binding moiety that binds to CD73 or CD39. Small molecules that are selective inhibitors of CD73 include, e.g., adenosine 5'-($\alpha,\beta$-methylene) diphosphate (APCP) and ZM241365. In some embodiments an anti-adenosine agent comprises an antibody or other binding moiety that binds to an A2aR and inhibits its activity by, e.g., blocking binding of adenosine.

In some embodiments, an agent that inhibits the biological activity of any T cell co-inhibitory receptor may be conjugated to cells to reduce loss of T cell proliferation and/or preserve functional activity and/or inhibit any immune checkpoint pathway. For example, antibodies or other binding moieties that bind to B7-H3, BTLA, A2aR, B7-H4, Tim-3, or LAG-3 may be conjugated to cells to be administered to a subject, e.g., a subject with cancer. In some embodiments an antagonist of B7-H3, BTLA, A2aR, B7-H4, Tim-3, or LAG-3, such as antibodies or other binding moieties that bind to B7-H3, BTLA, A2aR, B7-H4, Tim-3, or LAG-3 or to a ligand of B7-H3, BTLA, A2aR, B7-H4, Tim-3, or LAG-3 may be conjugated to cells to be administered to a subject, e.g., a subject with cancer. For example, the antibody or other binding moiety may bind to galectin-9 (ligand of Tim-3), HVEM, or adenosine. In some embodiments cells are sortagged with two or more different immune checkpoint inhibitors. The inhibitors may inhibit different immune checkpoint pathways. For example, cells may be sortagged with at least two inhibitors selected from PD-1 antagonists, CTLA-4 antagonists, B7-H3 antagonists, BTLA antagonists, A2aR antagonists or other anti-adenosine agents, B7-H4 antagonists, Tim-3 antagonists, or LAG-3 antagonists.

Cells may be sortagged with a mixture of agents, e.g., any of the afore-mentioned immune checkpoint inhibitor, or separate aliquots of cells may each be sortagged with a single immune checkpoint inhibitor and administered in combination to a subject, e.g., a subject in need of treatment for cancer. In some embodiments cells are sortagged with a first immune checkpoint inhibitor and then with a second immune checkpoint inhibitor or are sortagged with two or more immune checkpoint inhibitors at the same time. In some embodiments cells are sortagged with a first immune checkpoint inhibitor and administered in combination with a second immune checkpoint inhibitor. For example, cells may be sortagged with a PD-1 antagonist and administered in combination with a CTLA-4 antagonist not attached to cells. In some embodiments cells that have been sortagged with an immune checkpoint inhibitor are administered in combination with a targeted cancer therapy such as a protein kinase inhibitor, e.g., a VEGF receptor inhibitor, RAF inhibitor, ALK inhibitor, EGF receptor inhibitor, ERB-B1 inhibitor, ERB-B2 inhibitor, FGF receptor inhibitor, PDGF receptor inhibitor, etc.

Without wishing to be bound by any theory, and without limiting the invention in any way, the use of cells, e.g., RBCs or T cells, that are conjugated with a targeting moiety (e.g., an antibody) that binds to a tumor antigen, or that express an antigen receptor (e.g., a chimeric antigen receptor) that binds to a tumor antigen, to deliver one or multiple immune checkpoint inhibitors, may more effectively direct the immune checkpoint inhibitors to the tumor, increase local activity, and/or reduce unwanted systemic exposure and associated side effects as compared, for example, with administering the immune checkpoint inhibitors not attached to cells. For example, by combining an antibody directed to a tumor associated antigen with one or more immune checkpoint inhibitors, the checkpoint inhibitors may be more effectively directed to the tumor, increasing local activity, and reducing unwanted systemic exposure and associated side effects. Again without wishing to be bound by any theory, and without limiting the invention in any way, using cells, e.g., RBCs, T cells, NK cells, or others, that have been sortagged with agents such as bi-specific agents comprising one arm directed to a tumor associated antigen and another arm directed to CD3, to deliver such agents, the half-life of such agents may be extended, thereby improving their efficacy without increasing the amount or frequency of dosing and/or may allow a decrease in the amount or frequency of dosing without diminishing efficacy. In some embodiments the cells used to deliver a bispecific agent may be modified by sortase to carry one or more antibodies to tumor associated antigens.

In some embodiments a subject who is to be treated with cells that have been sortagged with an immune checkpoint inhibitor has a cancer that has been tested for expression of an immune checkpoint protein, e.g., a receptor or ligand that is a component of an immune checkpoint pathway. In some embodiments tumor cells, non-transformed cells in the tumor stroma, or both, express the immune checkpoint protein, or overexpress the immune checkpoint protein, as compared to its expression in normal cells outside the tumor. In some embodiments, a tumor or tumor sample (e.g., a biopsy or surgical sample) is analyzed to identify one or more immune checkpoint proteins that are expressed or overexpressed relative to normal cells by the tumor cells, non-transformed cells in the tumor stroma, or both. In some embodiments cells that are sortagged with an inhibitor of a particular immune checkpoint pathway that is identified as being active in a tumor are administered to the subject. In some embodiments cells that are sortagged with an antagonist of a particular immune checkpoint protein that is identified as being expressed or overexpressed in a tumor are administered to the subject. In some embodiments cells that are sortagged with an antagonist of a receptor or ligand of a particular immune checkpoint protein that is identified as being expressed or overexpressed in a tumor may be administered to the subject. In some embodiments a method comprises identifying an immune checkpoint pathway that is active or an immune checkpoint protein that is expressed in a tumor or tumor sample and administering cells that are sortagged with an agent that inhibits the immune checkpoint pathway or immune checkpoint protein to a subject in need of treatment for the tumor. Expression of the immune checkpoint protein or activity of the immune checkpoint pathway may be measured using any method known in the art. In some embodiments the level of mRNA encoding an immune checkpoint protein may be measured. In some embodiments the level of the protein may be measured, e.g., using an immunological assay such as an ELISA assay, immunohistochemistry, or other suitable methods.

In some embodiments a modulator of CTLA-4 activates CTLA-4 and may be referred to as a "CTLA-4 agonist". In some embodiments a CTLA-4 agonist is useful to reduce T cell proliferation and functional activity and/or promote tolerance, e.g., in a subject at risk or suffering from an autoimmune disease, GVHD, or transplant rejection.

In some embodiments, an agent comprises an activator of CD137 (CD137 agonist). CD137 (also known as 4-1BB), a member of the tumor necrosis factor (TNF) receptor superfamily and is a T cell costimulator molecule. Certain anti-CD137 monoclonal antibodies activate CD137 and are able to activate CD8+ T cells, causing them to produce interferon (IFN)-γ, and induce cytolytic markers. BMS-663513 (Urelumab), a humanized anti-CD137 antibody, is an example of a CD-137 agonist.

In some embodiments, cells are modified to comprise a targeting moiety and a second agent at their surface. Either the targeting moiety, second agent, or both, may be conjugated to the cells using sortase. In some embodiments, the cells are genetically engineered to express the targeting moiety and are conjugated with the second agent using sortase. In some embodiments, the cells are genetically engineered to express the second agent and are conjugated with the targeting moiety using sortase. In some embodiments, the targeting moiety, the second agent, or both, are conjugated via a sortase recognition sequence to an endogenous, non-genetically engineered polypeptide expressed by the cells. In some embodiments the cells are not genetically modified to express a polypeptide comprising an extracellular domain capable of serving as a sortase substrate or nucleophile in a sortase-catalyzed reaction. In some embodiments, the cells comprise a chimeric antigen receptor that comprises an antigen binding moiety that targets the cells to particular target cells, e.g., tumor cells, infected cells, or other undesired cells. The second agent can, in general, comprise any of the various agents described herein. In some embodiments the second agent comprises a targeting moiety. In some embodiments the second agent comprises at least a biologically active portion of a cytokine or chemokine. In some embodiments the second agent has a biological activity that enhances the biological activity of the administered cells, e.g., against target cells (e.g., tumor cells or infected cells) in the body of a subject. In some embodiments the biological activity is anti-tumor activity, costimulatory activity towards endogenous immune system cells or towards administered immune system cells or their descendants, or inhibitory activity towards endogenous immune system cells that contribute to an undesired immune response such as in autoimmune disease or transplant rejection. In some embodiments the second agent inhibits a biological activity that would otherwise inhibit or suppress activity of the administered cells or of endogenous cells, e.g., against target cells (e.g., tumor cells or infected cells) in the body of a subject.

In some embodiments a targeting moiety binds to a molecule expressed in tumor vasculature (a "tumor vasculature marker"). In some embodiments the tumor vasculature marker is overexpressed in tumor vasculature as compared with normal vasculature. In some embodiments the tumor vasculature marker is expressed at the luminal surface of endothelial cells in tumor vasculature. In some embodiments the molecule expressed on tumor vasculature is PD-1, VEGFR1, VEGFR2, tumor endothelial marker 1 (TEM1; also known as endosialin or CD248), or integrin αvβ3. In some embodiments the targeting moiety comprises one or more binding moieties, e.g., antibodies, that bind to PD-1, VEGFR1, VEGFR2, TEM1, or integrin αvβ3.

In some embodiments cells to be used in cancer therapy may be sortagged with an agent comprising a targeting moiety that binds to a tumor vasculature marker and administered to a subject. In some embodiments the cells are immune system cells, which in some embodiments may be sortagged with a second agent, wherein the second agent has anti-tumor activity, such as an immune checkpoint inhibitor. In some embodiments the cells are red blood cells that are sortagged with an agent that has anti-tumor activity, such as an immune checkpoint inhibitor. In some embodiments the cells are CAR cells.

In some aspects the disclosure provides a bispecific agent comprising (a) a first binding moiety that binds to a molecule on a target cell; (b) a second binding moiety that binds to a molecule on an immune system cell, e.g., a T cell, NK cell, or professional phagocyte (e.g., a monocyte, macrophage, or dendritic cell); and (c) a sortase recognition motif. In some embodiments the SRM is appropriately positioned to permit the agent to participate in a sortase-catalyzed reaction. In some aspects the disclosure provides a mammalian cell, e.g., a human cell, sortagged with such a bispecific agent. In some embodiments the target cell is a tumor cell, tumor-associated cell, pathogen-infected cell, or pathogen. In some embodiments the target cell is a tumor cell or tumor-associated cell, and the first binding moiety binds to a tumor antigen. In some embodiments the second moiety binds to a molecule on the surface of a T cell, e.g., CD3 (e.g., CD3 delta chain, CD3 epsilon chain, CD3 gamma chain, CD3 zeta chain, or other components of the TCR-CD3 complex, e.g., TCR alpha or TCR beta chains) or CD28. In some embodiments the second binding moiety binds to a molecule on the surface of an NK cell, dendritic cell, or macrophage, e.g., an Fc receptor, e.g., an Fcγ receptor, e.g., FcγRI (CD64) or FcγRIIIA (CD16a). Other molecules expressed at the surface of T cell, NK cells, and/or phagocytes are known to those of ordinary skill in the art.

In some embodiments the bispecific agent links the sortagged cell to the immune system cell and to the target cell. The immune system cell is thereby linked to the target cell via the sortagged cell. In some embodiments, linking the immune system cell to the target cell via the sortagged cell causes one or more effector functions of the immune system cell (e.g., cytotoxicity) to be directed towards the target cell. Alternatively, or additionally, in certain embodiments in which the sortagged cell is an immune system cell, one or more effector functions of the sortagged cell may be directed towards the target cell. In some embodiments, the individual or combined effect of attack by the immune system cell, the sortagged cell, or both, results in death of the target cell. In some embodiments two or more immune system cells are linked to the sortagged cell via the bispecific agents attached to the sortagged cell. An individual sortagged cell may thus tether multiple immune system cells to a target cell. It should be noted that multiple target cells may be located in close proximity to each other. For example, tumor cells are often located close to each other and/or close to tumor-associated cells in a tumor. An immune system cell that is linked to a target cell, e.g., via a sortagged cell, may attack other target cells in close proximity to the target cell to which it is linked.

In some embodiments, binding of the second binding moiety to a molecule on a T cell, NK cell, or phagocyte stimulates such cell. For example, binding of the second binding moiety to CD3 or CD28 on a T cell may stimulate the T cell to proliferate, become activated, secrete cytokines, phagocytose, or exert cytotoxic effects on a target cell by, e.g., releasing cytotoxins and/or inducing apoptosis. Binding of the second binding moiety to an Fc receptor on an NK cell, dendritic cell, or macrophage may stimulate such cell. For example, an NK cell may be stimulated to exert cytotoxic effects on a target cell; a DC may be stimulated to secrete cytokines and/or provide cell-cell interactions that stimulate other immune system cells; a macrophage may be stimulated to phagocytose a target cell. In some embodiments the sortagged cell stimulates the immune system cell to which it is bound, or vice versa. For example, either cell may secrete one or more cytokines or provide stimulation via cell-cell contact (e.g., one cell may express a ligand for a costimulatory receptor on the other cell). In some embodiments the sortagged cell is also sortagged with an agent that stimulates the immune system cell or inhibits immunosuppression of the immune system cell. In some embodiments, activation is at least in part dependent on the presence of cells expressing the target antigen to which the first binding moiety binds. For example, stimulation may occur when the T cell, NK cell, or phagocyte and the sortagged cell are localized at the site of a target cell. In some embodiments the sortagged cell is sortagged with two or more distinct bispecific agents, wherein the second binding moieties of the distinct bispecific agent differ in regard to the cell type or molecule to which they bind. An individual sortagged cell may thus bind to cells of two or more different cell types, e.g., a T cell and a dendritic cell, or a T cell and a macrophage, in addition to a target cell.

In some aspects the disclosure provides a trivalent agent comprising (a) a first binding moiety that binds to a molecule on a target cell; (b) a second binding moiety that binds to a molecule on an immune system cell, e.g., a T cell, NK cell, or phagocyte (e.g., a monocyte, macrophage, or dendritic cell); (c) a second binding moiety that binds to a molecule on an immune system cell, e.g., a T cell, NK cell, or professional phagocyte (e.g., a monocyte, macrophage, or dendritic cell); and (d) a sortase recognition motif. In some embodiments the SRM is appropriately positioned to permit the agent to participate in a sortase-catalyzed reaction. In some aspects the disclosure provides a mammalian cell, e.g., a human cell, sortagged with such a trivalent agent. The first binding moiety may be any binding moiety that binds to a molecule on a target cell. The second and third binding moieties may be the same or different and may be any binding moieties that bind to a T cell. NK cell, or professional phagocyte. The trivalent agent may link the sortagged cell to two other cells and to a target cell. The sortagged cell is linked to the target cell via the first binding moiety, and the two cells to which the second and third binding moieties bind are linked to the target cell via the sortagged cell.

In general, mammalian cell(s) to be sortagged with the bispecific or trivalent agent may be of any cell type or types in various embodiments. In some embodiments the cells comprise PBMCs, lymphocytes, NK cells, APCs, red blood cells, or platelets. The cells may be a purified population or may be a mixed population. In some embodiments at least 5%, 10%, 20%, 30%, 40%, or 50% of the cells are CD4+ T cells. In some embodiments no more than about 1%, 5%, 10%, 15%, 20%, 25%, 30%, 40%, or 50% of the cells are cytotoxic cells. In some embodiments the cells are not activated ex vivo to become effector cells. In some embodiments the cells are not genetically engineered. In some embodiments the cells are genetically engineered, e.g., they may be CAR cells, may express a recombinant gene product comprising a TCR, cytokine, cytokine receptor, costimulator, or costimulator receptor, or agent that inhibits the effect or production of immunosuppressive substances produced by tumors, pathogens, or Tregs. In certain embodiments the sortagged mammalian cells, in addition to being sortagged with the bispecific or trivalent agent, are also sortagged with one or more agents that inhibit the effect or production of immunosuppressive substances produced by tumors, pathogens, or Tregs. Suitable agents are discussed herein.

In some embodiments mammalian cells sortagged with the bispecific agent or trivalent agent are administered to a subject, and the second binding moiety (and, optionally, the third binding moiety, if present) binds to an immune system cell in vivo. In general, an immune system cell to which the second or third binding moiety binds may be an endogenous immune system cell of a subject or may be an exogenous cell that has been administered to a subject. If the immune system cell is an exogenous cell, the cell may in some embodiments have been sortagged and/or genetically engineered as described herein. For example, the cell may be a CAR cell, may produce a recombinant gene product comprising a cytokine, cytokine receptor, costimulator, costimulator receptor, adhesion molecule, etc.

In general, the binding moieties may be of any type, e.g., proteins (e.g., antibodies, antibody fragments), nucleic acid aptamers, small molecules, etc. In some embodiments, the first binding moiety, second moiety, or both, comprises an antibody, antibody fragment, scFv, single domain antibody, or any other moiety that comprises an antigen binding domain. In some embodiments the bispecific agent is a bispecific antibody. In some embodiments the bispecific antibody comprises two scFv, wherein a first scFv binds to a molecule on a target cell, and the second scFv binds to a molecule on the surface of an immune system cell, e.g., a T cell, NK cell, or professional phagocyte. In some embodiments the bispecific antibody comprises two single domain antibodies (sdAb), wherein a first sdAb binds to a molecule on a target cell, and the second sdAb binds to a molecule on the surface of an immune system cell, e.g., a T cell, NK cell, or professional phagocyte. In some embodiments the bispecific antibody comprises an scFv and an sdAb, wherein either the scFv or the sdAb binds to the target cell and the other binds to the immune system cell. In some embodiments the two scFv, two sdAbs, or scFv and sdAb are attached to each other using click chemistry to form the bispecific agent, and the bispecific agent is attached to the cell using sortase. In some embodiments, sortase is used to install click chemistry handles on the two scFv, two sdAbs, or scFv and sdAb, and the click chemistry handles are allowed to react, thus generating the bispecific agent. In some embodiments the two scFv, two sdAbs, or scFv and sdAb are produced as a fusion protein to form the bispecific agent, and the bispecific agent is attached to the cell using sortase. In some embodiments a single polypeptide chain comprising two VH and two VL regions, optionally separated by spacer regions, is produced, and the bispecific agent is attached to the cell using sortase. A sortase recognition motif may be located at or near a C-terminus of the agent, which may be used to attach the agent to the cell. In certain embodiments the bispecific agent is a bispecific antibody, in some embodiments a bispecific antibody comprising two sdAbs, which may in some embodiments be attached to each other using click chemistry, and then attached to the cell using sortase. In some embodiments, one arm of the bispecific agent recognizes an activating molecule on a T cell, such as CD3 on T cells, and the other arm recognizes an antigen on a target cell, such as a tumor cell. In some embodiments a bispecific agent comprises a first scFv that binds to CD3 epsilon chain and a second scFv that binds to CD19, EpCam, CD33, or any other tumor antigen. In some embodiments, for example, the bispecific antibody blinatumomab (anti-CD3/anti-CD19), MT103 (anti-CD3/anti-EpCam), or AMG330 may be modified to comprise a sortase recognition motif and used to sortag mammalian cells, e.g., human immune system cells. In some embodiments an scFv from any of the afore-mentioned bispecific antibodies may be combined with a scFv or other binding moiety that binds to any tumor antigen. In some embodiments a humanized anti-CD3 scFv may be used, e.g., a humanized OKT3 scFv (see, e.g., Woodle E S, et al. J Immunol 1992; 148:2756-63; Kipriyanov S M, et al. Protein Eng 1997; 10:445-53). In some embodiments a fully human anti-CD3 scFv may be used. In some embodiments a bispecific agent comprises two immune checkpoint inhibitors, optionally. that inhibit different immune checkpoint proteins. In some embodiments a bispecific agent comprises an immune checkpoint inhibitor and a targeting moiety. In some embodiments the targeting moiety targets the cell to tumor cells or tumor vasculature.

In some embodiments cells are sortagged with or administered in combination with an agent that enhances immune system cell infiltration, e.g., T cell infiltration, into tumors. In some embodiments the agent is an anti-angiogenic agent, e.g., a VEGF receptor inhibitor such as an antibody or other binding moiety that binds to a VEGF receptor and inhibits it by, e.g., blocking binding of VEGF; an antibody or other binding moiety that binds to one or more members of the VEGF family; an agent comprising a soluble VEGF receptor extracellular domain (e.g., VEGF-Trap). In some embodiments the agent enhances the expression of ICAM-1, ICAM-2, or VCAM-1 on endothelial cells. In some embodiments the agent binds to an endogenous molecule that may inhibit migration of immune system cells, e.g., lymphocytes, across the endothelial barrier. Examples of such molecules include endothelin B receptor. In some embodiments the agent is an endothelin B receptor inhibitor. In some embodiments the endothelin B receptor inhibitor is an antibody or other binding moiety that binds to the endothelin B receptor. In some embodiments the endothelin B receptor inhibitor is small molecule such as BQ-788. In some embodiments the cells are immune system cells, which in some embodiments may be sortagged with a second agent, wherein the second agent has anti-tumor activity, such as an immune checkpoint inhibitor. In some embodiments the cells are red blood cells that are sortagged with an agent that has anti-tumor activity, such as an immune checkpoint inhibitor. In some embodiments the cells are CAR cells.

In some aspects the invention provides compositions comprising any two or more cells or cell populations described herein, wherein at least one of the cells or cell populations comprises a non-genetically engineered polypeptide having an agent conjugated thereto by sortase. In some aspects the invention provides methods comprising using any two or more cells or cell populations described herein in the same method, e.g., administering any two or more cells or cell populations described herein to a subject, wherein at least one of the cells or cell populations comprises a non-genetically engineered polypeptide having an agent conjugated thereto by sortase. All different combinations are envisioned. In some embodiments the cells or cell populations are of the same cell type, e.g., two or more red blood cells or red blood cell populations conjugated with different agents, or two or more T cells or T cell populations conjugated with different agent. In some embodiments the cells or cell populations are of different cell types, e.g., red blood cells and lymphocytes (e.g., T cells). In some embodiments the two or more cells or cell populations are individually of use for the same purpose, e.g., anti-tumor therapy. In some embodiments the two or more cells or cell populations may have an additive or synergistic effect. In some embodiments a combination may comprise red blood cells comprising a non-genetically engineered polypeptide that is sortagged with a first agent in combination with immune system cells, e.g., lymphocytes, PBMCs, NK cells, sortagged with the same agent or a different agent. Without limiting the invention in any way, certain embodiments useful for cancer therapy may comprise (1) red blood cells that are sortagged with an immune checkpoint inhibitor or angiogenesis inhibitor in combination with immune system cells, e.g., T cells or PBMCs, sortagged with an agent comprising a binding moiety that binds to a tumor antigen; (2) red blood cells that are sortagged with an immune checkpoint inhibitor or angiogenesis inhibitor in combination with CAR cells that are sortagged with an agent that enhances immune system cell infiltration into tumors; (3) red blood cells that are sortagged with an immune checkpoint inhibitor or angiogenesis inhibitor in combination with CAR cells that comprise a CAR that binds to a first tumor antigen and are sortagged with an agent that binds to a second tumor antigen.

A subject may be treated with various preparative regimens prior to administration of sortagged cells. For example, lymphodepletion of the patient before adoptive cell transfer, which eliminates T regulatory cells and other lymphocytes, is a component of many ACT regimens for cancer (Dudley M E, et al. Adoptive cell transfer therapy following non-myeloablative but lymphodepleting chemotherapy for the treatment of patients with refractory metastatic melanoma. J. Clin. Oncol. 2005; 23:2346-2357). Such lymphocytes might otherwise compete with the transferred cells for homeostatic cytokines such as interleukin-7 (IL-7) and IL-15. Lymphodepletion before ACT may use total body irradiation or cytotoxic drugs to deplete the lymphoid compartment of patients. The transferred T cells may be administered with appropriate growth factors to stimulate their survival and expansion in vivo and/or such growth factors may be administered separately to the patient prior to or following administration of the cells. In some embodiments, molecules capable of stimulating endogenous antigen presenting cells, such as Toll-like receptor agonists may be administered. In some embodiments both T cells and APCs are administered.

In some embodiments cells may be sortagged with a detectable label so that they can be detected in vivo or in a sample subsequently removed from a subject.

In some aspects, methods of modulating the immune system of a mammalian subject are provided herein. In some embodiments a method of modulating the immune system comprises administering a living mammalian cell to a mammalian subject, wherein a moiety comprising an immunomodulator, antigen, or epitope, is conjugated to a living mammalian cell using sortase. In some embodiments a method of modulating the immune system comprises conjugating a moiety comprising an immunomodulator, antigen, or epitope to a living mammalian cell using sortase and administering the living mammalian cell to a mammalian subject.

In some embodiments, modulating the immune system comprises modulating one or more biological activities of one or more types of immune system cells. In some embodiments, modulating the immune system comprises modulating an immune response to an antigen. In some embodiments, modulating an immune response to an antigen comprises modulating one or more biological activities of one or more types of immune system cells exposed to the antigen. In some embodiments an immune response comprises migration, proliferation, or activation of one or more types of immune system cells. In some embodiments an immune response comprises development of immature immune system cells into mature, functional cells. In some embodiments an immune response comprises proliferation and/or activation of helper (CD4+) T cells specific for an antigen. In some embodiments an immune response comprises proliferation and/or activation of cytotoxic (CD8+) T lymphocytes (CTLs) specific for an antigen. In some embodiments an immune response to an antigen comprises production of cytokines by, e.g., immune system cells specific for the antigen. In some embodiments an immune response comprises proliferation and/or activation of antibody-producing cells (plasma cells) and/or production of antibodies by such cells, wherein the antibodies bind to an antigen. In some embodiments an immune response comprises production of memory T and/or B cells that are capable of providing a rapid immune response to an antigen upon subsequent exposure to the antigen that elicited their production. In some embodiments modulating an immune response comprises modulating any one or more biological activities of immune system cells. In some embodiments modulating an immune response to an antigen comprises modulating any one or more biological activities of immune system cells that are specific for the antigen. In some embodiments modulating an immune response to an antigen modulates an immune response to an entity comprising the antigen. For example, modulating an immune response to a pathogen-derived antigen modulates the immune response to a pathogen comprising the antigen or a cell expressing the antigen or displaying the antigen at its surface. The term "pathogen-derived antigen" encompasses any antigen that is naturally produced by and/or comprises a polypeptide or peptide that is naturally genetically encoded by a pathogen, e.g., any of the various pathogens mentioned herein. In some embodiments a pathogen-derived antigen is a polypeptide, a polysaccharide, a carbohydrate, a lipid, a nucleic acid, or combination thereof that is naturally produced by a pathogen. In some embodiments a pathogen-derived antigen is naturally encoded by a pathogen and is produced by an infected cell as a result of the introduction into the cell of the pathogen's genetic material that encodes the antigen. In some embodiments a pathogen-derived antigen is at least partly exposed at the surface of a cell membrane, cell wall, or capsule. In some embodiments a pathogen-derived antigen is a secreted virulence factor of a pathogen. In some embodiments a pathogen-derived antigen is an antigen that plays a role in entry of the pathogen into a host cell. For example, the antigen may bind to a cell surface molecule of a cell to be infected. In some embodiments a pathogen-derived antigen is a toxin. In some embodiments a pathogen may be an agent that rarely if ever causes disease in healthy, immunocompetent individuals, but that causes disease in at least some individuals who are susceptible, e.g., individuals who are immunocompromised.

In some embodiments, modulating an immune response comprises stimulating (enhancing, augmenting, eliciting) an immune response. In some embodiments "stimulating" an immune response encompasses causing development of an immune response, enhancing the capacity of a subject to mount an immune response, or increasing an immune response in a subject who is currently mounting an immune response. In some embodiments enhancing the capacity of a subject to mount an immune response results in a faster or more robust immune response. In some embodiments an immune response is directed towards foreign entities (e.g., pathogens), infected cells, cancer cells, or other undesirable (e.g., deleterious) cells or substances that comprise the antigen.

In general, a targeting moiety may comprise any of a variety of different moieties, which may be obtained using any suitable method. In some embodiments a targeting moiety comprises an antibody, an antibody chain, an antibody fragment, an scFv, a VHH domain, a single-domain antibody, protein, or an aptamer, wherein the antibody, antibody chain, antibody fragment, scFv, VHH domain, single-domain antibody, protein, or aptamer binds to the target.

In some embodiments, methods disclosed herein of modulating an immune response enhance an adaptive immune response against a pathogen, infected cell, tumor cell, or other undesired cell or substance. In some embodiments, methods disclosed herein of modulating an immune response enhance an innate immune response against a pathogen, infected cell, tumor cell, or other undesired cell or substance. In some embodiments, methods disclosed herein of modulating an immune response enhance both an adaptive immune response and an innate immune response. In some embodiments, methods disclosed herein enhance a T cell-mediated immune response, e.g., against a pathogen such as a virus (e.g., HIV), bacterium (e.g., *Mycobacterium*), fungus (e.g., *Aspergillus*) or parasite (e.g., *Plasmodium*), or against a tumor cell or other undesired cell. In some embodiments, methods disclosed herein enhance cell-mediated cytotoxicity towards a pathogen, infected cell, or tumor cell. For example, in some embodiments methods disclosed herein enhance activity of CD8+ cytotoxic T cells against a pathogen, infected cell, or tumor cell.

In some embodiments a composition comprises sortagged mammalian cells, wherein the cells are sortagged with any moiety of interest. In some embodiments a composition comprises mammalian cells, sortase, and a sortase substrate. In some embodiments a composition comprises up to about $10^{14}$ cells, e.g., about 10, $10^2$, $10^3$, $10^4$, $10^5$, $5 \times 10^5$, $10^6$, $5 \times 10^6$, $10^7$, $5 \times 10^7$, $10^8$, $5 \times 10^8$, $10^9$, $5 \times 10^9$, $10^{10}$, $5 \times 10^{10}$, $10^{11}$, $5 \times 10^{11}$, $10^{12}$, $5 \times 10^{12}$, $10^{13}$, $5 \times 10^{13}$, or $10^{14}$ cells. In some embodiments the number of cells may range between any two of the afore-mentioned numbers. In some embodiments a composition further comprises a growth factor, cytokine, adjuvant or costimulator. In some embodiments the one or more growth factors or cytokines promotes maturation, survival, proliferation, or activation of at least some of the cells. In some embodiments a cytokine is IL-2. In some embodiments a cytokine is IL-7, IL-12, IL-15, or IL-21. In some embodiments a cytokine is TNF-alpha. In some embodiments a composition in which immune system cells are cultured or maintained comprises an antibody or ligand of a T cell receptor or portion thereof, e.g., an antibody to CD3. In some embodiments a composition in which immune system cells are cultured or maintained comprises one or more adjuvants. In some embodiments a composition comprising immune system cells comprises one or more adjuvants that induces expression of a costimulator by at least some of the immune system cells. In some embodiments the one or more adjuvants comprises a TLR ligand, PAMP or PAMP mimic, CD40 ligand, or anti-CD40 antibody. In some embodiments a composition in which immune system cells are cultured or maintained comprises one or more costimulators. In some embodiments a costimulator is expressed at the surface of APCs, e.g., DCs. In some embodiments a costimulator is soluble. In some embodiments a costimulator is attached to a surface, e.g., a particle.

In some embodiments an immune response comprises maturation, proliferation and/or activation of lymphocytes, e.g., CD4+ helper T cells, that are specific for the antigen, i.e., that express receptors (TCR, BCR) that bind to the antigen, e.g., with high affinity. In some embodiments, cell activation results in increased expression of one or more cytokine genes.

Cells, e.g., sortagged mammalian cells, may be characterized or assessed, e.g., to determine whether they have one or more properties of interest, to determine the effect of sortagging, and/or to determine the effect of the cells when administered to a subject. In some embodiments, cells may be assessed for secretion of one or more cytokines, presence of a cell surface marker profile characteristic of an activated state, and/or possession of one or more functional activities such as cytotoxic activity. In some embodiments effector function of lymphocytes (e.g., T cells) may be demonstrated by IFNγ secretion after co-culture with target cells (e.g., tumor cells, infected cells, or cells that have been loaded with or caused to express a target antigen). In some embodiments effector function of lymphocytes may be demonstrated by increased expression of CD107a (LAMP-1), which may serve as a functional marker for the identification of CD8+ T cell and natural killer cell activity (e.g., degranulation). Cytokine secretion may be assessed using, e.g., ELISA assay, cytokine antibody arrays, etc. In some embodiments, presence or proliferation of T cells with specificity for a particular antigen may be assessed using peptide-MHC multimers (e.g., dimers, tetramers, pentamers, etc.) which can be used to identify or isolate T cells specific for the peptide, or in some embodiments using CD1-lipid multimers, which can be used to identify or isolate natural killer T cells specific for the lipid. Methods for generating peptide-MHC or CD1-lipid multimers are well known in the art.

A wide variety of assays are available to assess cell viability and/or proliferation. For example, a cell membrane integrity assay (e.g., ability to exclude a compound that is generally excluded from viable cells, such as trypan blue or 7-amino actinomycin D (7-AAD), cellular ATP-based assay, a mitochondrial reductase activity assay, calcein staining, a DNA content assay using a nucleic acid dye, a cellular metabolism assay such as resazurin (sometimes known as AlamarBlue, etc.), MTT, XTT, and CellTitre Glo, etc., a protein content assay such as SRB (sulforhodamine B) assay; nuclear fragmentation assays; cytoplasmic histone associated DNA fragmentation assay; PARP cleavage assay; TUNEL staining; annexin staining, CyQUANT® cell proliferation assays (Life Technologies). In some embodiments cytotoxicity may be assessed using a flow cytometry based assay, wherein a fluorochrome or other detectable label is used to stain non-viable or viable cells in a cell population, and the cells are subjected to flow cytometry and quantified.

In some embodiments cytotoxicity (e.g., cytotoxic effect of sortagged mammalian cells) may be assessed, if desired, using any suitable assay. In some embodiments a chromium-51 ($^{51}$Cr) release assay may be used. In a $^{51}$Cr assay, target cells are loaded with $^{51}$Cr and maintained under conditions in which cytolysis may occur. The label may then be released from the target cells by cytolysis. The label can be isolated by centrifuging the samples and collecting the supernatants. Supernatants from centrifugation can either be counted directly in a gamma counter, or mixed with scintillation fluid or dried on a substrate comprising a solid scintillant such as a LumaPlate™ and counted in a scintillation counter. Cytotoxicity assays utilizing similar principles to the chromium-51 release assay (loading cells with a compound or compound precursor and detecting compound subsequently released from lysed cells) may be used, such as the DELFIA® cytotoxicity assay (Perkin Elmer). The DELFIA is based on loading cells with an acetoxymethyl ester of a fluorescence enhancing ligand. After the ligand has penetrated the cell membrane the ester bonds are hydrolyzed within the cell to form a hydrophilic ligand, which no longer passes through the membrane. After cytolysis the released ligand is introduced to a europium solution to form a fluorescent chelate. The measured signal correlates directly with the amount of lysed cells. In some embodiments a cytotoxicity assay is used to measure cell-mediated cytotoxicity, e.g., cytotoxic activity of T cells or NK cells. In some embodiments the ability of cells to lyse target cells expressing particular peptides or other antigens may be tested using cells that have been loaded with or caused to express such peptides or antigens as target cells. In some embodiments a cytotoxic cell is characterized in that it produces perforin, granzyme(s) (e.g., granzyme A, granzyme B, granzyme 3/K), and/or granulysin. In some embodiments production of such enzymes may be detected by flow cytometry. In some embodiments, cytotoxicity may be observed using, e.g., time lapse microscopy.

In some embodiments pro-apoptotic activity (e.g., pro-apoptotic effect of sortagged mammalian cells) may be assessed, if desired, using any suitable assay. In some embodiments a TUNEL assay, DNA fragmentation assay, Annexin V assay, caspase assay, mitochondrial membrane potential assay, etc.

The ability of administered sortagged mammalian cells to produce a useful therapeutic effect may be assessed using standard methods for assessing the effect of therapies in the particular disease that the cells are intended to treat. For example, anti-tumor effect may be assessed in a variety of non-human animal tumor models, e.g., xenograft models, non-human animals with tumors that arise spontaneously or as a result of genetic engineering, etc. In some embodiments tumor(s) may be removed from the body (e.g., at necropsy) and assessed (e.g., tumors may be counted, weighed, and/or size (e.g., dimensions) measured). In some embodiments the size and/or number of tumors may be determined non-invasively. For example, in certain tumor models, tumor cells that are fluorescently labeled (e.g., by expressing a fluorescent protein such as GFP) can be monitored by various tumor-imaging techniques or instruments, e.g., non-invasive fluorescence methods such as two-photon microscopy. The size of a tumor implanted or developing subcutaneously can be monitored and measured underneath the skin. Any of a wide variety of methods and/or devices known in the art may be used to assess tumors in vivo in animals or in human subjects. Tumor number, size, growth rate, or metastasis may, for example, be assessed using various imaging modalities, e.g., 1,2, or 3-dimensional imaging (e.g., using X-ray, CT scan, ultrasound, or magnetic resonance imaging, etc.) and/or functional imaging (e.g., PET scan) may be used to detect or assess lesions (local or metastatic), e.g., to measure anatomical tumor burden, detect new lesions (e.g., metastases), etc. In human subjects, objective criteria such as the original or revised Response Evaluation Criteria In Solid Tumors (RECIST) (Therasse P, et al. J Natl Cancer Inst (2000) 92:205-16; Eisenhauer, E., et al., Eur J Cancer. (2009) 45(2):228-47) or in the case of lymphomas or leukemias, response criteria described in Cheson B D, et al. J Clin Oncol 2007; 10:579-86, may be used. As will be appreciated, in a clinical response may not be evident until a number of weeks or months after therapy. For example, in the case of a response to immune checkpoint inhibitor therapy, a regression in size of lesions may be slower (e.g., delayed by about 6 months after initiation of therapy) as compared with the timing that is typically seen in the case of responses to standard chemotherapeutic agents. Therapeutic effect against a pathogen may, e.g., be assessed based on symptoms of infection in pathogen-exposed animals or human subjects, and/or by detecting a reduction in the presence of pathogens or pathogen-infected cells in body fluids (e.g., blood), tissues, or organs in infected subjects that receive the therapy as compared with controls.

Animal models exist for a variety of different autoimmune diseases. For example, the Collagen Induced Arthritis (CIA) model is a commonly used model that shares immunological and pathological similarities to human rheumatoid arthritis. Arthritis is initiated by intradermal injections of Collagen Type II (CII) emulsified in Complete Freund's Adjuvant (CFA), e.g., in rodents, which causes an immune response generating antibodies to CII. There is both a T cell and B cell component to the pathology. Experimental autoimmune encephalomyelitis is an inflammatory demyelinating disease of the central nervous system (CNS) and is used as an animal model of human CNS demyelinating diseases, including multiple sclerosis and acute disseminated encephalomyelitis. EAE serves as a prototype for T-cell-mediated autoimmune disease in general. EAE can be induced in a number of species, including mice, rats, guinea pigs, rabbits and primates. Commonly used antigens in rodents are spinal cord homogenate (SCH), purified myelin, myelin protein such as MBP, PLP and MOG, or peptides of these proteins. It may also be induced by the passive transfer of T cells specifically reactive to these myelin antigens. Therapeutic efficacy may be assessed based on, e.g., clinical symptoms and signs, histopathology (e.g., lesions, tissue destruction), presence of self-reactive T cells, etc. Animal models of type I diabetes include, for example, non-obese diabetic (NOD), BDC2.5 transgenic, and humanized mice such as NOD.β2mnull.HHD mice, which lack murine-derived MHC I and instead transgenically express human HLA-A2.1 molecules.

Cells may be administered in an effective amount, by which is meant an amount sufficient to achieve a biological response or effect of interest, e.g., reducing one or more symptoms or manifestations of a disease or condition or modulating an immune response. In some embodiments a composition administered to a subject comprises up to about $10^{14}$ cells, e.g., about $10^3$, $10^4$, $10^5$, $10^6$, $10^7$, $10^8$, $10^9$, $10^{10}$, $10^{11}$, $10^{12}$, $10^{13}$ or $10^{14}$ cells, or any intervening number or range. In some embodiments between about $10^5$ and about $10^{12}$ cells are administered. In some embodiments between about $10^5$-$10^8$ cells and about $10^{11}$-$10^{13}$ cells are administered. In some embodiments a subject receives a single dose of cells. In some embodiments a subject receives multiple doses of cells, e.g., between 2 and 5, 10, 20, or more doses, over a course of treatment. In some embodiments a dose or total cell number may be expressed as cells/m$^2$ or cells/kg. For example, a dose may be about $10^3$, $10^4$, $10^5$, $10^6$, $10^7$, $10^8$, $10^9$, or $10^{10}$ cells/m$^2$ or cells/kg any intervening number of range. In some embodiments a course of treatment lasts for about 1-2 months, 2-6 months, 6-12 months, or more, e.g., indefinitely or until the subject is no longer in need of treatment. In some embodiments a subject may be treated about every 2-6 weeks. One of ordinary skill in the art will appreciate that the number of cells, doses, and/or dosing interval may be selected based on various factors such as the weight, surface area, and/or blood volume of the subject, the condition being treated, response of the subject, etc. The exact number of cells required may vary from subject to subject, depending on factors such as the species, age, weight, sex, and general condition of the subject, the severity of the disease or disorder, the particular cell(s), the identity and activity of agent(s) conjugated to the cells, mode of administration, concurrent therapies, and the like. It will be understood that the amount may be decided by the attending physician within the scope of sound medical judgment. In some embodiments both sortagged and non-sortagged cells may be administered.

In some embodiments one or more compounds is also administered once or more to the subject in addition to administering cells. In some embodiments a compound is administered at least once prior to and/or at least once after administration of the cells. In some embodiments a cytokine is administered, wherein the cytokine is capable of enhancing survival, proliferation, maturation, activation, or activity of immune system cells. In some embodiments the cytokine is IL-2. In some embodiments the cytokine is IL-7, IL-12, IL-15, or IL-21. In some embodiments an adjuvant is administered. In some embodiments the adjuvant is capable of inducing APCs to express a costimulator. In some embodiments the adjuvant and/or cytokine is administered in the same composition as the cells. In some embodiments the adjuvant, cytokine, and/or cells are administered in different compositions.

In general, cells may be administered using any suitable route of administration. In some embodiments cells are administered to the circulatory system, e.g., by infusion. In some embodiments cells are administered intravenously. In some embodiments cells are administered to or in the vicinity of a tumor or a site that may harbor tumor cells (e.g., a site from which a tumor was removed or rendered undetectable by treatment or to which a tumor is prone to metastasize), site of infection, or site of potential infection (e.g., a break in the skin such as a wound, indwelling device, surgical site, etc.), or any site at which an effect, e.g., a therapeutic effect, is desired. In some embodiments cells are administered into or in the vicinity of an organ that is affected by a condition for which the cells have a therapeutic effect. In some embodiments the organ is one in which a tumor is present or from which a tumor has been removed or to which a tumor is prone to metastasize. In some embodiments the tumor is a primary tumor. In some embodiments the tumor is a metastatic tumor. One of ordinary skill in the art will be aware that certain tumor types are prone to metastasize to particular organs, i.e., they metastasize to those organs commonly or at least more frequently than to many or most other organs. For example, breast tumors are prone to metastasize to bone, liver, lung and brain; colorectal cancers are prone to metastasize to the liver and lungs. In some embodiments the organ is the first, second, third, or fourth most common organ to which the particular tumor type that the individual has metastasizes. In some embodiments the tumor is a metastasis. In some embodiments cells are administered into the portal vein or hepatic artery to treat a liver condition, e.g., a liver cancer (e.g., hepatocellular carcinoma) or liver infection. In some embodiments cells are administered into the pancreatic artery to treat a condition affecting the pancreas, e.g., pancreatic cancer. In some embodiments cells are administered into the peritoneal cavity to treat a condition affecting the peritoneum, such as a tumor. Primary peritoneal cancer is a cancer of the cells lining the peritoneum and is a form of mesothelioma. The peritoneal cavity is a common site of ovarian cancer spread or recurrence. Peritoneal metastases may arise from a variety of primary cancer, such as gastrointestinal cancers. In some embodiments cells are administered into the pleural space or thoracic cavity to treat a condition affecting the lungs or pleura, such as a lung cancer or pleural mesothelioma. In some embodiments cells are administered into the spinal canal to treat a condition affecting the brain or meninges such as a tumor. In some embodiments cells are administered intraocularly to treat a condition affecting the eye, such as a tumor. In some embodiments cells are administered into or in the vicinity of an organ in which an infection has been detected or suspected of being present Presence of an infection in an organ may be suspected e.g., based at least in part on symptoms or signs experienced or exhibited by the subject, detection of the infectious agent or a component thereof (such as DNA, RNA, protein) in a sample obtained from the organ, or known propensity of the infectious agent to infect organs of that type. In some embodiments, "in the vicinity" of a site or organ refers to within a location outside the organ or site and within 1 cm, 2 cm, 3 cm, 4 cm, 5 cm from the edge of the organ or site. In some embodiments, "in the vicinity" of a site or organ refers to administration into a blood vessel that supplies the organ or site, either within the organ or site or at a location no more 5 cm, 10 cm, 15 cm, 20 cm, or 25 cm away from the point where the blood vessel (or one or more blood vessels that arise from the blood vessel) enter the organ or site. In certain embodiments cells may be introduced into a vessel that transports blood out of or away from the organ. In some embodiments, such administration may be useful to target tumor cells that arise from a tumor within the organ and enter the circulatory or lymphatic system.

In some embodiments, focused ultrasound (FUS) in the presence of a microbubble contrast agent may be used to deliver sortagged cells to the brain, e.g., for treatment of a tumor or infection in the brain using immune system cells targeted to an antigen expressed in the tumor, by infected cells, or by an infectious agent. The FUS disrupts the blood brain barrier (BBB), facilitating delivery of cells to the brain. In some embodiments the immune system cells are sortagged CAR cells. In some embodiments the cells are sortagged with a targeting moiety.

Cells may be administered in any physiologically acceptable vehicle. A vehicle compatible with cell viability and not causing adverse effects when administered to a subject may be selected by the ordinary skilled artisan. In some embodiments a vehicle comprises water, appropriate salt concentration, and may comprise a physiologically compatible buffer substance such as HEPES.

In some embodiments immune system cells are administered to a subject in need of prophylaxis or in need of treatment of an existing cancer or in need of delaying, inhibiting, or preventing recurrence of cancer. In some embodiments at least some of the introduced cells (or their descendants) mount an immune response against the cancer or against cancer cells remaining in or arising in the body, wherein the cancer or cancer cells comprise the tumor antigen. In some embodiments at least some of the introduced cells (or their descendants) stimulate maturation, proliferation, and/or activation of at least some endogenous immune system cells of the subject, e.g., endogenous T cells, wherein the endogenous immune system cells mount an immune response against the cancer or against cancer cells remaining in or arising in the body, wherein the cancer or cancer cells comprise the tumor antigen.

In some embodiments a method comprises identifying an antigen expressed by a tumor for which a subject is in need of treatment. The tumor or cells obtained from the tumor can be analyzed for expression of tumor antigens using standard methods such as immunohistochemistry, flow cytometry, etc. In some embodiments, immune system cells are sortagged with an agent comprising a targeting moiety that binds to the antigen. The immune system cells and/or descendants thereof are subsequently administered to the subject. In some embodiments immune system cells are obtained from a subject prior to treatment of the subject with chemotherapy or radiation. At least some of the immune system cells may be stored for future use in producing one or more cell preparations to be administered to the subject.

In some embodiments a subject, e.g., a subject to whom sortase-modified cells are administered, is immunocompetent, e.g., the subject has a normally functioning immune system. In some embodiments a subject is immunocompromised. A subject may be immunocompromised for any of a variety of reasons. Such reasons may include, e.g., age (e.g., infants or elderly individuals), genetic immunodeficiency disorders affecting one or more components of the innate and/or adaptive immune system, diseases such as cancer or infections that affect the immune system such as HIV infection, treatment with an immunosuppressive or cytotoxic drug, e.g., for cancer (e.g., cancer chemotherapy) or to prevent or inhibit transplant rejection or to treat an autoimmune disease. Immunosuppressive agents include, e.g., cytotoxic or cytostatic drugs, such as a variety of chemotherapeutic drugs used in the treatment of cancer, various drugs administered to reduce the likelihood of transplant rejection or to treat autoimmune diseases. Examples include, e.g., glucocorticoids, immunophilin-interacting agents such as rapamycin or rapamycin analogs, TNF alpha antagonists, etc.). In some embodiments a subject is at increased risk of infection as compared with a normal, average healthy individual, due, e.g., to hospitalization, surgery, chronic disease (e.g., diabetes, cancer, chronic obstructive pulmonary disease, cystic fibrosis), indwelling medical device (e.g., catheter, IV line), implant or prosthesis (e.g., heart valve replacement), physical trauma, burn, malnourishment, etc. In some embodiments sortase-modified cells are used to induce or augment an immune response in a subject who has undergone, is undergoing, or will undergo chemotherapy or radiation therapy. In some embodiments a subject is at increased risk of infection because the subject is less than about 1 year of age or is over about 60, 65, 70, 75, or 80 years of age.

In some embodiments, modulating an immune response comprises inhibiting the immune response. As used herein, "inhibiting" an immune response encompasses preventing or delaying development of an immune response to an antigen in a subject not currently exhibiting such response or reducing the intensity of a current or potential future immune response. In some embodiments an immune response is an unwanted immune response, e.g., an immune response that is deleterious to the subject in whom it occurs. In some embodiments, an unwanted immune response is directed against self tissues or cells, transplanted tissue or cells, non-living materials introduced into the body for diagnostic or therapeutic purposes, or an allergen.

In some embodiments an unwanted immune response is an immune response that is excessive or inappropriately prolonged, such that it is deleterious to the subject. For example, an immune response directed against an antigen derived from a pathogen that has infected a subject may initially be beneficial in terms of controlling the pathogen but may be too intense or prolonged, such that it causes tissue damage to the subject (e.g., cell-mediated or antibody-mediated tissue damage) or symptoms due to excessive cytokine release.

An unwanted immune response may be mounted by a subject against a transplanted tissue or organs or cells, such as blood cells, stem cells, blood vessel, bone marrow, solid organ (e.g., heart, lung, kidney, liver, pancreas), skin, intestine, or cells derived from any of the foregoing. For example, pancreatic tissue, e.g., pancreatic islets, or isolated pancreatic beta cells, may be transplanted from a donor into a subject in need of treatment of diabetes, e.g., type I diabetes. In some embodiments a transplant (also termed a "graft") comprises allogeneic cells or tissues (i.e., the donor and recipient are different individuals from the same species). In some embodiments a transplant comprises xenogeneic cells or tissues (i.e., the donor and recipient are of different species). The immune response may be directed, e.g., against one or more donor antigens, e.g., histocompatibility proteins (e.g., major or minor histocompatibility proteins) of the donor. An immune response directed against a graft may be referred to as "rejection". Rejection may result in damage to the graft, which may reduce its function, may lead to graft failure, and may ultimately require removal of the graft. In some embodiments sortagged mammalian cells comprise regulatory T cells conjugated with a moiety that targets them to cells, tissues, or organs at risk of or exhibiting evidence of rejection, e.g., acute graft rejection.

An unwanted immune response may comprise graft-versus-host disease (GvHD). GvHD may occur, for example, after an allogeneic stem cell transplant. In GvHD, grafted donor immune cells or their descendants recognize the recipient (e.g., recipient's cells) as foreign and mount an immune response thereto, e.g., a T cell-mediated immune response. Allogeneic hematopoietic stem cell transplantation can be a curative treatment in a variety of hematopoietic disorders, immunodeficiencies, and leukemias and finds use in treatment of a variety of cancers when chemotherapy has ablated the patient's immune system. GvHD can be a life-threatening complication of such transplants. In some embodiments sortagged mammalian cells may be used to treat, e.g., prophylactically, GvHD. In some embodiments sortagged mammalian cells comprise regulatory T cells conjugated with a moiety that targets them to cells, tissues, or organs at risk of or exhibiting evidence of GvHD. In some embodiments, regulatory T cells may be modified using sortase, e.g., with a targeting moiety that targets them to graft-derived immune cells and/or to sites at which such immune cells are active. Mesenchymal stem cells have been reported to have a variety of beneficial effects in treatment of graft-versus host disease (GvHD). For example, they have been reported to reduce proliferation of graft derived T-cells, inhibit alloreactive T-cell responses and support hematopoietic stem cell (HSC) engraftment. In some embodiments, MSCs may be modified using sortase, e.g., with a targeting moiety that targets them to graft-derived T cells and/or to sites at which such T cells are active. In some embodiments MSCs may be conjugated using sortase with a moiety that targets them to cells, tissues, or organs at risk of or exhibiting evidence of GvHD. In some embodiments the regulatory T cells and/or MSCs are targeted to the skin, liver, or gastrointestinal tract. In some embodiments the regulatory T cells and/or MSCs may be conjugated with an agent, e.g., a cytokine, that exerts an inhibitory effect on donor immune system cells involved in GvHD. In some embodiments the regulatory T cells and/or MSCs may be derived from the same donor as the original grafted cells.

In some embodiments an unwanted immune response comprises an immune response to an autoantigen (also referred to as a self antigen), e.g., in a subject suffering from an autoimmune disease. Such inappropriate immune responses may involve self-reactive T cells, autoantibodies, or both. One of ordinary skill in the art will be aware of various autoantigens involved in particular autoimmune diseases. Autoimmune diseases include, for example, acute disseminated encephalomyelitis, alopecia areata, antiphospholipid syndrome, autoimmune hepatitis, autoimmune myocarditis, autoimmune pancreatitis, autoimmune polyendocrine syndromes, autoimmune uveitis, inflammatory bowel disease (Crohn's disease, ulcerative colitis), type I diabetes mellitus (e.g., juvenile onset diabetes), multiple sclerosis, scleroderma, ankylosing spondylitis, sarcoid, pemphigus vulgaris, pemphigoid, psoriasis, myasthenia gravis, systemic lupus erythemotasus, rheumatoid arthritis, juvenile arthritis, psoriatic arthritis, Behcet's syndrome, Reiter's disease, Berger's disease, dermatomyositis, polymyositis, antineutrophil cytoplasmic antibody-associated vasculitides (e.g., granulomatosis with polyangiitis (also known as Wegener's granulomatosis), microscopic polyangiitis, and Churg-Strauss syndrome), scleroderma, Sjögren's syndrome, anti-glomerular basement membrane disease (including Goodpasture's syndrome), dilated cardiomyopathy, primary biliary cirrhosis, thyroiditis (e.g., Hashimoto's thyroiditis, Graves' disease), transverse myelitis, and Guillane-Barre syndrome. Examples of certain autoantigens that are involved in some of these diseases are discussed below. In some embodiments sortagged mammalian cells comprise regulatory T cells conjugated with a moiety that targets them to cells, tissues, or organs at risk of or exhibiting evidence of damage in an autoimmune disease.

In some embodiments, a method for inducing tolerance comprises generating tolerogenic DCs, e.g., DCs that either delete autoreactive T cells or induce regulatory T (Treg) cells, e.g., CD4+CD25−Foxp3+ regulatory T cells. In some embodiments, a method results in reduction in the number and/or activity of Th17 cells. In some embodiments tolerogenic DCs are generated in vitro and administered to a subject. In some embodiments tolerogenic DCs are generated by a method comprises exposing DCs, e.g., immature DCs, in vitro, to an agent comprising (a) a targeting moiety that binds to a DC cell surface protein and (b) an antigen, wherein the antigen comprises a self-antigen or allergenic antigen. In some embodiments inhibiting the immune response e.g., induction of tolerance or a tolerogenic state, is achieved by using a suitable concentration or amount of the agent and/or exposing cells or subjects to appropriate cytokines. In some embodiments targeting an antigen to DCs in the absence of an effective amount of an adjuvant inhibits the immune response to the antigen that would otherwise occur and thereby results in increased tolerance to the antigen. In some embodiments a method of inhibiting an immune response comprises administering to a subject an agent comprising a targeting moiety that binds to DCs and an antigen, wherein the antigen comprises a self-antigen or allergenic antigen. In some embodiments the antigen is one to which the subject has previously exhibited or continues to exhibit or is at risk of exhibiting an unwanted, e.g., deleterious, immune response. In some embodiments the agent is administered without administering an effective amount of an adjuvant. For example, the agent may be administered in a composition that is substantially free of adjuvants.

In some embodiments, a method for inducing or promoting tolerance comprises generating modified mammalian Treg cells ("Tregs") using sortase and administering the cells to a subject. As known in the art, Tregs are capable of regulating, e.g., inhibiting, immune responses by, for example, suppressing effector T cells. In some embodiments Tregs are modified by conjugating a targeting moiety to their surface using sortase, wherein the targeting moiety targets the Tregs to an organ, tissue, or site in the body of a subject where regulation, e.g., inhibition, of an immune response is desired. In some embodiments, the organ, tissue, or site is a graft. In some embodiments the Tregs are generated by obtaining Tregs from a subject and modifying the Tregs ex vivo using sortase. In some embodiments Tregs obtained from a subject are expanded ex vivo prior to modification by sortase. In some embodiments modified Tregs may be contacted with a graft ex vivo prior to transplanting the graft into a recipient. The Tregs may infiltrate the graft and inhibit development or limit the extent of an immune response after transplant. In some embodiments Tregs may be administered together with the graft and/or after the transplant. Tregs may be administered locally at or near the site of transplant and/or by introducing the cells into the bloodstream or lymphatic system. In some embodiments at least one cytokine is administered to the subject one or more times in combination with Tregs. A cytokine and Tregs may be administered at the same site, different sites, or both. A cytokine may be administered prior to, at the same time as, and/or after administration of the Tregs. If administered at the same time, the Tregs and cytokine(s) may be in the same composition as the Tregs or in a different composition. In some embodiments a cytokine is a cytokine that has anti-inflammatory properties, e.g., IL-2, IL-10, transforming growth factor-β (TGF-β), IL-27, IL-35 or IL-37. Such anti-inflammatory properties may comprise, e.g., inhibiting formation, maturation, expansion or activity of effector immune system cells; stimulating formation, maturation, expansion or activity of regulatory T cells, etc.

Tregs may be isolated and, if desired, expanded ex vivo using methods known in the art (see, e.g., and references therein for examples of such methods). Tregs may be identified based on a cell surface marker expression pattern of CD4+CD25+CD127lo. In some embodiments Tregs are characterized by high-level expression of CD25, FoxP3, CTLA-4, GITR, and CD62L and a very low or undetectable expression of CD127.

In some embodiments inhibiting an unwanted immune response comprises stimulating an immune response against one or more cellular components of the unwanted immune response. For example, in some embodiments an immune response directed against self-reactive immune system cells, e.g., self-reactive T cells, is stimulated. In some embodiments an immune response directed against immune system cells at least in part responsible for an immune-mediated disorder, e.g., allergy, is stimulated. In some embodiments an immune response directed against one or more cellular components of the unwanted immune response at least in part eliminates such cells, resulting in a reduction or inhibition of the unwanted immune response.

In some embodiments a composition, e.g., a composition to be used to induce tolerance in a subject, is substantially free or essentially free of any one or more substances, e.g., any one or more particular adjuvant(s), e.g., any one or more of the adjuvants or classes of adjuvants mentioned above or known in the art. In some embodiments the concentration or amount of adjuvant present, if any, is ineffective to enhance an immune response. In some embodiments the concentration or amount of adjuvant is less than or equal to 1%, 5%, 10%, 15%, 20%, or 25% of the concentration or amount that would be effective to stimulate an immune response, e.g., an amount that would be used by one of ordinary skill in the art seeking to generate or enhance an immune response against an antigen, e.g., in a vaccine. In some embodiments a composition is substantially free or essentially free of any one or more particular adjuvant(s), e.g., any one or more of the adjuvants or classes of adjuvants mentioned above or known in the art.

In some embodiments a method comprises identifying an antigen to which a subject is allergic or reactive (e.g., self-reactive) and conjugating an agent comprising the antigen to a mammalian cell using sortase. In some embodiments the cell is capable of inducing tolerance to the antigen. In some embodiments the cell is a Treg cell. In some embodiments the cell is administered to a subject in need of treatment of an allergy or in need of inhibition of immune response against the antigen. In some embodiments identifying an antigen comprises administering a test dose of one or more antigens to the subject, e.g., performing a skin test. In some embodiments identifying comprises determining the response of the subject to a test dose of one or more allergens or antigens. In some embodiments, if the response to an allergen is abnormally intense, the antigen is identified as one to which the subject is allergic or self-reactive. In some embodiments the subject harbors self-reactive T cells or B cells comprising a TCR or BRC that recognizes the antigen. In some embodiments the subject produces antibodies that bind to the antigen. In some embodiments a method comprises determining whether a subject produces antibodies that bind to an allergenic antigen or self-antigen. In some embodiments a sample comprising cells or serum from a subject is tested against a panel of candidate allergenic antigens or autoantigens in order, e.g., to identify one or more allergenic antigens or self-antigens at least in part responsible for causing an allergy or autoimmune disease.

In some embodiments cells are sortagged with an antigen to which the subject is allergic or self-reactive. In some embodiments at least some of the cells are administered to the subject. In some embodiments the cells promote or induce tolerance to the antigen. For example, in some embodiments, a method for inducing or promoting tolerance comprises generating modified mammalian cells using sortase, wherein the cells are not genetically engineered for sortagging, and administering the cells to a subject in need thereof, e.g., a subject suffering from or at risk of an autoimmune disease. The mammalian cells may be sortagged with any autoantigen or allergen of interest or fragment thereof. In some embodiments the mammalian cells may be obtained from the subject or from an immunocompatible donor. In some embodiments the mammalian cells comprise lymphocytes, PBMCs, splenocytes, or red blood cells. In some embodiments the antigen comprises a T cell epitope. In some embodiments the T cell epitope is a CD4+ epitope. In some embodiments the T cell epitope is a CD8+ epitope. Cells may be sortagged with an agent comprising a single epitope or multiple epitopes, which may be from the same or different antigens. In some embodiments multiple populations of cells, sortagged with agents comprising different epitopes, may be administered. In some embodiments a subject may be tested to identify autoantibodies and determine which antigen(s) they react with. An agent (or agents) comprising one or more epitopes from those particular antigens may be conjugated to cells using sortase, for subsequent administration to the subject. In some embodiments, inducing tolerance to an autoantigen may reduce the clinical severity (e.g., reduce the severity of one or more symptoms), reduce the rate of progression, reduce the number of flare-ups, induce a remission, reduce the level of one or more biomarkers or other indicators of the disease, or otherwise show evidence of beneficial effect.

In some embodiments an autoimmune disease to be treated is multiple sclerosis (MS). MS is an inflammatory demyelinating disease of the CNS characterized by the formation of multiple discrete inflammatory lesions and focal demyelination in perivascular and periventricular sites of CNS white matter (Nylander, A. & Hafler, D. A. (2012) J. Clin. Invest. 122, 1180-1188). These demyelinating lesions are marked by infiltration of activated mononuclear cells and are associated with the appearance of neurologic deficits. MS is believed to be an autoimmune disorder caused at least in part by T cells specific for immunodominant self-epitopes of myelin and other CNS antigens. It is thought that such autoreactive T cells migrate into the CNS and undergo re-activation upon T cell antigen recognition of endogenous CNS epitopes and secrete pro-inflammatory cytokines and chemokines which recruit inflammatory macrophages and other leukocytes from the blood to initiate focal demyelination and CNS dysfunction. In some embodiments the autoantigen is a myelin protein of the central nervous system (CNS) such as myelin basic protein (MBP), proteolipid protein (PLP), or myelin oligodendrocyte glycoprotein (MOG). In some embodiments mammalian cells, e.g., RBCs or PBMCs, are sortagged with an agent comprising any of these proteins or an agent, e.g., a peptide, comprising an epitope found in any of these proteins, and administered to a subject in need of treatment for MS. In some embodiments the peptide comprises MBP amino acids 89-99.

In some embodiments an autoimmune disease to be treated is type I diabetes (T1D). In some embodiments cells, e.g., RBCs or PBMCs, are sortagged with an agent that comprises insulin (INS), islet-specific G6Pase catalytic subunit-related protein (IGRP), heat shock protein 60 (HSP60), islet cell antigen 512 (IA-2), or other islet cell antigens, or an agent, e.g., a peptide, that comprises an epitope of any of these proteins. For example, the antigen may comprise insulin B amino acids 9-23. In some embodiments the cells may be administered to a subject in need of treatment for T1D. In some embodiments the cells may be administered to a subject with T1D who is to receive or has received a transplant comprising islet cells, e.g., isolated islet cells, islets, or pancreatic tissue comprising islets.

In some embodiments an autoimmune disease to be treated is an autoimmune blistering skin disease, which term refers to a group of diseases characterized by autoantibodies against structural components of the skin. Further details regarding these diseases and particular autoantigens and epitopes implicated in their pathogenesis may be found in Otten, J V, et al., Curr Mol Med. January 2014; 14(1): 69-95, and references cited therein. In pemphigus vulgaris (PV) autoantibodies react mainly with desmoglein 3 (Dsg3) alone and/or in combination with desmoglein 1 (Dsg1). In bullous pemphigoid (BP) autoantibodies frequently target two hemidesmosomal proteins, BP180 (collagen XVII) and BP230, but may also target other proteins such as plectin and α6 integrin. In mucous membrane pemphigoid autoantibodies target several autoantigens of the dermal-epidermal junction, including BP180, BP230, laminin 332, α6β4 integrin, and collagen VII. Autoimmunity to collagen VII is typically associated with the skin blistering disease epidermolysis bullosa acquisita (EBA), but also occurs occasionally in patients with systemic lupus erythematosus or inflammatory bowel disease. Anti-p200 pemphigoid is an autoimmune subepidermal blistering disease, characterized by autoantibodies against a 200-kDa protein (p200) of the epidermal basement membrane, which has been identified as the laminin γ1 chain. In some embodiments cells, e.g., RBCs or PBMCs, are sortagged with an agent comprising Dsg1, Dsg3, BP180, BP230, laminin yl, collagen VII, plectin, α6 integrin, laminin 332, or α6β4 integrin or an agent, e.g., a peptide, that comprises an epitope found in Dsg1, Dsg3, BP180, BP230, laminin yl, collagen VII, plectin, α6 integrin, laminin 332, or α6β4 integrin. In some embodiments the epitope is in the ectodomain of the relevant protein. The cells may be administered to a subject in need of treatment for the relevant autoimmune blistering skin disease, SLE, IBD, or other autoimmune disease.

In some embodiments an autoimmune disease to be treated is an inflammatory bowel disease, e.g., Crohn's disease and ulcerative colitis. Autoantibodies against exocrine pancreas (PAb) have been reported to be pathognomonic markers of Crohn's disease (CD). For example, the glycoproteins CUZD1 and GP2 are targets of PAb in patient with Crohn's disease. In some embodiments cells, e.g., RBCs or PBMCs, are sortagged with an agent comprising CUZD1 or GP2 or an agent, e.g., a peptide, that comprises an epitope found in CUZD1 or GP2. The cells may be administered to a subject in need of treatment for Crohn's disease.

In some embodiments an autoimmune disease to be treated is an inflammatory arthritis, e.g., rheumatoid arthritis (RA). Autoantibodies to type II collagen (CII), heat shock proteins such as the immunoglobulin binding protein (BiP), citrullinated peptides (anti-CCP) and other citrullinated proteins such as vimentin and fillagrin are found in patients with RA In some embodiments cells, e.g., RBCs or PBMCs, are sortagged with an agent comprising type II collagen (CII), heat shock proteins immunoglobulin binding protein (BiP), human chondrocyte glycoprotein 39, citrullinated peptides (anti-CCP) and citrullinated proteins such as citrullinated fillagrin or citrullinated vimentin or an agent, e.g., a peptide, that comprises an epitope found in any of these. The cells may be administered to a subject in need of treatment for an inflammatory arthritis, e.g., rheumatoid arthritis.

In some embodiments mammalian cells are sortagged with an agent that is capable of inhibiting or reducing the effect of (neutralizing) a toxic substance that may be present in the body of a subject, e.g., in the blood. A toxic substance is a substance that causes or is capable of causing death, injury, damage, or other physiological disturbance to organisms when a sufficient quantity is introduced into or onto or absorbed by a living organism. Toxic substances include those substances recognized as such in the art. The action of a toxic substance may be by chemical reaction or other activity on the molecular scale. In some embodiments a toxic substance exerts its effects when present in the blood or when transported via the circulatory system to one or more locations in the body. The agent may be, e.g., an antibody, at least a portion of a receptor that binds to the toxic substance, or any other binding agent that binds to the toxic substance.

As used herein, a "toxin" is a toxic substance produced within living cells or organisms. In some embodiments a toxin may be produced by or genetically encoded by a microbe, e.g., a pathogen and/or may be produced in the body as a result of infection by a pathogen. Toxins may be produced, e.g., by bacteria, fungi, plants, protozoa, and parasites. In some embodiments a toxin is an exotoxin, i.e., it is released, e.g., secreted, by cell(s) that produce it. Examples of toxins include $AB_n$ toxins, e.g., $AB_1$ toxins, $AB_5$ toxins. As used herein, an "$AB_1$ toxin" is a toxin that comprises an A subunit and a B subunit. It will be understood that a subunit, e.g., an A subunit, may be cleaved to produce two polypeptide chains, which may be linked by one or more disulfide bonds. Diphtheria toxin (C. diphtheriae) is an exemplary AB 1 toxin. Heparin-binding epidermal growth factor-like growth factor serves as a receptor for diphtheria toxin. Pseudomonas exotoxin A, another bacterial $AB_1$ toxin, utilizes the low density lipoprotein receptor-related protein, also known as the a2-macroglobulin receptor to enter cells. $AB_1$ toxins also include certain type II ribosome inactivating plant toxins such as ricin, abrin, cinnanomin, viscumin, ebulin, and nigrin b (Hartley, M R & Lord, J M, Cytotoxic ribosome-inactivating lectins from plants, Biochim Biophys Acta, 1701 (1-2): 1-14, 2004; Xu H, et al., Cinnamomin~a versatile type II ribosome-inactivating protein. Acta Biochim Biophys Sin (Shanghai) 36(3): 169-76). A complete $AB_5$ toxin complex contains six protein units, five B subunits that are similar or identical in structure and a single A subunit. The A subunit (or a portion thereof) of an $AB_5$ toxin is the portion of the complex responsible for toxicity. The B subunits form a pentameric (five-membered) ring, into which the A subunit extends and is held. The B subunits may protect the A subunit and mediate binding to cells. Examples of $AB_5$ toxins (and names of bacteria that produce them) include, e.g., campylobacter jejuni enterotoxin (C. jejuni), cholera toxin (V. cholerae), heat-labile enterotoxins LT and LT-II (Escherichia coli), pertussis toxin (B. pertussis), shiga toxin (S. dysenteriae), shiga-like toxin (also known verotoxin) SLT1 and SLT2 (certain E. coli). Other toxins of interest include, e.g., Botulinum neurotoxin (C. botulinum), tetanus neurotoxin (C. tetani), and the large clostridial toxins known as Toxin A and Toxin B (C. difficile)

In some embodiments a toxic substance, e.g., a toxin, is a cytolysin, which term refers to substances, e.g., proteins and lipids, that cause lysis of cells, e.g., by damaging their cell membrane. In some embodiments a toxin is a hemolysin, which term refers to substances that cause lysis of red blood cells Hemolysins can be identified by their ability to lyse red blood cells in vitro. In some embodiments a hemolysin may, in addition to affecting red blood cells, also affect other cells, such as leukocytes. In some embodiments a toxin is a pore-forming toxin (PFT). PFTs, which include certain cytolysins, can be divided into the following subcategories: alpha-pore-forming toxins (e.g., cytolysin A of E. coli, aerolysin (Aeromonas hydrophila), and Clostridial Epsilon-toxin), beta-pore-forming toxins (e.g., α-hemolysin, Panton-Valentine leukocidin, Vibrio cholerae cytolysin, and S. aureus gamma-hemolysin, Clostridium perfringens enterotoxin). Other cytolysins include, e.g., anthrax toxin, cholesterol-dependent cytolysins such as pneumolysin, and small pore-forming toxins such as gramicidin A.

In certain embodiments a toxin is a protein, e.g., an enzyme, that degrades or directly damages host cell molecules or tissues. Examples, include, e.g., hyaluronidase, proteases, coagulases, lipases, deoxyribonucleases. In certain embodiments a toxic substance is a superantigen or superantigen-like protein. Superantigens (SAgs) are a class of antigens that cause non-specific activation of T-cells resulting in polyclonal T cell activation and massive cytokine release. T cell activation is believed to result from SAg-mediated cross-linking of major histocompatibility complex (MHC) class II antigens and T-cell receptors (TCRs). SAgs contain distinct domains capable of binding to MHCII and TCR. SAgs can be produced by pathogenic microbes (e.g., certain bacteria) or may be endogenous and produced in response to infection by pathogenic microbes (e.g., certain viruses). Many SAgs are exotoxins, a number of which are produced by the Gram-positive organisms *Staphylococcus aureus* and *Streptococcus pyogenes*. SAgs are the causative agents in toxic shock syndrome, among other disorders. Many superantigens share a common architecture that is also shared by the superantigen-like proteins (SSL), another group of bacterial virulence factors. Certain Sags and SLLs are discussed in Fraser J D, Proft T. The bacterial superantigen and superantigen-like proteins. *Immunol Rev.* 2008; 225:226-43.

In some embodiments a toxin is an endotoxin, which refers to toxins that are typically not released from the cells that produce them (except in the case of destruction or damage to the cell, e.g., destruction of the bacterial cell wall). Examples of endotoxins are lipopolysaccharide (LPS) or lipooligosaccharide (LOS), found in the outer membrane of various Gram-negative bacteria. The toxic effects of endotoxins on vertebrate organisms are mediated by their interaction with receptors on immune system cells, which results in synthesis and/or release of immune mediators such as cytokines, nitric oxide, and eicosanoids, excessive amounts of which can damage the organism.

Further information regarding certain toxins discussed above and many others may be found, e.g., in Alouf, J E & Popoff, M R, (eds.) The Comprehensive Sourcebook of Bacterial Protein Toxins, Third Edition, Academic Press, 2006; Schmitt, M J & Schaffrath, R (eds.) Microbial Protein Toxins, Topics in Current Genetics 11, Berlin, N.Y.: Springer-Verlag, 2005; Proft, T. (ed.) Microbial toxins: molecular and cellular biology, Norfolk, England: BIOS Scientific, c2005.

In some embodiments a toxic substance may not be directly toxic but may enhance the effect of a toxic substance or may be required for its activity. For example, the substance may mediate entry of a toxic substance into cells. In some embodiments a substance may be converted into a toxic substance in the body.

In some embodiments a subject may be accidentally or deliberately exposed to a toxic substance. In some embodiments a toxic substance may be a pesticide (e.g., an insecticide or herbicide), a chemical used or produced in industrial processes, etc. In some embodiments a toxic substance may be a therapeutic agent that has been administered to a subject in an excessive amount and/or has been administered to a subject who has reduced (e.g., below normal) capacity to metabolize or excrete the substance.

In some embodiments a toxic substance may be produced by a subject's own cells, e.g., in response to infection or as part of a disease process. For example, certain cytokines and inflammatory mediators produced in response to infection or injury or in certain diseases may have damaging effects when present in excessive amounts. Examples include, e.g., pro-inflammatory cytokines such as interferon gamma, TNF-alpha, IL-1 (e.g., IL-1β), IL-6, and IL-17, and inflammatory mediators such as leukotrienes.

In some embodiments a toxic substance is a virulence factor or component thereof. Virulence factors are substances or structures produced or encoded by pathogens (bacteria, viruses, fungi, protozoa, or multicellular parasites) that play a role in establishing and/or maintaining an infection. A virulence factor may permit or increase the ability of a pathogen to achieve one or more of the following: colonization of a niche in the host, immunoevasion, evasion of the host's immune response, immunosuppression, entry into and/or exit out of cells or cellular compartments (if the pathogen is an intracellular one during at least part of its life cycle), obtain nutrition from the host. Virulence factors include, e.g., pathogen-produced toxins, adhesive molecules (e.g., adhesins), molecules that stimulate endocytosis, immunoglobulin-binding proteins, proteases that degrade immunoglobulins or other host cell molecules that play a role in the immune response, bacterial capsule, which may inhibit phagocytosis of the bacteria by host immune cells, complement inactivating molecules, structures such as pili or fimbriae. In some embodiments a virulence factor is a biofilm component. In some embodiments a virulence factor is encoded by a plasmid or bacteriophage.

Cells may be sortagged with any suitable moiety capable of binding to and/or inhibiting a toxic substance or virulence factor. In some embodiments an inhibitor of a toxic substance or virulence factor may bind to the substance or structure and thereby prevent it from acting on or interacting with its target, may inactivate the substance or structure (e.g., by cleaving it), etc. It will be understood that inhibition may be partial or complete. Examples of suitable inhibiting moieties include, e.g., proteins, aptamers, or other moieties that are capable of binding to the substance or structure, enzymes that are capable of cleaving the substance or structure, etc. In some embodiments an inhibitor of a toxic substance comprises a naturally occurring receptor for the substance or a fragment or variant of the receptor, wherein the variant or fragment is sufficient for binding the substance. A variety of agents capable of inhibiting toxic substances are known in the art and may be incorporated into agents that are used to sortag mammalian cells.

In some embodiments, cells may be sortagged with an agent capable of binding to a pathogen or pathogen-secreted molecule, e.g., any pathogen or pathogen-secreted molecule of interest. In some embodiments the pathogen is one that is typically present in the blood of a vertebrate, e.g., mammalian, host during all or part of the pathogen's life cycle. In some embodiments the pathogen-secreted molecule is secreted into the blood or gains entry into the blood of a vertebrate, e.g., mammalian, host infected by the pathogen.

In some embodiments living mammalian cells may be sortagged with a detectable label. The sortagged cells may be administered to a subject and subsequently detected in vivo or in a sample obtained from the subject. The detectable label may be selected to permit in vivo detection, e.g., by an imaging technique such as ultrasound, PET scan, MRI, fluorescence detection (e.g., near infrared). In some embodiments living mammalian cells may be sortagged with detectable label and a targeting moiety capable of targeting the cells to a target of interest, e.g., in the body of a subject. The cells become attached to the target, thereby concentrating the detectable moiety at the target. Detection of the detectable label may allow detection of the target. The target may be any molecule, cell, or structure in the body of a subject. In some embodiments the target may be a pathogen, pathogen component, or pathogen-secreted substance. In some embodiments the target may be a toxic substance.

In some embodiments living mammalian cells sortagged with a detectable label may be administered to a subject together with other cells of the same type that are not sortagged. The distribution and/or concentration of sortagged cells may be representative of the distribution and/or concentration of the administered population. Such sortagged cells may serve as tracking agents, e.g., detection and/or quantification of the sortagged cells provides an indication of the distribution and/or concentration of the administered population. For example, when administering cells for adoptive immunotherapy it may be of interest to determine where such cells localize and/or their average residence time in the body. In some embodiments a population of cells may be isolated based on any one or more criteria or properties of interest, such as a particular cell surface marker expression pattern, gene expression profile, functional activity, or based on their having been generated through or subjected to a particular protocol or exposed to particular agents. Cells may be sortagged with a detectable label and mixed with one or more other cell populations (which may or may not be sortagged, e.g., with different detectable label(s) or other moietie) or administered to a subject. The label(s) may be used to detect the cell in vitro or in vivo. For example, it may be of interest to monitor cell migration, cell-cell physical interactions, cell division, or cell distribution.

In some embodiments, sortase-modified mammalian may be used in regenerative medicine. Regenerative medicine as used herein refers to therapies that comprise replacing or regenerating mammalian, e.g., human, cells, tissues or organs to improve function, e.g., to restore or establish normal function and/or structure, by administering cells to the subject and/or by administering biologically active substances that act on endogenous cells or tissues to promote their healing or regeneration. Examples of regenerative medicine therapies include using implanted cartilage cells (e.g., chondrocytes) to restore cartilage, strategies to remuscularize the injured heart, e.g., using adult stem cells, pluripotent stem cells, or cardiomyoctes, ex vivo production of tissues or organs which may then be implanted into subjects, among others.

Sortase-modified mammalian cells may be used in regeneration of any of a wide variety of tissues and organs. Tissues and organs of interest include, e.g., cartilage, bone, heart, heart valve, blood vessel, esophagus, stomach, liver, gallbladder, pancreas, intestines, rectum, anus, endocrine gland (e.g., thyroid, parathyroid, adrenal, endocrine portion of pancreas, e.g., islets of Langerhans), skin, hair follicle, tooth, gum, lip, nose, mouth, thymus, spleen, skeletal muscle, smooth muscle, joint, brain, spinal cord, peripheral nerve, ovary, fallopian tube, uterus, vagina, mammary gland, testes, vas deferens, seminal vesicle, prostate, penis, pharynx, larynx, trachea, bronchi, lungs, kidney, ureter, bladder, urethra, eye (e.g., conjunctiva, retina, retinal pigment epithelium, cornea), or ear (e.g., organ of Corti). In some embodiments, a tissue is an epithelial layer, e.g., an epithelial layer lining the interior of a hollow organ. Regenerative medicine encompasses tissue engineering, i.e., the use of living cells seeded on a natural or synthetic extracellular substrate to create implantable structures, e.g., parts of an organism.

In some embodiments sortase is used to conjugate a moiety to a cell that is subsequently administered to a subject in need of regeneration, e.g., of a tissue or organ. In some embodiments the cell may be administered into, adjacent to, or near (e.g., within 5 cm, 10 cm, 20 cm, or 25 cm) a tissue or organ whose regeneration is desired. For example, if cardiac regeneration is desired, the cells may be administered to the heart. In some embodiments the cell may be administered into the circulatory system. In some embodiments a moiety comprises a targeting moiety binds to a target at a location in the body at which regeneration is desired. In some embodiments the target may be a cell-type specific marker expressed by cells in the tissue or organ to be regenerated. The targeting moiety may enhance attachment of the administered cell to a site where regeneration is desired or may enhance integration of the administered cell into a tissue or organ whose regeneration is desired. In some embodiments a moiety may promote survival, proliferation, or functional activity of the administered cell. In some embodiments the moiety may promote survival, proliferation, or functional activity of cells found in a tissue or organ whose regeneration is desired. In some embodiments the moiety may promote migration of circulating or resident adult stem cells to a tissue or organ whose regeneration is desired or may promote retention, functional integration, and/or differentiation of such adult stem cells. Examples of moieties that may be useful for regenerative medicine include, e.g., growth factors, survival factors, cell adhesion molecules, In some embodiments sortase-modified cells (e.g., conjugated with an agent that promotes cell survival, proliferation, functional activity, or tissue integration) may be used in the production of tissues or organs ex vivo, which may then be implanted into a subject. For example, they may be used, optionally in combination with unmodified cells, to seed two-dimensional or three-dimensional scaffolds (sometimes termed "matrices" or "constructs") ex vivo, or they may be used to provide appropriate stimulatory signals (e.g., growth or survival signals) to cells that are used in the production of tissues or organs ex vivo. A scaffold promote cell-biomaterial interactions, cell adhesion, and ECM deposition, may permit sufficient transport of gases, nutrients, and regulatory factors to allow cell survival, proliferation, and differentiation, and may in some embodiments biodegrade at a rate that approximates the rate of tissue regeneration under the culture conditions or in vivo conditions of interest. In some embodiments a scaffold is comprised of materials that provoke no or minimal degree of inflammation or toxicity in vivo. Scaffolds may comprise, e.g., decellularized structures such as decellularized blood vessels or organs, or may comprise synthetic scaffolds such as those produced using various synthetic polymers. Polymer scaffolds may be porous and/or biodegradable in certain embodiments. Examples of polymers or polymer compositions of natural origin of use in forming scaffolds include collagen, gelatin, fibrin, hyaluronic acid, alginate, and chitosan. Synthetic polymers of use in forming scaffolds include polyglycolide, poly(L-lactic acid), poly(l-lactide-co-glycolide), poly($\varepsilon$-caprolactone). It will be appreciated that derivatives, copolymers, and blends of natural and/or synthetic polymers may be used. Decellularization can provide an acellular, three-dimensional biologic scaffold that can be seeded with selected cell populations. A scaffold may be composed of ECM proteins typically found in the body. The three-dimension architecture of a scaffold may be similar to that of the original tissue or organ, which may thus confer appropriate mechanical and physical properties. Agents conjugated to sortase-modified cells may, e.g, promote cell attachment to a scaffold, may promote cell-cell adhesion, may promote cell survival, proliferation, and/or differentiation.

VII. Kits and Services for Sortagging Mammalian Cells and/or Other Eukaryotic Cells In some aspects, the invention provides kits useful for generating sortagged mammalian cells, wherein the cells are not genetically engineered for sortagging. In some embodiment a kit comprises (i) a sortase polypeptide, a nucleic acid or vector that encodes a sortase polypeptide, or a cell line that expresses sortase polypeptide; and (ii) one or more items useful in the preparation, characterization, and/or purification of sortagged mammalian cells. In s one or more items may be any of the items that are described herein with regard to methods of preparing, characterizing, and/or purifying sortagged living mammalian cells that are not genetically engineered for sortagging. In some embodiments the one or more additional items are selected from: (a) an agent comprising a transamidase recognition sequence; (b) mammalian cells that are not genetically engineered for sortagging; (c) a liquid composition, or components thereof, suitable for use as a reaction buffer in which to sortag living mammalian cells; (d) one or more reagents useful for separating sortagged cells from sortase; and (e) a control substance. In some embodiments a kit comprises instructions for preparing sortagged mammalian cells that are not genetically engineered for sortagging. In some embodiments instructions may be made available separately from the kit. For example, instructions may be provided or accessed via the Internet, e.g., on the World Wide Web ("web"). In some embodiments the agent comprising a transamidase recognition sequence comprises a binding moiety that binds to a tumor antigen. The agent may be used, e.g., to sortag cells that are to be administered to a subject in need of treatment for a tumor that expresses the TA. In some embodiments, any of the afore-mentioned kits may not comprise a sortase. For example, the agent comprising a transamidase recognition sequence may be provided alone or together with one or more of the afore-mentioned additional items.

In some embodiments, a kit comprises a plurality of distinct agents each comprising a transamidase recognition sequence, wherein distinct agents each comprise a different binding moiety. In some embodiments, each of a plurality of different binding moieties present in agents in the kit binds to a different tumor antigen. A health care facility, e.g., a hospital, that treats patients in need of treatment for tumors may obtain such a kit and may use it on site to sortag cells to be administered to the patient. The particular agents to be conjugated to cells may be selected from those present in the kit, based at least in part on results of analyzing expression of tumor antigens on a particular patient's tumor. In some embodiments, a kit comprises at least 5, 10, 15, 20, 25, 30, 40, or 50 different agents, e.g., up to about 100, 200, 500, or more agents, each comprising a binding moiety that binds to a different TA. Any one or more of the TAs mentioned above, in any combination, may be represented by agents in the kit. In some embodiments sortase is provided in the kit, optionally together with any one or more of the additional agents mentioned above. In some embodiments sortase may be provided separately.

In some aspects, the invention provides methods in which sortagging of eukaryotic cells, e.g., mammalian cells, may be performed as a service. An organization or individual that performs sortagging for other organizations and/or individuals, e.g., upon request, may be referred to as a "sortagging service provider". In some embodiments a sortagging service provider may be in the business of providing services, e.g., research services, manufacturing services, to the pharmaceutical industry, biotechnology industry, biomedical research community, etc. In some embodiments a sortagging service provider may have a website and may offer sortagging services on its website. In some embodiments a sortagging service provider receives a request (also referred to as an "order") for sortagged mammalian cells from a requestor, which may be any organization or individual that seeks to obtain sortagged mammalian cells. An organization may be a for-profit organization, a non-profit organization, a company, a corporation, a contract research organization, a research institution, an academic institution, etc. A request may be submitted, transmitted, received, and/or stored at least in part electronically or in electronic format. In some embodiments a request is submitted via a webpage and transmitted via the Internet. A request may indicate the type of cells and/or the agent(s) to be conjugated to the cells. In some embodiments a request may indicate one or more additional specification such as the number of cells, manufacturing conditions (e.g., research grade, clinical grade (e.g., GMP-compliant), storage conditions, shipping conditions, etc. In some embodiments the requestor may provide the cells and/or may provide one or more agent(s) to be conjugated to the cells or one or more moieties to be incorporated into agent(s) to be conjugated to cells. For example, in some embodiments a requestor may provide cells that originate from and/or are designated for administration to a particular subject. The sortagging service provider performs or arranges for sortagging according to the request and supplies sortagged cells, e.g., to the requestor or as indicated by the requestor. A sortagging service provider may perform the sortagging and/or providing itself and/or through arrangements with other organizations or individuals. In some embodiments a sortagging may be performed for a fee, under a contract, or according to a quote. A sortagging service provider may offer one or more ancillary services that may facilitate or support or may be useful in connection with generating or using sortagged mammalian cells. Examples include, e.g., cell expansion services, preparation of agents to be conjugated to mammalian cells, characterization of sortagged cells (e.g., assays of cell function or biological activity of an agent conjugated to the cells). In some embodiments, a sortagging service provider analyzes a tumor sample from a subject who is in need of treatment for a tumor and identifies one or more tumor antigens expressed by cells of the tumor, to which therapeutic cells are to be targeted. The sortagging service provider may sortag cells to be administered to the subject with one or more targeting moieties that bind to the tumor antigen(s). The sortagged cells may be transported to a location where they are administered to the subject.

In some embodiments, any of the above-mentioned kits and services may be used for the sortagging of non-mammalian eukaryotic cells, e.g., cells of non-mammalian vertebrate or invertebrate animals, fungal cells, or protozoal cells, in addition to or instead of mammalian cells. Thus, where the discussion of kits and services herein refers to mammalian cells, the invention provides embodiments that encompass non-mammalian eukaryotic cells.

VIII. Certain Aspects and Embodiments

Sortase-modified cells, e.g., sortase-modified mammalian cells, can be used to treat a wide variety of different diseases and disorders. In some embodiments sortase-modified cells conjugated with a therapeutic agent may be used to treat any disease or condition for which the unconjugated therapeutic agent is of use. Such methods of treatment are an aspect of the invention.

In some embodiments sortase-modified cells may be administered prophylactically, e.g., to a subject who does not exhibit signs or symptoms of the disease or disorder for which the cells are indicated (but may be at increased risk of developing the disorder or is expected to develop the disease or disorder). In some embodiments sortase-modified cells are administered to a subject who has developed one or more signs or symptoms of the disease or disorder, e.g., the subject has been diagnosed as having the disease or disorder. Optionally, a method comprises diagnosing a subject as having a disease or disorder for which sortase-modified cells are an appropriate treatment.

One of ordinary skill in the art will be aware of various indications for therapeutic agents that may be conjugated to mammalian cells. For example, interferons have a variety of uses, e.g., in the treatment of autoimmune diseases (e.g., multiple sclerosis) and certain infectious diseases (e.g., certain viral infections) and (often in combination with chemotherapy and radiation) as a treatment for many cancers.

In some embodiments sortagged mammalian cells or other sortagged eukaryotic cells (e.g., sortagged eukaryotic microorganisms) administered for treatment of a disease may be used in combination with any other therapy useful in treating the disease. When entities are administered "in combination" they may be administered in the same composition (if compatible) or in different compositions in various embodiments. When administered in different compositions any order of treatment is contemplated. Administration of or more doses of sortagged cells may be interspersed with administration of one or more doses of one or more other agents. Successive doses may be administered at times separated by time intervals of minutes, hours, days, weeks, or months. In some embodiments at least one dose of sortagged cells is administered within no more than 1, 2, 3, 4, 6, 8, 10, 12, 16, 20, 22, 24, 26, 30, 36, 42, 48, or 52 weeks before or after administration of one or more doses of a different therapeutic entity, e.g., any therapeutic agent useful in treating the disease. In some embodiments, a time interval between a dose of cells and a dose of a cytotoxic or anti-proliferative drug is selected so as to avoid significant effect, e.g., cytotoxic or anti-proliferative effect, of the cytotoxic or anti-proliferative drug on the cells.

In some embodiments sortagged mammalian cells administered for treatment of cancer may be used in combination with a chemotherapy drug and/or radiation therapy. The cells may be administered separately from the drug. In some embodiments cycles of drug and/or radiation therapy may be interspersed with cycles of cell therapy. In certain embodiments it is contemplated to administer sortagged cells in addition to any standard cancer treatment regimen, e.g., any standard chemotherapy and/or radiation regimen or instead of one or more components of such a regimen. In some embodiments a subject in need of treatment of cancer may undergo surgery to remove at least a portion of the tumor. The surgery may remove the entire tumor (to the extent the tumor is detectable) or may reduce the size of the tumor but not remove the entire tumor (e.g., if the tumor is too extensive to make complete surgical removal advisable or if attempting such surgical removal is otherwise not advisable within the judgement of the skilled artisan). In some embodiments sortagged cells may be administered to the subject one or more times prior to surgery, one or more times during surgery, and/or one or more times after surgery. The sortagged cells may reduce the size of a tumor and/or may eliminate tumor cells that were not removed during surgery (which may be located at the site of surgery or may have disseminated to other location(s) in the body.

Erythropoiesis stimulating agents such as EPO are of use to treat anemia, which may result from a variety of causes. For example, the anemia may be an anemia of chronic disease, anemia associated with medications (e.g., cancer chemotherapy), radiation, renal disease (e.g., diabetes), infectious diseases, or blood loss. Colony stimulating factors such as G-CSF, GM-CSF, and/or M-CSF may be used to treat leukopenia, e.g., neutropenia and/or lymphopenia, which may result, e.g., from medications (e.g., cancer chemotherapy), radiation, infectious disease, or blood loss.

Neurotrophic factor proteins may be used, e.g., to treat neurodegenerative diseases (e.g., amyotrophic lateral sclerosis, Huntington disease, Alzheimer disease, Parkinson disease), central or peripheral nervous system injury.

Interleukins are of use to modulate the immune response for a wide variety of purposes, e.g., to stimulate an immune response against an infectious agent or cancer or to limit the intensity and/or duration of innate and/or adaptive immune responses. Interleukins may be of use in treatment of autoimmune diseases, sepsis, or other conditions in which an aberrant or overactivated immune response can be deleterious.

Diseases caused by viruses, gram-positive or gram-negative bacteria, mycobacteria, fungi, or parasites are of interest in certain embodiments. For example, immune system cells may be sortagged with an agent that binds to such viruses, bacteria, fungi, or parasites, or may be sortagged with an agent that binds to mammalian cell infected by such viruses, bacteria, fungi, or parasites. Exemplary viruses, bacteria, fungi, and parasites are discussed above.

In general, a sortagged eukaryotic cell may be used for any purpose in which it is useful to have an agent attached to the surface of such cell. In some embodiments, the agent comprises a detectable label, thus facilitating detection of the sortagged eukaryotic cell. In some embodiments the cell is a microorganism that spends at least part of its life cycle as an intracellular parasite of a mammalian or avian host. Examples of such microorganisms include a variety of fungi and protozoa. In some embodiments, an intracellular parasite that has been labeled with sortase is contacted with a host cell, e.g., a mammalian or avian cell, in vitro. Processes such as attachment of the microorganism to the cell, entry of the microorganism, intracellular movement of the microorganism, or other activities of the microorganism may be monitored by detecting the label. In some embodiments a sortagged microorganism is of use in a method of identifying a candidate therapeutic agent for treating a disease caused by the microorganism. For example, in some embodiments, a candidate compound is contacted with the cell, and the ability of the candidate compound to inhibit one or more such activities is assessed. In some embodiments, if the candidate compound inhibits one or more such activities, the candidate compound is identified as a candidate therapeutic agent for treating a disease caused by the microorganism.

In some embodiments, a sortagged microorganism, e.g., a sortagged eukaryotic microorganism, is used to deliver an agent to a target cell, e.g., a tumor cell, tumor-associated cell, or pathogen-infected cell. In some embodiments the microorganism is sortagged with the agent, with a targeting moiety that binds to a molecule on the target cell, or both. In some embodiments the microorganism is one that is naturally capable of invading the target cell. For example, the microorganism may be an intracellular parasite (during at least one of its life cycle stages), e.g., an apicomplexan parasite such as *T. gondii*, a Trypanosomatid, a *Plasmodium*, a fungus such as *Histoplasma capsulatum* or *Cryptococcus neoformans*, and the target cell may be a vertebrate cell, e.g., a mammalian cell, e.g., a human cell, that is susceptible to invasion by the microorganism. Those of ordinary skill in the art will be aware of various strains of microorganisms and suitable methods of obtaining and propagating microorganisms. In some embodiments the microorganism is sortagged with a targeting moiety that binds to a tumor antigen and increases the binding of the microorganism to a cell that expresses the TA at its surface and, in some embodiments, increases subsequent invasion of the microorganism. In embodiments in which the microorganism is sortagged with a targeting moiety, the targeting moiety may be of any of the various types of binding moieties described herein. In some embodiments the targeting moiety comprises a single chain antibody (e.g., an scFv) or single domain antibody. For example, in some embodiments the targeting moiety comprises a VHH, some embodiments the targeting moiety comprises a single chain antibody (e.g., an scFv) or single domain antibody. For example, in some embodiments the binding moiety comprises a VHH. In some embodiments the microorganism is sortagged with an agent comprising a substance that is toxic to the target cell upon delivery to the surface of the cell or to the interior of the target cell. In some embodiments the microorganism is sortagged with an agent comprising a substance that is toxic to the target cell upon contact with the target cell surface. In some embodiments the toxic substance is a chemotherapy drug, e.g., a small molecule chemotherapy drug, a toxin, a protein comprising a cytolytic domain such as granzyme or perforin, a pro-apoptotic agent such as a protein comprising a pro-apoptotic domain. In some embodiments the microorganism is genetically engineered to produce one or more molecules, e.g., a substance that is toxic to the target cell, a cytokine, a costimulator, a targeting moiety. In some embodiments the microorganism secretes the molecule or expresses it at its cell surface. In some embodiments the microorganism is genetically engineered to lack expression or activity of one or more endogenous gene products. One or ordinary skill in the art will be aware of appropriate methods and vectors useful for creating genetically engineered microorganisms. In some embodiments, a strain, e.g., a T. gondii strain, that has a deficient non-homologous end joining pathway may be used (Fox B A, Eukaryot Cell. 2009; 8(4):520-9). For example, the strain may lack expression of a functional KU80 protein or homolog thereof, e.g., due to a disruption or deletion in the gene that encodes KU80 or homolog thereof. In some embodiments the microorganism is avirulent and/or can be effectively eliminated by treating the subject with an appropriate therapeutic agent.

In some embodiments the target cell is not a tumor cell or pathogen-infected cell. The target cell may be, e.g., a normal, healthy cell or an abnormal cell. In some embodiments the microorganism may be sortagged with an agent that modulates one or more biological activities or properties of the normal or abnormal cell, e.g., in a way that is beneficial to a subject to whom the cell is administered or in whom the cell exists. In some embodiments, the cell may be an immune system cell, and the agent may be, e.g., an immunomodulator. In some embodiments the microorganism is genetically engineered to produce a substance, e.g., a protein. The substance may be a therapeutic agent, enzyme, or any other substance the production of which is desired. In some embodiments the substance modulates one or more biological activities or properties of the cell. In some embodiments the cell is affected by a disease, and the substance ameliorates the effect of the disease on the cell. In some embodiments the microorganism is sortagged with a targeting moiety that binds to the normal or abnormal cell.

In some embodiments the microorganism is an attenuated strain. "Attenuated" refers to a strain that has reduced virulence relative to a wild type strain or parental strain from which an attenuated strain is generated. An attenuated strain may be weakened and/or less robust compared to a wild type strain or parental strain (i.e., a strain from which the attenuated strain was derived). In some embodiments an attenuated strain is avirulent. An attenuated strain may arise naturally and be identified by testing the virulence of the strain in a test system (e.g., in test cells or a test animal) or may be generated by man by, e.g., passaging the organism in a host or host cells that are not a natural host or host cell of the microorganism, by mutagenesis and selection, by irradiation, by exposure to a chemical agent, or by engineering. In some embodiments an attenuated strain has substantially reduced or absent ability to inflict damage on a host or host cell, has substantially reduced or absent ability to replicate or complete one or more stages of its life cycle in a particular host or host cell (e.g., humans or human cells), and/or has substantially reduced or absent transmissibility from one host to another as compared to a wild type strain or as compared to a parental strain. In some embodiments an attenuated strain has at least a 10-fold, $10^2$-fold, $10^3$-fold, $10^4$-fold, $10^5$-fold, $10^6$-fold, $10^7$-fold, or $10^8$-fold reduced ability to replicate as compared to a wild type strain or as compared to a parental strain. In general, replication ability may be measured using any suitable method. In some embodiments, replication ability may be measured as number of new individual organisms produced or amount of DNA synthesized by the organism and its descendants. In some embodiments an attenuated strain has at least a 10-fold, $10^2$-fold, $10^3$-fold, $10^4$-fold, $10^5$-fold, $10^6$-fold, $10^7$-fold, or $10^8$-fold reduced ability to cause death of a host or host cell as compared to a wild type strain or as compared to a parental strain. In some embodiments an attenuated strain is metabolically active. In some embodiments an attenuated strain retains ability to invade host cells, e.g., mammalian host cells, e.g., human host cells. If desired, invasion may be quantified using an invasion assay. One of ordinary skill in the art will be aware of suitable assays. The strain's ability to invade host cells may or may not be equivalent to that of a wild type strain or parental strain. In some embodiments the invasion ability is at least 10%, 20%, 30%, 40%, 50%, 60%, 70%, 80%, 90%, or 100% of that of a wild type strain or parental strain. In some embodiments an attenuated strain may have a normal or near normal level of virulence under certain conditions or in certain hosts but is avirulent or has substantially reduced virulence under other conditions, such as those existing in vivo in a subject, e.g., a human subject. In some embodiments, for example, an attenuated strain may be auxotrophic for one or more nutrients. The strain may replicate normally under conditions in which the nutrient is available (e.g., supplied in a culture medium) but may be unable to replicate under in vivo conditions in which the amount of the nutrient is insufficient to support replication. In some embodiments the nutrient is a precursor for nucleotide biosynthesis, e.g., a precursor for synthesis of a purine or pyrimidine. Attenuated strains are known in the art. For example, attenuated T. gondii strains are described in U.S. Pat. Pub. Nos. 20100203085 and/or 20120045477, which also describe methods and vectors useful for genetic engineering of T. gondii. In some embodiments an attenuated T. gondii strain has a defect in de novo pyrimidine synthesis, pyrimidine salvage, and/or transport of pyrimidine bases or nucleosides. For example, one or more genes in the de novo pyrimidine synthesis pathway, pyrimidine salvage pathway, or a transporter of pyrimidine bases or nucleosides may be disabled, e.g., by targeted insertional mutagenesis. In some embodiments the gene encodes carbamoyl phosphate synthetase II, aspartate transcarbamylase, dihydroorotase, dihydroorotase dehydrogenase, orotate phosphoribosyltransferase, or orotidine 5'-monophosphate decarboxylase, uridine phosphorylase (UP), uracil phosphoribosyltransferase, or purine nucleoside phosphorylase. In some embodiments an attenuated strain is the cps strain of T. gondii, which has a knockout of the gene that encodes carbamoyl phosphate synthetase II and exhibits uracil auxotrophy and extremely reduced virulence (B. A. Fox, D. J. Bzik. Nature. 2002; 415:926-929). The cps strain invades and replicates normally in vitro if uracil is supplied in the culture medium. As uracil is not present at an adequate concentration to support replication of the cps strain in mammals or mammalian cells, it invades mammalian host cells normally but does not replicate and exhibits greatly decreased virulence. In some embodiments a subject to whom a sortagged attenuated microorganism is administered is an individual who is infected with a non-attenuated strain of the microorganism. A variety of microorganisms have been used or proposed for use as live, attenuated vaccines, e.g., for protection against infection by non-attenuated strains of the microorganism, are known in the art. The present disclosure contemplates sortagging of any such microorganism.

In some embodiments a sortagged microorganism is contacted with target cells ex vivo. In some embodiments a sortagged microorganism is administered to a subject and encounters target cells in the subject. In some embodiments a subject to whom a sortagged attenuated microorganism is administered is an individual who is infected with a non-attenuated strain of the microorganism. In some embodiments, a sortagged microorganism is administered to a subject in need of treatment for a tumor. The microorganism may be sortagged with a targeting moiety that binds to a tumor antigen expressed by tumor cells in the tumor. In general, the tumor cells and tumor may be of any type. In some embodiments the tumor is an ovarian cancer, colon cancer, liver cancer, prostate cancer, lung cancer, bladder cancer, breast cancer, brain cancer, lymphoma, or melanoma. In some embodiments a subject to whom a sortagged microorganism is administered has a tumor composed at least in part of cells that the microorganism is capable of invading.

In some embodiments, tumor cells or pathogenic organisms, e.g., pathogenic eukaryotic organisms, are sortagged with an agent comprising a binding moiety that binds to a cell surface molecule expressed by an antigen presenting cell. In some embodiments the APC is a professional APC, such as a dendritic cell or macrophage. In general, the tumor cells may be derived from a tumor of any tumor type. In general, a pathogenic organism may be any organism capable of causing disease in a mammal, e.g., a human. In some embodiments the organism is a fungal cell or parasite. In some embodiments the organism is a microorganism. In some embodiments the microorganism is *T. gondii*. Those of ordinary skill in the art will be aware of various strains and suitable methods of obtaining and propagating pathogenic organisms. In some embodiments the binding moiety serves as a targeting moiety to target the tumor cells or pathogenic organism to APC. In some embodiments the APC is a phagocytic cell. In some embodiments the cell surface molecule is a receptor expressed by the APC. In some embodiments the cell surface molecule is an MHC Class II molecule, CD205 (DEC205), DNGR-1 (CLEC9A), CD207 (Langerin), CD11c, CD141, CD303, CD103, CD209 (DC-SIGN), CD68, or CD163. In general, the binding moiety may be of any of the various types of binding moieties described herein. In some embodiments the binding moiety comprises a single chain antibody (e.g., an scFv) or single domain antibody. For example, in some embodiments the binding moiety comprises a VHH, e.g., a VHH that binds to human MHC Class II or a VHH that binds to human DEC205. VHH4 is an exemplary VHH that binds to human MHC Class II (described in WO/2013/155526). Exemplary monoclonal antibodies that bind to human DEC205 are described in Park, C J, et al., J Immunol Methods. 2012; 377(1-2):15-22. In some embodiments the tumor cells are obtained from a subject suffering from a tumor. The tumor cells may be obtained by biopsy or surgery to remove at least a portion of the tumor or in a blood sample or other biological sample obtained from the subject. In some embodiments the tumor cells are from a tumor cell line, which may be derived from tumor cells obtained from a subject in need of treatment for a tumor or may be derived from a tumor of the same type as that of a subject. In some embodiments the tumor cells may express at least one tumor antigen.

In some embodiments tumor cells or pathogens that have been sortagged with a binding moiety that binds to a cell surface molecule expressed by an APC are processed. In some embodiments, processing renders the tumor cell non-viable, less viable (reduced lifespan), or incapable of proliferating. In some embodiments the processing renders the pathogen non-viable, less viable, attenuated, non-infectious, and/or incapable of proliferating. For example, the tumor cell or pathogen may be exposed to radiation or a toxic substance such as a pro-apoptotic agent. In some embodiments the processing may comprise physical or chemical fragmentation, lysis, or fractionation. For example, cells may be sonicated, subjected to bead beating, dounced, sheared, subjected to conditions of high or low osmolarity sufficient to induce cell lysis, exposed to a detergent, and/or exposed to a cytolytic agent. In some embodiments a cell membrane fraction may be isolated from the sortagged tumor cells or pathogens. In some embodiments, tumor cells or pathogens may be processed in any of the afore-mentioned ways prior to sortagging. Without wishing to be bound by any theory, fragmentation, lysis, or fractionation may produce portions of cells that are more readily phagocytosed or endocytosed than a whole cell.

In some embodiments a tumor cell or pathogen that has been sortagged with a binding moiety that binds to a cell surface molecule expressed by an APC is used to deliver an antigen expressed by the tumor cell or pathogen to APC that express the cell surface molecule. By binding to the APC, the binding moiety maintains the sortagged tumor cell or pathogen in close proximity to the APC, which may then internalize the tumor cell or pathogen or a portion thereof or a product thereof such as a molecule shed or released from the tumor cell or pathogen. For example, the APC may internalize the tumor cell, pathogen, or a portion or product thereof by phagocytosis or endocytosis. In some embodiments a pathogen is able to invade the APC and is thereby internalized. The APC may process the internalized tumor cell, pathogen, or portion or product thereof and present one or more antigens derived from the tumor cell, pathogen, or portion or product thereof on its surface in association with an MHC Class I or Class II molecule. For example, the APC may present a peptide comprising one or more epitopes derived from the tumor cell, pathogen, or portion of product thereof. In some embodiments tumor cells or pathogens that have been sortagged with a binding moiety that binds to a cell surface molecule expressed by an APC are administered to a subject, whereupon the binding moiety binds to APCs in the subject. In some embodiments tumor cells or pathogens that have been sortagged with a binding moiety that binds to a cell surface molecule expressed by an APC may be contacted with APCs ex vivo, e.g., by placing them in the same vessel, whereupon the binding moiety attached to the tumor cells or pathogens binds to the APCs. In some embodiments the APCs may subsequently be administered to a subject or may be contacted ex vivo with T cells that are subsequently administered to the subject. The APC may present the antigen to T cells ex vivo or in a subject. Presentation of the antigen by the APC may elicit or enhance a T cell response in the subject or ex vivo. The response may be directed toward cells that express the antigen, such as tumor cells or pathogens in the subject. An APC may thus elicit or promote an immune response against a tumor or pathogen in a subject. In some embodiments an APC may stimulate T cells by presenting an antigen derived from the sortagged tumor cell or pathogen to such cells. In some embodiments the T cells are naïve T cells. In some embodiments an APC may stimulate a cytotoxic T cell response, a helper T cell response, or both.

In some embodiments a tumor cell or pathogen that has been sortagged with a binding moiety that binds to a cell surface molecule expressed by an APC is also sortagged with a second agent. In some embodiments the second agent is capable of stimulating the functional maturation or at least one biological activity of an APC. In some embodiments the second agent comprises an adjuvant. In some embodiments a tumor cell or pathogen that has been sortagged with a binding moiety that binds to a cell surface molecule expressed by an APC is administered in combination with an adjuvant. The adjuvant may be in the same composition or may be administered separately.

In some embodiments a subject to whom sortagged tumor cells or portions thereof, sortagged pathogens or portions thereof, or APCs that have been contacted ex vivo with sortagged tumor cells, pathogens, or portions thereof, are administered is in need of treatment for a tumor or is in need of treatment for an infection caused by the pathogen. In some embodiments, the sortagged tumor cells or tumor cell portions are derived from the subject's tumor or from a tumor of the same type as that for which the subject needs treatment. For example, a subject in need of treatment for a melanoma may be treated with sortagged melanoma cells; a subject in need of treatment for a colon carcinoma may be treated with sortagged colon carcinoma cells, etc. In some embodiments tumor cells or pathogens that have been sortagged with a binding moiety that binds to a cell surface molecule expressed by an APC are processed prior to administration to a subject or prior to contacting them with APCs in vitro. In some embodiments tumor cells or pathogens are processed, and the resulting portions are sortagged, before administration to a subject or contacting with APC in vitro. Processing may comprise physical or chemical fragmentation, lysis, or fractionation, e.g., as described above. In some embodiments administration of tumor cells or pathogens or portions thereof that have been sortagged with a binding moiety that binds to APC results in accumulation of the tumor cells, pathogens, or portions thereof, in lymphoid tissue, e.g., in lymph nodes or other lymphoid organs. The tumor cells, pathogens, or portions thereof may come in contact with additional APC, or other immune system cells, in the lymphoid tissue. In some embodiments one or more doses of tumor cells or portions thereof that have been sortagged with a binding moiety that binds to a cell surface molecule expressed by an APC are administered to a subject prior to, concurrently with, and/or after surgery, radiation, or chemotherapy for treatment of a tumor.

In some embodiments, methods described above in which a eukaryotic organism is sortagged with an agent comprising a binding moiety that binds to an APC are applied using a eukaryotic organisms that is not pathogenic but expresses one or more proteins that is also expressed by a pathogenic eukaryotic organism or contains one or more epitopes of such a protein. In some embodiments cells derived from a multicellular pathogenic eukaryotic organism are used. It should be noted that the tumor cells or pathogenic eukaryotic organisms may in some embodiments be genetically engineered to produce one or more molecules, e.g., a cytokine, targeting moiety, costimulator, antigen, and/or toxic substance.

Sortagged tumor cells, microorganisms, pathogens, or portions thereof, may be prepared under appropriate conditions (e.g., in compliance with Good Manufacturing Practices) such that the resulting preparation is suitable for administration to a mammalian subject, e.g., a human subject. The sortagged tumor cells, microorganisms, pathogens, or portions thereof, may be mixed with a pharmaceutically acceptable carrier. Sortagged tumor cells or portions thereof, sortagged eukaryotic pathogens or portions thereof, may be administered to a subject using any suitable administration route. In some embodiments such cells or portions thereof are administered intravenously, orally, by inhalation, or topically. In some embodiments such cells or portions thereof are administered locally, e.g., directly to a tumor site, e.g., by injection into a tumor or intraperitoneally in the case of a peritoneal tumor, or locally to a site of infection (e.g., the lungs, liver, etc.) The number of cells to be administered in a dose and the number of doses to be administered can be determined using routine procedures known to those of ordinary skill in the art. In certain embodiments sortagged tumor cells or portions thereof, sortagged eukaryotic pathogens or portions thereof, are administered to a subject in combination with sortagged immune system cells, e.g., sortagged T cells.

The following working examples are intended to describe exemplary reductions to practice of certain methods, reagents, and compositions provided herein and do not limit the scope of the invention.

EXAMPLES

Example 1: Sortase-Catalyzed Conjugation of Biotin Probe to Non-Genetically Engineered Mammalian Cells Mouse red cell-depleted splenocytes were isolated using standard methods.

Figure 2:
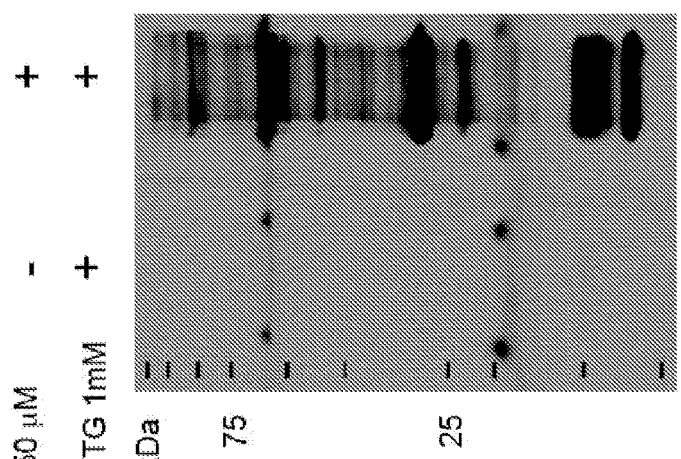
FIG. 2. Immunoblot demonstrating sortase-catalyzed conjugation of biotin to non-genetically engineered mammalian cells. The blot shows biotinylated proteins in cell lysate following incubation of mouse red cell-depleted splenocytes with a biotin-LPETG probe in the presence (right) or absence (left) of sortase.

Approximately 2 million cells were incubated with a biotin-LPETG probe (1 mM) either with or without sortase A (150 µM) from *Staphylococcus aureus* in 100 microliters DME without serum at 4° C. for 1 hour. Cells were then washed with PBS 5 times and lysed in Laemmli buffer. Samples were run on an SDS-PAGE gel. Approximately one quarter of the lysate from each incubation was loaded per lane. Biotinylated proteins were visualized by blotting with streptavidin-HRP using standard methods. The resulting immunoblot is shown in FIG. 2. The blot demonstrates labeling of a number of proteins with the biotin-LPETG probe. Based on other experiments, the prominent band of about 30 kD is believed to be sortase itself labeled with biotin-LPETG, while the band at about 60 kD is likely to be biotin-labeled sortase dimer.

Figure 3:
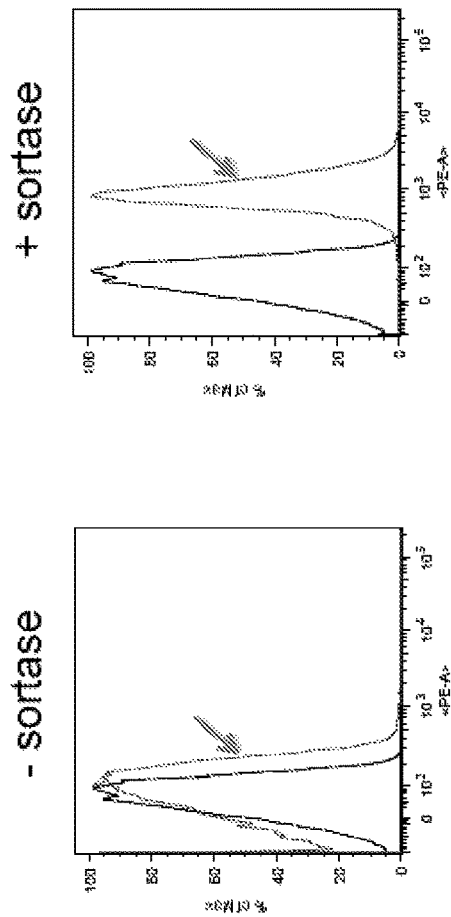
FIG. 3. Flow cytometry analysis demonstrating sortase-catalyzed conjugation of biotin to non-genetically engineered mammalian cells. Mouse red cell-depleted splenocytes were incubated with biotin-LPETG probe with or without sortase, washed with PBS, and incubated with phycoerythrin (PE)-conjugated strepavidin. Blue histograms (indicated with arrows) show PE signal gated on living cells incubated with (right) or without (left) sortase A. Black histograms (no arrow) show background staining on control splenocytes.

Flow cytometry analysis was used to confirm sortase-catalyzed labeling of non-genetically engineered mammalian cells with the biotin-LPETG probe (1 mM). Mouse red cell-depleted splenocytes isolated using standard methods were incubated with biotin-LPETG probe with or without sortase A (200 µM) from *Staphylococcus aureus* in DME without serum at 4° C. for 1 hour. Cells were then washed with PBS 5 times, incubated with phycoerythrin (PE)-conjugated streptavidin, and subjected to flow cytometry. Results are shown in FIG. 3. Blue histograms (indicated with arrows) show PE signal gated on living cells incubated with (right) or without (left) sortase A. Black histograms (no arrow) show background staining on control splenocytes. The results show specific binding of PE-conjugated streptavidin only to the cells that had been incubated with the biotin-LPETG probe in the presence of sortase, thus demonstrating the labeling of these cells by sortase-catalyzed conjugation of the probe thereto.

The production and purification of sortase used in this experiment is described in Popp, M W, et al., Nat Chem Biol. 2007; 3(11):707-8. Epub 2007 Sep. 23.

The biotin-LPETG probe was prepared according to the following protocol, which also describes preparation of a TAMRA-LPETG probe. These probes have two Gs at the C-terminus, i.e., biotin-LPETGG and TAMRA-LPETGG.

A) TAMRA-LPETGG Probe
Note: Use Fmoc-Ala-OH in place of Fmoc-Gly-OH to make probes for *S. pyogenes* sortase A
Resin Preparation TIMING 15 min
i Add 100 µmol of Rink amide resin (167 mg, 0.6 mmol/g) into a capped glass column with a fritted glass filter bottom, solvate the resin in dichloromethane (DCM) (7 mL) by shaking for 15 min in a wrist-action shaker and remove the DCM by vacuum filtration.
Deprotection TIMING 30 min
ii Add 20% piperidine solution in N-methyl-2-pyrrolidone (NMP) (7 mL) and shake for 15 min to remove the resin's Fmoc protecting groups.
Note: In all steps NMP may be replaced with DMF.
iii Remove the piperidine solution by vacuum filtration and wash the resin three times with NMP (7 mL, 1 min), three times with DCM (7 mL, 1 min) and an additional time with NMP (1 min).
Coupling Reaction TIMING 2-3 h Until Pause Point, 3.5 h Per Coupling Cycle
iv Dissolve Fmoc-Gly-OH (89 mg, 300 µmol), HBTU (114 mg, 300 µmol), and DIPEA (104 µL, 600 µmol) in NMP (7 mL) and add to the resin. Shake the suspension for 2 h at room temperature.
v Remove the reaction solution by vacuum filtration and wash the resin three times with NMP (7 mL, 1 min) and three times with DCM (7 mL, 1 min). The coupling reaction can be confirmed by performing a Kaiser test.
Note: If the reaction is incomplete repeat steps iv-v with half the amount of reagents used for a standard coupling and shake for 1 h.
PAUSE POINT: The resin can be stored at 4° C. after drying under vacuum. At this stage, store peptides in their Fmoc-protected form, if storage is desired.
vi Repeat steps i-v with Fmoc-Gly-OH (89 mg, 300 µmol), Fmoc-Thr(OtBu)-OH (119 mg, 300 µmol), Fmoc-Glu(OtBu)-OH (127 mg, 300 µmol), Fmoc-Pro-OH (101 mg, 300 µmol), Fmoc-Leu-OH (106 mg, 300 µmol), Fmoc-ε-aminocaproic acid (85 mg, 300 µmol).
Note: The Kaiser test does not work for verifying the extent of the Leu coupling, since the N-terminus of Pro is a secondary amine. To test this coupling reaction, one can use the chloroanil test or microcleavage. Note that the orthogonal protecting groups may not be fully removed during this abbreviated cleavage.
vii After removing the Fmoc on the ε-aminocaproic acid residue, add a solution of 5(6)-TAMRA (52 mg, 120 µmol), PyBOP (63 mg, 120 µmol), and DIPEA (42 µL, 240 µmol) in NMP (7 mL) and shake overnight at room temperature. To prevent photobleaching of the fluorophore, wrap the column in aluminum foil.
viii Repeat step v and perform the Kaiser test to check the TAMRA coupling.
Cleavage from Resin
ix Suspend the resin in cleavage solution consisting of 95% TFA, 2.5% $H_2O$, and 2.5% TIS (5 mL) for 2 h at room temperature.
x Elute the cleavage solution into 90 mL of ice cold (–0° C.) diethyl ether and rinse the resin with an additional 3 mL of the cleavage solution into the ether.
xi Store the ether solution at –20° C. for 20 min to precipitate the peptide. Centrifuge the suspension at 1,900 g for 15 min at 4° C., decant the supernatant and gently evaporate the remaining ether under reduced pressure.
Due to the flammable and volatile nature of diethyl ether it is desirable to use a spark-free freezer and centrifuge.
Pause point: The crude peptide can be stored as a solid at –20° C.
Critical step: The identity and purity can be verified by LC/MS analysis (linear gradient 545% LC/MS buffer B over 10 min). If LC/MS shows that the crude peptide is of sufficient purity, the next steps (xii-xiv) may be omitted and the peptide may be used directly in sortase reactions.
HPLC purification
xii Dissolve the dried peptide in $H_2O$ (2 mL) and centrifuge at 14,000 rpm for 10 min in a tabletop centrifuge to remove particulate matter.
Note: Up to 50% of tert-butanol may be added to peptides that do not dissolve in pure $H_2O$. Also spin filters or syringe filters may be used to remove particulate matter.
xiii Purify the centrifuged supernatant by reverse-phase HPLC on a C18 column using a 10-70% buffer B gradient over 15 min, followed by flushing at 90% buffer B for 5 min. We recommend a preliminary small 100 µL injection and adjusting the gradient accordingly for peptide purity and ease of separation. Once a good gradient is established, the remaining crude material may be purified with 400-600 µL injections.
xiv Analyze the fractions for product by LC/MS and lyophilize the desired fractions to dryness.
Note: TAMRA containing probes consist of a mixture of regio-isomers that will likely result in two product peaks during reverse phase HPLC purification. The different isomers have no effect on labeling.
The identity and purity can be verified by LC/MS analysis (linear gradient 545% LC/MS buffer B over 10 min) and NMR spectroscopy.
Pause point: The lyophilized peptide can be stored at –20° C. indefinitely.

B) Biotin-LPETGG Probe
i Use the same reaction conditions as for synthesis of the TAMRA-LPETGG probe through the Fmoc deprotection step of the Leu residue. At this point, add a solution of biotin (74 mg, 300 µmol), HBTU (114 mg, 300 µmol) and DIPEA (104 µL, 600 µmol) in NMP (7 mL); shake for 2 h.
ii Remove the reaction solution by vacuum filtration, wash the resin, and check the success of biotin coupling with a Kaiser test (remaining free amines).
iii Cleave the product from the resin as indicated in steps ix-xi for the TAMRA probe.
iv Purify by reverse phase HPLC as indicated in steps xii-xiv of the TAMRA probe The identity and purity can be verified by LC/MS analysis (linear gradient 545% B in 10 min) and NMR spectroscopy.
Pause point: The lyophilized peptide can be stored at –20° C. indefinitely.

Figure 4:
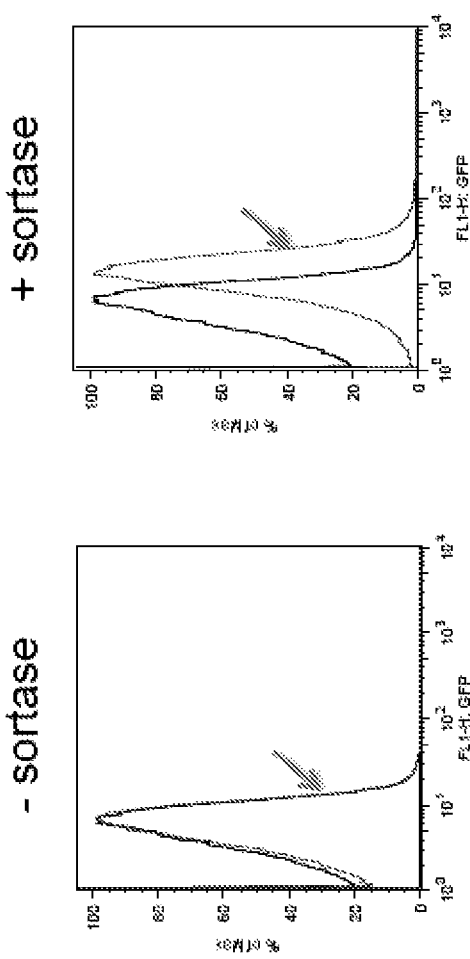
FIG. 4. Flow cytometry analysis demonstrating sortase-catalyzed conjugation of a GFP-specific VHH to non-genetically engineered mammalian cells. Mouse red cell-depleted splenocytes were incubated with a GFP-specific VHH that contains a C-terminal LPETG with or without sortase. Cells were then washed with PBS and incubated with GFP. Blue histograms (indicated with arrows) show GFP signal gated on living cells incubated with (right) or without (left) sortase A. Black histograms (no arrow) show background staining on control splenocytes.
Figure 5:
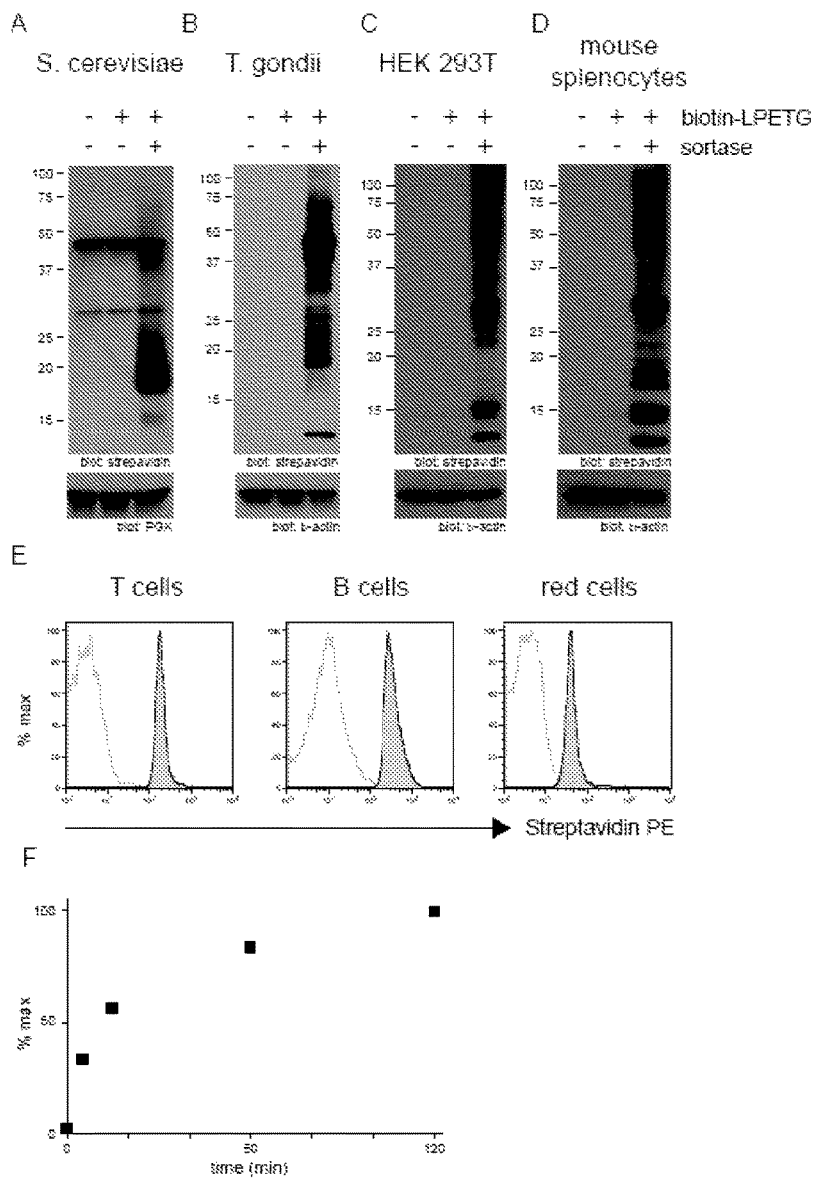
FIG. 5. (A)-(D) Immunoblots demonstrating sortase-catalyzed conjugation of a biotin-containing sortase substrate to non-genetically engineered *S. cerevesiae* cells (A), *T. gondii* cells (B), HEK-293T cells (C), and mouse splenocytes (D), as evidenced by streptavidin-based detection of protein. (E) Histograms showing flow cytometric analysis of non-genetically engineered splenocytes that were sortagged with a biotin-containing sortase substrate (biotin-LPETG) and subsequently exposed to streptavidin-phycoerythrin (streptavidin PE). The rightmost peak in each histogram represents streptavidin PE-labeled splenocytes. (F) erythrocyte-depleted splenocytes were incubated with 20 μM sortase A and 500 μM biotin-LPETG for the indicated times. Cells were washed and incubated with streptavidin-PE and analyzed by flow cytometry. Scatter plots show the mean fluorescence intensity of streptavidin-PE staining for each time point, normalized to maximum staining (120 minutes).

Example 2: Sortase-Catalyzed Conjugation of VHH Protein to Non-Genetically Engineered Mammalian Cells Approximately 2 million mouse red cell-depleted splenocytes isolated using standard methods were incubated with a GFP-specific VHH that contains a C-terminal LPETG (1001 µM) (see Kirchhofer, A., et al., Nat Struct Mol Biol. 2010 January; 17(1):133-8. doi: 10.1038/nsmb.1727. Epub 2009 Dec. 13 for description of the original GFP-specific VHH, which does not contain a C-terminal LPETG), either with or without sortase A (200 µM) from *Staphylococcus aureus*, in DME without serum at 4° C. for 1 hour. Cells were then washed with PBS 5 times, incubated with GFP for 30 minutes and subjected to flow cytometry. Results are shown in FIG. 4. Blue histograms show GFP signal gated on living cells that had been incubated with (right) or without (left) sortase A. Black histograms show background staining on control splenocytes incubated with GFP. The blue and black histograms in the left panel are virtually superimposable. The blue histogram in the right panel is indicated with an arrow. The results show specific binding of GFP only to the cells that had been incubated with the GFP-specific VHH in the presence of sortase, demonstrating the labeling of these cells by sortase-catalyzed conjugation of the VHH thereto.

Example 3: Sortase-Catalyzed Conjugation of VHH Protein to Non-Genetically Engineered Mammalian Cells Lymphocytes are isolated from mice using standard methods, and expanded and activated in vitro using appropriate antibodies (e.g., soluble or immobilized anti-CD3 mAb) and/or cytokines (e.g., IL-2) for T cell expansion and activation. An aliquot of the expanded and activated cells is incubated in culture medium with either a human tumor antigen (TA)-specific VHH (anti-TA VHH) containing a C-terminal LPETG or an anti-GFP VHH containing a C-terminal LPETG, either with or without sortase A from *Staphylococcus aureus* at 4° C. for 1 hour. Cells are then washed with PBS 5 times, incubated with a recombinant tumor antigen labeled with fluorescein isothiocyanate (FITC) fluorescent dye, and subjected to flow cytometry. Staining of the cells for FITC is compared with staining of control cells that had been incubated with the labeled recombinant tumor antigen but not with the VHH. Increased FITC signal from the cells that had been incubated with tumor-antigen specific VHH and sortase, followed by incubation with labeled tumor antigen, as compared with staining of control lymphocytes either (i) incubated with tumor-antigen specific VHH in the absence of sortase followed by followed by incubation with labeled tumor antigen; or (ii) incubated with anti-GFP VHH in the presence of sortase followed by incubation with labeled tumor antigen indicates successful sortase-mediated conjugation of the tumor-antigen specific VHH to the cells.

Cytotoxic activity of lymphocytes labeled with either anti-TA VHH or anti-GFP VHH towards target cells expressing the tumor antigen at their surface is assessed in vitro using standard methods such as chromium release assays and compared with cytotoxic activity of control lymphocytes.

Lymphocytes labeled with either anti-TA VHH or anti-GFP VHH are administered to separate groups of mice bearing xenografts of human tumor cells expressing the tumor antigen at their surface. Tumors are isolated after 2-6 weeks and their size and weight determined and compared among groups.

Example 4: Sortase-Catalyzed Conjugation of VHH Protein to Non-Genetically Engineered Mammalian Cells Lymphocytes are isolated from mice using standard methods, and expanded and activated in vitro using appropriate antibodies (e.g., soluble or immobilized anti-CD3 mAb) and/or cytokines (e.g., IL-2) for T cell expansion and activation, and incubated in culture medium with a human tumor antigen-specific VHH containing a C-terminal HA-LPETG or a GFP-specific VHH containing a C-terminal HA-LPETG, either with or without sortase A from *Staphylococcus aureus* at 4° C. for 1 hour. Cells are then washed with PBS 5 times, incubated with anti-HA antibody labeled with fluorescein isothiocyanate (FITC) fluorescent dye, and subjected to flow cytometry. Staining of the cells for FITC is compared with staining of control cells that had been incubated with the labeled recombinant tumor antigen but not with the VHH. Increased FITC signal from the cells that had been incubated with tumor-antigen specific VHH and sortase followed by incubation with labeled tumor antigen, as compared with background staining of control cells incubated with tumor-antigen specific VHH in the absence of sortase followed by followed by incubation with labeled tumor antigen indicates successful sortase-mediated conjugation of the tumor-antigen specific VHH to the cells.

Cytotoxic activity of lymphocytes with either HA-tagged anti-TA VHH or HA-tagged anti-GFP VHH conjugated thereto towards target cells expressing the tumor antigen at their surface is assessed in vitro using standard methods such as chromium release assays and compared.

Lymphocytes with HA-tagged anti-TA VHH or HA-tagged anti-GFP VHH conjugated thereto are administered to mice bearing xenografts of human tumor cells expressing the tumor antigen. Tumors are harvested 2 hours later and analyzed for presence of administered lymphocytes using immunohistochemistry, staining with antibodies against either the HA tag, CD3 (to detect T cells), or both. Increased number of T cells in the tumors of mice to which the lymphocytes sortagged with HA-tagged anti-TA VHH were administered as compared with the number of T cells in the tumors of mice to which lymphocytes sortagged with HA-tagged anti-GFP VHH were administered demonstrates tumor targeting of the lymphocytes In another experiment lymphocytes with either HA-tagged anti-TA VHH or HA-tagged anti-GFP VHH conjugated thereto are administered to separate groups of immunocompromised mice bearing xenografts of human tumor cells expressing the tumor antigen at their surface. Tumors are isolated after 2-6 weeks and their average and total size and weight are determined and compared among groups. Reduced average and/or total tumor size and weight in the mice to which the lymphocytes sortagged with the anti-TA VHH were administered as compared with the mice to which the lymphocytes sortagged with anti-GFP VHH were administered is indicative that sortagging with a tumor-targeting moiety can improve efficacy of adoptive anti-tumor immunotherapy.

Example 5: Sortase-Catalyzed Conjugation of VHH Protein to Non-Genetically Engineered Human Lymphocytes Peripheral blood mononuclear cells (PBMC) from a human donor are isolated using standard methods, expanded and activated in vitro using appropriate antibodies (e.g., soluble or immobilized anti-CD3 mAb) and/or cytokines (e.g., IL-2) for T cell expansion and activation. An aliquot of the expanded and activated cells is incubated in culture medium with a human tumor antigen-specific VHH containing a C-terminal LPETG or an anti-GFP VHH containing a C-terminal LPETG, either with or without sortase A from *Staphylococcus aureus* at 4° C. for 1 hour. Cells are then washed with PBS 5 times, incubated with a recombinant tumor antigen labeled with either fluorescein isothiocyanate (FITC) or Cy7.5 near-infrared fluorescent dye, and subjected to flow cytometry. Staining of the cells for FITC or Cy7.5 is compared with staining of control cells that had been incubated with the labeled recombinant tumor antigen but not with the VHH. Increased FITC or Cy7.5 signal from the cells that had been incubated with tumor-antigen specific VHH and sortase followed by incubation with labeled tumor antigen, as compared with background staining of control cells incubated with tumor-antigen specific VHH in the absence of sortase followed by followed by incubation with labeled tumor antigen indicates successful sortase-mediated conjugation of the tumor-antigen specific VHH to the cells.

Cytotoxic activity of lymphocytes labeled with either human anti-TA VHH or anti-GFP VHH towards target cells (e.g., human tumor cells) expressing the tumor antigen at their surface is assessed in vitro using standard methods such as chromium release assays.

Lymphocytes labeled with either human anti-TA VHH or anti-GFP VHH are administered to immunocompromised mice bearing human tumor xenografts that express the TA at their surface. Tumors are isolated after 2-6 weeks and their average and total size and weight are determined and compared among groups. Reduced average and/or total tumor size and weight in the mice to which the lymphocytes sortagged with the anti-TA VHH were administered as compared with the mice to which the lymphocytes sortagged with anti-GFP VHH were administered is indicative that sortagging with a tumor-targeting moiety can improve efficacy of adoptive anti-tumor immunotherapy.

Example 6: Sortase-Catalyzed Conjugation of Antibodies to Non-Genetically Engineered Mammalian Lymphocytes Examples 3-5 are repeated except that a conventional human antibody comprising a chain that contains a sortase recognition sequence is used instead of a VHH.

Example 7: Sortase-Catalyzed Conjugation of Antibodies to Non-Genetically Engineered Mammalian Lymphocytes Examples 3-5 are repeated except that an scFv comprising a sortase recognition sequence is used instead of a VHH.

Example 8: Sortase-Catalyzed Conjugation of Antibodies to Non-Genetically Engineered Mammalian Lymphocytes Examples 3-7 are repeated with the additional step(s) of (i) enriching for CD8+ cells using MACS beads prior to sortagging (using, e.g., CD8+ T Cell Isolation Kit, human (#130-096-495), Miltenyi Biotec); (ii) applying co-stimulation using an antibody to CD28 prior to administration of the sortagged lymphocytes; and/or (iii) assessing cytotoxic activity of a sample of the sortagged lymphocytes in vitro by measuring secretion of granzyme and/or perforin and/or by assessing CD107 cell surface expression using anti-CD107 mAbs.

Example 9: Sortase-Catalyzed Conjugation of Sortase Substrate to Genetically Unmanipulated Eukarotyic Cells of Diverse Species Antibodies used in Examples 9, 10, 11, and/or 28: Anti-PGK (clone 22C5D8, Invitrogen), anti-mouse/human actin (clone Ab-5, BD biosciences), anti-*Toxoplasma gondii* actin, horseradish peroxidase-conjugated goat anti-rabbit Ig (Southern Biotech, cat. number 4041-05), horseradish peroxidase-conjugated anti-mouse Ig (GE Healthcare, cat. number NXA931), anti-TCRbeta (clone H57, BD Pharmingen), anti-CD4 (clone GK1.5, ebiosciences), anti-CD19 (clone 1D4, BD Pharmingen), anti-TER119 (clone TER-119, BD Pharmingen), allophycocyanin-conjugated streptavidin (ebiosciences, cat. number 17-4317), phycoerythrin-conjugated streptavidin (Southern Biotech, cat. number 7100-09S). Propidium iodide (Sigma-Aldrich, cat. number P4864).

Results:

*Saccharomyces cerevisiae* (W303), *Toxoplasma gondii*, HEK 293 T cells, or total mouse splenocytes from WT C57BL/6 mice were incubated 1 hour at room temperature with or without 500 µM of biotin-LPETG and with or without 20 µM of a Ca2+-independent sortase A (see description in Example 11). HEK 293T cells were incubated at 20 million per milliliter, *Toxoplasma gondii* at 20 to 40 million per milliliter, and yeast at 6 OD 280 units per milliliter. Conjugation of biotin-LPETG probes was analyzed by SDS page followed by Western blotting using Streptavidin HRP. Results are presented in FIGS. 5(A)-(D). The right lane of each blot contains a number of bands clearly showing the sortase-catalyzed labeling of multiple proteins in each cell type.

Total mouse splenocytes (20-100 million cells per milliliter) from WT C57BL/6 mice were incubated 1 hour at room temperature with 500 µM of biotin-LPETG and with (dark grey histograms) or without (light grey histograms) 201 µM of sortase A. Conjugation of biotin-LPETG was analyzed by flow cytometry using fluorescently labeled streptavidin together with antibody specific for T (TCRb), B (CD19), or red cells (Ter119). Results are presented in FIG. 5(E) and clearly show the presence of labeled cells of each cell type. Biotin-LPETG probes labeled T and B cells equally well, and slightly less efficiently, red cells.

We measured by flow cytometry the kinetics with which biotin-LPETG was conjugated to red cell-depleted splenocytes by flow cytometry. Conjugation reached ~30% of maximum after 5 minutes and ~60% of maximum after 15 minutes (FIG. 5(F)). Collectively, our data show that all cells tested were efficiently sortagged in a time frame compatible with the investigation of many biological processes. Presumably the vast majority of cells have naturally exposed glycines at their cell surface and will therefore be amenable to direct sortagging.

Example 10: Measurement of Immune System Cell-Mediated Cytotoxicity Towards Specific Target Cells This example demonstrates that red cell-depleted splenocytes from OTI Rag$^{-/-}$ mice contain a cell population capable of exerting cell-mediated toxicity towards appropriate target cells upon stimulation and presents a method of quantifying the cytotoxic effect. Splenocytes are a mixed population of immune system cells containing a variety of cell populations such as lymphocytes, NK cells, and macrophages. OTI Rag$^{-/-}$ mice are deficient for Rag and are transgenic for a T cell receptor that recognizes the SIINFEKL peptide in the context of H2$^b$. These mice produce CD8$^+$ cells that are specific for SIINFEKL. Due to the Rag-deficient status of the mice, they lack B cells and CD4$^+$ T cells.

Splenocytes were isolated from OTI Rag$^{-/-}$ mice and depleted of splenocytes by osmotic shock using standard methods. Red cell-depleted splenocytes from OTI Rag$^{-/-}$ mice were incubated in complete RPMI (RPMI 1640 supplemented with 10% (vol/vol) inactivated FCS, β-mercaptoethanol, non essential amino acids, sodium pyruvate and penicillin-streptomycin) in a 24 well plate coated with anti-CD3 and anti-CD28 antibody (2 μg/ml in PBS, 30 min at 37° C.) to stimulate the T cell population. After 72 hours, cells were mixed with red-cell depleted C57BL/6 splenocytes (isogenic with the OTI Rag$^{-/-}$ mice but for the Rag mutations) that had been pre-incubated for 30 min at 37° C. in complete RPMI plus DMSO or plus DMSO+SIINFEKL peptide (final concentration 1 μg/ml). The purpose of the pre-incubation in the presence of SIINFEKL was to load cells within the C57BL/6 splenocyte population with SIINFEKL, causing it to be displayed at the cell surface. The cells were mixed in 96 U bottom well plates at a 1:1 ratio (200,000 each) in 200 ml complete RPMI. After 24 hours, B cell viability was measured by staining the cell population with antibody to CD19 (a marker expressed on B cells) and propidium iodide (PI) and subjecting the cells to flow cytometry. Cells that are negative for PI staining are viable.

Figure 6:
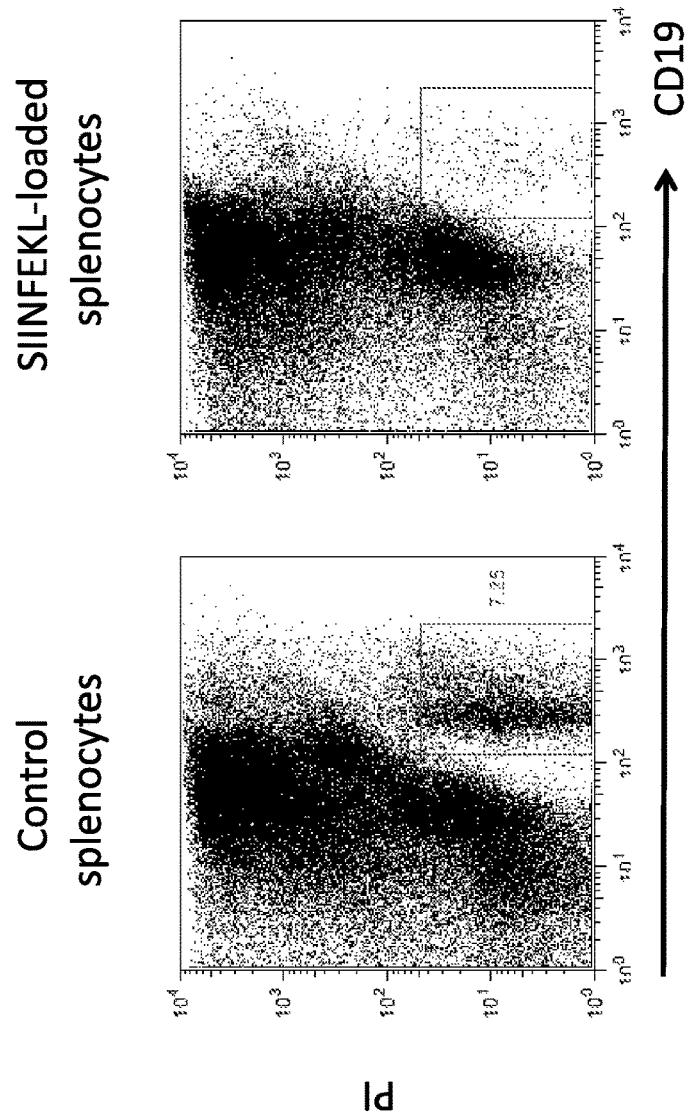
FIG. 6. Flow cytometry analysis demonstrating cytotoxicity of red cell depleted splenocytes from OTI Rag-/- mice (which express a T cell receptor specific for the SIINFELK peptide) towards splenocytes that display SIINFEKL peptide at their cell surface.

FIG. 6 shows dot plots showing viable C57BL/6 B cells (CD19+, PI−) (indicated in the boxed regions remaining after incubation of SIINFEKL-loaded (left panel) or control (right panel, not SIINFEKL-loaded) C57BL/6 splenocytes with the splenocytes from OTI Rag−/− mice (containing CD8+ cells specific for SIINFEKL). In the absence of SIINFEKL loading, about 7.5% of the C57BL/6 splenocytes detected (including both viable and non-viable cells) were viable B cells, while with SIINFEKL loading only about 1.1% of the C57BL/6 splenocytes were viable B cells. SIINFKEFL loading thus resulted in a dramatic reduction in the proportion of C57BL/6 splenocytes that were viable B cells following incubation with splenocytes from OTI Rag−/− mice (1.1% with SIINFEKL loading (right panel) versus 7.5% without SIINFEKL loading (left panel). This experiment confirms that splenocytes from OTI Rag−/− mice contain a population of cells that have the capacity to exert cell-mediated cytotoxicity towards target cells that bear a specific target antigen (in this case the peptide SIINFEKL) on their surface and that the approach described here is suitable to measure cell-mediated cytotoxicity towards target cells of interest.

Example 11: Non-Genetically Engineered Immune System Cells Sortagged with a Targeting Moiety Exhibit Cytotoxicity Specific for Target Cells This example demonstrates that attaching a targeting moiety to non-genetically engineered immune system cells using sortase increases their cytotoxicity specifically towards cells bearing a target to which the targeting moiety binds. As in Example 10, the experiment described in this example makes use of red cell-depleted splenocytes from OTI Rag$^{-/-}$ mice. The splenocytes were sortagged with a VHH (VHH7) that binds to mouse MHC Class I, and the ability of these cells to exert cytotoxic effects towards murine B cells expressing MHC Class I was assessed using a similar approach to that described in Example 9.

Red cell-depleted splenocytes from OTI Rag$^{-/-}$ mice were incubated in complete RPMI in a 24 well plate coated with anti-CD3 and anti-CD28 antibody as described in Example 10. After 72 hours the cells were washed and incubated with or without Enhancer VHH or VHH7 (5001 μM, 501 μM, or 51 μM) with or without sortase A (final concentration 201 μM mutated S. aureus srtA, Ca 2+ independent), in a total volume of 200 μl of PBS, 5×10$^6$ cell per reaction at room temperature for 1 hour, in order to conjugate the relevant VHH to the cell surface. The Ca2+ independent sortase that was used in this experiment is a 6×His tagged version with the following sequence:

(SEQ ID NO: 7)
MQAKPQIPKDKSKVAGYIEIPDADIKEPVYPGPATREQLNRGVSFAKENQ

SLDDQNISIAGHTFIDRPNYQFTNLKAAKKGSMVYFKVGNETRKYKMTSI

RNVKPTAVEVLDEQKGKDKQLTLITCDDYNEETGVWETRKIFVATEVKLE

HHHHHH

Enhancer VHH refers to a VHH that binds to GFP and has been modified to contain an LPETG sequence at its C-terminus, thus permitting the VHH to serve as a sortase substrate (see also Example 2). As noted above, VHH7 is a VHH that binds to murine MHC Class II molecules (PCT/US2013/036630 (WO/2013/155526; Witte, M D et al. (2012) PNAS, 109(30): 11993-11998). A version of VHH7 that contains a C-terminal LPETG was used in this experiment, thus permitting the VHH to serve as a sortase substrate. Where the terms "Enhancer VHH" and "VHH7" are used below and in FIG. 7 (which presents data from this Example), it should be assumed that the versions containing a C-terminal LPETG sequence were used.

Figure 7A:
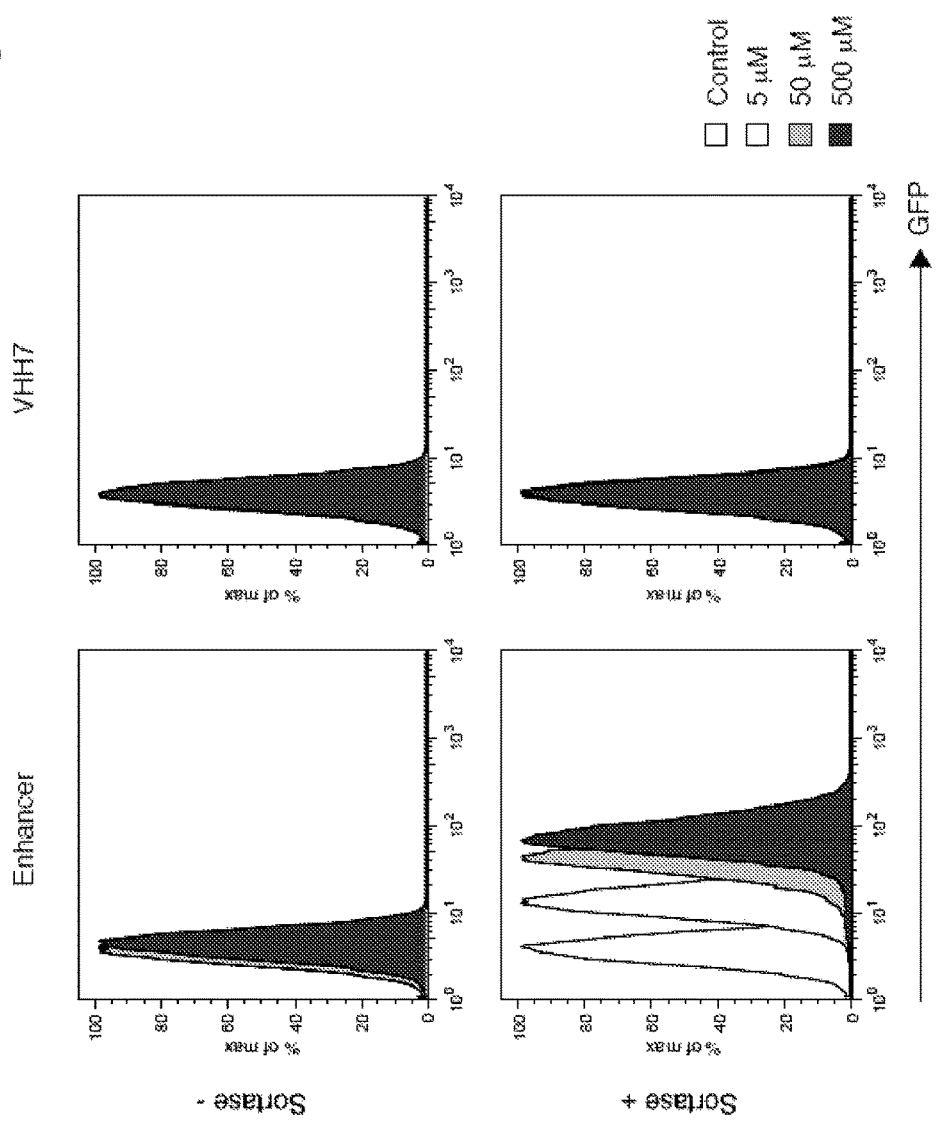
FIG. 7. Installation of VHHs on activated CD8+ T cells and demonstration of cytotoxicity of sortase-labeled CD8+ cells towards target cells expressing VHH target antigen. In vitro activated CD8+ T cells from OTI rag-/- mice were incubated for 1 hour at room temperature with or without 500 μM, 50 μM, or 5 μM of enhancer-LPETG or VHH7-LPETG and with or without 20 μM of sortase A, as indicated. (A) Control or sortagged cells were incubated with purified GFP protein. Binding of GFP through conjugated enhancer-LPETG was analyzed by flow cytometry. B) Control or sortagged cells were incubated with purified GFP protein. Amount of bound GFP was estimated by analyzing cell lysates by SDS-PAGE and Western blotting against GFP protein and comparing signal to a GFP standard (right lanes). C, D) Control (C) or sortagged cells (D) were incubated with splenocytes from WT mice for 20 hours. Histograms show the percentage of propidium iodide negative CD4 and CD19 cells as compared to cells incubated with unmanipulated activated OTI CD8 T cells. Enhancer VHH is a VHH that binds to GFP. VHH7 is a VHH that binds to MHC Class II but does not bind to GFP. Following incubation, cells were washed, contacted with GFP, and subjected to flow cytometry to detect GFP bound to the cells.

Following incubation with VHH7 or Enhancer VHH (or following control incubation without VHH), in each case either with or without sortase, red cell-depleted splenocytes from OTI Rag$^{-/-}$ mice were incubated with various concentrations of purified GFP protein or without GFP (Control). Binding of GFP through conjugated Enhancer-LPETG was analyzed by flow cytometry. As shown in FIG. 7(A), GFP binds to cells that were exposed to Enhancer in the presence of sortase (lower left panel) but does not bind to cells that were exposed to Enhancer in the absence of sortase or to cells that were exposed to VHH7 in the absence or presence of sortase (other 3 panels). To further demonstrate the sortase-catalyzed conjugation of VHHs to the cell surface, the amount of GFP bound to cells that had been incubated under each condition (i.e., in the absence or presence of sortase, in each case with either Enhancer or VHH7) was estimated by analyzing cell lysates by SDS-PAGE and Western blotting against GFP protein and comparing signal to a GFP standard (right lanes of FIG. 7(B)). As shown in FIG. 7(B), GFP binds only to the cells that were incubated with Enhancer in the presence of sortase. The number of VHHs installed was approximately proportional to the concentration of VHHs used for the reaction.

We estimated the number of VHHs installed per cell by measuring the number of bound GFP molecules by SDSPAGE and immunoblotting, using a solution of GFP of known concentration as standard (FIG. 7(B)). Sortagging of T cells in the presence of 500 μM of VHHs and sortase A resulted in the conjugation of ~1 million VHHs per cell.

Following incubation with VHH7 or Enhancer VHH (or following control incubation without VHH), in each case either with or without sortase, red cell-depleted splenocytes from OTI Rag$^{-/-}$ mice were washed and then incubated with red cell-depleted wild type C57BL/6 splenocytes for 24 h in U bottom 96 well plates at a 1:1 ratio (200,000 each) in 200 μl complete RPMI. After 24 hours, B cell viability among the red cell-depleted wild type C57BL/6 splenocytes was measured by staining with CD19 antibody and propidium iodide (PI) and subjecting the cells to flow cytometry. As a control, viability of CD4⁺ T cells among the red cell-depleted wild type splenocytes was measured by staining with CD4 antibody and propidium iodide (PI).

Figure 7D:
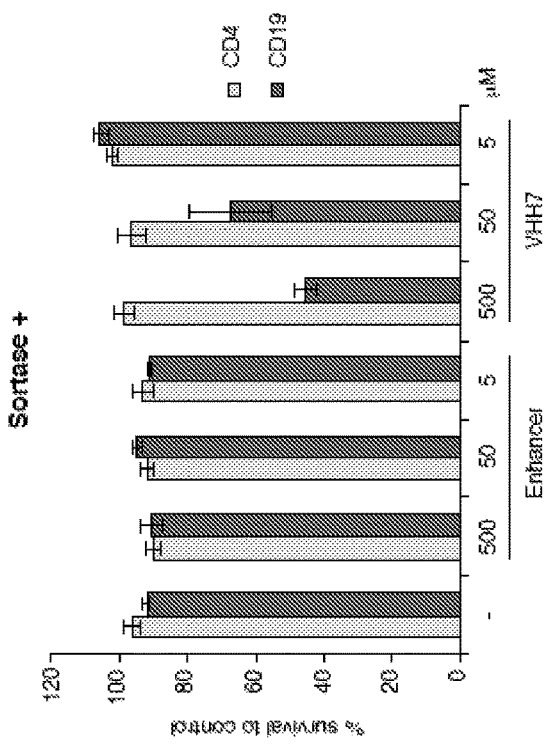
Figure 7C:
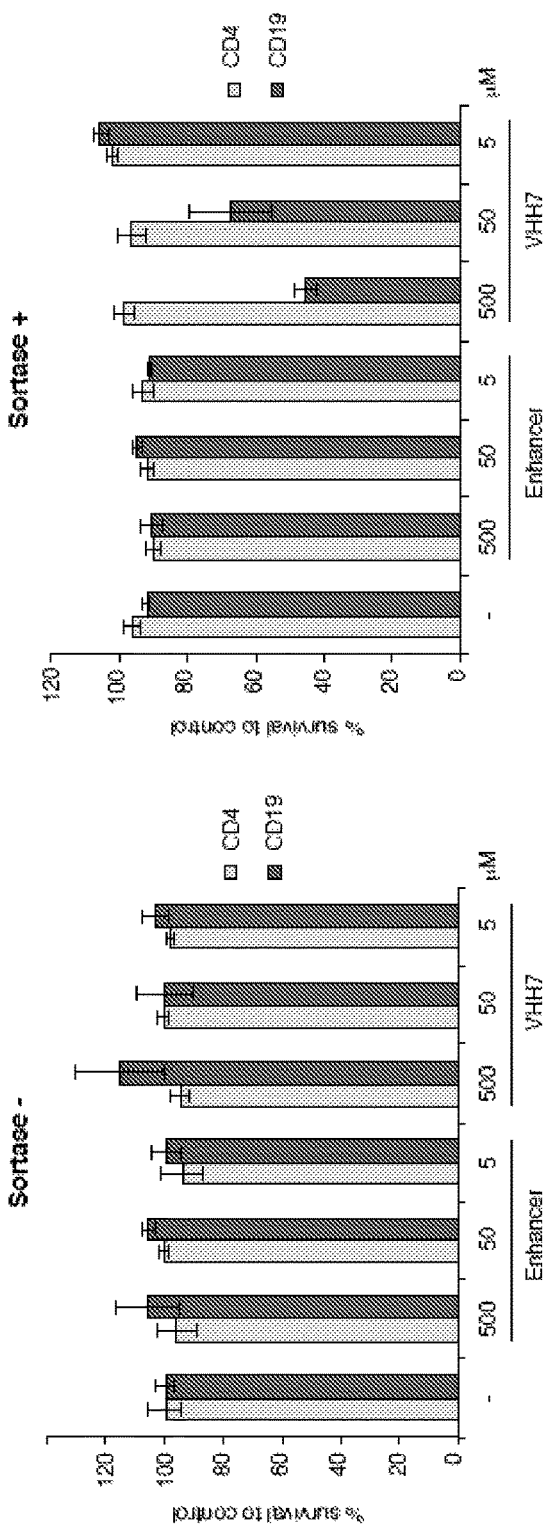

FIGS. 7(C) and 7(D) present bar graphs showing the percentage of viable C57BL/6 T cells (CD4+) and B cells (CD19⁺, PI⁻) in a representative experiment conducted with VHH7 either in the absence of sortase (left panel) or in the presence of sortase (right panel). The data indicate that non-sortagged splenocytes from OTI Rag$^{-/-}$ mice are not cytotoxic towards either C57BL/6 B cells or T cells i.e., approximately 100% of the C57BL/6 B cells and approximately 100% of the C57BL/6 T cells remain viable following incubation with non-sortagged splenocytes from OTI Rag$^{-/-}$ mice (regardless of whether such non-sortagged splenocytes from OTI Rag$^{-/-}$ mice had been incubated with VHH7, enhancer VHH, or no VHH). The data presented in FIG. 7(C) indicate that splenocytes from OTI Rag$^{-/-}$ mice that have been incubated with sortase alone (control) are not cytotoxic towards either C57BL/6 B cells or T cells i.e., approximately 100% of the C57BL/6 B cells and approximately 100% of the C57BL/6 T cells remain viable following incubation with splenocytes from OTI Rag$^{-/-}$ mice that had been incubated with sortase. The data presented in FIG. 7(D) indicate that splenocytes from OTI Rag$^{-/-}$ mice that have been incubated with sortase and Enhancer VHH are not cytotoxic towards either C57BL/6 B cells or T cells i.e., approximately 100% of the C57BL/6 B cells and approximately 100% of the C57BL/6 T cells remain viable following incubation with splenocytes from OTI Rag$^{-/-}$ mice that had been incubated with sortase and Enhancer VHH. The data presented in FIG. 7(D) also indicate that splenocytes from OTI Rag$^{-/-}$ mice that have been incubated with sortase and VHH7 (500 micromolar or 50 micromolar) are cytotoxic towards C57BL/6 B cells, but not towards C57BL/6 T cells. Thus, approximately 100% of the C57BL/6 T cells remain viable following incubation with splenocytes from OTI Rag$^{-/-}$ mice that had been incubated with sortase and Enhancer VHH, whereas only about 40% or 60% of the C57BL/6 B cells remain viable following incubation with splenocytes from OTI Rag$^{-/-}$ mice that had been incubated with sortase and 500 micromolar or 50 micromolar VHH7, respectively. These results demonstrate that non-genetically engineered cytotoxic immune system cells can be conjugated to a targeting moiety (in this case VHH7) using sortase and, as a result of such conjugation, exert cytotoxic effects specifically towards target cells that express the specific target of the binding moiety (in this case MHC Class II) at their cell surface.

Example 11A: Installation of Two Different Agents on Cells Using Sortase

Figure 11:
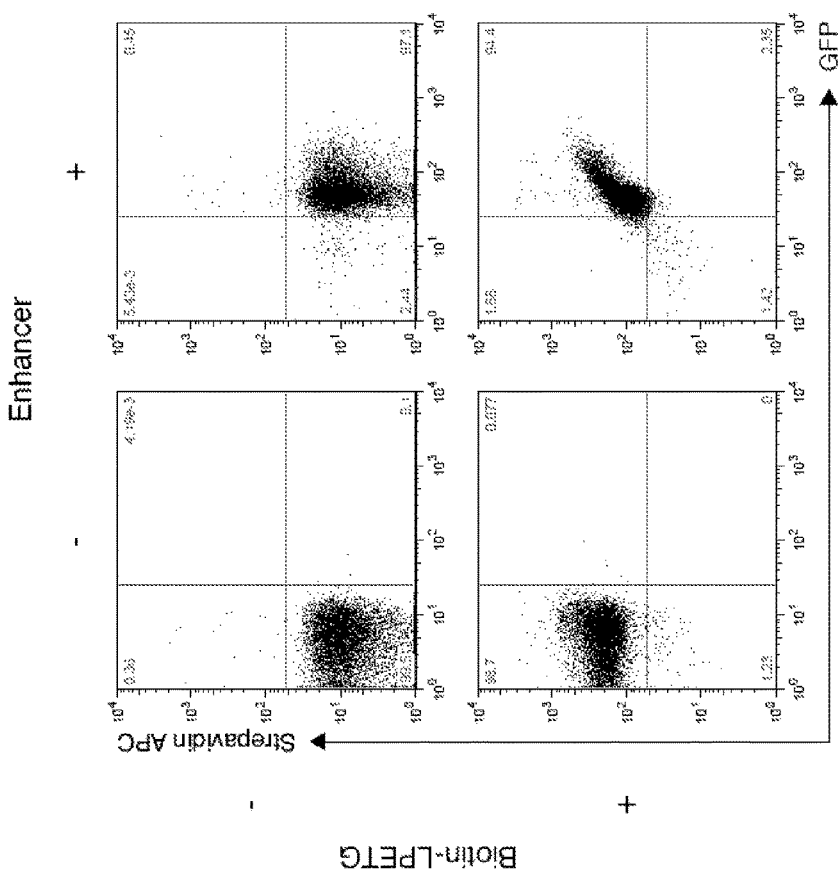
FIG. 11. Sequential installation of Enhancer first, then installation of LPETG-biotin, demonstrating that there are remaining sites on the cells that can serve as nucleophile to accept LPETG on cells already modified with Enhancer. Erythrocyte-depleted splenocytes were incubated with or without 500 μM enhancer-LPETG and 20 μM sortase A. After 60 minutes, 500 μM biotin-LPETG was added to reactions where indicated for a further 15 minutes. Dot plots show the binding of APC-conjugated streptavidin and GFP by sortagged cells after washing.

To investigate whether two different probes could be installed on lymphocytes, we incubated erythrocte-depleted splenocytes with or without enhancer-LPETG for 60 minutes in the presence of sortase A, followed by the addition of biotin-LPETG to the reaction for 15 minutes (FIG. 11). Cells incubated with enhancer-LPETG prior to biotin-LPETG had similar amounts of surface-conjugated biotin compared to cells incubated with biotin-LPTEG alone (FIG. 11). These data suggest that sortagging of VHHs to cells only minimally affects subsequent conjugation of biotin-LPETG. It is possible that the smaller LPETG-tagged probes may have more ready access to surface-displayed nucleophiles left unoccupied by larger LPETG-tagged proteins.

Example 12: Sortase Conjugation of CAR-Modified T Cells with Anti-PD-L1 Agent Human T cells obtained from a patient with B-cell chronic lymphoblastic leukemia are genetically modified to express a chimeric antigen receptor (anti-CD20 single chain Fv region fused to the transmembrane and intracellular domain of CD3-zeta, containing signaling domains of CD3-zeta and CD28). The cells are expanded for 10 days in culture with anti-CD3/anti-CD28 beads, then incubated with sortase and an agent comprising (i) the extracellular domain of PD-1 and (ii) a sortase recognition sequence, and transferred back into the patient. The effect of the administered cells on the leukemia is monitored.

Example 13: Sortase Conjugation of CAR-Modified T Cells with Anti-PD-1 Agent Human T cells obtained from a patient with B-cell chronic lymphoblastic leukemia are genetically modified to express a chimeric antigen cell receptor (anti-CD20 single chain Fv region fused to the transmembrane and intracellular domain of CD3-zeta, containing signaling domains of CD3-zeta and CD28). The cells are expanded for 10 days in culture with anti-CD3/anti-CD28 beads, then incubated with sortase and an agent comprising an scFv that binds to PD-1 that has been modified to comprise a sortase recognition sequence, and are then transferred into the patient. The effect of the administered cells on the leukemia is monitored.

Example 14: Treatment of Multiple Myeloma with Anti-CS1 or Anti-BCMA Conjugated NK Cells NK cells are isolated from a myeloma patient and expanded in culture. The cells are incubated with sortase and an anti-CS-1 or anti-BCMA antibody that has been modified to comprise a sortase recognition sequence, and are then transferred into the patient. The treatment is repeated weekly for 12 weeks. The effect of the administered cells on the multiple myeloma is monitored.

Example 15: Prevention of Metastasis with TRAIL-ES Conjugated PMBCs

PBMCs from a patient recently diagnosed with stage III colon carcinoma are isolated. The cells are incubated with sortase and an anti-CS-1 or anti-BCMA antibody that has been modified to comprise a sortase recognition sequence, and are then transferred into the patient. The treatment is repeated weekly for 12 weeks following colonic resection. The patient is monitored for presence of local recurrence or metastasis.

Example 16: Inhibition of Mesothelioma Tumor Growth in a Mouse Model by Mesothelin-Targeted T Cells A modified version of SS1 Fv, an Fv specific for mesothelin, is generated. The modified Fv has a sortase recognition sequence at the C-terminus. Human T cells (not genetically modified) are incubated with sortase and the modified SS1 Fv.

To assess the therapeutic effect of the SS1Fv-conjugated cells against established mesothelioma, mesothelioma tumors are established by intraperitoneal (i.p.) injection of 5 million LMB-H226-GL cells in 200 µl of growth media into the low abdomen or flank area of eight week old female athymic nude mice (ATHYMIC NCr-nu/nu) as described (Feng M, et al., J Cancer 2: 123-131). LMB-H226-GL cells are a human mesothelioma cell line LMB-H226-GL generated by Feng, et al by fluorescently labeling the NCI-H226 human mesothelioma cell line by a lentiviral vector harboring a luciferase-GFP (Luc/GFP) fusion gene driven by the RNA polymerase II promoter. After single-cell cloning by flow cytometry, a clone (named LMB-H226-GL) that stably expresses high levels of Luc/GFP was obtained. The labeled cells can be imaged in vivo, e.g., to monitor tumor growth. Following introduction of the mesothelioma cells, animals are imaged the following day and then once every week thereafter. The animals are divided into 5 groups; (1) Vehicle, (2) SS1P (0.4 mg/kg), (3) mesothelin-targeted T cells, (4) IL12-SS1 (Fv) (1.6 mg/kg body weight); (5) IL12-SS1 (Fv) (1.6 mg/kg body weight)+cells. IL12-SS1 (Fv) is a recombinant immunocytokine in which IL12 is fused to the anti-mesothelin antibody scFv (SS1). The p40 and p35 subunits of murine 1L12 are connected by flexible linker (Ser4Gly)3. IL12-SS1 is described further in Kim, H., et al., PLoS One. 2013 Nov. 15; 8(11):e81919. doi: 10.1371/journal.pone.00819190, The tumor-bearing mice are treated with the respective treatments or vehicle every the other day. The day when the mice were injected with the tumor cells is considered as day SS1P, anti-MSLN scFv conjugated with *Pseudomonas* toxin, is used as a positive control. The treatment groups and control group each contain 5 mice. Each mouse in the treatment groups receives 0.4 mg/kg body weight of SS1P, 0.4 mg/kg (low dose group). or 1.6 mg/kg (high dose group) of IL12-SS1 (Fv) every other day. The control group receives PBS as a vehicle control. Body weight and tumor growth are assessed twice a week, Assessment of tumor growth is performed. as follows: Two hundred microliters of 15 mg/mL D-luciferin (Caliper Life Sciences, Hanover, Md.) in PBS are injected i.p. before imaging. The luciferase activity of the tumor os alculated using Living Image 3.1.0 software (Caliper Life Sciences, Hanover, Md.), Intraperitoneal Tumor growth was assessed using photon intensity, photons per second (ph/sec) as luciferase activity as described (Feng, et a, cited earlier in this example). At the end of the treatment, three mice in each group are euthanized, Blood is taken for whole blood complete blood counts (CBC) and serum chemistry analysis. A full necropsy is performed, in which organs and tissues are weighed and examined for gross findings, Statistical analysis is performed with Prism (version 5) for Windows (GraphPad Software, La Jolla, Calif.). Raw data are analyzed by "analysis of variance" with Dunnett's and Newman-Keuls multiple comparison post tests, p values <. 0.05 are considered statistically significant.

Example 17: Treatment of Ovarian Cancer in a Mouse Model with Anti-CA125 Antibody Conjugated NK Cells Human NK cells are incubated with sortase and an anti-CA-125 antibody that has been modified to comprise a sortase recognition sequence. Following conjugation, NK cells are cultured with OVCAR cells (an epithelial ovarian cancer cell (EOC) line that expresses CA125 and mesothelin). Cells are stained with propidium iodide and analyzed by FACS. The ability of the CA-125-targeted NK cells to kill OVCAR cells in vitro is confirmed.

Efficacy of CA-125-targeted NK cell therapy in vivo either as single agent or in combination with docetaxel (DTX) (a standard chemotherapeutic agent used to treat ovarian cancer) is assessed in an intraperitoneal (i.p.) EOC mouse model that utilizes a subline of the OVCAR cell line termed OVCAR-3. (Further details of the OVCAR3 cells and model are described in Pourgholami M H, et al. Clin Cancer Res 12: 1928-1935 and Wang L, et al. PLoS ONE 6(9): e24405. doi:10.1371/journal.pone.0024405.). OVCAR-3 cells are implanted intraperitoneally in female athymic nude mice and allowed to grow tumor and ascites. Mice are then treated with various number of CA-125-targeted NK cells, various concentrations of DTX, combination test (CA-125-targteted NK cells and DTX), combination control (unconjugated human NK cells and DTX) or vehicle control i.p for 3 weeks. Treated mice are killed 4 weeks post-treatment. Ascites volume, tumor weight, CA125 levels from ascites, and survival of animals are assessed. The expression of MUC1 (tumor antigen expressed by OVCAR cells), CD31, Ki-67 (proliferation marker), TUNEL and apoptotic proteins in tumor xenografts was evaluated by immunohistochemistry. The ability of CA-125-targeted NK cells to inhibit i.p. tumor development, growth, and ascites production in a dose-dependent manner is assessed.

Example 18: Treatment of Ovarian Cancer in a Mouse Model with Anti-CA125 Antibody Conjugated T Cells The preceding example is repeated using human T cells obtained from the patient and expanded in culture.

Example 19: Treatment of Ovarian Cancer with Anti-CA125 and Anti-Mesothelin Antibody Conjugated NK Cells NK cells are isolated from a patient with stage III primary ovarian cancer and expanded in culture. An aliquot of the cells are incubated with sortase and an anti-CA-125 antibody that has been modified to comprise a sortase recognition sequence. A second aliquot of the cells is incubated with sortase and an anti-mesothelin antibody that has been modified to comprise a sortase recognition sequence.

Cells from each sortagged population are transferred back into the patient. The treatment is repeated weekly for 12 weeks following surgery. The effect of the administered cells on residual cancer and metastases is monitored. The patient is monitored for blood levels of CA-125 and is retreated with CA-125-targeted NK cells if an elevated CA-125 level is detected.

Example 20: Treatment of Ovarian Cancer with Anti-CA125 and Anti-Mesothelin Antibody Conjugated PBMCs The preceding example is repeated except that PBMCs obtained from the patient are used.

Example 21: Treatment of Ovarian Cancer with Anti-CA125 and Anti-Mesothelin Antibody Conjugated Allogeneic NK Cells The preceding example is repeated except that allogeneic NK cells, in this case NK-92 cells, are used Example 22: Treatment of Ovarian Cancer with IL-12-Conjugated CAR T Cells Human T cells obtained from a patient with stage III ovarian cancer are genetically modified to express a chimeric T cell receptor (anti-CA125 single chain Fv region fused to the transmembrane and intracellular domain of TCR, containing signaling domains of CD3-epsilon and CD28). The cells are expanded for 10 days in culture with CD3-CD28 beads and then incubated with sortase and a fusion protein that contains the two subunits of human interleukin-12 as a single polypeptide with a sortase recognition sequence at the C-terminus, and transferred back into the patient after surgery. Treatment is repeated weekly for 12 weeks. The effect of the administered cells on residual cancer and metastases is monitored. The patient is monitored for blood levels of CA-125 and is retreated if an elevated CA-125 level is detected.

Example 23: Treatment of Ovarian Cancer with T Cells Sortagged with a Bispecific Agent Single domain antibodies specific for CA-125 and CD3 epsilon are produced in a recombinant cell expression system. The sdAb specific for CD3 epsilon is produced with a sortase recognition motif incorporated at the C-terminus. Click chemistry handles are installed at the N-termini of each sdAb using sortase. The two sdAbs are then conjugated together to produce a bispecific antibody. Human T cells obtained from a patient with stage III ovarian cancer are expanded in culture with CD3-CD28 beads and then incubated with sortase and the bispecific antibody and are transferred back into the patient after surgery. Treatment is repeated weekly for 12 weeks. The effect of the administered cells on residual cancer and metastases is monitored. The patient is monitored for blood levels of CA-125 and is retreated if an elevated CA-125 level is detected.

Example 24: Treatment of Leukemia with Sortagged T Cells

Human T cells obtained from a patient with B-cell acute lymphoblastic leukemia are expanded for 10 days in culture with anti-CD3/anti-CD28 beads, then sortagged with an scFv that binds to CD19 and transferred into the patient. The effect of the administered cells on the leukemia is monitored.

Example 25: Treatment of Leukemia with Sortagged T Cells

Human T cells obtained from a patient with B-cell acute lymphoblastic leukemia are genetically modified to express a chimeric antigen cell receptor (anti-CD19 single chain Fv region fused to the transmembrane and intracellular domain of TCR, containing signaling domains of CD3-zeta and CD28). The cells are expanded for 10 days in culture with anti-CD3/anti-CD28 beads, then sortagged with an scFv that binds to CD22, and transferred into the patient. The effect of the administered cells on the leukemia is monitored.

Example 26: Treatment of Leukemia with Sortagged T Cells

Human T cells obtained from a patient with B-cell acute lymphoblastic leukemia are genetically modified to express a chimeric antigen cell receptor (anti-CD22 single chain Fv region fused to the transmembrane and intracellular domain of TCR, containing signaling domains of CD3-zeta and CD28). The cells are expanded for 10 days in culture with anti-CD3/anti-CD28 beads, then sortagged with an scFv that binds to CD19, and transferred into the patient. The effect of the administered cells on the leukemia is monitored.

Example 27: Clinical Trial of Treatment of Ovarian Cancer with Anti-CA125 Antibody Conjugated T Cells Patients with advanced ovarian cancer are randomized to receive, following surgery, either (1) standard adjuvant chemotherapy with platinum-taxane alone; (2) standard adjuvant chemotherapy with platinum-taxane and, in addition, therapy with intravenously administered autologous T cells conjugated with an anti-CA-125 antibody using sortase without genetic modification; or (3) standard adjuvant chemotherapy with platinum-taxane and, in addition, therapy with both intravenously and intraperitoneally administered autologous T cells conjugated with an anti-CA-125 antibody using sortase without genetic modification. Progression-free survival and 5 year survival rates of patients in the three treatment groups are monitored and compared.

Example 28: Sortase Conjugation of Red Blood Cells with Anti-PD-L1 Agent

Human red blood cells are obtained from a patient with B-cell chronic lymphoblastic leukemia or from an immunocompatible donor and incubated with sortase and an agent comprising (i) the extracellular domain of PD-1 and (ii) a sortase recognition sequence. Red blood cells are transferred into the patient after sortagging. The effect of the administered cells on the leukemia is monitored.

Example 29: Sortase Conjugation of Red Blood Cells with Anti-PD-1 Agent

Human red blood cells obtained from a patient with B-cell chronic lymphoblastic leukemia or from an immunocompatible donor are incubated with sortase and an agent comprising an scFv that binds to PD-1 and that has been modified to comprise a sortase recognition sequence. Red blood cells are transferred into the patient after sortagging. The effect of the administered cells on the leukemia is monitored.

Example 30: Treatment of Multiple Myeloma with Anti-CS1 or Anti-BCMA Conjugated Red Blood Cells Red blood cells are isolated from a myeloma patient or from an immunocompatible donor. The cells are incubated with sortase and an anti-CS-1 or anti-BCMA antibody that has been modified to comprise a sortase recognition sequence, and are then transferred into the patient. The treatment is repeated weekly for 12 weeks. The effect of the administered cells on the multiple myeloma is monitored.

Example 31: Prevention of Metastasis with TRAIL-ES Conjugated RBCs

Red blood cells are isolated from a patient recently diagnosed with stage III colon carcinoma or obtained from an immunocompatible donor. The cells are incubated with sortase and an anti-CS-1 or anti-BCMA antibody that has been modified to comprise a sortase recognition sequence, and are then transferred into the patient. The treatment is repeated weekly for 12 weeks following colonic resection. The patient is monitored for presence of local recurrence or metastasis.

Example 32: Treatment of EAE Using Red Blood Cells Sortagged with Peptide Fragment of Myelin Basic Protein Sortase is used to conjugate either myelin basic protein (MBP) that has been modified to comprise a sortase recognition sequence or ovalbumin that has been modified to comprise a sortase recognition sequence to non-genetically modified RBCs obtained from SJL mice.

Eight SJL mice are injected intravenously (iv) via tail vein with $1 \times 10^8$ RBC coupled to mouse MBP (MBP-RBC). Control mice receive $1 \times 10^8$ ovalbumin-coupled RBCs (OV-RBC), also prepared using sortase. One week later, all animals are immunized with syngeneic spinal cord homogenate in an emulsion in complete Freund's adjuvant to induce EAE according to standard methods.

Animals are weighed and examined daily from Day 7. Neurological deficit is graded according to the following scale: mild, a flaccid tail for 2 or more days with associated weight loss; or severe, definite paralysis, often with scissoring of the hind limbs. Animals are sacrificed 27 days after initial immunization. Brains are removed and fixed in 10% Formalin. Sections are made, stained with hematoxylin and eosin and scored on a scale from 1-5 in a blinded manner, according to the extent of meningeal inflammation and lymphocyte cuffing.

The clinical severity of EAE, pathologic severity of EAE, and weight loss are compared between the MBP-RBC and control groups. A lower level of clinical severity, lower level of pathological severity, and/or reduced weight loss (or weight gain instead of weight loss) in the MBC-RBC treated group as compared with the controls is evidence of effective inhibition of EAE.

Example 33: Treatment of Melanoma Using Sortagged T Cells

T cells isolated from a patient diagnosed with melanoma or obtained from an immunocompatible donor are expanded and sortagged with an antibody to a melanoma antigen, for example MART-1, and two checkpoint inhibitors, for example ipilimumab (anti-CTLA4) and anti-PD1 nivolumab. The sortagged T cells are administered to a patient with melanoma. The effect of the administered cells on the melanoma is monitored.

Example 34: Treatment of HER2 Positive Breast Cancer Using Sortagged Red Blood Cells RBCs isolated from a patient diagnosed with HER2 positive breast cancer or obtained from an immunocompatible donor are sortagged with Herceptin, anti-PD1 antibody, and anti-VEGFR2 antibody and are administered to the patient with HER2 positive breast cancer. The effect of the administered cells on the cancer is monitored.

Example 35: Treatment of HER2 Positive Breast Cancer Using Sortagged Red Blood Cells RBCs isolated from a patient diagnosed with HER2 positive breast cancer or obtained from an immunocompatible donor are sortagged with TRAIL and Herceptin and administered as an adjunct to standard chemotherapy/Herceptin therapy of HER-2 positive breast cancer. The effect of the administered cells on the cancer is monitored.

Example 36: Treatment of Relapsed/Refractory B-Precursor ALL

Relapsed/refractory B-precursor ALL in adult patients is an aggressive malignant disease with dismal prognosis and unmet medical need. Red blood cells sortagged to carry blinatumomab (a bispecific single-chain antibody construct designed to link B cells and T cells resulting in T cell activation and a cytotoxic T cell response against CD19 expressing cells) are administered to adult patients with relapsed/refractory B-precursor ALL. Patients receive up to five monthly cycles of intravenous RBC-blinatumomab treatment.

Example 37: Sortase-Catalyzed Installation of VHHs on *Toxoplasma gondii* Allows Cell-Specific Targeting As described above, modification of CD8 T cells through sortagging does not obviously interfere with cytotoxic functions. Invasion of host cells by parasites represents another type of cell-cell interaction. To investigate whether *Toxoplasma gondii* tachyzoites modified using sortase would be able to invade cells, we sortagged parasites with TAMRA-modified LPETG peptides and incubated them together with human foreskin fibroblasts. Tachyzoites (20 to 40 million per milliliter) were incubated with 5001 µM TAMRA-LPETG and 20 µM Ca2+-independent sortase A (same as used in Example 11) in HHE (Hanks buffer+Hepes+EDTA) for 15 minutes. Parasites were then washed and incubated with human foreskin fibroblasts (HFF). Sortagged parasites were visualized by fluorescence microscopy and their ability to invade the fibroblasts was monitored and recorded. We found that the sortagged parasites were perfectly capable of invading fibroblasts (FIG. 8(A); video available upon request).

Figure 8:
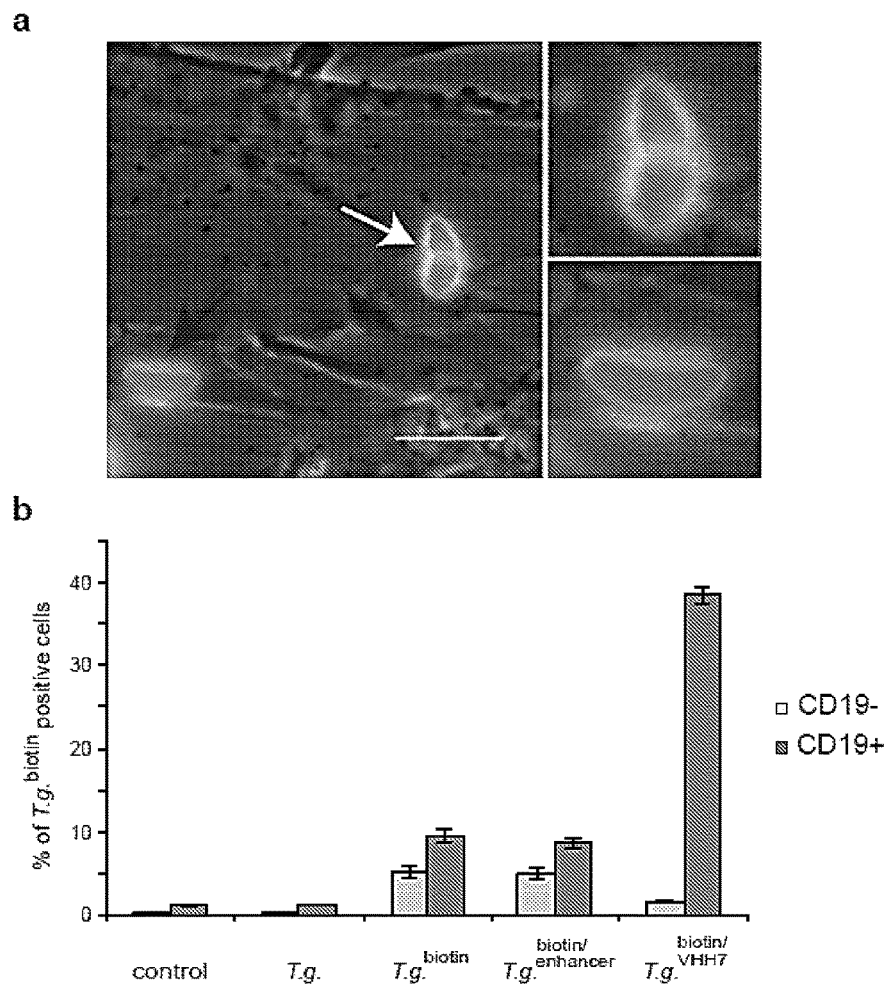
FIG. 8. (a) *Toxoplasma gondii* tachyzoites were incubated with 500 μM TAMRA-LPETG and 20 μM sortase A for 15 minutes. Parasites were then washed and incubated with human foreskin fibroblasts. Images show the juxtaposition of bright and fluorescent fields. Black arrow: intracellular parasite. White arrow: invading parasite. Scale bar: 10 micrometer. Right panels: zoomed images. (b) Histogram showing the percentage of sortagged *Toxoplasma* positive cells within CD19 negative (light gray bars) or CD19 positive (dark gray bars) splenocyte populations after incubation of Enhancer-sortagged or VHH-7 sortagged *Toxoplasma gondii* with mouse splenocytes. (c) Purified B cells from WT or class II MHC k.o. mice were incubated together with control *T. gondii* or *T. gondii* sortagged with enhancer or VHH7 at a multiplicity of infection of 5. Fifteen hours after infection, cell lysis was measured and normalized to uninfected (0%) and detergent-lysed B cells (100%). Error bars: standard deviation (n=3). **: p<0.01 at Student T-test.
Figure 8:
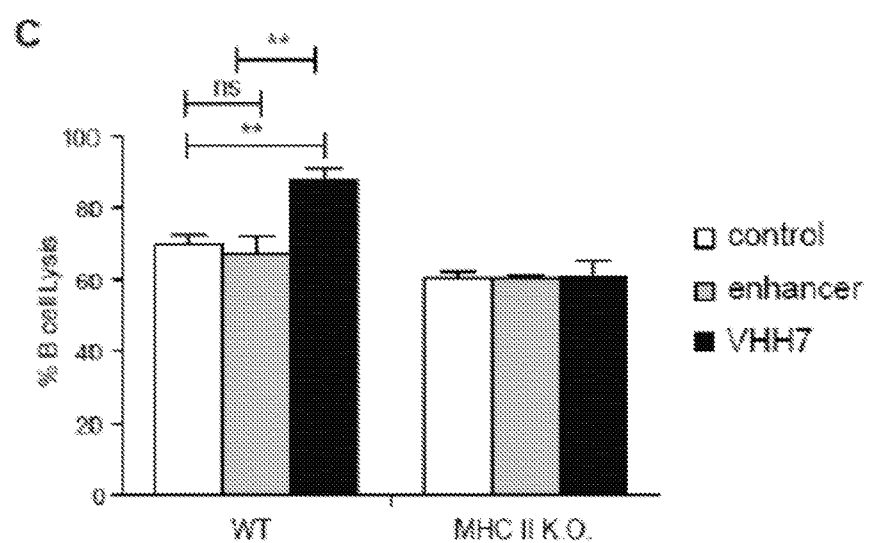
Figure 9:
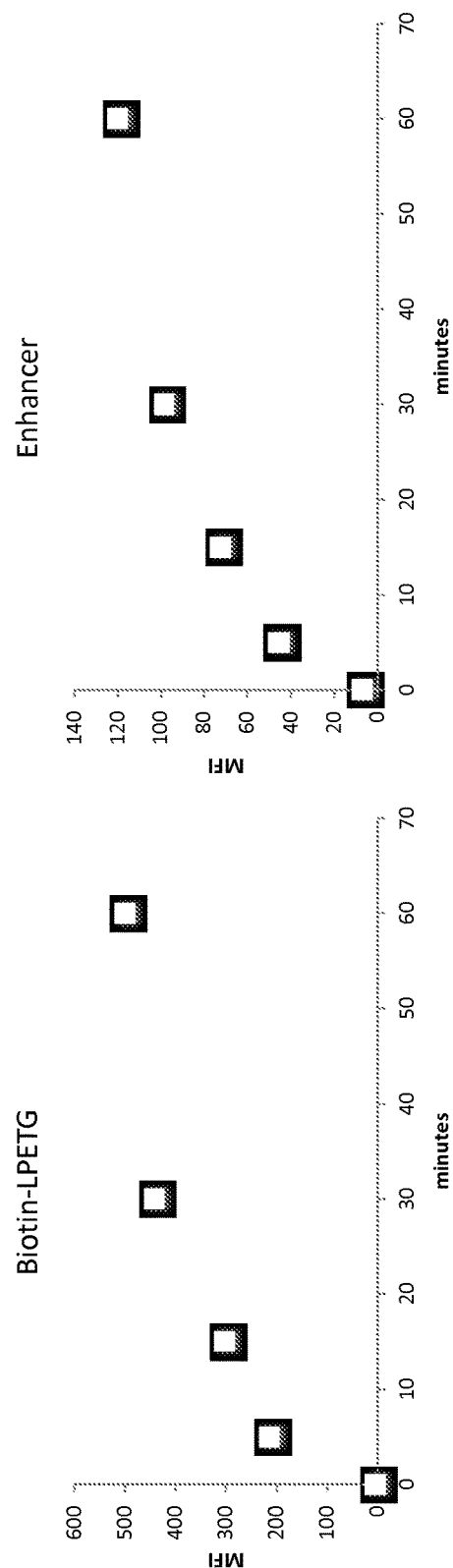
FIG. 9. Kinetic analysis showing installation of two substrates: LPETG-biotin and single domain anti-GFP VHH (Enhancer) on cells as a function of time at 37 degrees C.
Figure 10:
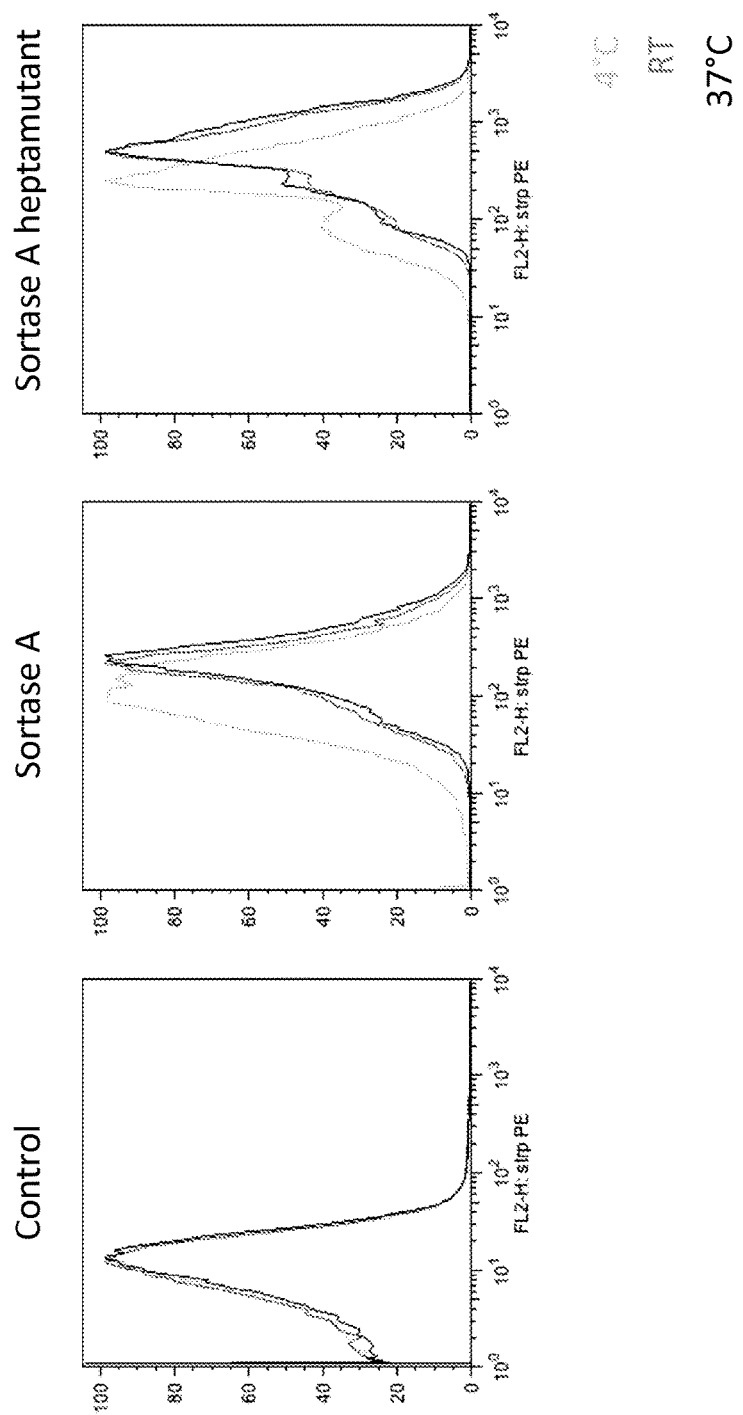
FIG. 10. Installation of LPETG-biotin on intact cells, followed by staining with streptavidin-PE. Panels show reaction with no enzyme (left panel), *S. aureus* Sortase A (middle panel) and $Ca^{2+}$-independent sortase heptamutant (right panel) at the indicated temperatures (bottom right). Mutations in heptamutant are shown in SEQ ID NOs: 4 and 7.

To address whether *Toxoplasma gondii* could be targeted to specific cells, we sortagged parasites with biotin or biotin plus Enhancer or VHH7 and incubated them with wild type splenocytes. *Toxoplasma gondii* tachyzoites were incubated with or without 50 µM enhancer-LPETG or VHH7-LPETG and 20 µM Ca2+-independent sortase A (same as used in Example 11) in HHE. After 20 minutes, biotin-LPETG was added for 15 minutes. Parasites were then washed and incubated with red-cell depleted splenocytes for 1 hour at a multiplicity of infection of 5. Cells were then washed and stained with a CD19-specific antibody and fluorescently labeled streptavidin. The percentages of CD19$^+$ and CD19$^-$ cells that were biotin positive (indicative of invasion by sortagged *T. gondii*) were quantified by FACS. The histogram in FIG. 8(B) shows the percentage of cells that were positive for sortagged *T. gondii* within the CD19 negative or positive populations. Sortagging of VHH7 to *Toxoplasma gondii* resulted in a dramatic increase of B cells targeted by *Toxoplasma gondii*, together with a significant decrease of binding of non-B cells suggesting very selective targeting. In addition, it enhanced the percentages of B cell lysed upon infection (FIG. 8(C)). The B cells lysis assay was performed as follows: *Toxoplasma gondii* tachyzoites were incubated with or without 50 µM enhancer- or VHH7-LPETG and 20 µM sortase A at room temperature in HHE buffer for 15 minutes. After washing *T. gondii* was incubated together with 0.5 million magnetic beads-purified splenic B cells from WT or class II MHC k.o. mice at a multiplicity of infection of 5 in 100 μl or complete RPMI in 96 flat bottom well plates. After 15 hours supernatants were harvested and cell lysis was measured using CytoTox 96 Non-Radioactive Cytotoxicity Assay kit (Promega, cat. G1781) according to manufacturer's instructions.

These results support the feasibility of using sortagging to target pathogens (e.g., cytolytic pathogens) to cells of interest, e.g., cancer cells.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments described herein, which fall within the scope of the claims. The scope of the present invention is not to be limited by or to embodiments or examples described above.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, sortase substrate, sortase, composition, amount, dose, administration route, cell type, species, target, cellular marker, antigen, epitope, targeting moiety, or combination thereof. In certain embodiments cells are not CHO cells. In certain embodiments cells are not HEK293T cells. In certain embodiments the sortase substrate used in a sortase reaction does not comprise an enhanced green fluorescent protein. In certain embodiments the sortase substrate used in a sortase reaction does not comprise an enhanced cyan fluorescent protein (ECFP). In certain embodiments the sortase substrate used in a sortase reaction does not comprise an AlexaFluor. In certain embodiments cells are not pre-incubated with sortase before being contacted with a sortase substrate in the presence of sortase. In certain embodiments cells are not pre-incubated with a nucleophilic acceptor sequence, e.g., an oligoglycine, e.g., triglycine, before being contacted with a sortase substrate in the presence of sortase. In certain embodiments if cells are pre-incubated with sortase and/or with a nucleophilic acceptor sequence, e.g., an oligoglycine, e.g., triglycine, before being contacted with a sortase substrate in the presence of sortase, such pre-incubation is for less than 15 minutes, less than 30 minutes, less than 60 minutes, or less than 120 minutes.

Embodiments in which any one or more limitations, elements, clauses, descriptive terms, etc., of any claim (or relevant description from elsewhere in the specification) is introduced into another claim are provided. For example, a claim that is dependent on another claim may be modified to include one or more elements or limitations found in any other claim that is dependent on the same base claim. It is expressly contemplated that any amendment to a genus or generic claim may be applied to any species of the genus or any species claim that incorporates or depends on the generic claim.

Where a claim recites a composition, methods of using the composition as disclosed herein are provided, and methods of making the composition according to any of the methods of making disclosed herein are provided. Where a claim recites a method, a composition for performing the method is provided. Where elements are presented as lists or groups, each subgroup is also disclosed. It should also be understood that, in general, where embodiments or aspects is/are referred to herein as comprising particular element(s), feature(s), agent(s), substance(s), step(s), etc., (or combinations thereof), certain embodiments or aspects may consist of, or consist essentially of, such element(s), feature(s), agent(s), substance(s), step(s), etc. (or combinations thereof). It should also be understood that, unless clearly indicated to the contrary, in any methods claimed herein that include more than one step or act, the order of the steps or acts of the method is not necessarily limited to the order in which the steps or acts of the method are recited. Any method of treatment may comprise a step of providing a subject in need of such treatment. Any method of treatment may comprise a step of providing a subject having a disease for which such treatment is warranted. Any method of treatment may comprise a step of diagnosing a subject as being in need of such treatment. Any method of treatment may comprise a step of diagnosing a subject as having a disease for which such treatment is warranted.

Where ranges are given herein, embodiments in which the endpoints are included, embodiments in which both endpoints are excluded, and embodiments in which one endpoint is included and the other is excluded, are provided. It should be assumed that both endpoints are included unless indicated otherwise. Unless otherwise indicated or otherwise evident from the context and understanding of one of ordinary skill in the art, values that are expressed as ranges can assume any specific value or subrange within the stated ranges in various embodiments, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise. Where a phrase such as "at least", "up to", "no more than", or similar phrases, precedes a series of numbers, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated.

What is claimed is:

1. A human cell having a binding moiety or therapeutic agent linked thereto via a sortase recognition sequence, wherein the binding moiety or therapeutic agent is linked to an endogenous, non-genetically engineered protein expressed by the human cell, and wherein the human cell has not been genetically engineered to express a polypeptide comprising a sortase recognition sequence, wherein the binding moiety or therapeutic agent comprises an immune checkpoint inhibitor.

2. The human cell of claim 1, wherein the human cell is an immune system cell.

3. The human cell of claim 1, wherein the sortase recognition sequence comprises LPXTG.

4. The human cell of claim 1, wherein the binding moiety comprises a targeting moiety that binds to an epitope or antigen of interest.

5. The human cell of claim 1, wherein the binding moiety comprises a monoclonal antibody, a single chain antibody, or a single domain antibody.

6. The human cell of claim 5, wherein the binding moiety comprises a VHH.

7. The human cell of claim 1, wherein the human cell is selected from the group consisting of a red blood cell, a peripheral blood mononuclear cell, a lymphocyte, a T cell, a NK cell, and a dendritic cell.

8. The human cell of claim 1, wherein the human cell is a non-immortalized cell.

9. The human cell of claim 1, wherein the human cell is a primary cell.

10. The human cell of claim 1, wherein the human cell has not been genetically engineered to express a polypeptide comprising a sequence comprising one or more N-terminal glycines.

11. The human cell of claim 1, wherein the human cell has not been genetically engineered.

12. A method of treating a subject in need of treatment for a disease, the method comprising administering at least one human cell of claim 1 to the subject, wherein the at least one cell is effective for treating the disease.

13. The method of claim 12, wherein the human cell originates from the subject and said subject is in need of evaluation or treatment for a disease of interest or from a donor who is immunocompatible with the subject.

14. The method of claim 13, wherein the human cell originates from the subject in need of evaluation or treatment for a disease characterized by the presence of abnormal or excessive cells or pathogens in the subject's body, or from a donor who is immunocompatible with the subject.

15. The method of claim 14, wherein the human cell originates from the subject in need of evaluation or treatment for cancer, an autoimmune disease, or an infection or from a donor who is immunocompatible with the subject.

16. A mammalian cell having a binding moiety or therapeutic agent linked thereto via a sortase recognition sequence, wherein the binding moiety or therapeutic agent is linked to an endogenous, non-genetically engineered protein expressed by the mammalian cell, and wherein the binding moiety or therapeutic agent comprises an immune checkpoint inhibitor.

17. A method of treating a subject in need of treatment for a disease, the method comprising administering the mammalian cell of claim 16 to the subject.

* * * * *